United States Patent
Platero et al.

(10) Patent No.: US 12,037,644 B2
(45) Date of Patent: *Jul. 16, 2024

(54) USE OF FGFR MUTANT GENE PANELS IN IDENTIFYING CANCER PATIENTS THAT WILL BE RESPONSIVE TO TREATMENT WITH AN FGFR INHIBITOR

(71) Applicant: Janssen Pharmaceutica NV, Beerse (BE)

(72) Inventors: Suso Jesus Platero, Washington Crossing, PA (US); Jayaprakash Karkera, Germantown, MD (US)

(73) Assignee: Janssen Pharmaceutica NV, Beerse (BE)

( * ) Notice: Subject to any disclaimer, the term of this patent is extended or adjusted under 35 U.S.C. 154(b) by 30 days.

This patent is subject to a terminal disclaimer.

(21) Appl. No.: 16/136,201

(22) Filed: Sep. 19, 2018

(65) Prior Publication Data

US 2019/0078166 A1  Mar. 14, 2019

Related U.S. Application Data

(63) Continuation of application No. 14/858,627, filed on Sep. 18, 2015, now abandoned.

(60) Provisional application No. 62/056,159, filed on Sep. 26, 2014.

(51) Int. Cl.
| | | |
|---|---|---|
| *A61P 35/00* | (2006.01) | |
| *A61K 31/415* | (2006.01) | |
| *A61K 31/498* | (2006.01) | |
| *C12Q 1/6886* | (2018.01) | |

(52) U.S. Cl.
CPC ..... *C12Q 1/6886* (2013.01); *C12Q 2600/106* (2013.01); *C12Q 2600/156* (2013.01)

(58) Field of Classification Search
CPC .......... A61P 35/00; A61P 35/02; A61P 35/04; A61K 31/415; A61K 31/498
See application file for complete search history.

(56) References Cited

U.S. PATENT DOCUMENTS

| | | | |
|---|---|---|---|
| 7,135,311 B1 | 11/2006 | David et al. | |
| 9,464,071 B2 | 10/2016 | Saxty et al. | |
| 11,077,106 B2 | 8/2021 | Stuyckens et al. | |
| 2007/0092878 A1* | 4/2007 | Martinez .............. | C12Q 1/6886 |
| | | | 435/6.13 |
| 2009/0048266 A1 | 2/2009 | Heise et al. | |
| 2010/0075337 A1 | 3/2010 | Graus Porta et al. | |
| 2010/0098696 A1 | 4/2010 | Sun et al. | |
| 2011/0275084 A1* | 11/2011 | Byron ................ | G01N 33/5011 |
| | | | 435/6.12 |
| 2011/0275087 A1 | 11/2011 | Breidenthal et al. | |
| 2012/0134993 A1 | 5/2012 | Pan et al. | |
| 2013/0072457 A1* | 3/2013 | Saxty .................. | C07D 401/14 |
| | | | 514/249 |
| 2013/0096021 A1 | 4/2013 | Chinnaiyan et al. | |
| 2013/0267525 A1 | 10/2013 | Saxty et al. | |
| 2013/0296326 A1 | 11/2013 | Pollock | |
| 2014/0248612 A1 | 9/2014 | Princen et al. | |
| 2015/0017637 A1 | 1/2015 | Chinnaiyan et al. | |
| 2015/0031703 A1 | 1/2015 | Suzuki et al. | |
| 2015/0307945 A1 | 10/2015 | Nakanishi et al. | |
| 2016/0090633 A1 | 3/2016 | Platero et al. | |
| 2016/0375023 A1 | 12/2016 | Suzuki et al. | |
| 2020/0208224 A1 | 7/2020 | Platero et al. | |

FOREIGN PATENT DOCUMENTS

| | | |
|---|---|---|
| CA | 2865388 A1 | 9/2013 |
| CN | 103370314 A | 10/2013 |
| EP | 1208231 A2 | 5/2002 |
| EP | 1659175 A1 | 5/2006 |
| EP | 1964837 A1 | 9/2008 |
| JP | 2006-515513 A | 6/2006 |
| JP | 2010-535480 A | 11/2010 |
| JP | 2013-528580 A | 7/2013 |
| WO | WO 2004/035803 A2 | 4/2004 |
| WO | 2006/000420 A1 | 1/2006 |
| WO | 2006/127926 A2 | 11/2006 |
| WO | 2008109465 A2 | 9/2008 |
| WO | 2008112408 A1 | 9/2008 |
| WO | WO 2009/019008 A1 | 2/2009 |
| WO | WO 2009/037490 A1 | 3/2009 |
| WO | WO 2011/027219 A1 | 3/2011 |
| WO | WO 2011/135376 A1 | 11/2011 |
| WO | 2013076186 A1 | 5/2013 |
| WO | 2013087725 A1 | 6/2013 |

(Continued)

OTHER PUBLICATIONS

Greulich et al. (Trends Mol Med. May 2011 ; 17(5): . doi:10.1016/j.molmed.2011.01.012.) (Year: 2011).*
Non-Final Office Action, U.S. Appl. No. 14/858,627, dated Mar. 20, 2018, entitled "Use of FGFR Mutant Gene Panels in Identifying Cancer Patients That Will be Responsive to Treatment With an FGFR Inhibitor".
International Preliminary Report on Patentability dated Mar. 28, 2017 for International Application No. PCT/US2015/050996, entitled "Use of FGFR Mutant Gene Panels in Identifying Cancer Patients That Will be Responsive to Treatment With an FGFR Inhibitor".
Parker, B.C., et al., "The tumorigenic FGFR3-TACC3 gene fusion escapes miR-99a regulation in glioblastoma," The Journal of Clinical Investigation, 123 (2), pp. 855-865, Feb. 1, 2013.

(Continued)

*Primary Examiner* — Jeffrey S Lundgren
*Assistant Examiner* — Chris E Simmons
(74) *Attorney, Agent, or Firm* — BakerHostetler

(57) ABSTRACT

Disclosed herein are methods of identifying a cancer patient that will be responsive to treatment with a fibroblast growth factor receptor (FGFR) inhibitor and methods of treating cancer patients. The methods involve evaluating a biological sample from the patient for the presence of one or more FGFR mutants from a FGFR mutant gene panel. Kits and primers for identifying the presence of one or more FGFR mutant genes in a biological sample are also disclosed herein.

25 Claims, 32 Drawing Sheets

Specification includes a Sequence Listing.

(56) References Cited

FOREIGN PATENT DOCUMENTS

| WO | 2013089882 A2 | 6/2013 |
| WO | 2013173480 A1 | 11/2013 |
| WO | 2013173485 A1 | 11/2013 |
| WO | 2013179034 A1 | 12/2013 |
| WO | 2014007369 A1 | 1/2014 |
| WO | 2014018673 A2 | 1/2014 |
| WO | 2014018841 A1 | 1/2014 |
| WO | 2014071419 A2 | 5/2014 |
| WO | 2014113729 A2 | 7/2014 |
| WO | WO 2014/1 13729 * 7/2014 |
| WO | 2014165710 A2 | 10/2014 |
| WO | 2014193229 A2 | 12/2014 |
| WO | 2013133351 A1 | 7/2015 |
| WO | 2016048833 A2 | 3/2016 |
| WO | 2014051022 A1 | 8/2016 |

OTHER PUBLICATIONS

Bello, et al., "E=3810 is a Potent Dual Inhibitor of VEGFR and FGFR that Exerts Antitumor Activity in Multiple Preclinical Models," vol. 71(4), pp. 1396-1405 (2011).

Database, Geneseq [Online], "FGFR3-TACC3 gene fusion PCR primer, FGFR3-TACC3(F18T11)_qPCR_F SEQ:15," XP002753027, Database accession No. BAT14432 (2013).

Database, Geneseq [Online], "Human FGFR 2 mRNA target sequence for mdRNA, Seq ID:3954," XP055257043, Database accession No. ATM46802.

Gavine, et al., "AZD4547: An Orally Bioavailable, Potent, and Selective Inhibitor of the Fibroblast Growth Factor Receptor Tyrosine Kinase Family," Cancer Research, vol. 72(8), pp. 2045-2056 (2012).

International Search Report from PCT/US2015/050996 dated Mar. 23, 2016.

Mengual, et al., BMC Research Notes 1:21, pp. 1-8 (Jun. 2008).

Millholland, et al., Research and Reports in Urology, 4: 33-40 (2012).

Sabnis, et al., "FGFR Fusions in the Driver's Seat," Cancer Discovery, vol. 3 (6), pp. 607-609 (2013).

Shinmura, et al., "A novel somatic FGFR3 mutation in primary lung cancer," Oncology Reports, vol. 31 (3), pp. 1219-1224 (2014).

Singh, et al., "Transforming Fusions of FGFR and TACC Genes in Human Glioblastoma," Science, vol. 337 (6099), pp. 1231-1235 (2012).

Trudel, et al., "Evaluation of XL999, a Potent Inhibitor of FGFR3, for the Potential Treatment of t(4;14) Positive Multiple Myeloma," Blood, vol. 110 (11), pp. 741A-742A (2007).

Williams, et al., "Oncogenic FGFR3 gene fusions in bladder cancer," Human Molecular Genetics, vol. 22 (4), pp. 795-803 (2013).

Wu, et al., "Identification of Targetable FGFR Gene Fusions in Diverse Cancers," Cancer Discovery, vol. 3 (6), pp. 636-647 (2013).

Bahleda, R. et al., "Phase 1 study of JNJ-42756493, a pan-fibroblast growth factor receptor (FGFR) inhibitor, in patients with advanced solid tumors," Journal of Clinical Oncology, vol. 32; Issue 15; Suppl; 4 pages (2014).

Miyake et al., "1-tert-Butyl-3-[6-(3,5-dimethoxy-phenyl)-2-(4-diethylamino-butylamino)-pyrido[2,3-d]pyrimidin-7-yl]-urea (PD173074), a Selective Tyrosine Kinase Inhibitor of Fibroblast Growth Factor Receptor-3 (FGFR3), Inhibits Cell Proliferation of Bladder Cancer Carrying the FGFR3 Gene Mutation along with Up-Regulation of p27/Kip1 and G1/G0 Arrest," Journal of Pharmacology and Experimental Therapeutics, vol. 332, No. 3, Dec. 2, 2009, pp. 795-802.

Qing et al., "Antibody-based targeting of FGFR3 in bladder carcinoma and t(4;14)-positive multiple myeloma in mice," Journal of Clinical Investigation, vol. 119, No. 5, May 1, 2009, pp. 1216-1229.

Wu, R. et al., "Somatic mutations of fibroblast growth factor receptor 3 (FGFR3) are uncommon in carcinomas of the uterine cervix," Oncogene, vol. 19; 5543-5546 (2000).

Dodurga, Y. et al., "Incidence of fibroblast growth factor receptor 3 gene (FGFR3) A248C, S249C, G372C, and T375C mutations in bladder cancer," Genetics and Molecular Research, vol. 10; No. 1; 86-95 (2011).

Non-Final Office Action, U.S. Appl. No. 16/723,975, dated Sep. 21, 2021.

Final Office Action, U.S. Appl. No. 16/723,975, dated Mar. 23, 2022.

Keegan, K. et al., "Isolation of an additional member of the fibroblast growth factor receptor family, FGFR-3," Proc. Natl. Acad. Sci., vol. 88; 1095-1099 (1991).

Liu, X. et al., "Clinical significance of fibroblast growth factor receptor-3 mutations in bladder cancer: a systematic review and meta-analysis," Genetics amd Molecular Research, vol. 13; No. 1; 1109-1120 (2014).

Mengual, L. et al., "Multiplex preamplification of specific cDNA targets prior to gene expression analysis by TaqMan Arrays," BMC Research Notes, vol. 1; No. 21; 8 pages (Jun. 2008).

Non-Final Office Action, U.S. Appl. No. 16/723,975, dated Jul. 21, 2022.

Advisory Action, U.S. Appl. No. 16/723,975, dated Jun. 7, 2022.

Bellmunt et al., "Pembrolizumab as second-line therapy for advanced urothelial carcinoma", N. England J. Med., Mar. 2017, 376, 1015-1026.

Dienstmann et al., "Genomic Aberrations in the FGFR Pathway: Opportunities for Targeted Therapies in Solid Tumors," Annals of Oncology, vol. 25, Nov. 20, 2013, No. 3, pp. 552-563.

Greulich et al., "Targeting mutant fibroblast growth factor receptors in cancer", Trends in Molecular Medicine, vol. 17, No. 5, pp. 283-292 (2011).

Joerger et al., "Rogaratinib in patients with advanced urothelial carcinomas prescreened for tumor FGFR mRNA expression and effects of mutations in the FGFR signaling pathway", J. Clin. Oncol.,May 2018, Suppl. 15, 4 pages.

Milowsky et al., "Phase 2 trial of dovitinib in patients with progressive FGFR3-mutated or FGFR3 wildtype advanced urothelial carcinoma", Eur. J. Cancer, Oct. 2014, 3145-3152.

Necchi et al., "Interim results of fight-201, a phase II, open-label, multicenter study of INCB054828 in patients (pts) with metastatic or surgically unrespectable urothelial carcinoma (UC) harboring fibroblast growth factor (FGF)/FGF receptor (FGFR) genetic alterations (GA)", Annals of Oncol., Oct. 2018, Suppl. 8, 2 pages.

Pal et al., "Efficacy of BGJ398, a fibroblast growth factor receptor 1-3 inhibitor, in patients with previously treated advanced urothelial carcinoma with FGFR3 alterations", Cancer Discovery, Jul. 2018, 8, 812-821.

Powles et al., "Atezolizumab versus chemotherapy in patients with platinum-treated locally advanced or metastatic urothelial carcinoma (IMvigor211): a multicentre, open-label, phase 3 randomised controlled trial", Lancet, Dec. 2017, 391, 748-757.

Advanced Organic Chemistry, by Jerry March, 4th Edition, Wiley Interscience, pages. More particularly, N-oxides can be made by the procedure ofL. W. Deady, Syn. Comm. 1977, 7, 509-514.

Balheda et al., "Multicenter Phase I Study of Erdafitinib (JNJ-42756493), Oral Pan-Fibroblast Growth Factor Receptor Inhibitor, in Patients with Advanced or Refractory Solid Tumors" Clinical Cancer Research 25(16): 4888-4896, Aug. 15, 2019.

Bello et al., "E-3810 Is a Potent Dual Inhibitor of VEG FR and FGFR that Exerts Antitumor Activity in Multiple Preclinical Models", Cancer Res., 2011, vol. 71, No. 4, pp. 1396-1405.

Branerjee et al, "AGN-241751, an Orally Bioavailable Positive NMDA Receptor Modulator, Exhibits Rapid and Sustained Antidepressant-Like Effects in Rodents", Biological Psychiatry, May 15, 2019, vol. 85, S348.

Deady. L.W. et al., "Ring Nitrogen Oxidation of Amino Substituted Nitrogen Heterocycles with m-Chloroperbenzoic Acid," Syn. Comm., vol. 7, 1977, pp. 509-514.

Heroult M. et al., "Fibroblast Growth Factor Receptor Signaling in Cancer Biology and Treatment", Current Signal Transduction Therapy, vol. 9, No. 1, 2014, pp. 15-25.

Javle et al., "Molecular characterization of gallbladder cancer using somatic mutation profiling", Hum Pathol., Apr. 2014, vol. 45, No. 4, pp. 701-708.

(56) References Cited

OTHER PUBLICATIONS

Parker et al., "Emergence of FGFR Family Gene Fusions as Therapeutic Targets in a Wide Spectrum of Solid Tumours," Journal of Pathology, Oct. 29, 2013, vol. 232, No. 1, pp. 4-15.

Williams S.V. et al., "Activation of FGFR3 by genomic fusion in urothelial carcinoma of the bladder", Cancer Res, 2013, vol. 73, 8_Supplement: 5310.

Ross et al., "New routes to targeted therapy of intrahepatic cholangiocarcinomas revealed by next-generation sequencing", Oncologist, 2014, vol. 19, No. 3, pp. 235-242.

* cited by examiner

FGFR3:TACC3 V1

Sample CNT14Y3

FGFR3:TACC3 V3

Sample CNT0RET

FGFR3:TACC3 Intron

Sample RT4

FGFR3:BAIAP2L1

Sample CNTORFE

FGFR2:AFF3

Sample CNT14QE

FGFR2:BICC1

Sample CNT0RLV

FGFR2:CASP7

Sample CNT06FT

FGFR2:CCDC6

Sample CNT06FT

FGFR2:OFD1

Sample Lu1656

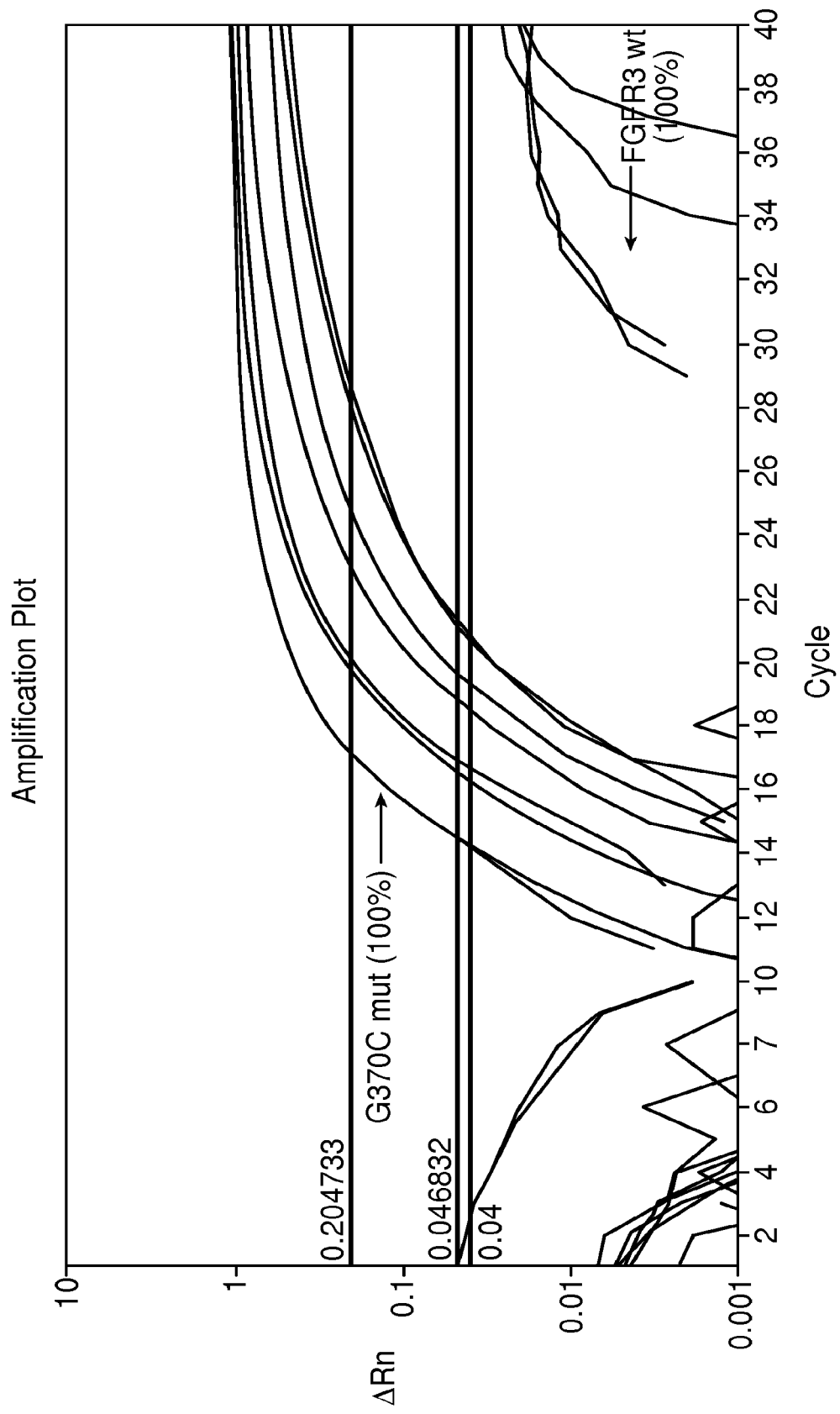

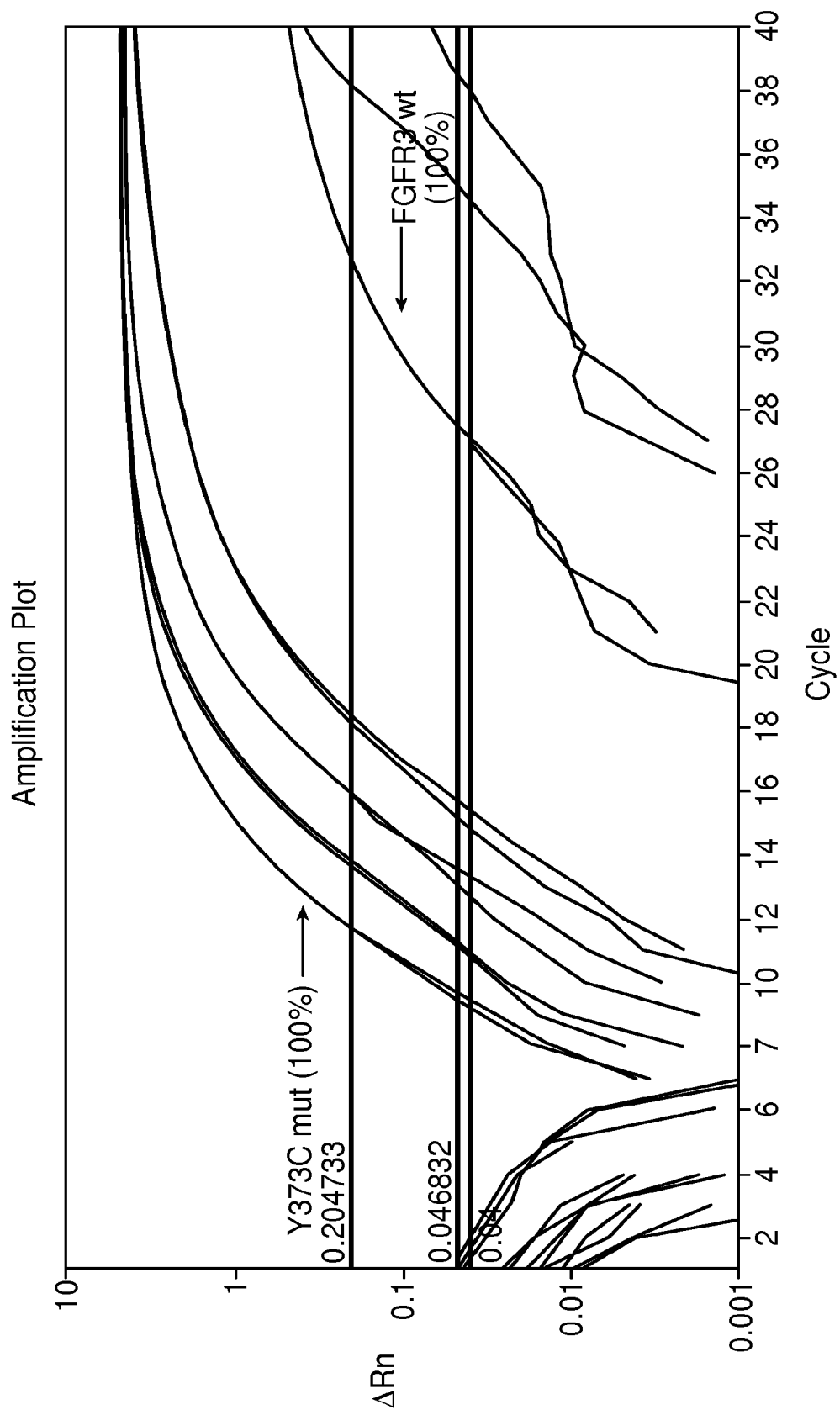

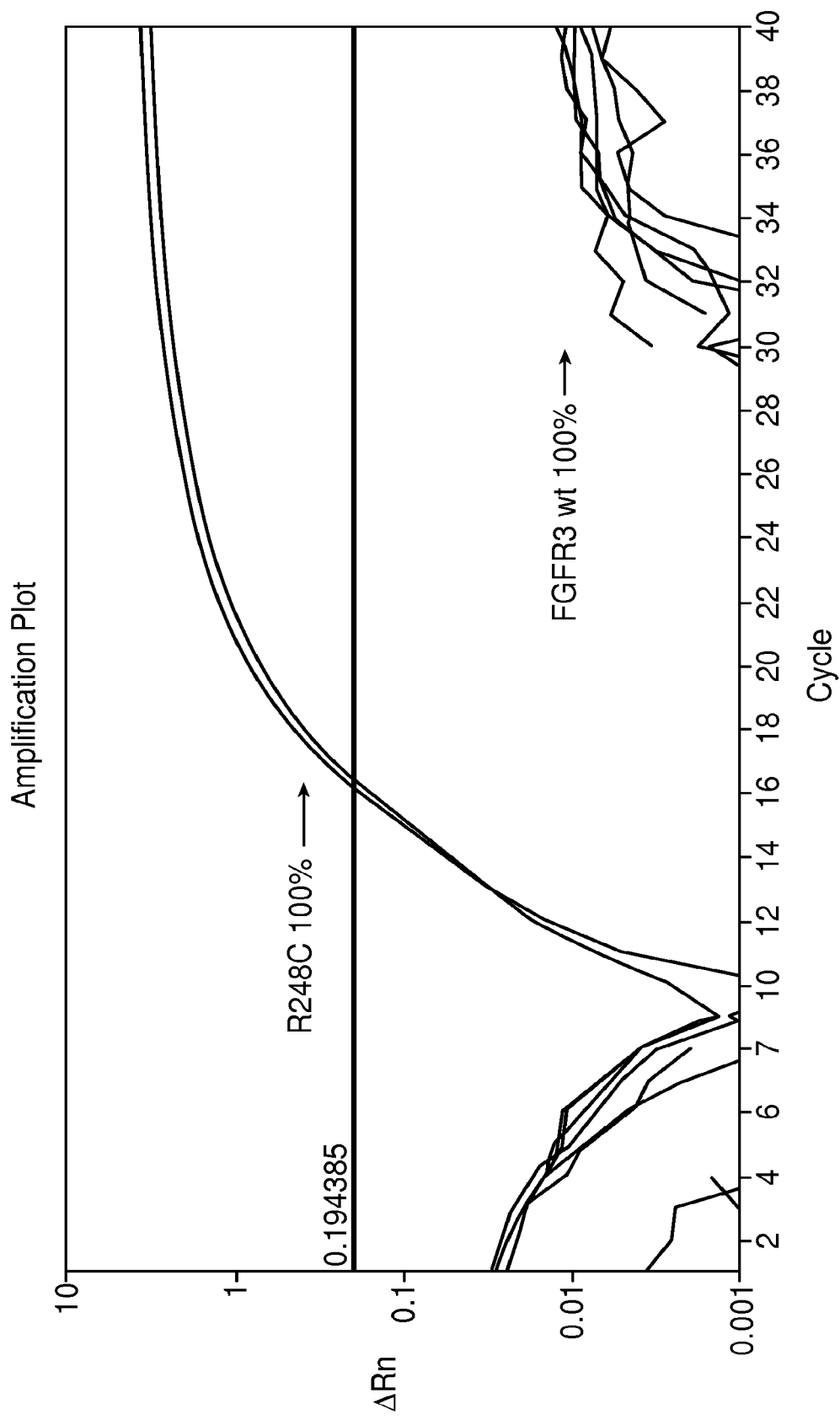

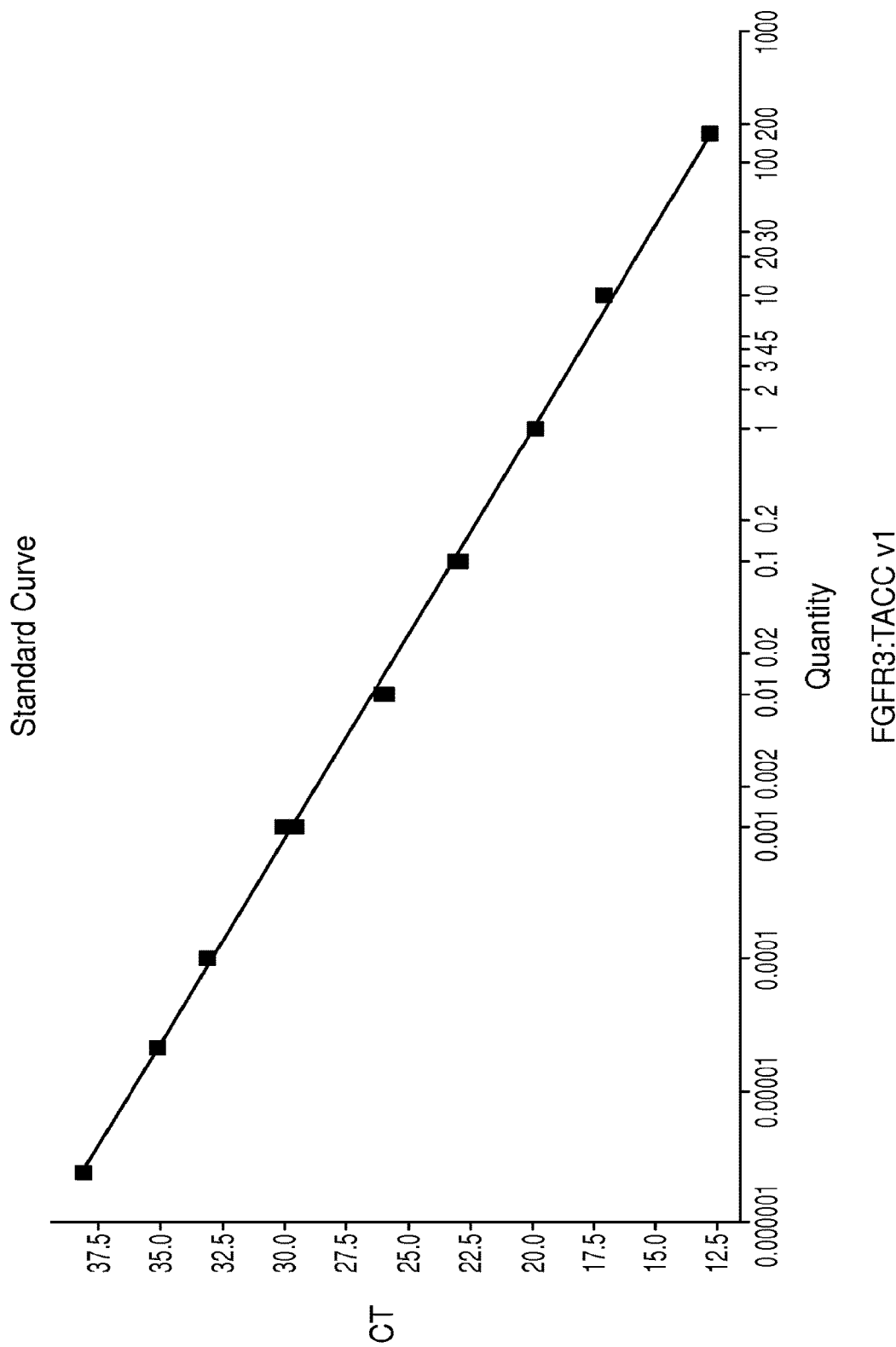

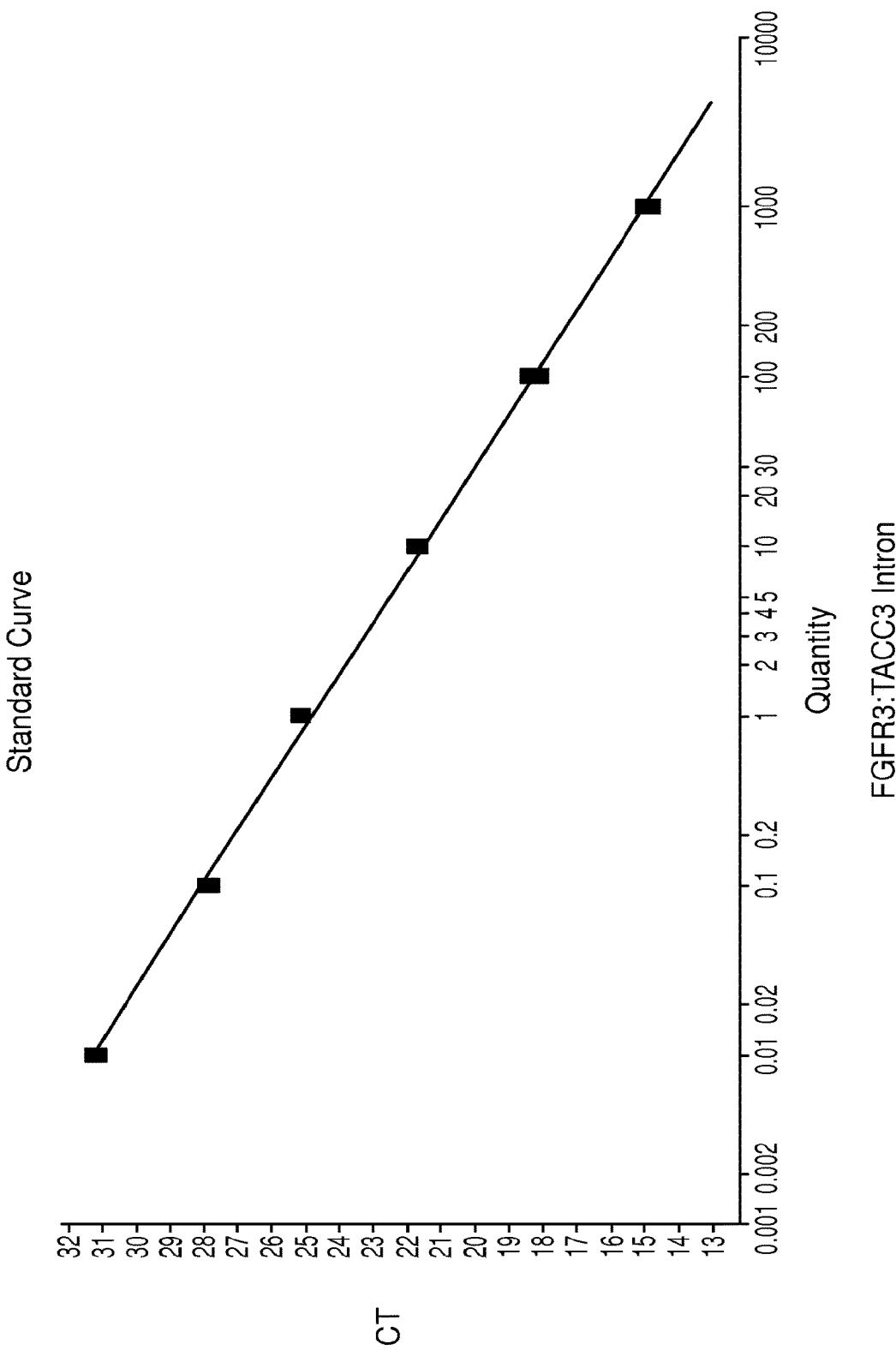

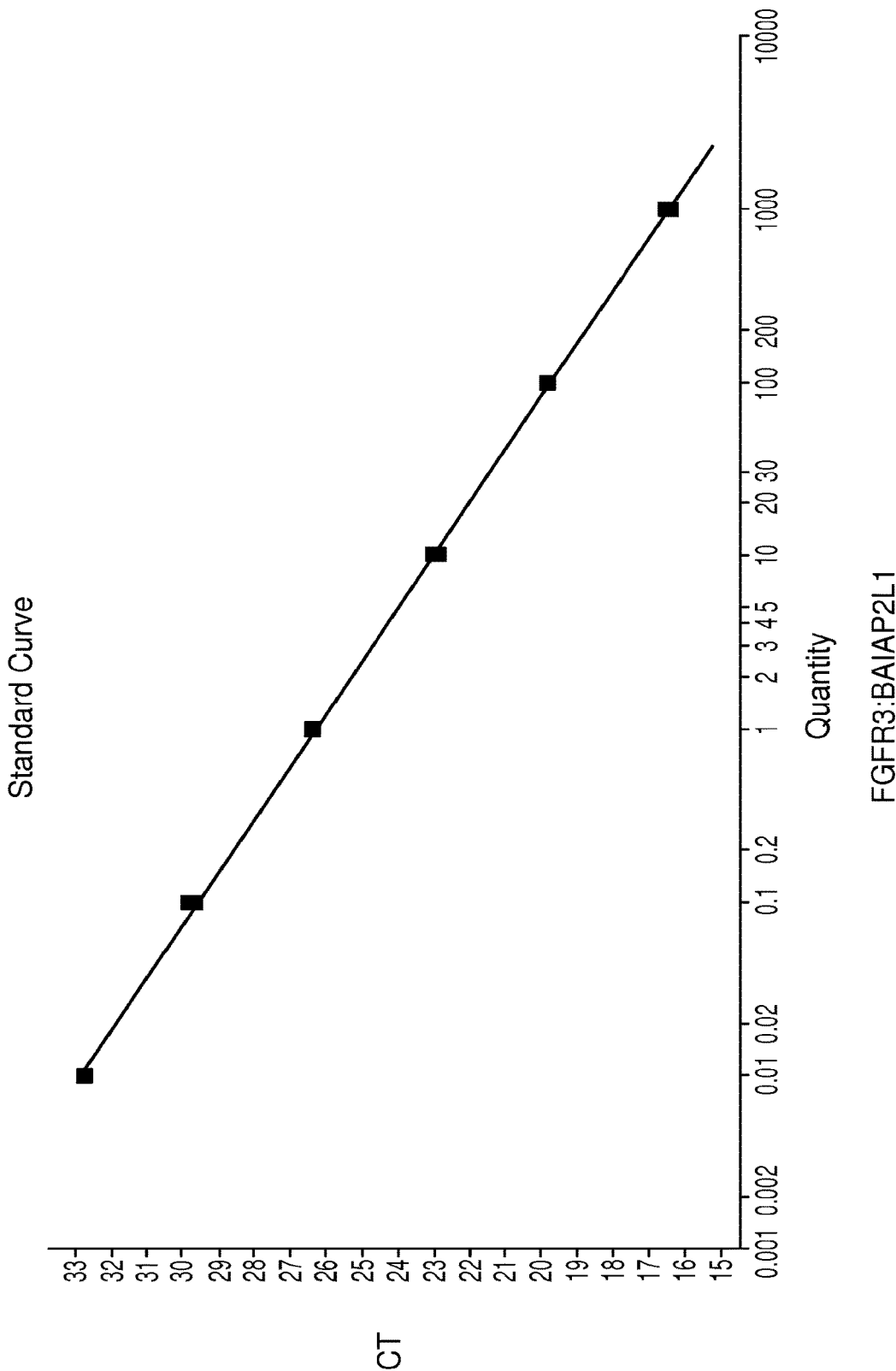

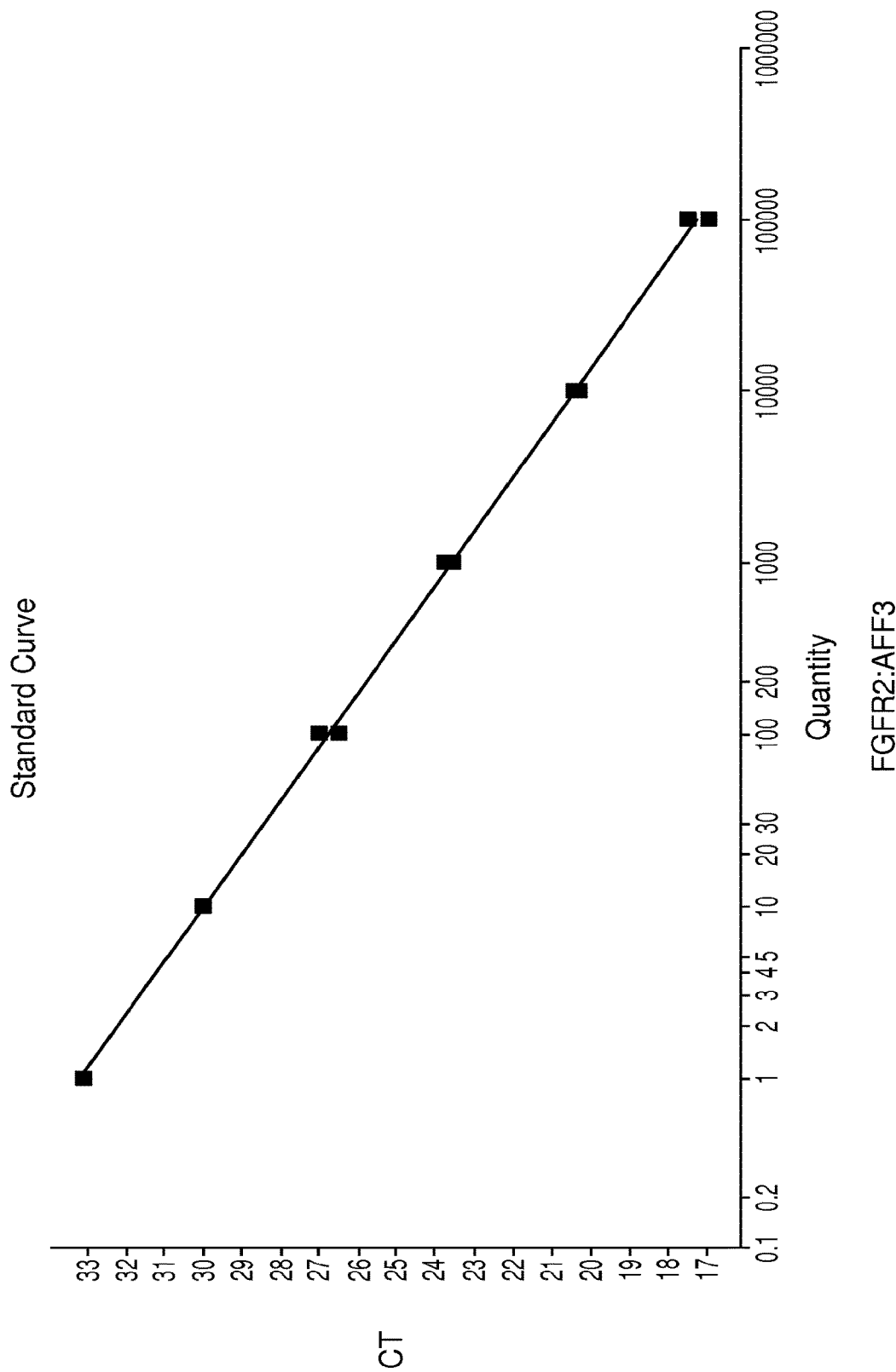

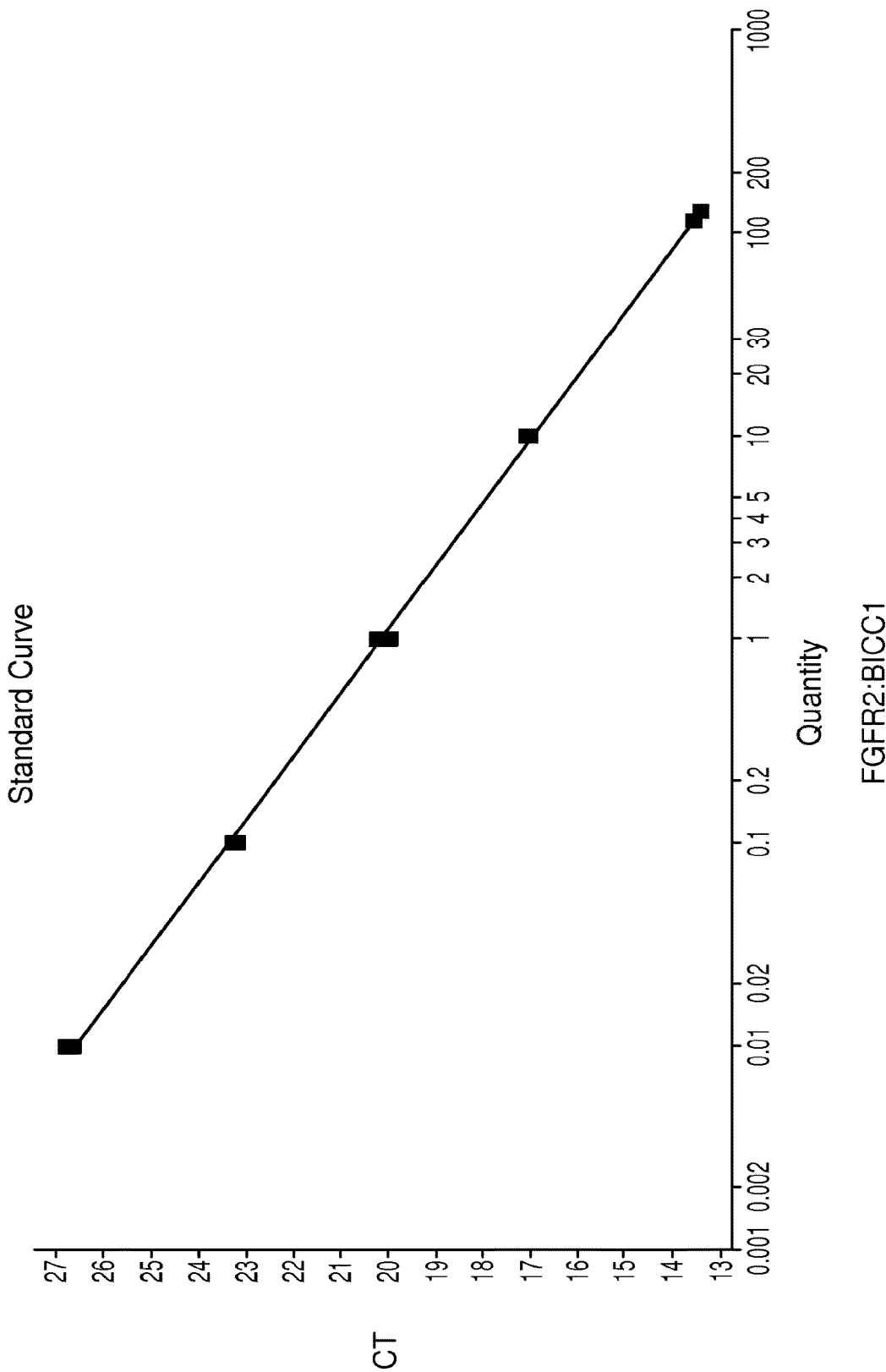

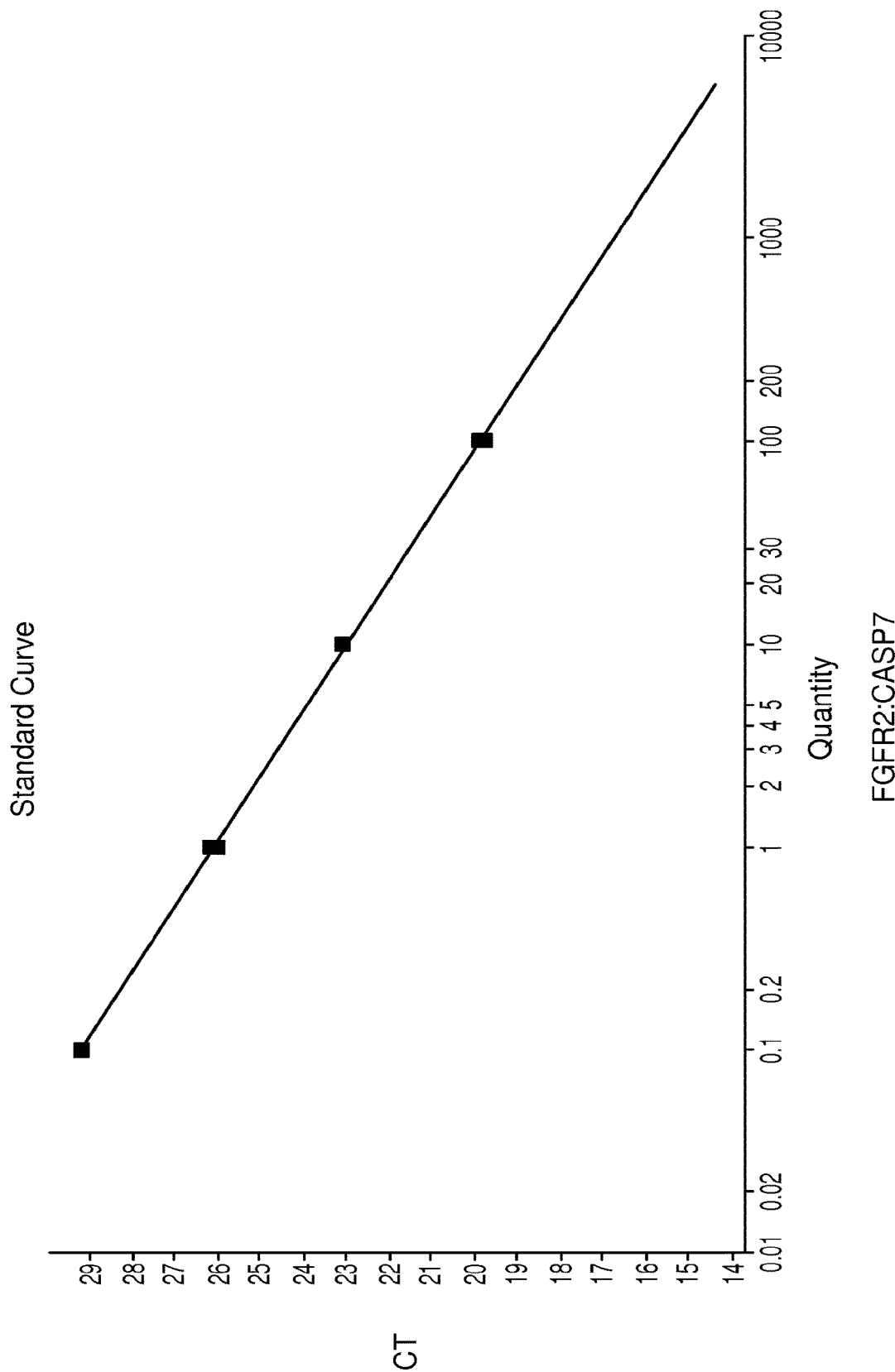

Standard Curve

Standard Curve

Results: Pt#340000115

FGFR3: TACC3 V3
exon 18: exon10
Amplification Plot

FGFR3: TACC3 V1
exon 18: exon11
Amplification Plot

FGFR2: CCDC6
Amplification Plot

| Assay | Sample Ct | St Ct |
|---|---|---|
| FGFR3: TACC3 V1 | 28.67 | 18.35 |
| FGFR3: TACC3 V3 | 35.0 | 24.89 |
| FGFR2: CCDC6 | 32.45 | 16.74 |

ST = Synthetic Template Assay Control
GAPDH = QC sample control

SEQUENCE LISTING

<160> NUMBER OF SEQ ID NOS: 73

<210> SEQ ID NO 1
<211> LENGTH: 268
<212> TYPE: DNA
<213> ORGANISM: Homo sapiens

<400> SEQUENCE: 1

```
tcggaccgcg gcaactacac ctgcgtcgtg gagaacaagt ttggcagcat ccggcagacg    60
tacacgctgg acgtgctgga gtgctccccg caccggccca tcctgcaggc ggggctgccg   120
gccaaccaga cggcggtgct gggcagcgac gtggagttcc actgcaaggt gtacagtgac   180
gcacagcccc acatccagtg gctcaagcac gtggaggtga atggcagcaa ggtgggcccg   240
gacggcacac cctacgttac cgtgctca                                       268
```

<210> SEQ ID NO 2
<211> LENGTH: 378
<212> TYPE: DNA
<213> ORGANISM: Homo sapiens

<400> SEQUENCE: 2

```
gaccgcggca actacacctg cgtcgtggag aacaagtttg gcagcatccg gcagacgtac    60
acgctggacg tgctgggtga gggccctggg gcggcgcggg ggtgggggcg gcagtggcgg   120
tggtggtgag ggagggggtg gcccctgagc gtcatctgcc cccacagagc gctgcccgca   180
ccggcccatc ctgcaggcgg ggctgccggc caaccagacg gcggtgctgg gcagcgacgt   240
ggagttccac tgcaaggtgt acagtgacgc acagccccac atccagtggc tcaagcacgt   300
ggaggtgaat ggcagcaagg tgggcccgga cggcacaccc tacgttaccg tgctcaaggt   360
gggccaccgt gtgcacgt                                                  378
```

<210> SEQ ID NO 3
<211> LENGTH: 234
<212> TYPE: DNA
<213> ORGANISM: Homo sapiens

<400> SEQUENCE: 3

```
gcgggcaatt ctattgggtt ttctcatcac tctgcgtggc tggtggtgct gccagccgag    60
gaggagctgg tggaggctga cgaggcgtgc agtgtgtatg caggcatcct cagctacggg   120
gtgggcttct tcctgttcat cctggtggtg gcggctgtga cgctctgccg cctgcgcagc   180 cccccccaaga aaggcctggg ctcccccacc gtgcacaaga tctcccgctt ccg         234
```

<210> SEQ ID NO 4
<211> LENGTH: 301
<212> TYPE: DNA
<213> ORGANISM: Homo sapiens

<400> SEQUENCE: 4

```
ctagaggttc tctccttgca caacgtcacc tttgaggacg ccggggagta cacctgcctg    60
gcgggcaatt ctattgggtt ttctcatcac tctgcgtggc tggtggtgct gccagccgag   120
gaggagctgg tggaggctga cgaggcgggc agtgtgtgtg caggcatcct cagctacggg   180
gtgggcttct tcctgttcat cctggtggtg gcggctgtga cgctctgccg cctgcgcagc   240 cccccccaaga aaggcctggg ctcccccacc gtgcacaaga tctcccgctt ccgctcaag   300 c                                                                   301
```

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5

```
gacctggacc gtgtccttac c                                              21
```

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

```
cttccccagt tccaggttct t                                              21
```

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7

```
aggacctgga ccgtgtcctt                                                20
```

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tataggtccg gtggacaggg                                              20

<210> SEQ ID NO 9
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ggccatcctg ccccc                                                   15

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gagcagtcca ggtcagccag                                              20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ctggaccgtg tccttaccgt                                              20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gcagcccagg attgaactgt                                              20

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tggatcgaat tctcactctc aca                                          23

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gccaagcaat ctgcgtattt g                                            21

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tggtagaaga cttggatcga attct                                          25

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tctcccggat tatttcttca aca                                            23

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gctcttcaat acagccctga tca                                            23

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
acttggatcg aattctcact ctca                                           24

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tggatcgaat tctcactctc aca                                            23

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gcaaagcctg aattttcttg aataa                                          25

```
<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
agggtgcatc aactcatgaa ttag                                           24

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
acttggatcg aattctcact ctca                                           24

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gcatccggca gacgtaca                                                  18

<210> SEQ ID NO 24
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ccccgcctgc aggat                                                     15

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gcatccggca gacgtaca                                                  18

<210> SEQ ID NO 26
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ccccgcctgc aggat                                                     15
```

```
<210> SEQ ID NO 27
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
aggagctggt ggaggctga                                                  19

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ccgtagctga ggatgcctg                                                  19

<210> SEQ ID NO 29
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ctggtggagg ctgacgag                                                   18

<210> SEQ ID NO 30
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
agcccacccc gtagct                                                     16

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gtcgtggaga acaagtttgg c                                               21

<210> SEQ ID NO 32
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gtctggttgg ccggcag                                                    17

<210> SEQ ID NO 33
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gtcgtggaga acaagtttgg c                                              21

<210> SEQ ID NO 34
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gtctggttgg ccggcag                                                   17

<210> SEQ ID NO 35
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
aggagctggt ggaggctga                                                 19

<210> SEQ ID NO 36
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ccgtagctga ggatgcctg                                                 19

<210> SEQ ID NO 37
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gacgaggcgg gcagtg                                                    16

<210> SEQ ID NO 38
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gaagaagccc accccgtag                                                 19

<210> SEQ ID NO 39
<211> LENGTH: 17
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
tggagcgctc cccgcac                                                   17

<210> SEQ ID NO 40
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
gacgtgctgg agrgctcc                                                  18

<210> SEQ ID NO 41
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ctgacgaggc gggcagc                                                   17

<210> SEQ ID NO 42
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
gtgtgtatgc aggcatcctc agc                                            23

<210> SEQ ID NO 43
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 43
tccaccgacg taaagg                                                    16

<210> SEQ ID NO 44
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 44
tccaccgacg tgccag                                                    16

<210> SEQ ID NO 45
<211> LENGTH: 18
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 45
ccaatgagat catggagg                                                    18

<210> SEQ ID NO 46
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 46
ccttctggcc caggtg                                                      16

<210> SEQ ID NO 47
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 47
caccgacaat gttatgg                                                     17

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 48
tcacaaccaa tgaggagagt                                                  20

<210> SEQ ID NO 49
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 49
ctgccatctc attggt                                                      16

<210> SEQ ID NO 50
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 50
aatgagcaag ccagggc                                                     17

<210> SEQ ID NO 51
<211> LENGTH: 19
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 51
aagttgtgtc tcattggtt                                                    19

<210> SEQ ID NO 52
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 52
ctggagtgct cccc                                                         14

<210> SEQ ID NO 53
<211> LENGTH: 13
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 53
agcgctgccc gca                                                          13

<210> SEQ ID NO 54
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 54
gcgtgcagtg tgtat                                                        15

<210> SEQ ID NO 55
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 55
ctgcacacac actgc                                                        15

<210> SEQ ID NO 56
<211> LENGTH: 2850
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56
atgggcgccc ctgcctgcgc cctcgcgctc tgcgtggccg tggccatcgt ggccggcgcc       60
tcctcggagt ccttggggac ggagcagcgc gtcgtggggc gagcggcaga agtcccgggc      120
ccagagcccg gccagcagga gcagttggtc ttcggcagcg gggatgctgt ggagctgagc      180
tgtcccccgc cgggggtgg tcccatgggg cccactgtct gggtcaagga tggcacaggg      240
```

```
ctggtgccct cggagcgtgt cctggtgggg ccccagcggc tgcaggtgct gaatgcctcc      300
cacgaggact ccggggccta cagctgccgg cagcggctca cgcagcgcgt actgtgccac      360
ttcagtgtgc gggtgacaga cgctccatcc tcgggagatg acgaagacgg ggaggacgag      420
gctgaggaca caggtgtgga cacaggggcc ccttactgga cacggcccga gcggatggac      480
aagaagctgc tggccgtgcc ggccgccaac accgtccgct tccgctgccc agccgctggc      540
aaccccactc cctccatctc ctggctgaag aacggcaggg agttccgcgg cgagcaccgc      600
attggaggca tcaagctgcg gcatcagcag tggagcctgg tcatggaaag cgtggtgccc      660
tcggaccgcg gcaactacac ctgcgtcgtg gagaacaagt tggcagcat ccggcagacg       720 tacacgctgg acgtgctgga gcgctccccg caccggccca tcctgcaggc ggggctgccg      780
gccaaccaga cggcggtgct gggcagcgac gtggagttcc actgcaaggt gtacagtgac      840
gcacagcccc acatccagtg gctcaagcac gtggaggtga atggcagcaa ggtgggcccg      900
gacggcacac cctacgttac cgtgctcaag acgcgggcg ctaacaccac cgacaaggag       960
ctagaggttc tctccttgca caacgtcacc tttgaggacg ccggggagta cacctgcctg     1020
gcgggcaatt ctattgggtt ttctcatcac tctgcgtggc tggtggtgct gccagccgag     1080
gaggagctgg tggaggctga cgaggcgggc agtgtgtatg caggcatcct cagctacggg     1140
gtgggcttct tcctgttcat cctggtggtg gcggctgtga cgctctgccg cctgcgcagc     1200
ccccccaaga aaggcctggg ctccccccacc gtgcacaaga tctcccgctt cccgctcaag    1260
cgacaggtgt ccctggagtc caacgcgtcc atgagctcca acacaccact ggtgcgcatc     1320
gcaaggctgt cctcagggga gggccccacg ctggccaatg tctccgagct cgagctgcct     1380
gccgacccca atgggagct gtctcgggcc cggctgaccc tgggcaagcc ccttggggag      1440
ggctgcttcg gccaggtggt catggcgag gccatcggca ttgacaagga ccgggccgcc      1500
aagcctgtca ccgtagccgt gaagatgctg aaagacgatg ccactgacaa ggacctgtcg     1560
gacctggtgt ctgagatgga gatgatgaag atgatcggga acacaaaaaa catcatcaac     1620
ctgctgggcg cctgcacgca gggcgggccc ctgtacgtgc tggtggagta cgcggccaag     1680
ggtaacctgc gggagtttct gcgggcgcgg cggccccgg gcctggacta ctccttcgac      1740
acctgcaagc cgcccgagga gcagctcacc ttcaaggacc tggtgtcctg tgcctaccag     1800
gtggcccggg gcatggagta cttggcctcc agaagtgca tccacaggga cctggctgcc    1860
cgcaatgtgc tggtgaccga ggacaacgtg atgaagatcg cagacttcgg gctggcccgg     1920
gacgtgcaca acctcgacta ctacaagaag acgaccaacg gccggctgcc cgtgaagtgg     1980
atggcgcctg aggccttgtt tgaccgagtc tacactcacc agagtgacgt ctggtccttt     2040
ggggtcctgc tctgggagat cttcacgctg ggggctccc cgtacccgg catccctgtg      2100 gaggagctct tcaagctgct gaaggagggc caccgcatgg acaagcccgc caactgcaca     2160
cacgacctgt acatgatcat gcgggagtgc tggcatgccg cgccctccca gaggcccacc     2220
ttcaagcagc tggtggagga cctggaccgt gtccttaccg tgacgtccac cgacgtaaag     2280
gcgacacagg aggagaaccg ggagctgagg agcaggtgtg aggagctcca cggaagaac     2340 ctggaactgg gaagatcat ggacaggttc gaagaggttg tgtaccaggc catggaggaa     2400
gttcagaagc agaaggaact ttccaaagct gaaatccaga aagttctaaa agaaaaagac   2460
caacttacca cagatctgaa ctccatggag aagtccttct ccgacctctt caagcgtttt    2520
gagaaacaga aagaggtgat cgagggctac cgcaagaacg aagagtcact gaagaagtgc   2580
gtggaggatt acctggcaag gatcacccag gagggccaga ggtaccaagc cctgaaggcc    2640
```

```
cacgcggagg agaagctgca gctggcaaac gaggagatcg cccaggtccg gagcaaggcc    2700
caggcggaag cgttggccct ccaggccagc ctgaggaagg agcagatgcg catccagtcg    2760
ctggagaaga cagtggagca gaagactaaa gagaacgagg agctgaccag gatctgcgac    2820
gacctcatct ccaagatgga gaagatctga                                     2850

<210> SEQ ID NO 57
<211> LENGTH: 2955
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57
atgggcgccc ctgcctgcgc cctcgcgctc tgcgtggccg tggccatcgt ggccggcgcc      60
tcctcggagt ccttggggac ggagcagcgc gtcgtggggc gagcggcaga agtcccgggc     120
ccagagcccg gccagcagga gcagttggtc ttcggcagcg gggatgctgt ggagctgagc     180 tgtccccgc ccggggggtgg tcccatgggg cccactgtct gggtcaagga tggcacaggg     240
ctggtgccct cggagcgtgt cctggtgggg cccagcggc tgcaggtgct gaatgcctcc     300
cacgaggact ccggggccta cagctgccgg cagcggctca cgcagcgcgt actgtgccac     360
ttcagtgtgc gggtgacaga cgctccatcc tcgggagatg acgaagacgg ggaggacgag     420
gctgaggaca caggtgtgga cacaggggcc ccttactgga cacggcccga gcggatggac     480
aagaagctgc tggccgtgcc ggccgccaac accgtccgct tccgctgccc agccgctggc     540
aaccccactc cctccatctc ctggctgaag aacggcaggg agttccgcgg cgagcaccgc     600
attggaggca tcaagctgcg gcatcagcag tggagcctgg tcatggaaag cgtggtgccc     660
tcggaccgcg gcaactacac ctgcgtcgtg gagaacaagt ttggcagcat ccggcagacg     720
tacacgctgg acgtgctgga cgctccccg caccggccca tcctgcaggc ggggctgccg     780
gccaaccaga cggcggtgct gggcagcgac gtggagttcc actgcaaggt gtacagtgac     840
gcacagcccc acatccagtg gctcaagcac gtggaggtga atggcagcaa ggtgggcccg     900
gacggcacac cctacgttac cgtgctcaag acggcgggcg ctaacaccac cgacaaggag     960
ctagaggttc tctccttgca caacgtcacc tttgaggacg ccggggagta cacctgcctg    1020
gcgggcaatt ctattgggtt ttctcatcac tctgcgtggc tggtggtgct gccagccgag    1080
gaggagctgg tggaggctga cgaggcgggc agtgtgtatg caggcatcct cagctacggg    1140
gtgggcttct tcctgttcat cctggtggtg gcggctgtga cgctctgccg cctgcgcagc    1200
ccccccaaga aaggcctggg ctcccccacc gtgcacaaga tctcccgctt cccgctcaag    1260
cgacaggtgt ccctggagtc caacgcgtcc atgagctcca acacaccact ggtgcgcatc    1320
gcaaggctgt cctcagggga gggccccacg ctggccaatg tctccgagct cgagctgcct    1380
gccgacccca aatgggagct gtctcgggcc cggctgaccc tgggcaagcc ccttgggga    1440 ggctgcttcg gccaggtggt catggcggag gccatcggca ttgacaagga ccgggccgcc    1500
aagcctgtca ccgtagccgt gaagatgctg aaagacgatg ccactgacaa ggacctgtcg    1560
gacctggtgt ctgagatgga gatgatgaag atgatcggga aacacaaaaa catcatcaac    1620
ctgctgggcg cctgcacgca gggcgggccc ctgtacgtgc tggtggagta cgcggccaag    1680
ggtaacctgc gggagtttct gcgggcgcgg cggccccgg gcctggacta ctccttcgac    1740
acctgcaagc cgcccgagga gcagctcacc ttcaaggacc tggtgtcctg tgcctaccag    1800
```

```
gtggcccggg gcatggagta cttggcctcc cagaagtgca tccacaggga cctggctgcc    1860
cgcaatgtgc tggtgaccga ggacaacgtg atgaagatcg cagacttcgg gctggcccgg    1920
gacgtgcaca acctcgacta ctacaagaag acgaccaacg ccggctgccc cgtgaagtgg    1980
atggcgcctg aggccttgtt tgaccgagtc tacactcacc agagtgacgt ctggtccttt    2040
ggggtcctgc tctgggagat cttcacgctg ggggctccc cgtaccccgg catccctgtg    2100
gaggagctct tcaagctgct gaaggagggc accgcatgg acaagcccgc caactgcaca    2160
cacgacctgt acatgatcat gcgggagtgc tggcatgccg cgccctccca gaggcccacc    2220
ttcaagcagc tggtggagga cctggaccgt gtccttaccg tgacgtccac cgacgtgcca    2280
ggcccacccc caggtgttcc cgcgcctggg ggcccacccc tgtccaccgg acctatagtg    2340
gacctgctcc agtacagcca gaaggacctg gatgcagtgg taaaggcgac acaggaggag    2400
aaccgggagc tgaggagcag gtgtgaggag ctccacggga agaacctgga actggggaag    2460
atcatggaca ggttcgaaga ggttgtgtac caggccatgg aggaagttca gaagcagaag    2520
gaactttcca agctgaaat ccagaaagtt ctaaagaaa aagaccaact taccacagat    2580
ctgaactcca tggagaagtc cttctccgac ctcttcaagc gttttgagaa acagaaagag    2640
gtgatcgagg gctaccgcaa gaacgaagag tcactgaaga agtgcgtgga ggattacctg    2700
gcaaggatca cccaggaggg ccagaggtac caagccctga aggcccacgc ggaggagaag    2760
ctgcagctgg caaacgagga gatcgcccag gtccggagca aggcccaggc ggaagcgttg    2820
gccctccagg ccagcctgag gaaggagcag atgcgcatcc agtcgctgga aagacagtg    2880 gagcagaaga ctaaagagaa cgaggagctg accaggatct gcgacgacct catctccaag    2940
atggagaaga tctga                                                    2955

<210> SEQ ID NO 58
<211> LENGTH: 4462
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58
atgggcgccc ctgcctgcgc cctcgcgctc tgcgtggccg tggccatcgt ggccggcgcc      60
tcctcggagt ccttggggac ggagcagcgc gtcgtggggc gagcggcaga agtcccgggc     120
ccagagcccg ccagcagga gcagttggtc ttcggcagcg gggatgctgt ggagctgagc     180 tgtccccgc ccggggtgg tcccatgggg cccactgtct gggtcaagga tggcacaggg     240
ctggtgccct cggagcgtgt cctggtgggg cccagcggc tgcaggtgct gaatgcctcc     300
cacgaggact ccggggccta cagctgccgg cagcggctca cgcagcgcgt actgtgccac     360
ttcagtgtgc gggtgacaga cgctccatcc tcgggagatg acgaagacgg ggaggacgag     420
gctgaggaca caggtgtgga cacagggggcc ccttactgga cacggcccga gcggatggac     480
aagaagctgc tggccgtgcc ggccgccaac accgtccgct tccgctgccc agccgctggc     540
aaccccactc cctccatctc ctggctgaag aacggcaggg agttccgcgg cgagcaccgc     600
attggaggca tcaagctgcg gcatcagcag tggagcctgg tcatggaaag cgtggtgccc     660
tcggaccgcg gcaactacac ctgcgtcgtg gagaacaagt ttggcagcat ccggcagacg     720
tacacgctga acgtgctgga gcgctccccg caccggccca tcctgcaggc ggggctgccg     780
gccaaccaga cggcggtgct gggcagcgac gtggagttcc actgcaaggt gtacagtgac     840
```

```
gcacagcccc acatccagtg gctcaagcac gtggaggtga atggcagcaa ggtgggcccg      900
gacggcacac cctacgttac cgtgctcaag acggcgggcg ctaacaccac cgacaaggag      960
ctagaggttc tctccttgca caacgtcacc tttgaggacg ccggggagta cacctgcctg     1020
gcgggcaatt ctattgggtt ttctcatcac tctgcgtggc tggtggtgct gccagccgag     1080
gaggagctgg tggaggctga cgaggcgggc agtgtgtatg caggcatcct cagctacggg     1140
gtgggcttct tcctgttcat cctggtggtg gcggctgtga cgctctgccg cctgcgcagc     1200
cccccccaaga aaggcctggg ctcccccacc gtgcacaaga tctcccgctt cccgctcaag     1260
cgacaggtgt ccctggagtc caacgcgtcc atgagctcca acacaccact ggtgcgcatc     1320
gcaaggctgt cctcagggga gggccccacg ctggccaatg tctccgagct cgagctgcct     1380
gccgacccca atgggagct gtctcgggcc cggctgaccc tggcaagcc ccttggggag     1440
ggctgcttcg ccaggtggt catggcggag ccatcggca ttgacaagga ccgggccgcc     1500
aagcctgtca ccgtagccgt gaagatgctg aaagacgatg ccactgacaa ggacctgtcg     1560
gacctggtgt ctgagatgga gatgatgaag atgatcggga aacacaaaaa catcatcaac     1620
ctgctgggcg cctgcacgca gggcgggccc ctgtacgtgc tggtggagta cgcggccaag     1680
ggtaacctgc gggagtttct gcgggcgcgg cggcccccgg gcctggacta ctccttcgac     1740
acctgcaagc cgcccgagga gcagctcacc ttcaaggacc tggtgtcctg tgcctaccag     1800
gtggcccggg gcatggagta cttggcctcc cagaagtgca tccacaggga cctggctgcc     1860
cgcaatgtgc tggtgaccga ggacaacgtg atgaagatcg cagacttcgg gctggcccgg     1920
gacgtgcaca acctcgacta ctacaagaag acgaccaacg gccggctgcc cgtgaagtgg     1980
atggcgcctg aggccttgtt tgaccgagtc tacactcacc agagtgacgt ctggtccttt     2040
ggggtcctgc tctgggagat cttcacgctg ggggggctccc cgtaccccgg catccctgtg     2100
gaggagctct tcaagctgct gaaggagggc caccgcatgg acaagcccgc caactgcaca     2160
cacgacctgt acatgatcat gcgggagtgc tggcatgccg cgccctccca gaggcccacc     2220
ttcaagcagc tggtggagga cctggaccgt gtccttaccg tgacgtccac cgacgtgagt     2280
gctggctctg gcctggtgcc acccgccat gcccctcccc ctgccgtccc cggccatcct     2340
gccccccaga gtgctgaggt gtggggcggg ccttctggc ccaggtgccc tggctgacct     2400
ggactgctca agctcttccc agagcccagg aagttctgag aaccaaatgg tgtctccagg     2460
aaaagtgtct ggcagccctg agcaagccgt ggaggaaaac cttagttcct attccttaga     2520
cagaagagtg acacccgcct ctgagaccct agaagaccct tgcaggacag agtcccagca     2580
caaagcggag actccgcacg gagccgagga agaatgcaaa gcggagactc cgcacggagc     2640
cgaggaggaa tgccggcacg gtggggtctg tgctcccgca gcagtggcca cttcgcctcc     2700
tggtgcaatc cctaaggaag cctgcggagg agcaccctg cagggtctgc ctggcgaagc     2760
cctgggctgc cctgcgggtg tgggcacccc cgtgccagca gatggcactc agacccttac     2820
ctgtgcacac acctctgctc ctgagagcac agccccaacc aaccacctgg tggctggcag     2880
ggccatgacc ctgagtcctc aggaagaagt ggctgcaggc caaatggcca gctcctcgag     2940
gagcggacct gtaaaactag aatttgatgt atctgatggc gccaccagca aagggcacc     3000
cccaccaagg agactgggag agaggtccgg cctcaagcct cccttgagga aagcagcagt     3060
gaggcagcaa aaggccccgc aggaggtgga ggagacgac ggtaggagcg gagcaggaga     3120
ggaccccccc atgccagctt ctcggggctc ttaccacctc gactgggaca aaatggatga     3180
```

```
cccaaacttc atcccgttcg gaggtgacac caagtctggt tgcagtgagg cccagccccc    3240
agaaagccct gagaccaggc tgggccagcc agcggctgaa cagttgcatg ctgggcctgc    3300
cacggaggag ccaggtccct gtctgagcca gcagctgcat tcagcctcag cggaggacac    3360
gcctgtggtg cagttggcag ccgagacccc aacagcagag agcaaggaga gagccttgaa    3420
ctctgccagc acctcgcttc ccacaagctg tccaggcagt gagccagtgc ccacccatca    3480
gcaggggcag cctgccttgg agctgaaaga ggagagcttc agagacccg ctgaggttct     3540 aggcacgggc gcggaggtgg attacctgga gcagtttgga acttcctcgt ttaaggagtc    3600
ggccttgagg aagcagtcct tatacctcaa gttcgacccc ctcctgaggg acagtcctgg    3660
tagaccagtg cccgtggcca ccgagaccag cagcatgcac ggtgcaaatg agactccctc    3720
aggacgtccg cgggaagcca agcttgtgga gttcgatttc ttgggagcac tggacattcc    3780
tgtgccaggc ccacccccag gtgttcccgc gcctggggc ccacccctgt ccaccggacc     3840
tatagtggac ctgctccagt acagccagaa ggacctggat gcagtggtaa aggcgacaca    3900
ggaggagaac cgggagctga ggagcaggtg tgaggagctc cacgggaaga acctggaact    3960
ggggaagatc atggacaggt tcgaagaggt tgtgtaccag gccatggagg aagttcagaa    4020
gcagaaggaa ctttccaaag ctgaaatcca gaaagttcta aaagaaaaag accaacttac    4080
cacagatctg aactccatgg agaagtcctt ctccgacctc ttcaagcgtt ttgagaaaca    4140
gaaagaggtg atcgagggct accgcaagaa cgaagagtca ctgaagaagt gcgtggagga    4200
ttacctggca aggatcaccc aggagggcca gaggtaccaa gccctgaagg cccacgcgga    4260
ggagaagctg cagctggcaa cgaggagat cgcccaggtc cggagcaagg cccaggcgga     4320
agcgttggcc ctccaggcca gcctgaggaa ggagcagatg cgcatccagt cgctggagaa    4380
gacagtggag cagaagacta agagaacga ggagctgacc aggatctgcg acgacctcat     4440
ctccaagatg gagaagatct ga                                            4462
```

<210> SEQ ID NO 59
<211> LENGTH: 3765
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59

```
atgggcgccc ctgcctgcgc cctcgcgctc tgcgtggccg tggccatcgt ggccggcgcc      60
tcctcggagt ccttggggac ggagcagcgc gtcgtggggc gagcggcaga agtcccgggc     120
ccagagcccg ccagcagga gcagttggtc ttcggcagcg gggatgctgt ggagctgagc      180 tgtccccgc ccgggggtgg tcccatgggg cccactgtct gggtcaagga tggcacaggg      240
ctggtgccct cggagcgtgt cctggtgggg ccccagcggc tgcaggtgct gaatgcctcc     300
cacgaggact ccggggccta cagctgccgg cagcggctca cgcagcgcgt actgtgccac     360
ttcagtgtgc gggtgacaga cgctccatcc tcgggagatg acgaagacgg ggaggacgag     420
gctgaggaca caggtgtgga cacaggggcc ccttactgga cacggcccga gcggatggac     480
aagaagctgc tggccgtgcc ggccgccaac acctccgct ccgctgccc agccgctggc      540 aaccccactc cctccatctc tggctgaag aacggcaggg agttccgcgg cgagcaccgc      600
attggaggca tcaagctgcg gcatcagcag tggagcctgg tcatgaaag cgtggtgccc      660 tcggaccgcg gcaactacac ctgcgtcgtg gagaacaagt ttggcagcat ccggcagacg     720
```

```
tacacgctgg acgtgctgga gcgctccccg caccggccca tcctgcaggc ggggctgccg    780
gccaaccaga cggcggtgct gggcagcgac gtggagttcc actgcaaggt gtacagtgac    840
gcacagcccc acatccagtg gctcaagcac gtggaggtga atggcagcaa ggtgggcccg    900
gacggcacac cctacgttac cgtgctcaag tcctggatca gtgagagtgt ggaggccgac    960
gtgcgcctcc gcctggccaa tgtgtcggag cgggacgggg gcgagtacct ctgtcgagcc   1020
accaatttca taggcgtggc cgagaaggcc ttttggctga cgttcacgg ccccgagca     1080
gccgaggagg agctggtgga ggctgacgag gcgggcagtg tgtatgcagg catcctcagc   1140
tacggggtgg gcttcttcct gttcatcctg gtggtggcgg ctgtgacgct ctgccgcctg   1200
cgcagccccc ccaagaaagg cctgggctcc cccaccgtgc acaagatctc ccgcttcccg   1260
ctcaagcgac aggtgtccct ggagtccaac gcgtccatga gctccaacac accactggtg   1320
cgcatcgcaa ggctgtcctc aggggagggc cccacgctgg ccaatgtctc cgagctcgag   1380
ctgcctgccg accccaaatg ggagctgtct cgggcccggc tgaccctggg caagccccctt  1440
ggggagggct gcttcggcca ggtggtcatg gcggaggcca tcggcattga caaggaccgg   1500
gccgccaagc ctgtcaccgt agccgtgaag atgctgaaag acgatgccac tgacaaggac   1560
ctgtcggacc tggtgtctga gatggagatg atgaagatga tcgggaaaca caaaaacatc   1620
atcaacctgc tgggcgcctg cacgcagggc gggcccctgt acgtgctggt ggagtacgcg   1680
gccaagggta acctgcggga gtttctgcgg gcgcggcggc ccccgggcct ggactactcc   1740
ttcgacacct gcaagccgcc cgaggagcag ctcaccttca aggacctggt gtcctgtgcc   1800
taccaggtgg cccggggcat ggagtacttg gcctcccaga agtgcatcca cagggacctg   1860
gctgcccgca atgtgctggt gaccgaggac aacgtgatga agatcgcaga cttcgggctg   1920
gcccgggacg tgcacaacct cgactactac aagaagacga ccaacggccg gctgcccgtg   1980
aagtggatgg cgcctgaggc cttgtttgac cgagtctaca ctcaccagag tgacgtctgg   2040
tcctttgggg tcctgctctg ggagatcttc acgctggggg gctccccgta ccccggcatc   2100
cctgtggagg agctcttcaa gctgctgaag gagggccacc gcatggacaa gcccgccaac   2160
tgcacacacg acctgtacat gatcatgcgg gagtgctggc atgccgcgcc ctcccagagg   2220
cccaccttca gcagctggt ggaggacctg gaccgtgtcc ttaccgtgac gtccaccgac    2280
aatgttatgg aacagttcaa tcctgggctg cgaaatttaa taaacctggg gaaaaattat   2340
gagaaagctg taaacgctat gatcctggca ggaaaagcct actacgatgg agtggccaag   2400
atcggtgaga ttgccactgg gtccccccgtg tcaactgaac tgggacatgt cctcatagag  2460
atttcaagta cccacaagaa actcaacgag agtcttgatg aaaattttaa aaaattccac   2520
aaagagatta tccatgagct ggagaagaag atagaacttg acgtgaaata tatgaacgca   2580
actctaaaaa gataccaaac agaacacaag aataaattag agtctttgga gaaatcccaa   2640
gctgagttga agaagatcag aaggaaaagc caaggaagcc gaaacgcact caaatatgaa   2700
cacaaagaaa ttgagtatgt ggagaccgtt acttctcgtc agagtgaaat ccagaaattc   2760
attgcagatg gttgcaaaga ggctctgctt gaagagaaga ggcgcttctg ctttctggtt   2820
gataagcact gtggctttgc aaaccacata cattattatc acttacagtc tgcagaacta   2880
ctgaattcca agctgcctcg gtggcaggag acctgtgttg atgccatcaa agtgccagag   2940
aaaatcatga atatgatcga agaaataaag accccagcct ctaccccgt gtctggaact    3000
cctcaggctt cacccatgat cgagagaagc aatgtggtta ggaaagatta cgacacccct   3060
tctaaatgct caccaaagat gccccccgct ccttcaggca gagcatatac cagtcccttg   3120
```

| | |
|---|---|
| atcgatatgt ttaataaccc agccacggct gccccgaatt cacaaagggt aaataattca | 3180 |
| acaggtactt ccgaagatcc cagtttacag cgatcagttt cggttgcaac gggactgaac | 3240 |
| atgatgaaga agcagaaagt gaagaccatc ttcccgcaca ctgcgggctc caacaagacc | 3300 |
| ttactcagct ttgcacaggg agatgtcatc acgctgctca tccccgagga aaggatggc | 3360 |
| tggctctatg gagaacacga cgtgtccaag gcgaggggtt ggttcccgtc gtcgtacacg | 3420 |
| aagttgctgg aagaaaatga gacagaagca gtgaccgtgc ccacgccaag ccccacacca | 3480 |
| gtgagaagca tcagcaccgt gaacttgtct gagaatagca gtgttgtcat ccccccaccc | 3540 |
| gactacttgg aatgcttgtc catggggca gctgccgaca ggagagcaga ttcggccagg | 3600 |
| acgacatcca cctttaaggc cccagcgtcc aagcccgaga ccgcggctcc taacgatgcc | 3660 |
| aacgggactg caaagccgcc ttttctcagc ggagaaaacc cctttgccac tgtgaaactc | 3720 |
| cgcccgactg tgacgaatga tcgctcggca cccatcattc gatga | 3765 |

<210> SEQ ID NO 60
<211> LENGTH: 4989
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60

| | |
|---|---|
| atggtcagct ggggtcgttt catctgcctg gtcgtggtca ccatggcaac cttgtccctg | 60 |
| gcccggccct ccttcagttt agttgaggat accacattag agccagaaga gccaccaacc | 120 |
| aaataccaaa tctctcaacc agaagtgtac gtggctgcgc caggggagtc gctagaggtg | 180 |
| cgctgcctgt tgaaagatgc cgccgtgatc agttggacta aggatgggt gcacttgggg | 240 |
| cccaacaata ggacagtgct tattgggag tacttgcaga taaagggcgc cacgcctaga | 300 |
| gactccggcc tctatgcttg tactgccagt aggactgtag acagtgaaac ttggtacttc | 360 |
| atggtgaatg tcacagatgc catctcatcc ggagatgatg aggatgacac cgatggtgcg | 420 |
| gaagattttg tcagtgagaa cagtaacaac aagagagcac catactggac caacacagaa | 480 |
| aagatggaaa agcggctcca tgctgtgcct gcggccaaca ctgtcaagtt tcgctgccca | 540 |
| gccgggggga acccaatgcc aaccatgcgg tggctgaaaa acgggaagga gtttaagcag | 600 |
| gagcatcgca ttggaggcta caaggtacga aaccagcact ggagcctcat tatggaaagt | 660 |
| gtggtcccat ctgacaaggg aaattatacc tgtgtagtgg agaatgaata cgggtccatc | 720 |
| aatcacacgt accacctgga tgttgtggag cgatcgcctc accggcccat cctccaagcc | 780 |
| ggactgccgg caaatgcctc cacagtggtc ggaggagacg tagagtttgt ctgcaaggtt | 840 |
| tacagtgatg cccagcccca catccagtgg atcaagcacg tggaaaagaa cggcagtaaa | 900 |
| tacgggcccg acgggctgcc ctacctcaag gttctcaagg ccgccggtgt taacaccacg | 960 |
| gacaaagaga ttgaggttct ctatattcgg aatgtaactt ttgaggacgc tggggaatat | 1020 |
| acgtgcttgg cgggtaattc tattgggata cctttcact ctgcatggtt gacagttctg | 1080 |
| ccagcgcctg aagagaaaaa ggagattaca gcttccccag actacctgga gatagccatt | 1140 |
| tactgcatag gggtcttctt aatcgcctgt atggtggtaa cagtcatcct gtgccgaatg | 1200 |
| aagaacacga ccaagaagcc agacttcagc agccagccgg ctgtgcacaa gctgaccaaa | 1260 |
| cgtatccccc tgcggagaca ggtaacagtt tcggctgagt ccagctcctc catgaactcc | 1320 |
| aacacccgc tggtgaggat aacaacacgc ctctcttcaa cggcagacac ccccatgctg | 1380 |

```
gcaggggtct ccgagtatga acttccagag gacccaaaat gggagtttcc aagagataag     1440
ctgacactgg gcaagcccct gggagaaggt tgctttgggc aagtggtcat ggcggaagca     1500
gtgggaattg acaaagacaa gcccaaggag gcggtcaccg tggccgtgaa gatgttgaaa     1560
gatgatgcca cagagaaaga cctttctgat ctggtgtcag agatggagat gatgaagatg     1620
attgggaaac acaagaatat cataaatctt cttggagcct gcacacagga tgggcctctc     1680
tatgtcatag ttgagtatgc ctctaaaggc aacctccgag aatacctccg agcccggagg     1740
ccacccggga tggagtactc ctatgacatt aaccgtgttc ctgaggagca gatgaccttc     1800
aaggacttgg tgtcatgcac ctaccagctg gccagaggca tggagtactt ggcttcccaa     1860
aaatgtattc atcgagattt agcagccaga aatgttttgg taacagaaaa caatgtgatg     1920
aaaatagcag actttggact cgccagagat atcaacaata tagactatta caaaaagacc     1980
accaatgggc ggcttccagt caagtggatg gctccagaag ccctgtttga tagagtatac     2040
actcatcaga gtgatgtctg gtccttcggg gtgttaatgt gggagatctt cactttaggg     2100
ggctcgccct acccagggat tcccgtggag gaacttttta agctgctgaa ggaaggacac     2160
agaatggata agccagccaa ctgcaccaac gaactgtaca tgatgatgag ggactgttgg     2220
catgcagtgc cctcccagag accaacgttc aagcagttgg tagaagactt ggatcgaatt     2280
ctcactctca caaccaatga gatcatggag gaaacaaata cgcagattgc ttggccatca     2340
aaactgaaga tcggagccaa atccaagaaa gatccccata ttaaggtttc tggaaagaaa     2400
gaagatgtta aagaagccaa ggaaatgatc atgtctgtct tagacacaaa aagcaatcga     2460
gtcacactga agatggatgt ttcacataca gaacattcac atgtaatcgg caaaggtggc     2520
aacaatatta aaaagtgat ggaagaaacc ggatgccata tccactttcc agattccaac     2580
aggaataacc aagcagaaaa aagcaaccag gtatctatag cgggacaacc agcaggagta     2640
gaatctgccc gagttagaat tcgggagctg cttcctttgg tgctgatgtt tgagctacca     2700
attgctggaa ttcttcaacc ggttcctgat cctaattccc cctctattca gcatatatca     2760
caaacgtaca atatttcagt atcatttaaa cagcgttccc gaatgtatgg tgctactgtc     2820
atagtacgag ggtctcagaa taacactagt gctgtgaagg aaggaactgc catgctgtta     2880
gaacatcttg ctgggagctt agcatcagct attcctgtga gcacacaact agatattgca     2940
gctcaacatc atctctttat gatgggtcga atgggagca acatcaaaca tatcatgcag     3000
agaacaggtg ctcagatcca ctttcctgat cccagtaatc cacaaaagaa atctaccgtc     3060
tacctccagg gcaccattga gtctgtctgt cttgcaaggc aatatctcat gggttgtctt     3120
cctcttgtgt tgatgtttga tatgaaggaa gaaattgaag tagatccaca attcattgcg     3180
cagttgatgg aacagcttga tgtcttcatc agtattaaac caaagcccaa acagccaagc     3240
aagtctgtga ttgtgaaaag tgttgagcga atgccttaa atatgtatga agcaaggaaa     3300
tgtctcctcg gacttgaaag cagtgggggtt accatagcaa ccagtccatc cccagcatcc     3360
tgccctgccg gcctggcatg tcccagcctg gatatcttag cttcagcagg ccttggactc     3420
actggactag gtcttttggg acccaccacc ttatctctga acacttcaac aaccccaaac     3480
tcactcttga atgctcttaa tagctcagtc agtcctttgc aaagtccaag ttctggtaca     3540
cccagcccca cattatgggc accccacctt gctaatactt caagtgccac aggttttttct     3600 gctataccac accttatgat tccatctact gcccaagcca cattaactaa tattttgttg     3660
tctggagtgc ccacctatgg gcacacagct ccatctcccc ctcctggctt gactcctgtt     3720
```

```
gatgtccata tcaacagtat gcagaccgaa ggcaaaaaaa tctctgctgc tttaaatgga      3780
catgcacagt ctccagatat aaaatatggt gcaatatcca cttcatcact tggagaaaaa      3840
gtgctgagtg caaatcacgg ggatccgtcc atccagacaa gtgggtctga gcagacatct      3900
cccaaatcaa gccccactga aggttgtaat gatgcttttg ttgaagtagg catgcctcga      3960
agtccttccc attctgggaa tgctggtgac ttgaaacaga tgatgtgtcc ctccaaggtt      4020
tcctgtgcca aaaggcagac agtggaacta ttgcaaggca cgaaaaactc acacttacac      4080
agcactgaca ggttgctctc agaccctgaa ctgagtgcta ccgaaagccc tttggctgac      4140
aagaaggctc cagggagtga gcgcgctgca gagagggcag cagctgccca gcaaaactcc      4200
gaaagggccc accttgctcc acggtcatca tatgtcaaca tgcaggcatt tgactatgaa      4260
cagaagaagc tattagccac caaagctatg ttaaagaaac cagtggtgac ggaggtcaga      4320
acgcccacaa atacctggag tggcctgggt ttttctaaat ccatgccagc tgaaactatc      4380
aaggagttga aagggccaa tcatgtgtcc tataagccca caatgacaac cacttatgag      4440
ggctcatcca tgtcccttc acggtccaac agtcgtgagc acttgggagg tggaagcgaa      4500
tctgataact ggagagaccg aaatggaatt ggacctggaa gtcatagtga atttgcagct      4560
tctattggca gccctaagcg taaacaaaac aaatcaacgg aacactatct cagcagtagc      4620
aattacatgg actgcatttc ctcgctgaca ggaagcaatg gctgtaactt aaatagctct      4680
ttcaaaggtt ctgacctccc tgagctcttc agcaaactgg gctgggcaa atacacagat      4740 gttttccagc aacaagagat cgatcttcag acattcctca ctctcacaga tcaggatctg      4800
aaggagctgg aataactac ttttggtgcc aggaggaaaa tgctgcttgc aatttcagaa      4860
ctaaataaaa accgaagaaa gcttttgaa tcgccaaatg cacgcacctc tttcctggaa      4920
ggtggagcga gtggaaggct accccgtcag tatcactcag acattgctag tgtcagtggc      4980
cgctggtag                                                              4989

<210> SEQ ID NO 61
<211> LENGTH: 5109
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61
atggtcagct ggggtcgttt catctgcctg gtcgtggtca ccatggcaac cttgtccctg        60
gcccggccct ccttcagttt agttgaggat accacattag agccagaaga gccaccaacc       120
aaataccaaa tctctcaacc agaagtgtac gtggctgcgc cagggagtc gctagaggtg       180 cgctgcctgt tgaaagatgc cgccgtgatc agttggacta aggatgggt gcacttgggg       240 cccaacaata ggacagtgct tattgggag tacttgcaga taaagggcgc cacgcctaga       300
gactccggcc tctatgcttg tactgccagt aggactgtag acagtgaaac ttggtacttc       360
atggtgaatg tcacagatgc catctcatcc ggagatgatg aggatgacac cgatggtgcg       420
gaagattttg tcagtgagaa cagtaacaac aagagagcac catactggac caacacagaa       480
aagatggaaa gcggctcca tgctgtgcct gcggccaaca ctgtcaagtt cgctgcccca       540
gccgggggga acccaatgcc aaccatgcgg tggctgaaaa acgggaagga gtttaagcag       600
gagcatcgca ttgaggcta caaggtacga aaccagcact ggagcctcat tatgaaagt        660 gtggtcccat ctgacaaggg aaattatacc tgtgtagtgg agaatgaata cgggtccatc       720
```

```
aatcacacgt accacctgga tgttgtggag cgatcgcctc accggcccat cctccaagcc    780
ggactgccgg caaatgcctc cacagtggtc ggaggagacg tagagtttgt ctgcaaggtt    840
tacagtgatg cccagcccca catccagtgg atcaagcacg tggaaaagaa cggcagtaaa    900
tacgggcccg acgggctgcc ctacctcaag gttctcaagg ccgccggtgt taacaccacg    960
gacaaagaga ttgaggttct ctatattcgg aatgtaactt ttgaggacgc tggggaatat   1020
acgtgcttgg cgggtaattc tattgggata tcctttcact ctgcatggtt gacagttctg   1080
ccagcgcctg gaagagaaaa ggagattaca gcttccccag actacctgga gatagccatt   1140
tactgcatag gggtcttctt aatcgcctgt atggtggtaa cagtcatcct gtgccgaatg   1200
aagaacacga ccaagaagcc agacttcagc agccagccgg ctgtgcacaa gctgaccaaa   1260
cgtatccccc tgcggagaca ggtaacagtt tcggctgagt ccagctcctc catgaactcc   1320
aacaccccgc tggtgaggat aacaacacgc ctctcttcaa cggcagacac ccccatgctg   1380
gcaggggtct ccgagtatga acttccagag acccaaaat gggagtttcc aagagataag   1440
ctgacactgg caagcccct gggagaaggt tgctttgggc aagtggtcat ggcggaagca   1500
gtgggaattg acaaagacaa gcccaaggag gcggtcaccg tggccgtgaa gatgttgaaa   1560
gatgatgcca cagagaaaga cctttctgat ctggtgtcag agatggagat gatgaagatg   1620
attgggaaac acaagaatat cataaatctt cttggagcct gcacacagga tgggcctctc   1680
tatgtcatag ttgagtatgc ctctaaaggc aacctccgag aatacctccg agcccggagg   1740
ccacccggga tggagtactc ctatgacatt aaccgtgttc ctgaggagca gatgaccttc   1800
aaggacttgg tgtcatgcac ctaccagctg gccagaggca tggagtactt ggcttcccaa   1860
aaatgtattc atcgagattt agcagccaga aatgttttgg taacagaaaa caatgtgatg   1920
aaaatagcag acttttggac tcgccagaga tcaacaata tagactatta caaaagacc   1980
accaatgggc ggcttccagt caagtggatg gctccagaag ccctgtttga tagagtatac   2040
actcatcaga gtgatgtctg gtccttcggg gtgttaatgt gggagatctt cacttttaggg   2100
ggctcgccct acccagggat tccgtggag gaactttta agctgctgaa ggaaggacac   2160
agaatggata agccagccaa ctgcaccaac gaactgtaca tgatgatgag ggactgttgg   2220
catgcagtgc cctcccagag accaacgttc aagcagttgg tagaagactt ggatcgaatt   2280
ctcactctca caaccaatga ggagagtaga tctggagaaa ccaacagctg tgttgaagaa   2340
ataatccggg agatgacctg gcttccacca ctttctgcta ttcaagcacc tggcaaagtg   2400
gaaccaacca aatttccatt tccaaataag gactctcagc ttgtatcctc tggacacaat   2460
aatccaaaga aggtgatgc agagccagag agtccagaca gtggcacatc gaatacatca   2520
atgctggaag atgaccttaa gctaagcagt gatgaagagg agaatgaaca gcaggcagct   2580
cagagaacgg ctctccgcgc tctctctgac agcgccgtgg tccagcagcc caactgcaga   2640
acctcggtgc cttccagcaa gggcagcagc agcagcagca gcagcggcag cagcagctcc   2700
tccagcgact cagagagcag ctccggatct gactcggaga ccgagagcag ctccagcgag   2760
agtgagggca gcaagccccc ccacttctcc agccccgagg ctgaaccggc atcctctaac   2820
aagtggcagc tggataaatg gctaaacaaa gttaatcccc acaagcctcc tattctgatc   2880
caaaatgaaa gccacgggtc agagagcaat cagtactaca acccggtgaa agaggacgtc   2940
caggactgtg ggaaagtccc cgacgtttgc cagcccagcc tgagagagaa ggagatcaag   3000
agcacttgca aggaggagca aaggccaagg acagccaaca aggcccctgg gagtaaaggc   3060
gtgaagcaga agtccccgcc cgcggccgtg gccgtggcgg tgagcgcagc cgccccgcca   3120
```

```
cccgcagtgc cctgtgcgcc cgcggagaac gcgcccgcgc ctgcccggag gtccgcgggc    3180
aagaagccca ccaggcgcac cgagaggacc tcagccgggg acggcgccaa ctgccaccgg    3240
cccgaggagc ccgcggccgc ggacgcgctg gggacgagcg tggtggtccc cccggagccc    3300
accaaaacca ggcccgtgtgg caacaacaga gcgagccacc gcaaggagct gcgctcctcc    3360
gtgacctgcg agaagcgccg cacgcggggg ctaagcagga tcgtccccaa atccaaggag    3420
ttcattgaga cagagtcgtc atcttcatcc tcctcctcgg actccgacct ggagtccgag    3480
caggaggagt accctctgtc caaagcacag accgtggctg cctctgcctc ctccgggaat    3540
gatcagaggc tgaaggaggc cgctgccaac gggggcagtg gtcctagggc ccctgtaggc    3600
tccatcaacg ccaggaccac cagtgacatc gccaaggagc tggaggagca gttctacaca    3660
ctggtcccct ttggccggaa cgaacttctc tcccctctaa aggacagtga tgagatcagg    3720
tctctctggg tcaaaatcga cctgaccctc ctgtccagga tcccagaaca cctgccccag    3780
gagccagggg tattgagcgc ccctgccacc aaggactctg agagcgcacc gcccagccac    3840
acctcggaca cacctgcaga aaaggctttg ccaaaatcca gaggaaacg caagtgtgac    3900 aacgaagacg actacaggga gatcaagaag tcccagggag agaaagacag ctcttcaaga    3960
ctggccacct ccaccagtaa tactttgtct gcaaaccact gcaacatgaa catcaacagt    4020
gtggcaatac caataaataa aaatgaaaaa atgcttcggt cgcccatctc accectctct    4080 gatgcatcta aacacaaata caccagcgag gacttaactt cttccagccg acctaatggc    4140
aacagtttgt ttacttcagc ctcttccagc aaaaagccta aggccgacag ccagctgcag    4200
cctcacggcg gagacctcac gaaagcagct cacaacaatt ctgaaaacat tcccctccac    4260
aagtcacggc cgcagacgaa gccgtggtct ccaggctcca acggcacag ggactgcaag    4320 aggcagaaac ttgtcttcga tgatatgcct cgcagtgccg attatttat gcaagaagct    4380 aaacgaatga agcataaagc agatgcaatg gtggaaaagt ttggaaaggc tttgaactat    4440
gctgaagcag cattgtcgtt tatcgagtgt ggaaatgcaa tggaacaagg ccccatggaa    4500
tccaaatctc cttatacgat gtattcagaa acagtagagc tcatcaggta tgctatgaga    4560
ctaaaaaccc actcaggccc caatgccaca ccagaagaca acaactggc tgcattatgt    4620 taccgatgcc tggccctcct gtactggcgg atgtttcgac tcaaaaggga ccacgctgta    4680
aagtattcaa aagcactaat cgactatttc aagaactcat ctaaagccgc caagccccca    4740
tctccgtggg gggccagtgg aaagagcact ggaaccccat ccccatgtc tcccaaccccc    4800 tctcccgcca gctccgtggg gtctcaggc agcctctcca acgccagcgc cctgtccccg    4860
tcgaccatcg tcagcatccc acagcgcatc caccagatgg cggccaacca cgtcagcatc    4920
accaacagca tcctgcacag ctacgactac tgggagatgg ccgacaacct ggccaaggaa    4980
aaccgagaat tcttcaacga cctggatctg ctcatggggc cggtcaccct gcacagcagc    5040
atggagcacc tggtccagta ctcccaacag ggcctgcact ggctgcggaa cagcgcccac    5100
ctgtcatag                                                          5109
```

<210> SEQ ID NO 62
<211> LENGTH: 3213
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62

```
atggtcagct ggggtcgttt catctgcctg gtcgtggtca ccatggcaac cttgtccctg      60
gcccggccct ccttcagttt agttgaggat accacattag agccagaaga gccaccaacc     120
aaataccaaa tctctcaacc agaagtgtac gtggctgcgc caggggagtc gctagaggtg     180
cgctgcctgt tgaaagatgc cgccgtgatc agttggacta aggatggggt gcacttgggg     240
cccaacaata ggacagtgct tattgggag tacttgcaga taaagggcgc cacgcctaga      300
gactccggcc tctatgcttg tactgccagt aggactgtag acagtgaaac ttggtacttc     360
atggtgaatg tcacagatgc catctcatcc ggagatgatg aggatgacac cgatggtgcg     420
gaagattttg tcagtgagaa cagtaacaac aagagagcac catactggac caacacagaa     480
aagatggaaa agcggctcca tgctgtgcct gcggccaaca ctgtcaagtt tcgctgccca     540
gccggggga acccaatgcc aaccatgcgg tggctgaaaa acgggaagga gtttaagcag     600
gagcatcgca ttggaggcta caaggtacga aaccagcact ggagcctcat tatggaaagt     660
gtggtcccat ctgacaaggg aaattatacc tgtgtagtgg agaatgaata cgggtccatc     720
aatcacacgt accacctgga tgttgtggag cgatcgcctc accggcccat cctccaagcc     780
ggactgccgg caaatgcctc cacagtggtc ggaggagacg tagagtttgt ctgcaaggtt     840
tacagtgatg cccagcccca catccagtgg atcaagcacg tggaaaagaa cggcagtaaa     900
tacgggcccg acgggctgcc ctacctcaag gttctcaagg ccgccggtgt taacaccacg     960
gacaaagaga ttgaggttct ctatattcgg aatgtaactt ttgaggacgc tggggaatat    1020
acgtgcttgg cggtaattc tattgggata tcctttcact ctgcatggtt gacagttctg    1080
ccagcgcctg aagagaaaa ggagattaca gcttccccag actacctgga gatagccatt    1140
tactgcatag gggtcttctt aatcgcctgt atggtggtaa cagtcatcct gtgccgaatg    1200
aagaacacga ccaagaagcc agacttcagc agccagccgg ctgtgcacaa gctgaccaaa    1260
cgtatccccc tgcggagaca ggtaacagtt tcggctgagt ccagctcctc catgaactcc    1320
aacaccccgc tggtgaggat aacaacacgc ctctcttcaa cggcagacac ccccatgctg    1380
gcagggggtct ccgagtatga acttccagag gacccaaaat gggagtttcc aagagataag    1440
ctgacactgg gcaagcccct gggagaaggt tgctttgggc aagtggtcat ggcggaagca    1500
gtgggaattg acaaagacaa gcccaaggag gcggtcaccg tggccgtgaa gatgttgaaa    1560
gatgatgcca cagagaaaga cctttctgat ctggtgtcag agatggagat gatgaagatg    1620
attgggaaac acaagaatat cataaatctt cttggagcct gcacacagga tgggcctctc    1680
tatgtcatag ttgagtatgc ctctaaaggc aacctccgag aatacctccg agcccggagg    1740
ccacccggga tggagtactc ctatgacatt aaccgtgttc ctgaggagca gatgaccttc    1800
aaggacttgg tgtcatgcac ctaccagctg gccagaggca tggagtactt ggcttcccaa    1860
aaatgtattc atcgagattt agcagccaga atgtttttgg taacagaaaa caatgtgatg    1920
aaaatagcag actttggact cgccagagat atcaacaata tagactatta caaaaagacc    1980
accaatgggc ggcttccagt caagtggatg gctccagaag ccctgtttga tagagtatac    2040
actcatcaga gtgatgtctg gtccttcggg gtgttaatgt gggagatctt cacttttaggg    2100
ggctcgccct acccagggat tcccgtggag gaacttttta gctgctgaa ggaaggacac    2160
agaatggata gccagccaa ctgcaccaac gaactgtaca tgatgatgag ggactgttgg    2220
catgcagtgc cctcccagag accaacgttc aagcagttgg tagaagactt ggatcgaatt    2280
ctcactctca caaccaatga gatggcagat gatcagggct gtattgaaga gcaggggtt    2340
```

```
gaggattcag caaatgaaga ttcagtggat gctaagccag accggtcctc gtttgtaccg    2400
tccctcttca gtaagaagaa gaaaaatgtc accatgcgat ccatcaagac cacccgggac    2460
cgagtgccta catatcagta aacatgaatt tttgaaaagc tgggcaaatg catcataata    2520
aacaacaaga actttgataa agtgacaggt atgggcgttc gaaacggaac agacaaagat    2580
gccgaggcgc tcttcaagtg cttccgaagc ctgggttttg acgtgattgt ctataatgac    2640
tgctcttgtg ccaagatgca agatctgctt aaaaaagctt ctgaagagga ccatacaaat    2700
gccgcctgct tcgcctgcat cctcttaagc catggagaag aaaatgtaat ttatgggaaa    2760
gatggtgtca caccaataaa ggatttgaca gcccacttta gggggatag atgcaaaacc    2820 cttttagaga aacccaaact cttcttcatt caggcttgcc gagggaccga gcttgatgat    2880
ggcatccagg ccgactcggg gcccatcaat gacacagatg ctaatcctcg atacaagatc    2940
ccagtggaag ctgacttcct cttcgcctat tccacggttc caggctatta ctcgtggagg    3000
agcccaggaa gaggctcctg gtttgtgcaa gccctctgct ccatcctgga ggagcacgga    3060
aaagacctgg aaatcatgca gatcctcacc agggtgaatg acagagttgc caggcacttt    3120
gagtctcagt ctgatgaccc acacttccat gagaagaagc agatcccctg tgtggtctcc    3180
atgctcacca aggaactcta cttcagtcaa tag                                 3213
```

<210> SEQ ID NO 63
<211> LENGTH: 3423
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63

```
atggtcagct ggggtcgttt catctgcctg gtcgtggtca ccatggcaac cttgtccctg      60
gcccggccct ccttcagttt agttgaggat accacattag agccagaaga gccaccaacc     120
aaataccaaa tctctcaacc agaagtgtac gtggctgcgc caggggagtc gctagaggtg     180
cgctgcctgt tgaaagatgc cgccgtgatc agttggacta aggatggggt gcacttgggg     240
cccaacaata ggacagtgct tattggggag tacttgcaga taaagggcgc cacgcctaga     300
gactccggcc tctatgcttg tactgccagt aggactgtag acagtgaaac ttggtacttc     360
atggtgaatg tcacagatgc catctcatcc ggagatgatg aggatgacac cgatggtgcg     420
gaagattttg tcagtgagaa cagtaacaac aagagagcac catactggac caacacagaa     480
aagatggaaa agcggctcca tgctgtgcct gcggccaaca ctgtcaagtt cgctgccca    540 gccgggggga acccaatgcc aaccatgcgg tggctgaaaa acgggaagga gtttaagcag     600
gagcatcgca ttgaggcta caaggtacga accagcact ggagcctcat tatggaaagt     660
gtggtcccat ctgacaaggg aaattatacc tgtgtagtgg agaatgaata cgggtccatc     720
aatcacacgt accacctgga tgttgtggag cgatcgcctc accggcccat cctccaagcc     780
ggactgccgg caaatgcctc cacagtggtc ggaggagacg tagagtttgt ctgcaaggtt     840
tacagtgatg cccagcccca catccagtgg atcaagcacg tggaaaagaa cggcagtaaa     900
tacgggcccg acgggctgcc ctacctcaag gttctcaagg ccgccggtgt aacaccacg     960 gacaaagaga ttgaggttct ctatattcgg aatgtaactt ttgaggacgc tgggggaatat    1020 acgtgcttgg cgggtaattc tattgggata tcctttcact ctgcatggtt gacagttctg    1080
ccagcgcctg aagagaaaa ggagattaca gcttccccag actacctgga gatagccatt    1140
```

```
tactgcatag gggtcttctt aatcgcctgt atggtggtaa cagtcatcct gtgccgaatg   1200
aagaacacga ccaagaagcc agacttcagc agccagccgg ctgtgcacaa gctgaccaaa   1260
cgtatccccc tgcggagaca ggtaacagtt tcggctgagt ccagctcctc catgaactcc   1320
aacaccccgc tggtgaggat aacaacacgc ctctcttcaa cggcagacac ccccatgctg   1380 gcagggtct ccgagtatga acttccagag acccaaaat gggagtttcc aagagataag    1440
ctgacactgg gcaagcccct gggagaaggt tgctttgggc aagtggtcat ggcggaagca   1500
gtgggaattg acaaagacaa gcccaaggag gcggtcaccg tggccgtgaa gatgttgaaa   1560
gatgatgcca cagagaaaga cctttctgat ctggtgtcag agatggagat gatgaagatg   1620
attgggaaac acaagaatat cataaatctt cttggagcct gcacacagga tgggcctctc   1680
tatgtcatag ttgagtatgc ctctaaaggc aacctccgag aatacctccg agcccggagg   1740
ccacccggga tggagtactc ctatgacatt aaccgtgttc ctgaggagca gatgaccttc   1800
aaggacttgg tgtcatgcac ctaccagctg gccagaggca tggagtactt ggcttcccaa   1860
aaatgtattc atcgagattt agcagccaga atgttttgg taacagaaaa caatgtgatg   1920
aaaatagcag actttggact cgccagagat atcaacaata tagactatta caaaaagacc   1980
accaatgggc ggcttccagt caagtggatg gctccagaag ccctgtttga tagagtatac   2040
actcatcaga gtgatgtctg gtccttcggg gtgttaatgt gggagatctt cactttaggg   2100
ggctcgccct acccagggat tcccgtggag gaactttta agctgctgaa ggaaggacac   2160
agaatggata agccagccaa ctgcaccaac gaactgtaca tgatgatgag ggactgttgg   2220
catgcagtgc cctcccagag accaacgttc aagcagttgg tagaagactt ggatcgaatt   2280
ctcactctca caaccaatga gcaagccagg gctgagcagg aagaagaatt cattagtaac   2340
actttattca agaaaattca ggctttgcag aaggagaaag aaacccttgc tgtaaattat   2400
gagaaagaag aagaattcct cactaatgag ctctccagaa aattgatgca gttgcagcat   2460
gagaaagccg aactagaaca gcatcttgaa caagagcagg aatttcaggt caacaaactg   2520
atgaagaaaa ttaaaaaact ggagaatgac accatttcta gcaacttac attagaacag   2580 ttgagacggg agaagattga ccttgaaaat acattggaac aagaacaaga agcactagtt   2640
aatcgcctct ggaaaaggat ggataagctt gaagctgaaa agcgaatcct gcaggaaaaa   2700
ttagaccagc ccgtctctgc tccaccatcg cctagagata tctccatgga gattgattct   2760
ccagaaaata tgatgcgtca catcaggttt ttaaagaatg aagtggaacg gctgaagaag   2820
caactgagag ctgctcagtt acagcattca gagaaaatgg cacagtatct ggaggaggaa   2880
cgtcacatga gagaagagaa cttgaggctc cagaggaagc tgcagaggga gatggagaga   2940
agagaagccc tctgtcgaca gctctccgag agtgagtcca gcttagaaat ggacgacgaa   3000
aggtatttta atgagatgtc tgcacaagga ttaagacctc gcactgtgtc cagcccgatc   3060
ccttacacac cttctccgag ttcaagcagg cctatatcac ctggtctatc atatgcaagt   3120
cacacggttg gtttcacgcc accaacttca ctgactagag ctggaatgtc ttattacaat   3180
tccccgggtc ttcacgtgca gcacatggga acatcccatg gtatcacaag gccttcacca   3240
cggagaagca acagtcctga caaattcaaa cggcccacgc cgcctccatc tcccaacaca   3300
cagaccccag tccagccacc tccgcctcca cctccgccac ccatgcagcc cacggtcccc   3360
tcagcagcca cctcgcagcc tactccttcg caacattcgg cgcacccctc ctcccagcct   3420
taa                                                                3423
```

<210> SEQ ID NO 64
<211> LENGTH: 5229
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64

| | | | | | |
|---|---|---|---|---|---|
| atggtcagct | ggggtcgttt | catctgcctg | gtcgtggtca | ccatggcaac | cttgtccctg | 60 |
| gcccggccct | ccttcagttt | agttgaggat | accacattag | agccagaaga | gccaccaacc | 120 |
| aaataccaaa | tctctcaacc | agaagtgtac | gtggctgcgc | caggggagtc | gctagaggtg | 180 |
| cgctgcctgt | tgaaagatgc | cgccgtgatc | agttggacta | aggatggggt | gcacttgggg | 240 |
| cccaacaata | ggacagtgct | tattggggag | tacttgcaga | taaagggcgc | cacgcctaga | 300 |
| gactccggcc | tctatgcttg | tactgccagt | aggactgtag | acagtgaaac | ttggtacttc | 360 |
| atggtgaatg | tcacagatgc | catctcatcc | ggagatgatg | aggatgacac | cgatggtgcg | 420 |
| gaagattttg | tcagtgagaa | cagtaacaac | aagagagcac | catactggac | caacacagaa | 480 |
| aagatggaaa | agcggctcca | tgctgtgcct | gcggccaaca | ctgtcaagtt | tcgctgccca | 540 |
| gccgggggga | acccaatgcc | aaccatgcgg | tggctgaaaa | acgggaagga | gtttaagcag | 600 |
| gagcatcgca | ttggaggcta | caaggtacga | aaccagcact | ggagcctcat | tatggaaagt | 660 |
| gtggtcccat | ctgacaaggg | aaattatacc | tgtgtagtgg | agaatgaata | cggtccatc | 720 |
| aatcacacgt | accacctgga | tgttgtggag | cgatcgcctc | accggcccat | cctccaagcc | 780 |
| ggactgccga | caaatgcctc | cacagtggtc | ggaggagacg | tagagtttgt | ctgcaaggtt | 840 |
| tacagtgatg | cccagcccca | catccagtgg | atcaagcacg | tggaaaagaa | cggcagtaaa | 900 |
| tacgggcccg | acgggctgcc | ctacctcaag | gttctcaagg | ccgccggtgt | aacaccacg | 960 |
| gacaaagaga | ttgaggttct | ctatattcgg | aatgtaactt | ttgaggacgc | tggggaatat | 1020 |
| acgtgcttgg | cggtaattc | tattgggata | tcctttcact | ctgcatggtt | gacagttctg | 1080 |
| ccagcgcctg | gaagagaaaa | ggagattaca | gcttccccag | actacctgga | gatagccatt | 1140 |
| tactgcatag | gggtcttctt | aatcgcctgt | atggtggtaa | cagtcatcct | gtgccgaatg | 1200 |
| aagaacacga | ccaagaagcc | agacttcagc | agccagccgg | ctgtgcacaa | gctgaccaaa | 1260 |
| cgtatccccc | tgcggagaca | ggtaacagtt | tcggctgagt | ccagctcctc | catgaactcc | 1320 |
| aacacccgc | tggtgaggat | aacaacacgc | ctctcttcaa | cggcagacac | ccccatgctg | 1380 |
| gcagggtct | ccgagtatga | acttccagag | gacccaaaat | gggagtttcc | aagagataag | 1440 |
| ctgacactgg | gcaagcccct | gggagaaggt | tgctttgggc | aagtggtcat | ggcggaagca | 1500 |
| gtgggaattg | acaaagacaa | gcccaaggag | gcggtcaccg | tggccgtgaa | gatgttgaaa | 1560 |
| gatgatgcca | cagagaaaga | cctttctgat | ctggtgtcag | agatggagat | gatgaagatg | 1620 |
| attgggaaac | acaagaatat | cataaatctt | cttggagcct | gcacacagga | tgggcctctc | 1680 |
| tatgtcatag | ttgagtatgc | ctctaaaggc | aacctccgag | aatacctccg | agcccggagg | 1740 |
| ccacccggga | tggagtactc | ctatgacatt | aaccgtgttc | ctgaggagca | gatgaccttc | 1800 |
| aaggacttgg | tgtcatgcac | ctaccagctg | gccagaggca | tggagtactt | ggcttcccaa | 1860 |
| aaatgtattc | atcgagattt | agcagccaga | aatgttttgg | taacagaaaa | caatgtgatg | 1920 |
| aaaatagcag | actttggact | cgccagagat | atcaacaata | tagactatta | caaaaagacc | 1980 |
| accaatgggc | ggcttccagt | caagtggatg | gctccagaag | ccctgtttga | tagagtatac | 2040 |
| actcatcaga | gtgatgtctg | gtccttcggg | gtgttaatgt | gggagatctt | cactttaggg | 2100 |

```
ggctcgccct acccagggat tcccgtggag gaactttttta agctgctgaa ggaaggacac    2160
agaatggata agccagccaa ctgcaccaac gaactgtaca tgatgatgag ggactgttgg    2220
catgcagtgc cctcccagag accaacgttc aagcagttgg tagaagactt ggatcgaatt    2280
ctcactctca caaccaatga gacacaactt cgaaaccagc taattcatga gttgatgcac    2340
cctgtattga gtggagaact gcagcctcgg tccatttcag tagaagggag ctccctctta    2400
ataggcgcct ctaactcttt agtggcagat cacttacaaa gatgtggcta tgaatattca    2460
ctttctgttt tctttccaga aagtggtttg gcaaagaaaa aggtatttac tatgcaggat    2520
ctattacaac tcattaaaat caaccctact tccagtctct acaaatcact ggtttcagga    2580
tctgataaag aaaatcaaaa aggttttctt atgcattttt taaaagaatt ggcagaatat    2640
catcaagcta aagagagttg taatatggaa actcagacaa gttcgacatt taacagagat    2700
tctctggctg agaagcttca gcttattgat gatcagtttg cagatgctta ccctcagcgt    2760
atcaagttcg aatctttaga aataaagcta aatgagtata agagagaaat agaagagcaa    2820
cttcgggcag aaatgtgtca aaagttgaag tttttttaaag ataccgagat agcaaaaatt    2880
aaaatggaag caaaaaaaaa gtatgaaaag gagttaacca tgttccagaa tgatttttgaa    2940 aaagcttgtc aagcaaaatc tgaagctctc gttcttcggg aaaagagtac ccttgaaaga    3000
attcacaagc accaagagat tgaaacaaaa gaaatttatg ctcaaaggca acttttacta    3060
aaagatatgg atttgctaag aggaagagaa gcagagctga agcaaagagt tgaagctttt    3120
gaattgaacc agaagctcca ggaagaaaaa cataaaagca taactgaggc acttaggaga    3180
caggagcaga atataaagag ttttgaggag acctatgacc gaaagctcaa gaatgaactt    3240
ctaaagtatc aacttgaact gaaggatgac tacatcatta gaactaatcg actgattgaa    3300
gatgaaagga agaataaaga aaaagctgtt catttgcaag aggagctcat agctattaat    3360
tcaaaaaagg aggaactcaa tcaatctgta aatcgtgtga agaacttga gcttgaatta    3420 gagtctgtca agcccagtc tttggcaata acaaaacaaa accatatgct gaatgaaaag    3480
gttaaagaga tgagtgatta ttcactacta aaagaagaga aactggagct tctggcacaa    3540
aataaattac ttaaacaaca actggaagag agtagaaatg aaaacctgcg tctcctaaac    3600
cgcctagctc agccggctcc tgaacttgca gtctttcaga aagaactacg gaaagccgaa    3660
aaggctatag tggttgagca tgaggagttc gaaagctgca ggcaagctct gcacaaacaa    3720
ctgcaagacg aaattgagca ttctgcacag ctgaaggccc agattctagg ttacaaagct    3780
tctgtaaaga gtttaactac tcaggttgcc gatttaaaat tgcaactgaa gcaaactcag    3840
acagccctag agaatgaagt gtactgcaat ccaaagcagt ctgtgatcga tcgttctgtc    3900
aatggattaa taaatggcaa tgtggtgcct tgcaatggtg agataagtgg ggatttcttg    3960
aacaatcctt ttaaacagga aaacgttcta gcacgtatgg ttgcatcaag gatcacaaat    4020
tatccaactg catgggtgga gggtagttcc cctgattctg accttgagtt tgtagccaat    4080
actaaggcaa gggtcaaaga gcttcagcaa gaggccgaac gcttggaaaa ggcttttcaga    4140 agttaccatc ggagagtcat taaaaactct gccaaaagcc cactagcagc aaagagccca    4200
ccatctctgc acttgctgga agccttcaaa acattactt ccagttcccc ggaaagacat    4260
atttttggag aggacagagt tgtctctgag cagcctcaag tgggcacact tgaagaaagg    4320
aatgacgtcg tggaagcact gacaggcagt gcagcctcga ggctccgcgg gggcacttcc    4380
tccagacgcc tctcttccac accccttcca aaagcaaaaa gaagcctcga aagtgaaatg    4440
```

```
tatctggaag gtctgggcag atcacacatt gcttccccca gtccttgtcc tgacagaatg    4500
cccctaccat cacccactga gtctaggcac agcctctcca tccctcctgt ctccagccct    4560
ccggagcaga aagtgggtct ttatcgaaga caaactgaac ttcaagacaa aagtgaattt    4620
tcagatgtgg acaagctagc ttttaaggat aatgaggagt ttgaatcatc ttttgaatct    4680
gcagggaaca tgccaaggca gttggaaatg ggcgggcttt ctcctgccgg ggatatgtct    4740
catgtggacg ctgctgcagc tgctgtgccc ctctcatatc agcacccaag tgtagatcag    4800
aaacaaattg aagaacaaaa ggaagaagaa aaaatacggg aacagcaagt gaaagaacga    4860
aggcagagag aagaaagaag gcagagtaac ctacaagaag ttttagaaag ggaacgaaga    4920
gaactagaaa aactgtatca ggaaaggaag atgattgaag aatcactgaa gattaaaata    4980
aaaaaggaat tagaaatgga aaatgaatta gaaatgagta atcaagaaat aaaagacaaa    5040
tctgctcaca gtgaaaatcc tttagagaaa tacatgaaaa tcatccagca ggagcaagac    5100
caggagtcgg cagataagag ctcaaaaaag atggtccaag aaggctccct agtggacacg    5160
ctgcaatcta gtgacaaagt cgaaagttta acaggctttt ctcatgaaga actagacgac    5220
tcttggtaa                                                            5229

<210> SEQ ID NO 65
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
tccaccgacg taaaggcg                                                    18

<210> SEQ ID NO 66
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
taccgtgacg tccaccga                                                    18

<210> SEQ ID NO 67
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
gccttctggc ccaggtgc                                                    18

<210> SEQ ID NO 68
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
tccaccgaca atgttatg                                                    18
```

<210> SEQ ID NO 69
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
accaatgagg agagtaga                                                18

<210> SEQ ID NO 70
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
accaatgaga tcatggag                                                18

<210> SEQ ID NO 71
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
accaatgaga tggcag                                                  16

<210> SEQ ID NO 72
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
accaatgagc aagccagg                                                18

<210> SEQ ID NO 73
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
accaatgaga cacaactt                                                18

USE OF FGFR MUTANT GENE PANELS IN IDENTIFYING CANCER PATIENTS THAT WILL BE RESPONSIVE TO TREATMENT WITH AN FGFR INHIBITOR

RELATED APPLICATIONS

This application is a continuation of U.S. application Ser. No. 14/858,627, filed Sep. 18, 2015, which claims the benefit of U.S. Provisional Application No. 62/056,159, filed on Sep. 26, 2014.

The entire teachings of the above applications are incorporated herein by reference.

SEQUENCE LISTING

The instant application contains a Sequence Listing which has been submitted electronically in ASCII format and is hereby incorporated by reference in its entirety. Said ASCII copy, created on Sep. 19, 2018, is named 01482032001_Sequence_Listing.txt and is 64 KB in size.

TECHNICAL FIELD

Provided herein are methods of identifying a cancer patient that will be responsive to treatment with a fibroblast growth factor receptor inhibitor and methods of treating the same.

BACKGROUND

The identification of genetic abnormalities can be useful in selecting the appropriate therapeutic(s) for cancer patients. This is also useful for cancer patients failing the main therapeutic option (front-line therapy) for that cancer type, particularly if there is no accepted standard of care for second and subsequent-line therapy. Fibroblast growth factor receptors (FGFRs) are a family of receptor tyrosine kinases involved in regulating cell survival, proliferation, migration and differentiation. FGFR alterations have been observed in some cancers. To date, there are no approved therapies that are efficacious in patients with FGFR alterations.

SUMMARY

Disclosed herein are methods of identifying a cancer patient that will be responsive to treatment with a fibroblast growth factor receptor (FGFR) inhibitor comprising: evaluating a biological sample from the patient for a FGFR mutant from a FGFR mutant gene panel, wherein the FGFR mutant is a FGFR fusion gene or a FGFR single nucleotide polymorphism, and wherein said evaluating comprises amplifying cDNA with a pair of primers that bind to and amplify one or more FGFR mutants from the FGFR mutant gene panel; and determining whether the one or more FGFR mutants from the gene panel are present in the sample, wherein the presence of the one or more FGFR mutants indicates that the patient will be responsive to treatment with the FGFR inhibitor.

Also disclosed are methods of treating cancer in a patient comprising: evaluating a biological sample from the patient for the presence of one or more FGFR mutants from a FGFR mutant gene panel; and treating the patient with an FGFR inhibitor if one or more FGFR mutants are present in the sample.

Kits and primers for identifying the presence of one or more FGFR mutant genes in a biological sample are further provided herein.

BRIEF DESCRIPTION OF THE DRAWINGS

The summary, as well as the following detailed description, is further understood when read in conjunction with the appended drawings. For the purpose of illustrating the disclosed methods, kits, and primers, there are shown in the drawings exemplary embodiments of the methods, kits, and primers; however, the methods, kits, and primers are not limited to the specific embodiments disclosed. In the drawings:

FIGS. 2A-2I represent Sanger sequencing results from FFPET samples positive for: FIG. 2A) FGFR3:TACC3 v1; FIG. 2B) FGFR3:TACC3 v3; FIG. 2C) FGFR3:TACC3 Intron; FIG. 2D) FGFR3:BAIAP2L1; FIG. 2E) FGFR2:AFF3; FIG. 2F) FGFR2:BICC1; FIG. 2G) FGFR2:CASP7; FIG. 2H) FGFR2:CCDC6; and FIG. 2I) FGFR2:OFD1.

FIGS. 5A-5D illustrate SNP-specific PCR with dideoxy WT blocker for (FIG. 5A) G370C, (FIG. 5B) Y373C, (FIG. 5C) S249C, and (FIG. 5D) R248C.

FIGS. 6A-6I represent efficiency standard curves for the FGFR fusion gene assays: FIG. 6A) FGFR3:TACC3 v1; FIG. 6B) FGFR3:TACC3 v3; FIG. 6C) FGFR3:TACC3 Intron; FIG. 6D) FGFR3:BAIAP2L1; FIG. 6E) FGFR2:AFF3; FIG. 6F) FGFR2:BICC1; FIG. 6G) FGFR2:CASP7; FIG. 6H) FGFR2:CCDC6; and FIG. 6I) FGFR2:OFD1.

FIGS. 9A-9D represent exemplary results from phase I patient samples. Assays were performed using synthetic template assay control (ST), primers for GAPDH (quality control sample), or primers specific for: FIG. 9A) FGFR2:BICC1 fusions; FIG. 9B) FGFR3:TACC3 (exon 18:exon 1) fusions; FIG. 9C) FGFR2:CCDC6 fusions; or FIG. 9D) FGFR3:TACC3 v1, FGFR3:TACC3 v3, or FGFR2:CCDC6 fusions. Patient samples are as follows: FIG. 9A—urothelial carcinoma; FIG. 9B—bladder cancer; FIG. 9C—cholangiocarcinoma; and FIG. 9D—adrenal carcinoma.

(FIG. 13A) 0.1% cresyl crystal violet stained 6-well chambers and (FIG. 13B) bar graph illustrating the number of colonies/100 cells plated. Results are representative of two independent experiments.

DETAILED DESCRIPTION OF ILLUSTRATIVE EMBODIMENTS

Figure 1:
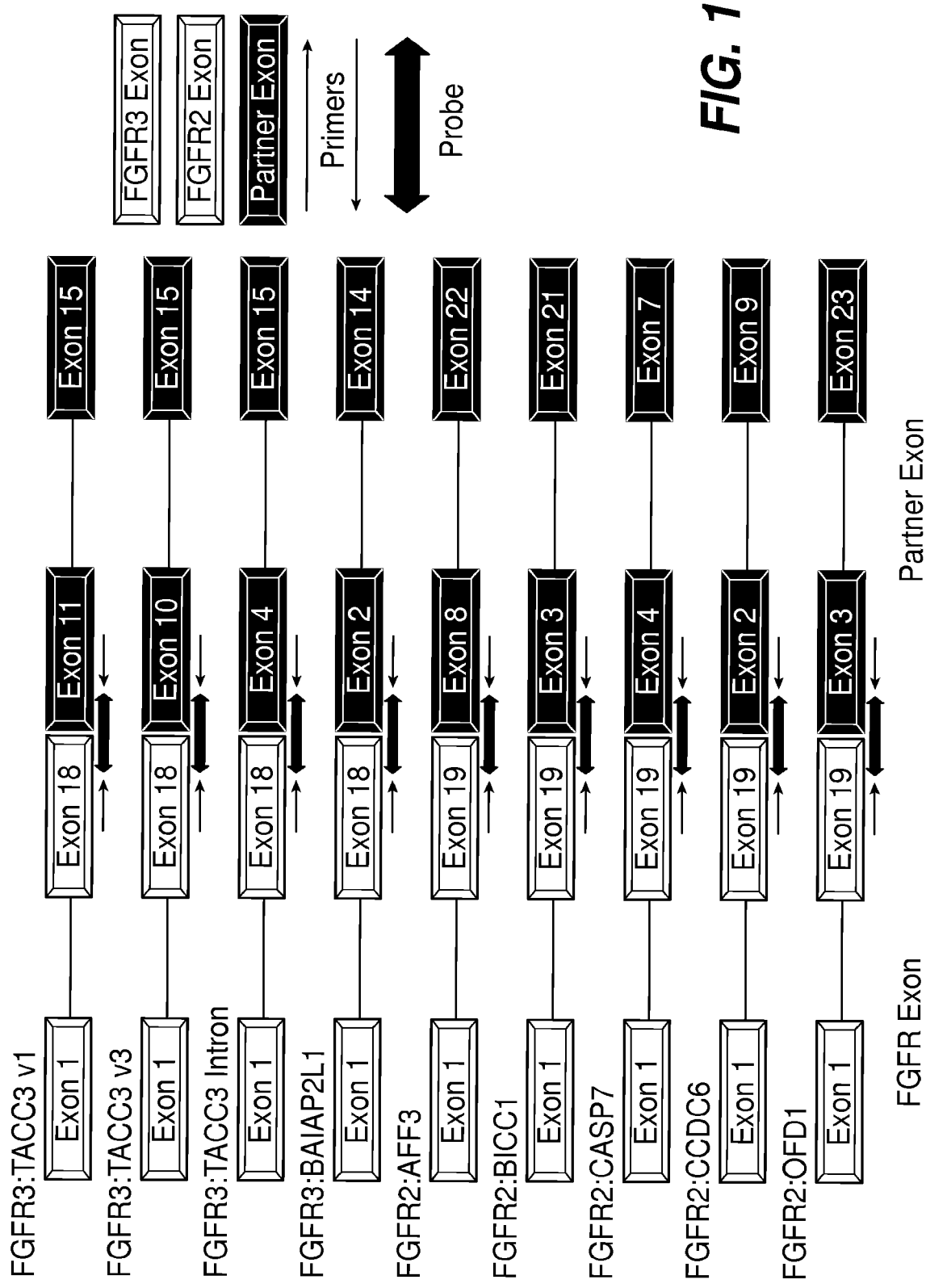
FIG. 1 is an illustration of exemplary FGFR fusion genes, the presence of at least one of which indicates that a patient will be responsive to treatment with an FGFR inhibitor. Also illustrated (small arrows) are exemplary primer locations for amplifying the fusion genes.
Figure 2A:
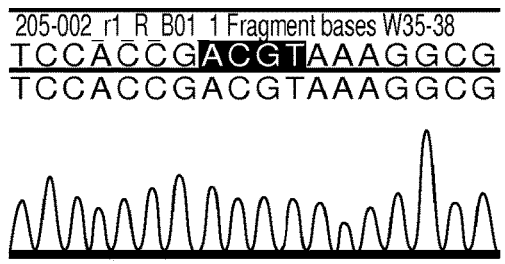
Figure 2B:
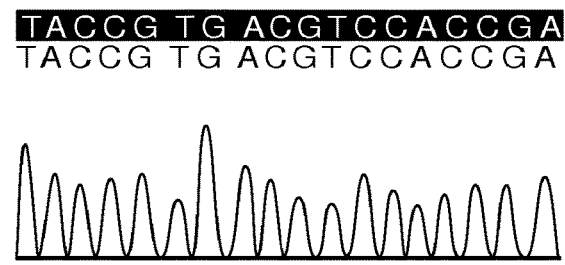
Figure 2C:
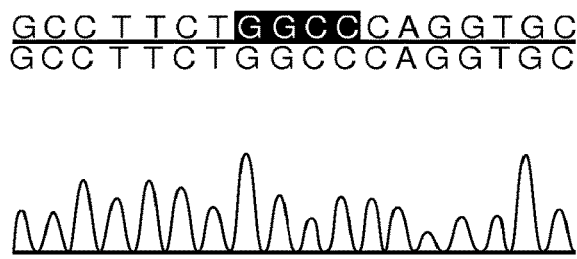
Figure 2D:
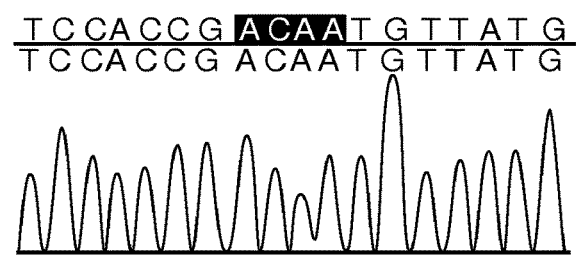
Figure 2E:
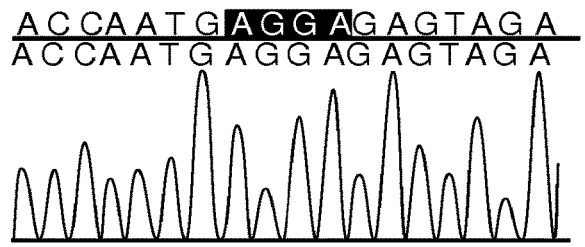
Figure 2F:
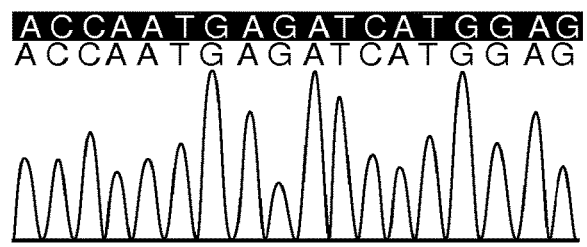
Figure 2G:
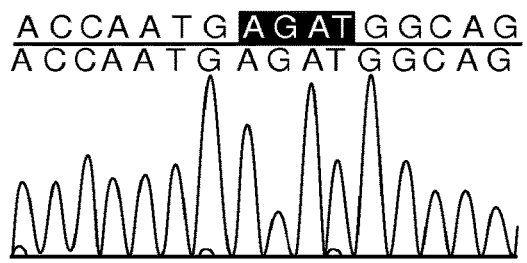
Figure 2H:
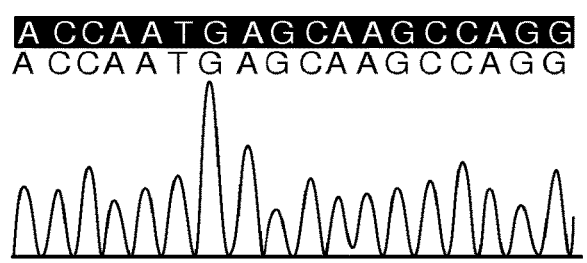
Figure 2I:
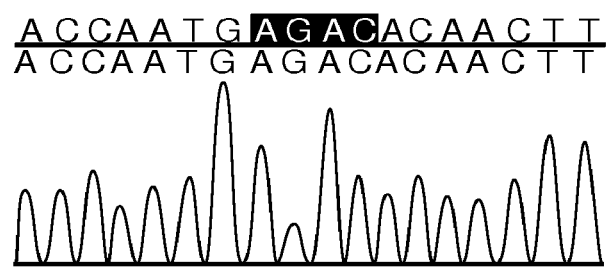

The disclosed methods, kits, and primers may be understood more readily by reference to the following detailed description taken in connection with the accompanying figures, which form a part of this disclosure. It is to be understood that the disclosed methods, kits, and primers are not limited to the specific methods, kits, and primers described and/or shown herein, and that the terminology used herein is for the purpose of describing particular embodiments by way of example only and is not intended to be limiting of the claimed methods, kits, and primers.

Reference to a particular numerical value includes at least that particular value, unless the context clearly dictates otherwise. When a range of values is expressed, another embodiment includes from the one particular value and/or to the other particular value. Further, reference to values stated in ranges include each and every value within that range. All ranges are inclusive and combinable.

It is to be appreciated that certain features of the disclosed methods, kits, and primers which are, for clarity, described herein in the context of separate embodiments, may also be provided in combination in a single embodiment. Conversely, various features of the disclosed methods, kits, and primers that are, for brevity, described in the context of a single embodiment, may also be provided separately or in any subcombination.

As used herein, the singular forms "a," "an," and "the" include the plural.

The following abbreviations are used throughout the specification: FGFR (fibroblast growth factor receptor); LLOQ (lower limit of quantitation); FGFR3:TACC3 (fusion between genes encoding FGFR3 and transforming acidic coiled-coil containing protein 3); FGFR3:BAIAP2L1 (fusion between genes encoding FGFR3 and brain-specific angiogenesis inhibitor 1-associated protein 2-like protein 1); FGFR2:AFF3 (fusion between genes encoding FGFR2 and AF4/FMR2 family, member 3); FGFR2:BICC1 (fusion between genes encoding FGFR2 and bicaudal C homolog 1); FGFR2: CASP7 (fusion between genes encoding FGFR2 and caspase 7); FGFR2:CCDC6 (fusion between genes encoding FGFR2 and coiled-coil domain containing 6); FGFR2:OFD1 (fusion between genes encoding FGFR2 and oral-facial-digital syndrome 1); FFPET (Formalin-Fixed Paraffin-Embedded Tissue); SNP (single nucleotide polymorphism); NSCLC (Non-small-cell lung cancer), ct (cycle threshold).

As used herein, "treating" and like terms refer to reducing the severity and/or frequency of cancer symptoms, eliminating cancer symptoms and/or the underlying cause of said symptoms, reducing the frequency or likelihood of cancer symptoms and/or their underlying cause, and improving or remediating damage caused, directly or indirectly, by cancer.

"Biological samples" refers to any sample from a patient in which cancerous cells can be obtained and RNA can be isolated. Suitable biological samples include, but are not limited to, blood, lymph fluid, bone marrow, a solid tumor sample, or any combination thereof. In some embodiments, the biological sample can be FFPET.

As used herein, "pre-amplification" refers to a PCR procedure that is performed prior to the amplifying step in order to increase the quantity of template cDNA for the amplification step. A pre-amplification step can be performed, for example, using the TaqMan® PreAmp Master Mix (Life Technologies/Applied Biosystems® product #4391128).

As used herein, "amplifying," "amplify," and like terms refer to the generation of numerous identical copies of a nucleic acid sample. Suitable techniques for amplifying a nucleic acid sample include, but are not limited to, polymerase chain reaction (PCR) and real-time polymerase chain reaction (RT-PCR). In some embodiments, the amplifying step comprises RT-PCR.

FGFR Mutants

As used herein, the phrase "FGFR mutant" refers to a FGFR fusion gene, a FGFR single nucleotide polymorphism, or both.

"FGFR fusion" or "FGFR fusion gene" refers to a gene encoding FGFR (e.g., FGRF2 or FGFR3), or a portion thereof, and one of the herein disclosed fusion partners, or portion thereof, created by a translocation between the two genes. The presence of one or more of the following FGFR fusion genes in a biological sample from a patient can be determined using the disclosed methods: FGFR3:TACC3 v1, FGFR3:TACC3 v3, FGFR3:TACC3 Intron, FGFR3:BAIAP2L1, FGFR2:BICC1, FGFR2:AFF3, FGFR2:CASP7, FGFR2:CCDC6, FGFR2:OFD1, or any combination thereof. Table 1 provides the FGFR fusion genes and the FGFR and fusion partner exons that are fused. FIG. 1 provides an illustration of the various FGFR fusion genes. The sequences of the individual FGFR fusion genes are disclosed in Table 16.

TABLE 1

| Fusion Gene | FGFR Exon | Partner Exon |
|---|---|---|
| FGFR3:TACC3 v1 | 18 | 11 |
| FCFR3:TACC3 v3 | 18 | 10 |
| FGFR3:TACC3 Intron | 18 | 4 |
| FGFR3:BAIAP2L1 | 18 | 2 |
| FGFR2:AFF3 | 19 | 8 |
| FGFR2:BICC1 | 19 | 3 |
| FGFR2:CASP7 | 19 | 4 |
| FGFR2:CCDC6 | 19 | 2 |
| FGFR2:OFD1 | 19 | 3 |

"FGFR single nucleotide polymorphism" (SNP) refers to a FGFR2 or FGFR3 gene in which a single nucleotide differs among individuals. In particular, FGFR single nucleotide polymorphism" (SNP) refers to a FGFR3 gene in which a single nucleotide differs among individuals. The presence of one or more of the following FGFR SNPs in a biological sample from a patient can be determined using the disclosed methods: FGFR3 R248C, FGFR3 S249C, FGFR3 G370C, FGFR3 Y373C, or any combination thereof. The sequences of the FGFR SNPs are provided in Table 2.

TABLE 2

| FGFR3 mutant | Sequence |
|---|---|
| FGFR3 R248C | TCGGACCGCGGCAACTACACCTGCGTCGTGGAGAAC<br>AAGTTTGGCAGCATCCGGCAGACGTACACGCTGGAC<br>GTGCTGGAG(T)GCTCCCCGCACCGGCCCATCCTGC<br>AGGCGGGGCTGCCGGCCAACCAGACGGCGGTGCTGG<br>GCAGCGACGTGGAGTTCCACTGCAAGGTGTACAGTG<br>ACGCACAGCCCCACATCCAGTGGCTCAAGCACGTGG<br>AGGTGAATGGCAGCAAGGTGGGCCCGGACGGCACAC<br>CCTACGTTACCGTGCTCA<br>(SEQ ID NO: 1) |
| FGFR3 S249C | GACCGCGGCAACTACACCTGCGTCGTGGAGAACAAG<br>TTTGGCAGCATCCGGCAGACGTACACGCTGGACGTG<br>CTGGGTGAGGGCCCTGGGGCGGCGCGGGGTGGGGG<br>CGGCAGTGGCGGTGGTGGTGAGGGAGGGGGTGGCCC<br>CTGAGCGTCATCTGCCCCCACAGAGCGT(G)CCCGC<br>ACCGGCCCATCCTGCAGGCGGGGCTGCCGGCCAACC<br>AGACGGCGGTGCTGGGCAGCGACGTGGAGTTCCACT<br>GCAAGGTGTACAGTGACGCACAGCCCCACATCCAGT<br>GGCTCAAGCACGTGGAGGTGAATGGCAGCAAGGTGG<br>GCCCGGACGGCACACCCTACGTTACCGTGCTCAAGG<br>TGGGCCACCGTGTGCACGT<br>(SEQ ID NO: 2) |
| FGFR3 G370G | GCGGGCAATTCTATTGGGTTTTCTCATCACTCTGCG<br>TGGCTGGTGGTGCTGCCAGCCGAGGAGGAGCTGGTG<br>GAGGCTGACGAGGCG(T)GCAGTGTGTATGCAGGCA<br>TCCTCAGCTACGGGGTGGGCTTCTTCCTGTTCATCC<br>TGGTGGTGGCGGCTGTGACGCTCTGCCGCCTGCGCA<br>GCCCCCCCAAGAAAGGCCTGGGCTCCCCCACCGTGC<br>ACAAGATCTCCCGCTTCCCG<br>(SEQ ID NO: 3) |
| RGFR3 Y373C* | CTAGAGGTTCTCTCCTTGCACAACGTCACCTTTGAG<br>GACGCCGGGGAGTACACCTGCCTGGCGGGCAATTCT<br>ATTGGGTTTTCTCATCACTCTGCGTGGCTGGTGGTG<br>CTGCCAGCCGAGGAGGAGCTGGTGGAGGCTGACGAG<br>GCGGGCAGTGTGT(G)TGCAGGCATCCTCAGCTACG<br>GGGTGGGCTTCTTCCTGTTCATCCTGGTGGTGGCGG<br>CTGTGACGCTCTGCCGCCTGCGCAGCCCCCCCAAGA<br>AAGGCCTGGGCTCCCCCACCGTGCACAAGATCTCCC<br>GCTTCCCGCTCAAGC<br>(SEQ ID NO: 4) |

Sequences correspond to nucleotides 920-1510 of FGFR3 (GenBank ID # NM_000142.4).
Nucleotides in bold underline represent the SNP.
*Sometimes mistakenly referred to as Y375C in the literature.

As used herein, "FGFR mutant gene panel" includes one or more of the above listed FGFR mutants. In some embodiments, the FGFR mutant gene panel is dependent upon the patient's cancer type.

The FGFR mutant panel that is used in the evaluating step of the disclosed methods is based, in part, on the patient's cancer type. For patients with bladder cancer, a suitable FGFR mutant gene panel can comprise FGFR3:TACC3 v1, FGFR3:TACC3 v3, FGFR3:BAIAP2L1, FGFR2:BICC1, FGFR2:AFF3, FGFR2:CASP7, FGFR3 R248C, FGFR3 S249C, FGFR3 G370C, or FGFR3 Y373C, or any combination thereof.

For patients with metastatic bladder cancer, a suitable FGFR mutant gene panel can comprise FGFR3:TACC3 v1, FGFR3:TACC3 v3, FGFR3:BAIAP2L1, FGFR2:BICC1, FGFR2:AFF3, FGFR2:CASP7, FGFR3 R248C, FGFR3 S249C, FGFR3 G370C, or FGFR3 Y373C, or any combination thereof.

For patients with ovarian cancer, a suitable FGFR mutant gene panel can comprise FGFR3:TACC3 v1, FGFR3:TACC3 v3, FGFR3:BAIAP2L1, FGFR2:BICC1, FGFR2:AFF3, FGFR2:CASP7, FGFR3 R248C, FGFR3 S249C, FGFR3 G370C, or FGFR3 Y373C, or any combination thereof.

For patients with head and neck cancer, a suitable FGFR mutant gene panel can comprise FGFR3:BAIAP2L1, FGFR2:CASP7, FGFR3 R248C, FGFR3 S249C, FGFR3 G370C, or FGFR3 Y373C, or any combination thereof.

For patients with metastatic head and neck cancer, a suitable FGFR mutant gene panel can comprise FGFR3:BAIAP2L1, FGFR2:CASP7, or FGFR2:OFD1, or any combination thereof.

For patients with esophageal cancer, a suitable FGFR mutant gene panel can comprise FGFR3:TACC3 v1, FGFR3:TACC3 v3, FGFR2:BICC1, FGFR2:CASP7, FGFR3 R248C, FGFR3 S249C, FGFR3 G370C, or FGFR3 Y373C, or any combination thereof.

For patients with metastatic esophageal cancer, a suitable FGFR mutant gene panel can comprise FGFR3:TACC3 v1, FGFR3:TACC3 v3, FGFR3:TACC3 Intron, FGFR3:BAIAP2L1, FGFR2:BICC1, FGFR2:AFF3, FGFR2:CASP7, FGFR2:CCD6, or FGFR2:OFD1, or any combination thereof.

For patients with non-small-cell lung adenocarcinoma, a suitable FGFR mutant gene panel can comprise FGFR3:TACC3 v1, FGFR3:TACC3 v3, FGFR3:TACC3 Intron, FGFR3:BAIAP2L1, FGFR2:AFF3, FGFR2:CASP7, FGFR3 R248C, FGFR3 S249C, FGFR3 G370C, or FGFR3 Y373C, or any combination thereof.

For patients with non-small cell lung squamous cell carcinoma, a suitable FGFR mutant gene panel can comprise FGFR3:TACC3 v1, FGFR3:TACC3 v3, FGFR3:BAIAP2L1, FGFR2:BICC1, FGFR2:AFF3, FGFR2:CASP7, FGFR2:CCDC6, FGFR3 R248C, FGFR3 S249C, FGFR3 G370C, or FGFR3 Y373C, or any combination thereof.

For patients with metastatic endometrial cancer, a suitable FGFR mutant gene panel can comprise FGFR3:TACC3 v1, FGFR3:TACC3 v3, FGFR3:TACC3 Intron, FGFR3:BAIAP2L1, FGFR2:CASP7, FGFR2:CCDC6, or FGFR2:OFD1, or any combination thereof.

For patients with breast cancer, a suitable FGFR mutant gene panel can comprise FGFR3:TACC3 v1, FGFR3:TACC3 v3, FGFR3:TACC3 Intron, FGFR3:BAIAP2L1, FGFR2:BICC1, FGFR2:AFF3, FGFR2:CASP7, FGFR2:CCD6, or FGFR2:OFD1, or any combination thereof.

Primers for Amplifying FGFR Mutants

One skilled in the art knows that amplification of nucleic acid requires primers that are complementary, and bind to, a 5' and 3' region of the nucleic acid strand that flanks the region sought to be amplified. As used herein, "pair of primers" refers to the forward and reverse primers used in an amplifying step. Pairs of primers suitable for performing the disclosed methods are listed in Table 3.

TABLE 3

| Target | Forward Primer | Reverse Primer 5'-3' |
|---|---|---|
| FGFR3: TACC3 V1 | GACCTGGACCGTGTCCTTACC (SEQ ID NO: 5) | CTTCCCCAGTTCCAGGTTCTT (SEQ ID NO: 6) |
| FGFR3: TACC3 V3 | AGGACCTGGACCGTGTCCTT (SEQ ID NO: 7) | TATAGGTCCGGTGGACAGGG (SEQ ID NO: 8) |
| FGFR3: TACC3 Intron | GGCCATCCTGCCCCC (SEQ ID NO: 9) | GAGCAGTCCAGGTCAGCCAG (SEQ ID NO: 10) |
| FGFR3: BAIAP2L1 | CTGGACCGTGTCCTTACCGT (SEQ ID NO: 11) | GCAGCCCAGGATTGAACTGT (SEQ ID NO: 12) |
| FGFR2: BICC1 | TGGATCGAATTCTCACTCTCACA (SEQ ID NO: 13) | GCCAAGCAATCTGCGTATTTG (SEQ ID NO: 14) |
| FGFR2: AFF3 | TGGTAGAAGACTTGGATCGAATTCTTCTCCCGGATTATTTCTTCAACA (SEQ ID NO: 15) | (SEQ ID NO: 16) |
| FGFR2: CASP7 | GCTCTTCAATACAGCCCTGATCA (SEQ ID NO: 17) | ACTTGGATCGAATTCTCACTCTCA (SEQ ID NO: 18) |
| FGFR2: CCDC6 | TGGATCGAATTCTCACTCTCACA (SEQ ID NO: 19) | GCAAAGCCTGAATTTTCTTGAATAA (SEQ ID NO: 20) |
| FGFR2: OFD1 | AGGGTGCATCAACTCATGAATTAG (SEQ ID NO: 21) | ACTTGGATCGAATTCTCACTCTCA (SEQ ID NO: 22) |
| FGFR3 R248C | GCATCCGGCAGACGTACA (SEQ ID NO: 23) | CCCCGCCTGCAGGAT (SEQ ID NO: 24) |
| FGFR3 S249C | GCATCCGGCAGACGTACA (SEQ ID NO: 25) | CCCCGCCTGCAGGAT (SEQ ID NO: 26) |
| FGFR3 G370C | AGGAGCTGGTGGAGGCTGA (SEQ ID NO: 27) | CCGTAGCTGAGGATGCCTG (SEQ ID NO: 28) |
| FGFR3 Y373C | CTGGTGGAGGCTGACGAG (SEQ ID NO: 29) | AGCCCACCCCGTAGCT (SEQ ID NO: 30) |
| FGFR3 R248C | GTCGTGGAGAACAAGTTTGGC (SEQ ID NO: 31) | GTCTGGTTGGCCGGCAG (SEQ ID NO: 32) |
| FGFR3 S249C | GTCGTGGAGAACAAGTTTGGC (SEQ ID NO: 33) | GTCTGGTTGGCCGGCAG (SEQ ID NO: 34) |
| FGFR3 G370C | AGGAGCTGGTGGAGGCTGA (SEQ ID NO: 35) | CCGTAGCTGAGGATGCCTG (SEQ ID NO: 36) |
| FGFR3 Y373C | GACGAGGCGGGCAGTG (SEQ ID NO: 37) | GAAGAAGCCCACCCCGTAG (SEQ ID NO: 38) |

Disclosed herein are primers having the nucleic acid sequence of SEQ TD NO: 5, SEQ ID NO: 6, SEQ ID NO: 7, SEQ ID NO: 8, SEQ TD NO: 9, SEQ ID NO: 10, SEQ ID NO: 11, SEQ ID NO: 12, SEQ ID NO: 13, SEQ ID NO: 14, SEQ TD NO: 15, SEQ ID NO: 16, SEQ ID NO: 17, SEQ ID NO: 18, SEQ ID NO: 19, SEQ ID NO:20, SEQ ID NO:21, SEQ ID NO:22, SEQ ID NO:23, SEQ ID NO:24, SEQ ID NO:25, SEQ TD NO:26, SEQ ID NO:27, SEQ TD NO:28, SEQ ID NO: 29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, or any combination thereof.

Also disclosed herein are sets of primers having the sequences of SEQ ID NO:5 and SEQ ID NO:6, SEQ ID NO:7 and SEQ ID NO:8, SEQ ID NO:9 and SEQ ID NO:10, SEQ ID NO:11 and SEQ ID NO:12, SEQ ID NO:13 and SEQ ID NO:14, SEQ ID NO:15 and SEQ ID NO:16, SEQ ID NO:17 and SEQ ID NO:18, SEQ ID NO:19 and SEQ ID NO:20, SEQ ID NO:21 and SEQ ID NO:22, SEQ ID NO:23 and SEQ ID NO:24, SEQ ID NO:25 and SEQ ID NO:26, SEQ ID NO:27 and SEQ ID NO:28, SEQ ID NO:29 and SEQ ID NO:30, SEQ ID NO:31 and SEQ ID NO:32, SEQ ID NO:33 and SEQ ID NO:34, SEQ ID NO:35 and SEQ ID NO:36, SEQ ID NO:37 and SEQ ID NO:38, or any combination thereof.

In some embodiments, the set of primers can have the sequence of SEQ ID NO:5 and SEQ ID NO:6. In some embodiments, the set of primers can have the sequence of SEQ ID NO:7 and SEQ ID NO:8. In some embodiments, the set of primers can have the sequence of SEQ ID NO:9 and SEQ ID NO:10. In some embodiments, the set of primers can have the sequence of SEQ ID NO:11 and SEQ ID NO:12. In some embodiments, the set of primers can have the sequence of SEQ ID NO:13 and SEQ ID NO:14. In some embodiments, the set of primers can have the sequence of SEQ ID NO:15 and SEQ ID NO:16. In some embodiments, the set of primers can have the sequence of SEQ ID NO:17 and SEQ ID NO:18. In some embodiments, the set of primers can have the sequence of SEQ ID NO:19 and SEQ ID NO:20. In some embodiments, the set of primers can have the sequence of SEQ ID NO:21 and SEQ ID NO:22. In some embodiments, the set of primers can have the sequence of SEQ ID NO:23 and SEQ ID NO:24. In some embodiments, the set of primers can have the sequence of SEQ ID NO:25 and SEQ ID NO:26. In some embodiments, the set of primers can have the sequence of SEQ ID NO:27 and SEQ ID NO:28. In some embodiments, the set of primers can have the sequence of SEQ ID NO:29 and SEQ ID NO:30. In some embodiments, the set of primers can have the sequence of SEQ ID NO:31 and SEQ ID NO:32. In some embodiments, the set of primers can have the sequence of SEQ ID NO:33 and SEQ ID NO:34. In some embodiments, the set of primers can have the sequence of SEQ ID NO:35 and SEQ ID NO:36. In some embodiments, the set of primers can have the sequence of SEQ ID NO:37 and SEQ ID NO:38. In some embodiments, the set of primers can have the sequences of any combination of the above sets of primers.

FGFR Inhibitors for Use in the Disclosed Methods

Suitable FGFR inhibitors for use in the disclosed methods are provided herein.

In some embodiments, if one or more FGFR mutants are present in the sample, the patient can be treated with a FGFR inhibitor disclosed in U.S. Publ. No. 2013/0072457 A1 (incorporated herein by reference), including any tautomeric or stereochemically isomeric form thereof, and a N-oxide thereof, a pharmaceutically acceptable salt thereof, or a solvate thereof (suitable R groups are also disclosed in U.S. Publ. No. 2013/0072457 A1). In some aspects, for example, the patient can be treated with N-(3,5-dimethoxyphenyl)-N'-(1-methylethyl)-N-[3-(1-methyl-1H-pyrazol-4-yl)quinoxalin-6-yl]ethane-1,2-diamine (referred to herein as "JNJ-42756493" or "JNJ493"):

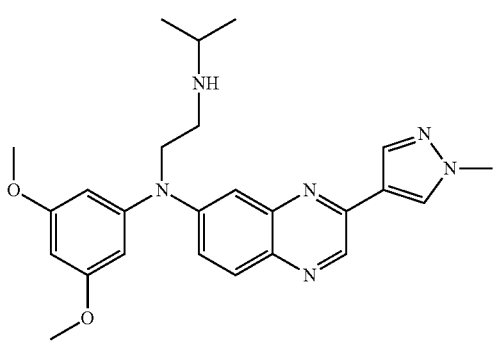

(I)

including a N-oxide thereof, a pharmaceutically acceptable salt thereof, or a solvate thereof. In some aspects, the pharmaceutically acceptable salt is a HCl salt. In some aspects, the patient can be treated with JNJ493 base.

In some embodiments, the patient can be treated with a FGFR inhibitor if one or more FGFR mutants are present in the sample, wherein the FGFR inhibitor is N-[5-[2-(3,5-Dimethoxyphenyl)ethyl]-2H-pyrazol-3-yl]-4-(3,5-diemthylpiperazin-1-yl)benzamide (AZD4547), as described in Gavine, P. R., et al., AZD4547: An Orally Bioavailable, Potent, and Selective Inhibitor of the Fibroblast Growth Factor Receptor Tyrosine Kinase Family, Cancer Res. Apr. 15, 2012 72; 2045:

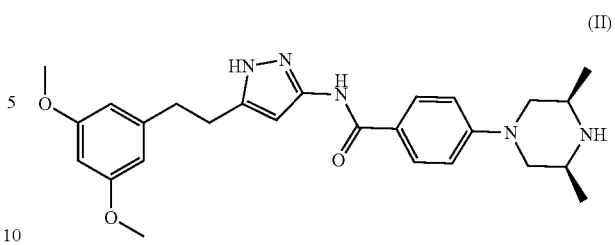

(II)

including, when chemically possible, any tautomeric or stereochemically isomeric form thereof, and a N-oxide thereof, a pharmaceutically acceptable salt thereof, or a solvate thereof.

In some embodiments, the patient can be treated with a FGFR inhibitor if one or more FGFR mutants are present in the sample, wherein the FGFR inhibitor is 3-(2,6-Dichloro-3,5-dimethoxy-phenyl)-1-{6-[4-(4-ethyl-piperazin-1-yl)-phenylamino]-pyrimid-4-yl}-1-methyl-urea (NVP-BGJ398) as described in Int'l Publ. No. WO2006/000420:

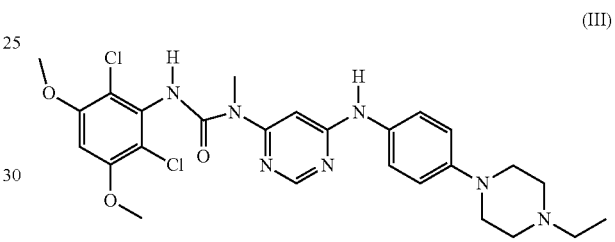

(III)

including, when chemically possible, any tautomeric or stereochemically isomeric form thereof, and a N-oxide thereof, a pharmaceutically acceptable salt thereof, or a solvate thereof.

In some embodiments, the patient can be treated with a FGFR inhibitor if one or more FGFR mutants are present in the sample, wherein the FGFR inhibitor is 4-amino-5-fluoro-3-[6-(4-methylpiperazin-1-yl)-1H-benzimidazol-2-yl]-1H-quinolin-2-one (dovitinib) as described in Int't Publ. No. WO2006/127926:

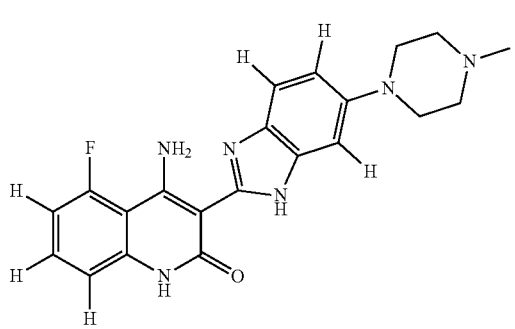

(IV)

including, when chemically possible, any tautomeric or stereochemically isomeric form thereof, and a N-oxide thereof, a pharmaceutically acceptable salt thereof, or a solvate thereof.

In some embodiments, the patient can be treated with a FGFR inhibitor if one or more FGFR mutants are present in the sample, wherein the FGFR inhibitor is 6-(7-((1-Aminocyclopropyl)-methoxy)-6-methoxyquinolin-4-yloxy)-N-methyl-1-naphthamide (AL3810) (lucitanib; E-3810), as described in Bello, E. et al., E-3810 Is a Potent Dual Inhibitor of VEGFR and FGFR that Exerts Antitumor Activity in Multiple Preclinical Models, Cancer Res Feb. 15, 2011 71(A)1396-1405 and Int'l Publ. No. WO2008/112408:

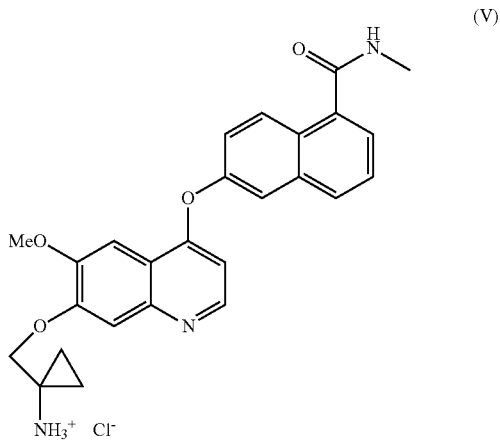

(V)

including, when chemically possible, any tautomeric or stereochemically isomeric form thereof, and a N-oxide thereof, a pharmaceutically acceptable salt thereof, or a solvate thereof.

In some embodiments, the patient can be treated with a FGFR inhibitor if one or more FGFR mutants are present in the sample, wherein the FGFR inhibitor is an anti-FGFR2 antibody such as that described in WO2013/076186.

Additional suitable FGFR inhibitors include BAY1163877 (Bayer), BAY1179470 (Bayer), TAS-120 (Taiho), ARQ087 (ArQule), ASP5878 (Astellas), FF284 (Chugai), FP-1039 (GSK/FivePrime), Blueprint, LY-2874455 (Lilly), RG-7444 (Roche), or any combination thereof, including, when chemically possible, any tautomeric or stereochemically isomeric forms thereof, N-oxides thereof, pharmaceutically acceptable salts thereof, or solvates thereof.

In some embodiments, the patient can be treated with a FGFR inhibitor if one or more FGFR mutants are present in the sample, wherein the FGFR inhibitor is BAY1163877 (Bayer), including, when chemically possible, any tautomeric or stereochemically isomeric form thereof, N-oxide thereof, pharmaceutically acceptable salt thereof, or solvate thereof.

In some embodiments, the patient can be treated with a FGFR inhibitor if one or more FGFR mutants are present in the sample, wherein the FGFR inhibitor is BAY1179470 (Bayer), including, when chemically possible, any tautomeric or stereochemically isomeric form thereof, N-oxide thereof, pharmaceutically acceptable salt thereof, or solvate thereof.

In some embodiments, the patient can be treated with a FGFR inhibitor if one or more FGFR mutants are present in the sample, wherein the FGFR inhibitor is TAS-120 (Taiho), including, when chemically possible, any tautomeric or stereochemically isomeric form thereof, N-oxide thereof, pharmaceutically acceptable salt thereof, or solvate thereof.

In some embodiments, the patient can be treated with a FGFR inhibitor if one or more FGFR mutants are present in the sample, wherein the FGFR inhibitor is ARQ087 (ArQule), including, when chemically possible, any tautomeric or stereochemically isomeric form thereof, N-oxide thereof, pharmaceutically acceptable salt thereof, or solvate thereof.

In some embodiments, the patient can be treated with a FGFR inhibitor if one or more FGFR mutants are present in the sample, wherein the FGFR inhibitor is ASP5878 (Astellas), including, when chemically possible, any tautomeric or stereochemically isomeric form thereof, N-oxide thereof, pharmaceutically acceptable salt thereof, or solvate thereof.

In some embodiments, the patient can be treated with a FGFR inhibitor if one or more FGFR mutants are present in the sample, wherein the FGFR inhibitor is FF284 (Chugai), including, when chemically possible, any tautomeric or stereochemically isomeric form thereof, N-oxide thereof, pharmaceutically acceptable salt thereof, or solvate thereof.

In some embodiments, the patient can be treated with a FGFR inhibitor if one or more FGFR mutants are present in the sample, wherein the FGFR inhibitor is FP-1039 (GSK/FivePrime), including, when chemically possible, any tautomeric or stereochemically isomeric form thereof, N-oxide thereof, pharmaceutically acceptable salt thereof, or solvate thereof.

In some embodiments, the patient can be treated with a FGFR inhibitor if one or more FGFR mutants are present in the sample, wherein the FGFR inhibitor is Blueprint, including, when chemically possible, any tautomeric or stereochemically isomeric form thereof, N-oxide thereof, pharmaceutically acceptable salt thereof, or solvate thereof.

In some embodiments, the patient can be treated with a FGFR inhibitor if one or more FGFR mutants are present in the sample, wherein the FGFR inhibitor is LY-2874455 (Lilly), including, when chemically possible, any tautomeric or stereochemically isomeric form thereof, N-oxide thereof, pharmaceutically acceptable salt thereof, or solvate thereof.

In some embodiments, the patient can be treated with a FGFR inhibitor if one or more FGFR mutants are present in the sample, wherein the FGFR inhibitor is RG-7444 (Roche), including, when chemically possible, any tautomeric or stereochemically isomeric form thereof, N-oxide thereof, pharmaceutically acceptable salt thereof, or solvate thereof.

Salts can be synthesized from a parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002, which is incorporated herein by reference. Generally, such salts can be prepared by reacting the free acid or base forms of these compounds with the appropriate base or acid in water or in an organic solvent, or in a mixture of the two; generally, nonaqueous media such as ether, ethyl acetate, ethanol, isopropanol, or acetonitrile are used. The FGFR inhibitors for use in the disclosed methods may exist as mono- or di-salts depending upon the pKa of the acid from which the salt is formed.

Acid addition salts may be formed with a wide variety of acids, both inorganic and organic. Examples of acid addition salts include salts formed with an acid including, but not limited to, acetic, 2,2-dichloroacetic, adipic, alginic, ascorbic (e.g. L-ascorbic), L-aspartic, benzenesulphonic, benzoic, 4-acetamidobenzoic, butanoic, (+) camphoric, camphor-sulphonic, (+)-(1S)-camphor-10-sulphonic, capric, caproic, caprylic, cinnamic, citric, cyclamic, dodecylsulphuric, ethane-1,2-disulphonic, ethanesulphonic, 2-hydroxyethanesulphonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrobromic, hydrochloric, hydriodic, isethionic, lactic (e.g. (+)-L-lactic, (±)-DL-lactic), lactobionic, maleic, malic, (−)-L-malic, malonic, (±)-DL-mandelic, methanesulphonic, naphthalenesulphonic (e.g. naphthalene-2-sulphonic), naphthalene-1,5-disulphonic, 1-hydroxy-2-naphthoic, nicotinic, nitric, oleic, orotic, oxalic, palmitic, pamoic, phosphoric, propionic, L-pyroglutamic, pyruvic, salicylic, 4-amino-salicylic, sebacic, stearic, succinic, sulphuric, tannic, (+)-L-tartaric, thiocyanic, toluenesulphonic (e.g. p-toluenesulphonic), undecylenic and valeric acids, as well as acylated amino acids and cation exchange resins.

One particular group of salts consists of salts formed from acetic, hydrochloric, hydriodic, phosphoric, nitric, sulphuric, citric, lactic, succinic, maleic, malic, isethionic, fumaric, benzenesulphonic, toluenesulphonic, methanesulphonic (mesylate), ethanesulphonic, naphthalenesulphonic, valeric, propanoic, butanoic, malonic, glucuronic and lactobionic acids. Another group of acid addition salts includes salts formed from acetic, adipic, ascorbic, aspartic, citric, DL-Lactic, fumaric, gluconic, glucuronic, hippuric, hydrochloric, glutamic, DL-malic, methanesulphonic, sebacic, stearic, succinic and tartaric acids.

If the compound is anionic, or has a functional group which may be anionic (e.g., —COOH may be —COO$^-$), then a salt may be formed with a suitable cation. Examples of suitable inorganic cations include, but are not limited to, alkali metal ions such as Na$^+$ and K$^+$, alkaline earth metal cations such as Ca$^{2+}$ and Mg$^{2+}$, and other cations such as Al3+. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$).

Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

Where the compounds contain an amine function, these may form quaternary ammonium salts, for example by reaction with an alkylating agent according to methods well known to the skilled person. Such quaternary ammonium compounds are within the scope of the disclosed compounds. Compounds containing an amine function may also form N-oxides. A reference herein to a compound that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g. a peroxycarboxylic acid), see for example Advanced Organic Chemistry, by Jerry March, 4$^{th}$ Edition, Wiley Interscience, pages. More particularly, N-oxides can be made by the procedure of L. W. Deady (Syn. Comm. (1977), 7, 509-514) in which the amine compound is reacted with m-chloroperoxybenzoic acid (MCPBA), for example, in an inert solvent such as dichloromethane.

As used herein, the term "solvate" means a physical association of the compound with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include the disclosed compounds in combination with water, isopropanol, ethanol, methanol, DMSO, ethyl acetate, acetic acid, ethanolamine and the like. The compound may exert its biological effects while in solution.

Solvates are well known in pharmaceutical chemistry. They can be important to the processes for the preparation of a substance (e.g. in relation to their purification), the storage of the substance (e.g. its stability) and the ease of handling of the substance, and are often formed as part of the isolation or purification stages of a chemical synthesis. A person skilled in the art can determine by means of standard and long used techniques whether a hydrate or other solvate has formed by the isolation conditions or purification conditions used to prepare a given compound. Examples of such techniques include thermogravimetric analysis (TGA), differential scanning calorimetry (DSC), X-ray crystallography (e.g. single crystal X-ray crystallography or X-ray powder diffraction) and Solid State NMR (SS-NMR, also known as Magic Angle Spinning NMR or MAS-NMR). Such techniques are as much a part of the standard analytical toolkit of the skilled chemist as NMR, IR, HPLC and MS. Alternatively the skilled person can deliberately form a solvate using crystallisation conditions that include an amount of the solvent required for the particular solvate. Thereafter the standard methods described above, can be used to establish whether solvates had formed. Also encompassed are any complexes (e.g. inclusion complexes or clathrates with compounds such as cyclodextrins, or complexes with metals) of the FGFR inhibitor.

Furthermore, the compound may have one or more polymorph (crystalline) or amorphous forms.

The compounds include compounds with one or more isotopic substitutions, and a reference to a particular element includes within its scope all isotopes of the element. For example, a reference to hydrogen includes within its scope $^1$H, $^2$H (D), and $^3$H (T). Similarly, references to carbon and oxygen include within their scope respectively $^{12}$C, $^{13}$C and $^{14}$C and $^{16}$O and $^{18}$O. The isotopes may be radioactive or non-radioactive. In one embodiment, the compounds contain no radioactive isotopes. Such compounds are preferred for therapeutic use. In another embodiment, however, the compound may contain one or more radioisotopes. Compounds containing such radioisotopes may be useful in a diagnostic context.

In some embodiments, the patient is treated with a FGFR inhibitor if one or more FGFR mutants are present in the sample, wherein the FGFR inhibitor is N-(3,5-dimethoxyphenyl)-N'-(1-methylethyl)-N-[3-(1-methyl-1H-pyrazol-4-yl)quinoxalin-6-yl]ethane-1,2-diamine (referred to herein "JNJ-42756493"), or a pharmaceutically acceptable salt thereof or a solvate thereof.

Methods of Treating Cancer in a Patient

Disclosed herein are methods of treating cancer in a patient comprising: evaluating a biological sample from the patient for the presence of one or more FGFR mutants from a FGFR mutant gene panel; and treating the patient with an FGFR inhibitor if one or more FGFR mutants are present in the sample.

The disclosed methods can be used to treat a variety of cancer types including, but not limited to, bladder cancer, metastatic bladder cancer, ovarian cancer, head and neck cancer, metastatic head and neck cancer, esophageal cancer, metastatic esophageal cancer, non-small-cell lung adenocarcinoma, non-small cell lung squamous cell carcinoma, prostate cancer, lung cancer, gastric cancer, urothelial carcinoma, small cell lung cancer, breast cancer, endometrial cancer, metastatic endometrial cancer, cholangiocarcinoma, hepatocellular carcinoma, glioblastoma, gliomas, colon carcinoma, sarcomas, solid tumors of squamous origin, and multiple myeloma.

The FGFR mutant panel that is used in the evaluating step is based, in part, on the patient's cancer type. For patients with bladder cancer, for example, a suitable FGFR mutant gene panel can comprise FGFR3:TACC3 v1, FGFR3:TACC3 v3, FGFR3:BAIAP2L1, FGFR2:BICC1, FGFR2:AFF3, FGFR2:CASP7, FGFR3 R248C, FGFR3 S249C, FGFR3 G370C, or FGFR3 Y373C, or any combination thereof. Accordingly, in some embodiments, a patient having bladder cancer is treated with an FGFR inhibitor if FGFR3:TACC3 v1 is present in the sample. In some embodiments, a patient having bladder cancer is treated with an FGFR inhibitor if FGFR3:TACC3 v3 is present in the sample. In some embodiments, a patient having bladder cancer is treated with an FGFR inhibitor if FGFR3:BAIAP2L1 is present in the sample. In some embodiments, a patient having bladder cancer is treated with an FGFR inhibitor if FGFR2:BICC1 is present in the sample. In some embodiments, a patient having bladder cancer is treated with an FGFR inhibitor if FGFR2:AFF3 is present in the sample. In some embodiments, a patient having bladder cancer is treated with an FGFR inhibitor if FGFR2:CASP7 is present in the sample. In some embodiments, a patient having bladder cancer is treated with an FGFR inhibitor if FGFR3 R248C is present in the sample. In some embodiments, a patient having bladder cancer is treated with an FGFR inhibitor if FGFR3 S249C is present in the sample. In some embodiments, a patient having bladder cancer is treated with an FGFR inhibitor if FGFR3 G370C is present in the sample. In some embodiments, a patient having bladder cancer is treated with an FGFR inhibitor if FGFR3 Y373C is present in the sample. In some embodiments, a patient having bladder cancer is treated with an FGFR inhibitor if any combination of the above FGFR mutants is present in the sample.

For patients with metastatic bladder cancer, for example, a suitable FGFR mutant gene panel can comprise FGFR3:TACC3 v1, FGFR3:TACC3 v3, FGFR3:BAIAP2L1, FGFR2:BICC1, FGFR2:AFF3, FGFR2:CASP7, FGFR3 R248C, FGFR3 S249C, FGFR3 G370C, or FGFR3 Y373C, or any combination thereof. Accordingly, in some embodiments, a patient having metastatic bladder cancer is treated with an FGFR inhibitor if FGFR3:TACC3 v1 is present in the sample. In some embodiments, a patient having metastatic bladder cancer is treated with an FGFR inhibitor if FGFR3:TACC3 v3 is present in the sample. In some embodiments, a patient having metastatic bladder cancer is treated with an FGFR inhibitor if FGFR3:BAIAP2L1 is present in the sample. In some embodiments, a patient having metastatic bladder cancer is treated with an FGFR inhibitor if FGFR2:BICC1 is present in the sample. In some embodiments, a patient having metastatic bladder cancer is treated with an FGFR inhibitor if FGFR2:AFF3 is present in the sample. In some embodiments, a patient having metastatic bladder cancer is treated with an FGFR inhibitor if FGFR2:CASP7 is present in the sample. In some embodiments, a patient having metastatic bladder cancer is treated with an FGFR inhibitor if FGFR3 R248C is present in the sample. In some embodiments, a patient having metastatic bladder cancer is treated with an FGFR inhibitor if FGFR3 S249C is present in the sample. In some embodiments, a patient having metastatic bladder cancer is treated with an FGFR inhibitor if FGFR3 G370C is present in the sample. In some embodiments, a patient having metastatic bladder cancer is treated with an FGFR inhibitor if FGFR3 Y373C is present in the sample. In some embodiments, a patient having metastatic bladder cancer is treated with an FGFR inhibitor if any combination of the above FGFR mutants is present in the sample.

For patients with ovarian cancer, for example, a suitable FGFR mutant gene panel can comprise FGFR3:TACC3 v1, FGFR3:TACC3 v3, FGFR3:BAIAP2L1, FGFR2:BICC1, FGFR2:AFF3, FGFR2:CASP7, FGFR3 R248C, FGFR3 S249C, FGFR3 G370C, or FGFR3 Y373C, or any combination thereof. Accordingly, in some embodiments, a patient having ovarian cancer is treated with an FGFR inhibitor if FGFR3:TACC3 v1 is present in the sample. In some embodiments, a patient having ovarian cancer is treated with an FGFR inhibitor if FGFR3:TACC3 v3 is present in the sample. In some embodiments, a patient having ovarian cancer is treated with an FGFR inhibitor if FGFR3:BAIAP2L1 is present in the sample. In some embodiments, a patient having ovarian cancer is treated with an FGFR inhibitor if FGFR2:BICC1 is present in the sample. In some embodiments, a patient having ovarian cancer is treated with an FGFR inhibitor if FGFR2:AFF3 is present in the sample. In some embodiments, a patient having ovarian cancer is treated with an FGFR inhibitor if FGFR2:CASP7 is present in the sample. In some embodiments, a patient having ovarian cancer is treated with an FGFR inhibitor if FGFR3 R248C is present in the sample. In some embodiments, a patient having ovarian cancer is treated with an FGFR inhibitor if FGFR3 S249C is present in the sample. In some embodiments, a patient having ovarian cancer is treated with an FGFR inhibitor if FGFR3 G370C is present in the sample. In some embodiments, a patient having ovarian cancer is treated with an FGFR inhibitor if FGFR3 Y373C is present in the sample. In some embodiments, a patient having ovarian cancer is treated with an FGFR inhibitor if any combination of the above FGFR mutants is present in the sample.

For patients with head and neck cancer, for example, a suitable FGFR mutant gene panel can comprise FGFR3:BAIAP2L1, FGFR2:CASP7, FGFR3 R248C, FGFR3 S249C, FGFR3 G370C, or FGFR3 Y373C, or any combination thereof. Accordingly, in some embodiments, a patient having head and neck cancer is treated with an FGFR inhibitor if FGFR3:BAIAP2L1 is present in the sample. In some embodiments, a patient having head and neck cancer is treated with an FGFR inhibitor if FGFR2:CASP7 is present in the sample. In some embodiments, a patient having head and neck cancer is treated with an FGFR inhibitor if FGFR3 R248C is present in the sample. In some embodiments, a patient having head and neck cancer is treated with an FGFR inhibitor if FGFR3 S249C is present in the sample. In some embodiments, a patient having head and neck cancer is treated with an FGFR inhibitor if FGFR3 G370C is present in the sample. In some embodiments, a patient having head and neck cancer is treated with an FGFR inhibitor if FGFR3 Y373C is present in the sample. In some embodiments, a patient having head and neck cancer is treated with an FGFR inhibitor if any combination of the above FGFR mutants is present in the sample.

For patients with metastatic head and neck cancer, for example, a suitable FGFR mutant gene panel can comprise FGFR3:BAIAP2L1, FGFR2:CASP7, or FGFR2:OFD1, or any combination thereof. Accordingly, in some embodiments, a patient having metastatic head and neck cancer is treated with an FGFR inhibitor if FGFR3:BAIAP2L1 is present in the sample. In some embodiments, a patient having metastatic head and neck cancer is treated with an FGFR inhibitor if FGFR2:CASP7 is present in the sample. In some embodiments, a patient having metastatic head and neck cancer is treated with an FGFR inhibitor if FGFR2: OFD1 is present in the sample. In some embodiments, a patient having metastic head and neck cancer is treated with an FGFR inhibitor if any combination of the above FGFR mutants is present in the sample.

For patients with esophageal cancer, for example, a suitable FGFR mutant gene panel can comprise FGFR3:TACC3 v1, FGFR3:TACC3 v3, FGFR2:BICC1, FGFR2:CASP7, FGFR3 R248C, FGFR3 S249C, FGFR3 G370C, or FGFR3 Y373C, or any combination thereof. Accordingly, in some embodiments, a patient having esophageal cancer is treated with an FGFR inhibitor if FGFR3:TACC3 v1 is present in the sample. In some embodiments, a patient having esophageal cancer is treated with an FGFR inhibitor if FGFR3: TACC3 v3 is present in the sample. In some embodiments, a patient having esophageal cancer is treated with an FGFR inhibitor if FGFR2:BICC1 is present in the sample. In some embodiments, a patient having esophageal cancer is treated with an FGFR inhibitor if FGFR2:CASP7 is present in the sample. In some embodiments, a patient having esophageal cancer is treated with an FGFR inhibitor if FGFR3 R248C is present in the sample. In some embodiments, a patient having esophageal cancer is treated with an FGFR inhibitor if FGFR3 S249C is present in the sample. In some embodiments, a patient having esophageal cancer is treated with an FGFR inhibitor if FGFR3 G370C is present in the sample. In some embodiments, a patient having esophageal cancer is treated with an FGFR inhibitor if FGFR3 Y373C is present in the sample. In some embodiments, a patient having esophageal cancer is treated with an FGFR inhibitor if any combination of the above FGFR mutants is present in the sample.

For patients with metastatic esophageal cancer, for example, a suitable FGFR mutant gene panel can comprise FGFR3:TACC3 v1, FGFR3:TACC3 v3, FGFR3:TACC3 Intron, FGFR3:BAIAP2L1, FGFR2:BICC1, FGFR2:AFF3, FGFR2:CASP7, FGFR2:CCD6, or FGFR2:OFD1, or any combination thereof. Accordingly, in some embodiments, a patient having metastatic esophageal cancer is treated with an FGFR inhibitor if FGFR3:TACC3 v1 is present in the sample. In some embodiments, a patient having metastatic esophageal cancer is treated with an FGFR inhibitor if FGFR3:TACC3 v3 is present in the sample. In some embodiments, a patient having metastatic esophageal cancer is treated with an FGFR inhibitor if FGFR3:TACC3 Intron is present in the sample. In some embodiments, a patient having metastatic esophageal cancer is treated with an FGFR inhibitor if FGFR3:BAIAP2L1 is present in the sample. In some embodiments, a patient having metastatic esophageal cancer is treated with an FGFR inhibitor if FGFR2:BICC1 is present in the sample. In some embodiments, a patient having metastatic esophageal cancer is treated with an FGFR inhibitor if FGFR2:AFF3 is present in the sample. In some embodiments, a patient having metastatic esophageal cancer is treated with an FGFR inhibitor if FGFR2:CASP7 is present in the sample. In some embodiments, a patient having metastatic esophageal cancer is treated with an FGFR inhibitor if FGFR2:CCD6 is present in the sample. In some embodiments, a patient having metastatic esophageal cancer is treated with an FGFR inhibitor if FGFR2:OFD1 is present in the sample. In some embodiments, a patient having metastatic esophageal cancer is treated with an FGFR inhibitor if any combination of the above FGFR mutants is present in the sample.

For patients with non-small cell lung (NSCL) adenocarcinoma, for example, a suitable FGFR mutant gene panel can comprise FGFR3:TACC3 v1, FGFR3:TACC3 v3, FGFR3:TACC3 Intron, FGFR3:BAIAP2L1, FGFR2:AFF3, FGFR2:CASP7, FGFR3 R248C, FGFR3 S249C, FGFR3 G370C, or FGFR3 Y373C, or any combination thereof. Accordingly, in some embodiments, a patient having NSCL adenocarcinoma is treated with an FGFR inhibitor if FGFR3:TACC3 v1 is present in the sample. In some embodiments, a patient having NSCL adenocarcinoma is treated with an FGFR inhibitor if FGFR3:TACC3 v3 is present in the sample. In some embodiments, a patient having NSCL adenocarcinoma is treated with an FGFR inhibitor if FGFR3:TACC3 Intron is present in the sample. In some embodiments, a patient having NSCL adenocarcinoma is treated with an FGFR inhibitor if FGFR3: BAIAP2L1 is present in the sample. In some embodiments, a patient having NSCL adenocarcinoma is treated with an FGFR inhibitor if FGFR2:AFF3 is present in the sample. In some embodiments, a patient having NSCL adenocarcinoma is treated with an FGFR inhibitor if FGFR2:CASP7 is present in the sample. In some embodiments, a patient having NSCL adenocarcinoma is treated with an FGFR inhibitor if FGFR3 R248C is present in the sample. In some embodiments, a patient having NSCL adenocarcinoma is treated with an FGFR inhibitor if FGFR3 S249C is present in the sample. In some embodiments, a patient having NSCL adenocarcinoma is treated with an FGFR inhibitor if FGFR3 G370C is present in the sample. In some embodiments, a patient having NSCL adenocarcinoma is treated with an FGFR inhibitor if FGFR3 Y373C is present in the sample. In some embodiments, a patient having NSCL adenocarcinoma is treated with an FGFR inhibitor if any combination of the above FGFR mutants is present in the sample.

For patients with non-small cell lung (NSCL) squamous cell carcinoma, for example, a suitable FGFR mutant gene panel can comprise FGFR3:TACC3 v1, FGFR3:TACC3 v3, FGFR3:BAIAP2L1, FGFR2:BICC1, FGFR2:AFF3, FGFR2:CASP7, FGFR2:CCDC6, FGFR3 R248C, FGFR3 S249C, FGFR3 G370C, or FGFR3 Y373C, or any combination thereof. Accordingly, in some embodiments, a patient having NSCL squamous cell carcinoma is treated with an FGFR inhibitor if FGFR3:TACC3 v1 is present in the sample. In some embodiments, a patient having NSCL squamous cell carcinoma is treated with an FGFR inhibitor if FGFR3:TACC3 v3 is present in the sample. In some embodiments, a patient having NSCL squamous cell carcinoma is treated with an FGFR inhibitor if FGFR3: BAIAP2L1 is present in the sample. In some embodiments, a patient having NSCL squamous cell carcinoma is treated with an FGFR inhibitor if FGFR2:BICC1 is present in the sample. In some embodiments, a patient having NSCL squamous cell carcinoma is treated with an FGFR inhibitor if FGFR2:AFF3 is present in the sample. In some embodiments, a patient having NSCL squamous cell carcinoma is treated with an FGFR inhibitor if FGFR2:CASP7 is present in the sample. In some embodiments, a patient having NSCL squamous cell carcinoma is treated with an FGFR inhibitor if FGFR2:CCDC6 is present in the sample. In some embodiments, a patient having NSCL squamous cell carcinoma is treated with an FGFR inhibitor if FGFR3 R248C is present in the sample. In some embodiments, a patient having NSCL squamous cell carcinoma is treated with an FGFR inhibitor if FGFR3 S249C is present in the sample. In some embodiments, a patient having NSCL squamous cell carcinoma is treated with an FGFR inhibitor if FGFR3 G370C is present in the sample. In some embodiments, a patient having NSCL squamous cell carcinoma is treated with an FGFR inhibitor if FGFR3 Y373C is present in the sample. In some embodiments, a patient having NSCL squamous cell carcinoma is treated with an FGFR inhibitor if any combination of the above FGFR mutants is present in the sample.

For patients with metastatic endometrial cancer, for example, a suitable FGFR mutant gene panel can comprise FGFR3:TACC3 v1, FGFR3:TACC3 v3, FGFR3:TACC3 Intron, FGFR3:BAIAP2L1, FGFR2:CASP7, FGFR2:CCDC6, or FGFR2:OFD1, or any combination thereof. Accordingly, in some embodiments, a patient having metastatic endometrial cancer is treated with an FGFR inhibitor if FGFR3:TACC3 v1 is present in the sample. In some embodiments, a patient having metastatic endometrial cancer is treated with an FGFR inhibitor if FGFR3:TACC3 v3 is present in the sample. In some embodiments, a patient having metastatic endometrial cancer is treated with an FGFR inhibitor if FGFR3:TACC3 Intron is present in the sample. In some embodiments, a patient having metastatic endometrial cancer is treated with an FGFR inhibitor if FGFR3:BAIAP2L1 is present in the sample. In some embodiments, a patient having metastatic endometrial cancer is treated with an FGFR inhibitor if FGFR2:CASP7 is present in the sample. In some embodiments, a patient having metastatic endometrial cancer is treated with an FGFR inhibitor if FGFR2:CCDC6 is present in the sample. In some embodiments, a patient having metastatic endometrial cancer is treated with an FGFR inhibitor if FGFR2:OFD1 is present in the sample. In some embodiments, a patient having metastatic endometrial cancer is treated with an FGFR inhibitor if any combination of the above FGFR mutants is present in the sample.

For patients with breast cancer, for example, a suitable FGFR mutant gene panel can comprise FGFR3:TACC3 v1, FGFR3:TACC3 v3, FGFR3:TACC3 Intron, FGFR3:BAIAP2L1, FGFR2:BICC1, FGFR2:AFF3, FGFR2:CASP7, FGFR2:CCD6, or FGFR2:OFD1, or any combination thereof. Accordingly, in some embodiments, a patient having breast cancer is treated with an FGFR inhibitor if FGFR3:TACC3 v1 is present in the sample. In some embodiments, a patient having breast cancer is treated with an FGFR inhibitor if FGFR3:TACC3 v3 is present in the sample. In some embodiments, a patient having breast cancer is treated with an FGFR inhibitor if FGFR3:TACC3 Intron is present in the sample. In some embodiments, a patient having breast cancer is treated with an FGFR inhibitor if FGFR3:BAIAP2L1 is present in the sample. In some embodiments, a patient having breast cancer is treated with an FGFR inhibitor if FGFR2:BICC1 is present in the sample. In some embodiments, a patient having breast cancer is treated with an FGFR inhibitor if FGFR2:AFF3 is present in the sample. In some embodiments, a patient having breast cancer is treated with an FGFR inhibitor if FGFR2:CASP7 is present in the sample. In some embodiments, a patient having breast cancer is treated with an FGFR inhibitor if FGFR2:CCD6 is present in the sample. In some embodiments, a patient having breast cancer is treated with an FGFR inhibitor if FGFR2:OFD1 is present in the sample. In some embodiments, a patient having breast cancer is treated with an FGFR inhibitor if any combination of the above FGFR mutants is present in the sample.

For patients with hepatocellular carcinoma, for example, a suitable FGFR mutant gene panel can comprise FGFR3:TACC3 v1, FGFR3:TACC3 v3, FGFR3:TACC3 Intron, FGFR3:BAIAP2L1, FGFR2:BICC1, FGFR2:AFF3, FGFR2:CASP7, FGFR2:CCDC6, FGFR2:OFD1, FGFR3 R248C, FGFR3 S249C, FGFR3 G370C, or FGFR3 Y373C, or any combination thereof. Accordingly, in some embodiments, a patient having hepatocellular carcinoma is treated with an FGFR inhibitor if FGFR3:TACC3 v1 is present in the sample. In some embodiments, a patient having hepatocellular carcinoma is treated with an FGFR inhibitor if FGFR3:TACC3 v3 is present in the sample. In some embodiments, a patient having hepatocellular carcinoma is treated with an FGFR inhibitor if FGFR3:TACC3 Intron is present in the sample. In some embodiments, a patient having hepatocellular carcinoma is treated with an FGFR inhibitor if FGFR3:BAIAP2L1 is present in the sample. In some embodiments, a patient having hepatocellular carcinoma is treated with an FGFR inhibitor if FGFR2:BICC1 is present in the sample. In some embodiments, a patient having hepatocellular carcinoma is treated with an FGFR inhibitor if FGFR2:AFF3 is present in the sample. In some embodiments, a patient having hepatocellular carcinoma is treated with an FGFR inhibitor if FGFR2:CASP7 is present in the sample. In some embodiments, a patient having hepatocellular carcinoma is treated with an FGFR inhibitor if FGFR2:CCDC6 is present in the sample. In some embodiments, a patient having hepatocellular carcinoma is treated with an FGFR inhibitor if FGFR2:OFD1 is present in the sample. In some embodiments, a patient having hepatocellular carcinoma is treated with an FGFR inhibitor if FGFR3 R248C is present in the sample. In some embodiments, a patient having hepatocellular carcinoma is treated with an FGFR inhibitor if FGFR3 S249C is present in the sample. In some embodiments, a patient having hepatocellular carcinoma is treated with an FGFR inhibitor if FGFR3 G370C is present in the sample. In some embodiments, a patient having hepatocellular carcinoma is treated with an FGFR inhibitor if FGFR3 Y373C is present in the sample. In some embodiments, a patient having hepatocellular carcinoma is treated with an FGFR inhibitor if any combination of the above FGFR mutants is present in the sample.

In some embodiments, the evaluating step comprises: isolating RNA from the biological sample; synthesizing cDNA from the isolated RNA; pre-amplifying the cDNA; and amplifying the pre-amplified cDNA with a pair of primers that bind to and amplify one or more FGFR mutants from the FGFR mutant gene panel.

Isolating RNA from the biological sample can be performed by a number of procedures known to one skilled in the art. In one embodiment, RNA can be isolated from the biological sample using an AllPrep DNA/RNA FFPE Kit from Qiagen (product #80234)

Synthesizing cDNA from isolated RNA can be performed by a number of procedures known to one skilled in the art. In one embodiment, cDNA can be synthesized from isolated RNA using a High Capacity cDNA Reverse Transcriptase Kit with RNase Inhibitor from ABI (product #4374966).

Pre-amplification of cDNA can be performed by a number of procedures known to one skilled in the art. Amplification procedures are well known in the art. In one embodiment, cDNA can be pre-amplified using a TaqMan® PreAmp Master Mix (Life Technologies/Applied Biosystems® product #4391128).

In some embodiments, the amplifying step can comprise performing real-time PCR (qRT-PCR). Exemplary qRT-PCR procedures are discussed in the Example section herein. In some aspects, the qRT-PCR can be a Taqman® Real-Time PCR assay. qRT-PCR procedures can involve the use of probes to increase the specificity of the assay. Suitable probes for use in the qRT-PCR assay include any of the probes disclosed herein, for example, the probes disclosed in Table 15. In some embodiments, for example, the real-time PCR can be performed with one or more probes comprising SEQ ID NO: 43, SEQ ID NO:44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, and/or SEQ ID NO: 55. In other embodiments, the real-time PCR can be performed with one or more probes consisting essentially of SEQ ID NO: 43, SEQ ID NO:44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, and/or SEQ ID NO: 55. In other embodiments, the real-time PCR can be performed with one or more probes consisting of SEQ ID NO: 43, SEQ ID NO:44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, and/or SEQ ID NO: 55. In other embodiments, the real-time PCR can be performed with one or more probes having SEQ ID NO: 43, SEQ ID NO:44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, and/or SEQ ID NO: 55.

The qRT-PCR can be performed with one or more 3' blocking oligonucleotides. Exemplary qRT-PCR procedures using 3' blocking oligonucleotides are disclosed in the Example section herein. Suitable 3' blocking oligonucleotides include, for example, those disclosed in Table 8. In some embodiments, the qRT-PCR can be performed with one or more 3' blocking oligonucleotides comprising SEQ ID NO: 39, SEQ ID NO: 40, SEQ ID NO: 41, and/or SEQ ID NO: 42. In some embodiments, the qRT-PCR can be performed with one or more 3' blocking oligonucleotides consisting essentially of SEQ ID NO: 39, SEQ ID NO: 40, SEQ ID NO: 41, and/or SEQ ID NO: 42. In some embodiments, the qRT-PCR can be performed with one or more 3' blocking oligonucleotides consisting of SEQ ID NO: 39, SEQ ID NO: 40, SEQ ID NO: 41, and/or SEQ ID NO: 42. In some embodiments, the qRT-PCR can be performed with one or more 3' blocking oligonucleotides having SEQ ID NO: 39, SEQ ID NO: 40, SEQ ID NO: 41, and/or SEQ ID NO: 42.

Suitable pairs of primers for use in the amplifying step include those disclosed in Table 3. For example, in some embodiments, the FGFR mutant and pair of primers can be FGFR3:TACC3 v1 and primers having the amino acid sequences of SEQ ID NO:5 and SEQ ID NO:6. In some embodiments, the FGFR mutant and pair of primers can be FGFR3:TACC3 v3 and primers having the amino acid sequences of SEQ ID NO:7 and SEQ ID NO:8. In some embodiments, the FGFR mutant and pair of primers can be FGFR3:TACC3 Intron and primers having the amino acid sequences of SEQ ID NO:9 and SEQ ID NO:10. In some embodiments, the FGFR mutant and pair of primers can be FGFR3: BAIAP2L1 and primers having the amino acid sequences of SEQ ID NO:11 and SEQ ID NO:12. In some embodiments, the FGFR mutant and pair of primers can be FGFR2:BICC1 and primers having the amino acid sequences of SEQ ID NO:13 and SEQ ID NO:14. In some embodiments, the FGFR mutant and pair of primers can be FGFR2:AFF3 and primers having the amino acid sequences of SEQ ID NO:15 and SEQ ID NO:16. In some embodiments, the FGFR mutant and pair of primers can be FGFR2: CASP7 and primers having the amino acid sequences of SEQ ID NO:17 and SEQ ID NO:18. In some embodiments, the FGFR mutant and pair of primers can be FGFR2: CCDC6 and primers having the amino acid sequences of SEQ ID NO:19 and SEQ ID NO:20. In some embodiments, the FGFR mutant and pair of primers can be FGFR2:OFD1 and primers having the amino acid sequences of SEQ ID NO:21 and SEQ ID NO:22. In some embodiments, the FGFR mutant and pair of primers can be R248C and primers having the amino acid sequences of SEQ ID NO:23 and SEQ ID NO:24 or SEQ ID NO:31 and SEQ ID NO:32. In some embodiments, the FGFR mutant and pair of primers can be S249C and primers having the amino acid sequences of SEQ ID NO:25 and SEQ ID NO:26 or SEQ ID NO:33 and SEQ ID NO:34. In some embodiments, the FGFR mutant and pair of primers can be G370C and primers having the amino acid sequences of SEQ ID NO:27 and SEQ ID NO:28 or SEQ ID NO:35 and SEQ ID NO:36. In some embodiments, the FGFR mutant and pair of primers can be Y373C and primers having the amino acid sequences of SEQ ID NO:29 and SEQ ID NO:30 or SEQ ID NO:37 and SEQ ID NO:38. In some embodiments, the FGFR mutant and pair of primers can be any combination of the above disclosed FGFR mutants and corresponding pair of primers.

In some embodiments, the amplifying step can be performed with the following:

a. the pair of primers have the sequences SEQ ID NO:5 and SEQ ID NO:6 and the probe has the sequence of SEQ ID NO:43;

b. the pair of primers have the sequences SEQ ID NO:7 and SEQ ID NO:8 and the probe has the sequence of SEQ ID NO:44;

c. the pair of primers have the sequences SEQ ID NO:9 and SEQ ID NO:10 and the probe has the sequence of SEQ ID NO:46;

d. the pair of primers have the sequences SEQ ID NO:11 and SEQ ID NO:12 and the probe has the sequence of SEQ ID NO:47;

e. the pair of primers have the sequences SEQ ID NO:13 and SEQ ID NO:14 and the probe has the sequence of SEQ ID NO:45;

f. the pair of primers have the sequences SEQ ID NO:15 and SEQ ID NO:16 and the probe has the sequence of SEQ ID NO:48;

g. the pair of primers have the sequences SEQ ID NO:17 and SEQ ID NO:18 and the probe has the sequence of SEQ ID NO:49;

h. the pair of primers have the sequences SEQ ID NO:19 and SEQ ID NO:20 and the probe has the sequence of SEQ ID NO:50;

i. the pair of primers have the sequences SEQ ID NO:21 and SEQ ID NO:22 and the probe has the sequence of SEQ ID NO:51;

j. the pair of primers have the sequences SEQ ID NO:23 and SEQ ID NO:24 and the probe has the sequence of SEQ ID NO:52;

k. the pair of primers have the sequences SEQ ID NO:25 and SEQ ID NO:26 and the probe has the sequence of SEQ ID NO:53;

l. the pair of primers have the sequences SEQ ID NO:27 and SEQ ID NO:28 and the probe has the sequence of SEQ ID NO:54;

m. the pair of primers have the sequences SEQ ID NO:29 and SEQ ID NO:30 and the probe has the sequence of SEQ ID NO:55;

n. the pair of primers have the sequences SEQ ID NO:31 and SEQ ID NO:32, the probe has the sequence of SEQ ID NO:52, and the 3' blocking oligonucleotide has the sequence of SEQ ID NO:39;

o. the pair of primers have the sequences SEQ ID NO:33 and SEQ ID NO:34, the probe has the sequence of SEQ ID NO:53, and the 3' blocking oligonucleotide has the sequence of SEQ ID NO:40;

p. the pair of primers have the sequences SEQ ID NO:35 and SEQ ID NO:36, the probe has the sequence of SEQ ID NO:54, and the 3' blocking oligonucleotide has the sequence of SEQ ID NO:41;

q. the pair of primers have the sequences SEQ ID NO:37 and SEQ ID NO:38, the probe has the sequence of SEQ ID NO:55, and the 3' blocking oligonucleotide has the sequence of SEQ ID NO:42; or r. any combination thereof.

The disclosed methods comprise treating a patient if one or more FGFR mutants are present in the sample. The presence of one or more FGFR mutants in the sample can be determined by, for example, sequencing the amplified cDNA.

Suitable FGFR inhibitors for use in the treatment methods include those previously described herein.

Also disclosed are FGFR inhibitors for use in the treatment of cancer in a patient wherein the patient is identified as being responsive to treatment with the FGFR inhibitor by evaluating a biological sample obtained from the patient for the presence of one or more FGFR mutants from a FGFR mutant gene panel, wherein the presence of the one or more FGFR mutants in the sample is detected.

Further disclosed are FGFR inhibitors for use in the treatment of cancer in a patient wherein the patient is identified as being responsive to treatment with the FGFR inhibitor by evaluating a biological sample obtained from the patient for the presence of one or more FGFR mutants from a FGFR mutant gene panel, wherein the one or more FGFR mutants are a FGFR fusion gene or a FGFR SNP, wherein the presence of the one or more FGFR mutants in the sample is detected, and wherein said evaluating comprises amplifying cDNA with a pair of primers that bind to and amplify one or more FGFR mutants from the FGFR mutant gene panel.

Further disclosed are FGFR inhibitors for use in the treatment of cancer in a patient wherein the patient is identified as being responsive to treatment with the FGFR inhibitor by evaluating a biological sample obtained from the patient for the presence of one or more FGFR mutants from a FGFR mutant gene panel, wherein the FGFR mutant is a FGFR fusion gene or a FGFR SNP, wherein the presence of one or more FGFR mutants in the sample is detected, and wherein said evaluating comprises amplifying a pre-amplified cDNA with a pair of primers that bind to and amplify one or more FGFR mutants from the FGFR mutant gene panel.

Methods of Identifying a Cancer Patient that Will be Responsive to Treatment with a Fibroblast Growth Factor Receptor (FGFR) Inhibitor Disclosed herein are methods of identifying a cancer patient that will be responsive to treatment with a fibroblast growth factor receptor (FGFR) inhibitor comprising: evaluating a biological sample from the patient for a FGFR mutant from a FGFR mutant gene panel, wherein the FGFR mutant is a FGFR fusion gene or a FGFR single nucleotide polymorphism, and wherein said evaluating comprises amplifying cDNA with a pair of primers that bind to and amplify one or more FGFR mutants from the FGFR mutant gene panel and determining whether the one or more FGFR mutants from the gene panel are present in the sample, wherein the presence of the one or more FGFR mutants indicates that the patient will be responsive to treatment with the FGFR inhibitor.

Also provided are methods of identifying a cancer patient that is responsive to treatment with a fibroblast growth factor receptor (FGFR) inhibitor comprising: evaluating a biological sample from the patient for a FGFR mutant from a FGFR mutant gene panel, wherein the FGFR mutant is a FGFR fusion gene or a FGFR single nucleotide polymorphism, and wherein said evaluating comprises amplifying cDNA with a pair of primers that bind to and amplify one or more FGFR mutants from the FGFR mutant gene panel and determining whether the one or more FGFR mutants from the gene panel are present in the sample, wherein the presence of the one or more FGFR mutants indicates that the patient is responsive to treatment with the FGFR inhibitor.

Further provided are methods of identifying a cancer patient that is responsive to treatment with a fibroblast growth factor receptor (FGFR) inhibitor comprising evaluating a biological sample from the patient for the presence of one or more FGFR mutant from a FGFR mutant gene panel, wherein the FGFR mutant is a FGFR fusion gene or a FGFR single nucleotide polymorphism, wherein the presence of the one or more FGFR mutants indicates that the patient is responsive to treatment with the FGFR inhibitor.

In some embodiments, the evaluating can comprise amplifying cDNA with a pair of primers that bind to and amplify one or more FGFR mutants from the FGFR mutant gene panel. In some embodiments, the cDNA can be pre-amplified cDNA.

In some embodiments, the evaluating step comprises: isolating RNA from the biological sample and synthesizing cDNA from the isolated RNA. In some aspects, the evaluating step can be performed on preamplified cDNA. Thus, the evaluating step can further comprise pre-amplifying the cDNA prior to said amplifying step. Isolating RNA from a biological sample can be performed by a number of procedures known to one skilled in the art. In one embodiment, RNA can be isolated from the biological sample using an AllPrep DNA/RNA FFPE Kit from Qiagen (for example, product #80234). Synthesizing cDNA from isolated RNA can be performed by a number of procedures known to one skilled in the art. In one embodiment, cDNA can be synthesized from isolated RNA using a High Capacity cDNA Reverse Transcriptase Kit with RNase Inhibitor from ABI (for example, product #4374966). Pre-amplification of cDNA can be performed by a number of procedures known to one skilled in the art. Amplification procedures are well known in the art. In one embodiment, cDNA can be pre-amplified using a TaqMan® PreAmp Master Mix (Life Technologies/Applied Biosystems® product #4391128).

The disclosed methods can be used to identify patients with a number of different types of cancer that will be responsive to treatment with a fibroblast growth factor receptor (FGFR) inhibitor including, but not limited to, bladder cancer, metastatic bladder cancer, ovarian cancer, head and neck cancer, esophageal cancer, non-small-cell lung adenocarcinoma, non-small cell lung squamous cell carcinoma, prostate cancer, lung cancer, gastric cancer, urothelial carcinoma, small cell lung cancer, breast cancer, endometrial cancer, cholangiocarcinoma, hepatocellular carcinoma, glioblastoma, gliomas, colon carcinoma, sarcomas, solid tumors of squamous origin, and multiple myeloma.

The FGFR mutant panel that is used in the evaluating step is based, in part, on the patient's cancer type. For patients with bladder cancer, for example, a suitable FGFR mutant gene panel can comprise FGFR3:TACC3 v1, FGFR3:

TACC3 v3, FGFR3:BAIAP2L1, FGFR2:BICC1, FGFR2:AFF3, FGFR2:CASP7, FGFR3 R248C, FGFR3 S249C, FGFR3 G370C, or FGFR3 Y373C, or any combination thereof. Accordingly, in some embodiments, the evaluating step comprises determining whether FGFR3:TACC3 v1 is present in a biological sample from a patient having bladder cancer. In some embodiments, the evaluating step comprises determining whether FGFR3:TACC3 v3 is present in a biological sample from a patient having bladder cancer. In some embodiments, the evaluating step comprises determining whether FGFR3:BAIAP2L1 is present in a biological sample from a patient having bladder cancer. In some embodiments, the evaluating step comprises determining whether FGFR2:BICC1 is present in a biological sample from a patient having bladder cancer. In some embodiments, the evaluating step comprises determining whether FGFR2:AFF3 is present in a biological sample from a patient having bladder cancer. In some embodiments, the evaluating step comprises determining whether FGFR2:CASP7 is present in a biological sample from a patient having bladder cancer. In some embodiments, the evaluating step comprises determining whether FGFR3 R248C is present in a biological sample from a patient having bladder cancer. In some embodiments, the evaluating step comprises determining whether FGFR3 S249C is present in a biological sample from a patient having bladder cancer. In some embodiments, the evaluating step comprises determining whether FGFR3 G370C is present in a biological sample from a patient having bladder cancer. In some embodiments, the evaluating step comprises determining whether FGFR3 Y373C is present in a biological sample from a patient having bladder cancer. In some embodiments, the evaluating step comprises determining whether any combination of the above FGFR mutants are present in a biological sample from a patient having bladder cancer.

For patients with metastatic bladder cancer, for example, a suitable FGFR mutant gene panel can comprise FGFR3:TACC3 v1, FGFR3:TACC3 v3, FGFR3:BAIAP2L1, FGFR2:BICC1, FGFR2:AFF3, FGFR2:CASP7, FGFR3 R248C, FGFR3 S249C, FGFR3 G370C, or FGFR3 Y373C, or any combination thereof. Accordingly, in some embodiments, the evaluating step comprises determining whether FGFR3:TACC3 v1 is present in a biological sample from a patient having metastatic bladder cancer. In some embodiments, the evaluating step comprises determining whether FGFR3:TACC3 v3 is present in a biological sample from a patient having metastatic bladder cancer. In some embodiments, the evaluating step comprises determining whether FGFR3:BAIAP2L1 is present in a biological sample from a patient having metastatic bladder cancer. In some embodiments, the evaluating step comprises determining whether FGFR2:BICC1 is present in a biological sample from a patient having metastatic bladder cancer. In some embodiments, the evaluating step comprises determining whether FGFR2:AFF3 is present in a biological sample from a patient having metastatic bladder cancer. In some embodiments, the evaluating step comprises determining whether FGFR2:CASP7 is present in a biological sample from a patient having metastatic bladder cancer. In some embodiments, the evaluating step comprises determining whether FGFR3 R248C is present in a biological sample from a patient having metastatic bladder cancer. In some embodiments, the evaluating step comprises determining whether FGFR3 S249C is present in a biological sample from a patient having metastatic bladder cancer. In some embodiments, the evaluating step comprises determining whether FGFR3 G370C is present in a biological sample from a patient having metastatic bladder cancer. In some embodiments, the evaluating step comprises determining whether FGFR3 Y373C is present in a biological sample from a patient having metastatic bladder cancer. In some embodiments, the evaluating step comprises determining whether any combination of the above FGFR mutants are present in a biological sample from a patient having metastatic bladder cancer.

For patients with ovarian cancer, for example, a suitable FGFR mutant gene panel can comprise FGFR3:TACC3 v1, FGFR3:TACC3 v3, FGFR3:BAIAP2L1, FGFR2:BICC1, FGFR2:AFF3, FGFR2:CASP7, FGFR3 R248C, FGFR3 S249C, FGFR3 G370C, or FGFR3 Y373C, or any combination thereof. Accordingly, in some embodiments, the evaluating step comprises determining whether FGFR3:TACC3 v1 is present in a biological sample from a patient having ovarian cancer. In some embodiments, the evaluating step comprises determining whether FGFR3:TACC3 v3 is present in a biological sample from a patient having ovarian cancer. In some embodiments, the evaluating step comprises determining whether FGFR3:BAIAP2L1 is present in a biological sample from a patient having ovarian cancer. In some embodiments, the evaluating step comprises determining whether FGFR2:BICC1 is present in a biological sample from a patient having ovarian cancer. In some embodiments, the evaluating step comprises determining whether FGFR2:AFF3 is present in a biological sample from a patient having ovarian cancer. In some embodiments, the evaluating step comprises determining whether FGFR2:CASP7 is present in a biological sample from a patient having ovarian cancer. In some embodiments, the evaluating step comprises determining whether FGFR3 R248C is present in a biological sample from a patient having ovarian cancer. In some embodiments, the evaluating step comprises determining whether FGFR3 S249C is present in a biological sample from a patient having ovarian cancer. In some embodiments, the evaluating step comprises determining whether FGFR3 G370C is present in a biological sample from a patient having ovarian cancer. In some embodiments, the evaluating step comprises determining whether FGFR3 Y373C is present in a biological sample from a patient having ovarian cancer. In some embodiments, the evaluating step comprises determining whether any combination of the above FGFR mutants is present in a biological sample from a patient having ovarian cancer.

For patients with head and neck cancer, for example, a suitable FGFR mutant gene panel can comprise FGFR3:BAIAP2L1, FGFR2:CASP7, FGFR3 R248C, FGFR3 S249C, FGFR3 G370C, or FGFR3 Y373C, or any combination thereof. Accordingly, in some embodiments, the evaluating step comprises determining whether FGFR3:BAIAP2L1 is present in a biological sample from a patient having head and neck cancer. In some embodiments, the evaluating step comprises determining whether FGFR2:CASP7 is present in a biological sample from a patient having head and neck cancer. In some embodiments, the evaluating step comprises determining whether FGFR3 R248C is present in a biological sample from a patient having head and neck cancer. In some embodiments, the evaluating step comprises determining whether FGFR3 S249C is present in a biological sample from a patient having head and neck cancer. In some embodiments, the evaluating step comprises determining whether FGFR3 G370C is present in a biological sample from a patient having head and neck cancer. In some embodiments, the evaluating step comprises determining whether FGFR3 Y373C is present in a biological sample from a patient having head and neck cancer. In some embodiments, the evaluating step comprises determining whether any combination of the above FGFR mutants is present in a biological sample from a patient having head and neck cancer.

For patients with metastatic head and neck cancer, for example, a suitable FGFR mutant gene panel can comprise FGFR3:BAIAP2L1, FGFR2:CASP7, or FGFR2:OFD1, or any combination thereof. Accordingly, in some embodiments, a patient having metastatic head and neck cancer is treated with an FGFR inhibitor if FGFR3:BAIAP2L1 is present in the sample. In some embodiments, a patient having metastatic head and neck cancer is treated with an FGFR inhibitor if FGFR2:CASP7 is present in the sample. In some embodiments, a patient having metastatic head and neck cancer is treated with an FGFR inhibitor if FGFR2:OFD1 is present in the sample. In some embodiments, a patient having metastic head and neck cancer is treated with an FGFR inhibitor if any combination of the above FGFR mutants is present in the sample.

For patients with esophageal cancer, for example, a suitable FGFR mutant gene panel can comprise FGFR3:TACC3 v1, FGFR3:TACC3 v3, FGFR2:BICC1, FGFR2:CASP7, FGFR3 R248C, FGFR3 S249C, FGFR3 G370C, or FGFR3 Y373C, or any combination thereof. Accordingly, in some embodiments, the evaluating step comprises determining whether FGFR3:TACC3 v1 is present in a biological sample from a patient having esophageal cancer. In some embodiments, the evaluating step comprises determining whether FGFR3:TACC3 v3 is present in a biological sample from a patient having esophageal cancer. In some embodiments, the evaluating step comprises determining whether FGFR2:BICC1 is present in a biological sample from a patient having esophageal cancer. In some embodiments, the evaluating step comprises determining whether FGFR2:CASP7 is present in a biological sample from a patient having esophageal cancer. In some embodiments, the evaluating step comprises determining whether FGFR3 R248C is present in a biological sample from a patient having esophageal cancer. In some embodiments, the evaluating step comprises determining whether FGFR3 S249C is present in a biological sample from a patient having esophageal cancer. In some embodiments, the evaluating step comprises determining whether FGFR3 G370C is present in a biological sample from a patient having esophageal cancer. In some embodiments, the evaluating step comprises determining whether FGFR3 Y373C is present in a biological sample from a patient having esophageal cancer. In some embodiments, the evaluating step comprises determining whether any combination of the above FGFR mutants is present in a biological sample from a patient having esophageal cancer.

For patients with metastatic esophageal cancer, for example, a suitable FGFR mutant gene panel can comprise FGFR3:TACC3 v1, FGFR3:TACC3 v3, FGFR3:TACC3 Intron, FGFR3:BAIAP2L1, FGFR2:BICC1, FGFR2:AFF3, FGFR2:CASP7, FGFR2:CCD6, or FGFR2:OFD1, or any combination thereof. Accordingly, in some embodiments, a patient having metastatic esophageal cancer is treated with an FGFR inhibitor if FGFR3:TACC3 v1 is present in the sample. In some embodiments, a patient having metastatic esophageal cancer is treated with an FGFR inhibitor if FGFR3:TACC3 v3 is present in the sample. In some embodiments, a patient having metastatic esophageal cancer is treated with an FGFR inhibitor if FGFR3:TACC3 Intron is present in the sample. In some embodiments, a patient having metastatic esophageal cancer is treated with an FGFR inhibitor if FGFR3:BAIAP2L1 is present in the sample. In some embodiments, a patient having metastatic esophageal cancer is treated with an FGFR inhibitor if FGFR2:BICC1 is present in the sample. In some embodiments, a patient having metastatic esophageal cancer is treated with an FGFR inhibitor if FGFR2:AFF3 is present in the sample. In some embodiments, a patient having metastatic esophageal cancer is treated with an FGFR inhibitor if FGFR2:CASP7 is present in the sample. In some embodiments, a patient having metastatic esophageal cancer is treated with an FGFR inhibitor if FGFR2:CCD6 is present in the sample. In some embodiments, a patient having metastatic esophageal cancer is treated with an FGFR inhibitor if FGFR2:OFD1 is present in the sample. In some embodiments, a patient having metastatic esophageal cancer is treated with an FGFR inhibitor if any combination of the above FGFR mutants is present in the sample.

For patients with non-small-cell lung (NSCL) adenocarcinoma, for example, a suitable FGFR mutant gene panel can comprise FGFR3:TACC3 v1, FGFR3:TACC3 v3, FGFR3:TACC3 Intron, FGFR3:BAIAP2L1, FGFR2:AFF3, FGFR2:CASP7, FGFR3 R248C, FGFR3 S249C, FGFR3 G370C, or FGFR3 Y373C, or any combination thereof. Accordingly, in some embodiments, the evaluating step comprises determining whether FGFR3:TACC3 v1 is present in a biological sample from a patient having NSCL adenocarcinoma. In some embodiments, the evaluating step comprises determining whether FGFR3:TACC3 v3 is present in a biological sample from a patient having NSCL adenocarcinoma. In some embodiments, the evaluating step comprises determining whether FGFR3:TACC3 Intron is present in a biological sample from a patient having NSCL adenocarcinoma. In some embodiments, the evaluating step comprises determining whether FGFR3:BAIAP2L1 is present in a biological sample from a patient having NSCL adenocarcinoma. In some embodiments, the evaluating step comprises determining whether FGFR2:AFF3 is present in a biological sample from a patient having NSCL adenocarcinoma. In some embodiments, the evaluating step comprises determining whether FGFR2:CASP7 is present in a biological sample from a patient having NSCL adenocarcinoma. In some embodiments, the evaluating step comprises determining whether FGFR3 R248C is present in a biological sample from a patient having NSCL adenocarcinoma. In some embodiments, the evaluating step comprises determining whether FGFR3 S249C is present in a biological sample from a patient having NSCL adenocarcinoma. In some embodiments, the evaluating step comprises determining whether FGFR3 G370C is present in a biological sample from a patient having NSCL adenocarcinoma. In some embodiments, the evaluating step comprises determining whether FGFR3 Y373C is present in a biological sample from a patient having NSCL adenocarcinoma. In some embodiments, the evaluating step comprises determining whether any combination of the above FGFR mutants is present in a biological sample from a patient having NSCL adenocarcinoma.

For patients with non-small cell lung (NSCL) squamous cell carcinoma, for example, a suitable FGFR mutant gene panel can comprise FGFR3:TACC3 v1, FGFR3:TACC3 v3, FGFR3:BAIAP2L1, FGFR2:BICC1, FGFR2:AFF3, FGFR2:CASP7, FGFR2:CCDC6, FGFR3 R248C, FGFR3 S249C, FGFR3 G370C, or FGFR3 Y373C, or any combination thereof. Accordingly, in some embodiments, the evaluating step comprises determining whether FGFR3:TACC3 v1 is present in a biological sample from a patient having NSCL squamous cell carcinoma. In some embodiments, the evaluating step comprises determining whether FGFR3:TACC3 v3 is present in a biological sample from a patient having NSCL squamous cell carcinoma. In some embodiments, the evaluating step comprises determining whether FGFR3:BAIAP2L1 is present in a biological sample from a patient having NSCL squamous cell carcinoma. In some embodiments, the evaluating step comprises determining whether FGFR2:BICC1 is present in a biological sample from a patient having NSCL squamous cell carcinoma. In some embodiments, the evaluating step comprises determining whether FGFR2:AFF3 is present in a biological sample from a patient having NSCL squamous cell carcinoma. In some embodiments, the evaluating step comprises determining whether FGFR2:CASP7 is present in a biological sample from a patient having NSCL squamous cell carcinoma. In some embodiments, the evaluating step comprises determining whether FGFR2:CCDC6 is present in a biological sample from a patient having NSCL squamous cell carcinoma. In some embodiments, the evaluating step comprises determining whether FGFR3 R248C is present in a biological sample from a patient having NSCL squamous cell carcinoma. In some embodiments, the evaluating step comprises determining whether FGFR3 S249C is present in a biological sample from a patient having NSCL squamous cell carcinoma. In some embodiments, the evaluating step comprises determining whether FGFR3 G370C is present in a biological sample from a patient having NSCL squamous cell carcinoma. In some embodiments, the evaluating step comprises determining whether FGFR3 Y373C is present in a biological sample from a patient having NSCL squamous cell carcinoma. In some embodiments, the evaluating step comprises determining whether any combination of the above FGFR mutants is present in a biological sample from a patient having NSCL squamous cell carcinoma.

For patients with metastatic endometrial cancer, for example, a suitable FGFR mutant gene panel can comprise FGFR3:TACC3 v1, FGFR3:TACC3 v3, FGFR3:TACC3 Intron, FGFR3:BAIAP2L1, FGFR2:CASP7, FGFR2:CCD6, or FGFR2:OFD1, or any combination thereof. Accordingly, in some embodiments, a patient having metastatic endometrial cancer is treated with an FGFR inhibitor if FGFR3:TACC3 v1 is present in the sample. In some embodiments, a patient having metastatic endometrial cancer is treated with an FGFR inhibitor if FGFR3:TACC3 v3 is present in the sample. In some embodiments, a patient having metastatic endometrial cancer is treated with an FGFR inhibitor if FGFR3:TACC3 Intron is present in the sample. In some embodiments, a patient having metastatic endometrial cancer is treated with an FGFR inhibitor if FGFR3:BAIAP2L1 is present in the sample. In some embodiments, a patient having metastatic endometrial cancer is treated with an FGFR inhibitor if FGFR2:CASP7 is present in the sample. In some embodiments, a patient having metastatic endometrial cancer is treated with an FGFR inhibitor if FGFR2:CCDC6 is present in the sample. In some embodiments, a patient having metastatic endometrial cancer is treated with an FGFR inhibitor if FGFR2:OFD1 is present in the sample. In some embodiments, a patient having metastatic endometrial cancer is treated with an FGFR inhibitor if any combination of the above FGFR mutants is present in the sample.

For patients with breast cancer, for example, a suitable FGFR mutant gene panel can comprise FGFR3:TACC3 v1, FGFR3:TACC3 v3, FGFR3:TACC3 Intron, FGFR3:BAIAP2L1, FGFR2:BICC1, FGFR2:AFF3, FGFR2:CASP7, FGFR2:CCD6, or FGFR2:OFD1, or any combination thereof. Accordingly, in some embodiments, a patient having breast cancer is treated with an FGFR inhibitor if FGFR3:TACC3 v1 is present in the sample. In some embodiments, a patient having breast cancer is treated with an FGFR inhibitor if FGFR3:TACC3 v3 is present in the sample. In some embodiments, a patient having breast cancer is treated with an FGFR inhibitor if FGFR3:TACC3 Intron is present in the sample. In some embodiments, a patient having breast cancer is treated with an FGFR inhibitor if FGFR3:BAIAP2L1 is present in the sample. In some embodiments, a patient having breast cancer is treated with an FGFR inhibitor if FGFR2:BICC1 is present in the sample. In some embodiments, a patient having breast cancer is treated with an FGFR inhibitor if FGFR2:AFF3 is present in the sample. In some embodiments, a patient having breast cancer is treated with an FGFR inhibitor if FGFR2:CASP7 is present in the sample. In some embodiments, a patient having breast cancer is treated with an FGFR inhibitor if FGFR2:CCD6 is present in the sample. In some embodiments, a patient having breast cancer is treated with an FGFR inhibitor if FGFR2:OFD1 is present in the sample. In some embodiments, a patient having breast cancer is treated with an FGFR inhibitor if any combination of the above FGFR mutants is present in the sample.

For patients with hepatocellular carcinoma, for example, a suitable FGFR mutant gene panel can comprise FGFR3:TACC3 v1, FGFR3:TACC3 v3, FGFR3:TACC3 Intron, FGFR3:BAIAP2L1, FGFR2:BICC1, FGFR2:AFF3, FGFR2:CASP7, FGFR2:CCDC6, FGFR2:OFD1, FGFR3 R248C, FGFR3 S249C, FGFR3 G370C, or FGFR3 Y373C, or any combination thereof. Accordingly, in some embodiments, a patient having hepatocellular carcinoma is treated with an FGFR inhibitor if FGFR3:TACC3 v1 is present in the sample. In some embodiments, a patient having hepatocellular carcinoma is treated with an FGFR inhibitor if FGFR3:TACC3 v3 is present in the sample. In some embodiments, a patient having hepatocellular carcinoma is treated with an FGFR inhibitor if FGFR3:TACC3 Intron is present in the sample. In some embodiments, a patient having hepatocellular carcinoma is treated with an FGFR inhibitor if FGFR3:BAIAP2L1 is present in the sample. In some embodiments, a patient having hepatocellular carcinoma is treated with an FGFR inhibitor if FGFR2:BICC1 is present in the sample. In some embodiments, a patient having hepatocellular carcinoma is treated with an FGFR inhibitor if FGFR2:AFF3 is present in the sample. In some embodiments, a patient having hepatocellular carcinoma is treated with an FGFR inhibitor if FGFR2:CASP7 is present in the sample. In some embodiments, a patient having hepatocellular carcinoma is treated with an FGFR inhibitor if FGFR2:CCDC6 is present in the sample. In some embodiments, a patient having hepatocellular carcinoma is treated with an FGFR inhibitor if FGFR2:OFD1 is present in the sample. In some embodiments, a patient having hepatocellular carcinoma is treated with an FGFR inhibitor if FGFR3 R248C is present in the sample. In some embodiments, a patient having hepatocellular carcinoma is treated with an FGFR inhibitor if FGFR3 S249C is present in the sample. In some embodiments, a patient having hepatocellular carcinoma is treated with an FGFR inhibitor if FGFR3 G370C is present in the sample. In some embodiments, a patient having hepatocellular carcinoma is treated with an FGFR inhibitor if FGFR3 Y373C is present in the sample. In some embodiments, a patient having hepatocellular carcinoma is treated with an FGFR inhibitor if any combination of the above FGFR mutants is present in the sample.

Suitable pairs of primers for use in the amplifying step include those disclosed in Table 3. For example, in some embodiments, the FGFR mutant and pair of primers can be FGFR3:TACC3 v1 and primers having the amino acid sequences of SEQ ID NO:5 and SEQ ID NO:6. In some embodiments, the FGFR mutant and pair of primers can be FGFR3:TACC3 v3 and primers having the amino acid sequences of SEQ ID NO:7 and SEQ ID NO:8. In some embodiments, the FGFR mutant and pair of primers can be FGFR3:TACC3 Intron and primers having the amino acid sequences of SEQ ID NO:9 and SEQ ID NO:10. In some embodiments, the FGFR mutant and pair of primers can be FGFR3:BAIAP2L1 and primers having the amino acid sequences of SEQ ID NO:11 and SEQ ID NO: 12. In some embodiments, the FGFR mutant and pair of primers can be FGFR2:BICC1 and primers having the amino acid sequences of SEQ ID NO:13 and SEQ ID NO:14. In some embodiments, the FGFR mutant and pair of primers can be FGFR2:AFF3 and primers having the amino acid sequences of SEQ ID NO:15 and SEQ ID NO:16. In some embodiments, the FGFR mutant and pair of primers can be FGFR2:CASP7 and primers having the amino acid sequences of SEQ ID NO:17 and SEQ ID NO:18. In some embodiments, the FGFR mutant and pair of primers can be FGFR2:CCDC6 and primers having the amino acid sequences of SEQ ID NO:19 and SEQ ID NO:20. In some embodiments, the FGFR mutant and pair of primers can be FGFR2:OFD1 and primers having the amino acid sequences of SEQ ID NO:21 and SEQ ID NO:22. In some embodiments, the FGFR mutant and pair of primers can be R248C and primers having the amino acid sequences of SEQ ID NO:23 and SEQ ID NO:24 or SEQ ID NO:31 and SEQ ID NO:32. In some embodiments, the FGFR mutant and pair of primers can be S249C and primers having the amino acid sequences of SEQ ID NO:25 and SEQ ID NO:26 or SEQ ID NO:33 and SEQ ID NO:34. In some embodiments, the FGFR mutant and pair of primers can be G370C and primers having the amino acid sequences of SEQ ID NO:27 and SEQ ID NO:28 or SEQ ID NO:35 and SEQ ID NO:36. In some embodiments, the FGFR mutant and pair of primers can be Y373C and primers having the amino acid sequences of SEQ ID NO:29 and SEQ ID NO:30 or SEQ ID NO:37 and SEQ ID NO:38. In some embodiments, the FGFR mutant and pair of primers can be any combination of the above disclosed FGFR mutants and corresponding pair of primers.

The disclosed methods comprise determining whether the one or more FGFR mutants from the gene panel are present in the sample. In some embodiments, the determining step comprises sequencing the amplified cDNA.

In some embodiments, the method further comprises treating the patient with an FGFR inhibitor if the one or more FGFR mutants from the gene panel are present in the sample. Suitable FGFR inhibitors for use in the treatment methods include those previously described herein, in particular JNJ-42756493.

Kits for Identifying the Presence of FGFR Mutant Genes

Further disclosed are kits for identifying the presence of one or more FGFR mutant genes in a biological sample comprising: pairs of primers having the sequences of SEQ ID NO:5 and SEQ ID NO:6, SEQ ID NO:7 and SEQ ID NO:8, SEQ ID NO:9 and SEQ ID NO:10, SEQ ID NO:11 and SEQ ID NO:12, SEQ ID NO:13 and SEQ ID NO:14, SEQ ID NO:15 and SEQ ID NO:16, SEQ ID NO:17 and SEQ ID NO:18, SEQ ID NO:19 and SEQ ID NO:20, SEQ ID NO:21 and SEQ ID NO:22, SEQ ID NO:23 and SEQ ID NO:24, SEQ ID NO:25 and SEQ ID NO:26, SEQ ID NO:27 and SEQ ID NO:28, SEQ ID NO:29 and SEQ ID NO:30, SEQ ID NO:31, SEQ ID NO:32, SEQ ID NO:33, SEQ ID NO:34, SEQ ID NO:35 and SEQ ID NO:36, SEQ ID NO:37, SEQ ID NO:38, or any combination thereof, and instructions for performing an assay to detect one or more FGFR mutant genes.

The kits can further comprise one or more probes, one or more 3' blocking oligonucleotides, or both. In some embodiments, the kits can further comprise one or more probes, for example, any one or more of the probes disclosed in Table 15. In some embodiments, the kits can further comprise one or more 3' blocking oligonucleotides, for example, any one or more of the 3' blocking oligonucleotides disclosed in Table 8. In some embodiments, the kits can further comprise one or more probes and one or more 3' blocking oligonucleotides. For example, in some embodiments, the kits can further comprise:

a. the pair of primers have the sequences SEQ ID NO:5 and SEQ ID NO:6 and the probe has the sequence of SEQ ID NO:43;
b. the pair of primers have the sequences SEQ ID NO:7 and SEQ ID NO:8 and the probe has the sequence of SEQ ID NO:44;
c. the pair of primers have the sequences SEQ ID NO:9 and SEQ ID NO:10 and the probe has the sequence of SEQ ID NO:46;
d. the pair of primers have the sequences SEQ ID NO:11 and SEQ ID NO:12 and the probe has the sequence of SEQ ID NO:47;
e. the pair of primers have the sequences SEQ ID NO:13 and SEQ ID NO:14 and the probe has the sequence of SEQ ID NO:45;
f. the pair of primers have the sequences SEQ ID NO:15 and SEQ ID NO:16 and the probe has the sequence of SEQ ID NO:48;
g. the pair of primers have the sequences SEQ ID NO:17 and SEQ ID NO:18 and the probe has the sequence of SEQ ID NO:49;
h. the pair of primers have the sequences SEQ ID NO:19 and SEQ ID NO:20 and the probe has the sequence of SEQ ID NO:50;
i. the pair of primers have the sequences SEQ ID NO:21 and SEQ ID NO:22 and the probe has the sequence of SEQ ID NO:51;
j. the pair of primers have the sequences SEQ ID NO:23 and SEQ ID NO:24 and the probe has the sequence of SEQ ID NO:52;
k. the pair of primers have the sequences SEQ ID NO:25 and SEQ ID NO:26 and the probe has the sequence of SEQ ID NO:53;
l. the pair of primers have the sequences SEQ ID NO:27 and SEQ ID NO:28 and the probe has the sequence of SEQ ID NO:54;
m. the pair of primers have the sequences SEQ ID NO:29 and SEQ ID NO:30 and the probe has the sequence of SEQ ID NO:55;
n. the pair of primers have the sequences SEQ ID NO:31 and SEQ ID NO:32, the probe has the sequence of SEQ ID NO:52, and the 3' blocking oligonucleotide has the sequence of SEQ ID NO: 39;
o. the pair of primers have the sequences SEQ ID NO:33 and SEQ ID NO:34, the probe has the sequence of SEQ ID NO:53, and the 3' blocking oligonucleotide has the sequence of SEQ ID NO:40;
p. the pair of primers have the sequences SEQ ID NO:35 and SEQ ID NO:36, the probe has the sequence of SEQ ID NO:54, and the 3' blocking oligonucleotide has the sequence of SEQ ID NO:41;
q. the pair of primers have the sequences SEQ ID NO:37 and SEQ ID NO:38, the probe has the sequence of SEQ ID NO:55, and the 3' blocking oligonucleotide has the sequence of SEQ ID NO:42; or r. any combination thereof.

Oligonucleotide Probes

Also disclosed are oligonucleotide probes having the sequence of any one of SEQ ID NOs:43-55. In some embodiments, the oligonucleotide probe can have the sequence of SEQ ID NO:43. In some embodiments, the oligonucleotide probe can have the sequence of SEQ ID NO:44. In some embodiments, the oligonucleotide probe can have the sequence of SEQ ID NO:45. In some embodiments, the oligonucleotide probe can have the sequence of SEQ ID NO:46. In some embodiments, the oligonucleotide probe can have the sequence of SEQ ID NO:47. In some embodiments, the oligonucleotide probe can have the sequence of SEQ ID NO: 48. In some embodiments, the oligonucleotide probe can have the sequence of SEQ ID NO:49. In some embodiments, the oligonucleotide probe can have the sequence of SEQ ID NO:50. In some embodiments, the oligonucleotide probe can have the sequence of SEQ ID NO:51. In some embodiments, the oligonucleotide probe can have the sequence of SEQ ID NO:52. In some embodiments, the oligonucleotide probe can have the sequence of SEQ ID NO:53. In some embodiments, the oligonucleotide probe can have the sequence of SEQ ID NO:54. In some embodiments, the oligonucleotide probe can have the sequence of SEQ ID NO:55.

3' Blocking Oligonucleotide

Also disclosed herein are oligonucleotides having the sequence of any one of SEQ ID NOs:39-42. In some embodiments, the 3' blocking oligonucleotide can have the sequence of SEQ ID NO:39. In some embodiments, the 3' blocking oligonucleotide can have the sequence of SEQ ID NO:40. In some embodiments, the 3' blocking oligonucleotide can have the sequence of SEQ ID NO:41. In some embodiments, the 3' blocking oligonucleotide can have the sequence of SEQ ID NO:42.

EXAMPLES

Example 1—Plasmid DNA Isolation and Purification

Below is an exemplary procedure for preparing FGFR fusion plasmid DNA.

Required equipment: centrifuge, capable of 1500×g; microcentrifuge; pipettors, positive-displacement or air-displacement; vortexer; nanodrop Spectrophotometer; 37° C. shaker/incubator; and an oven set to 37° C.

Required materials: frozen glycerol bacterial stock containing plasmid DNA; Kanamycin LB agar plates (Teknova #L1155); LB broth (Life Technologies #10855-021); Kanamycin (Sigma #K0254); plasmid purification kit (Qiagen #12123); absolute ethanol (Sigma Aldrich #E7023); isopropanol (Sigma Aldrich #W292907); Nuclease Free Water (Non-DEPC treated) (from IDT or Ambion #AM9932); RNase-free Barrier (Filter) Tips; RNase-free Microtube (1.5 to 2 mL VWR #10011-724); serological pipettes; and 14 ml Round bottom tubes (VWR #352057).

To recover bacteria from the glycerol stock, frozen bacteria were scraped off of the top of a glycerol stock tube using a sterile pipet tip, streaked onto a LB agar plate, and placed upside down in the oven at 37° C. overnight.

DNA plasmids were purified using Qiagen Plasmid DNA Purification protocol. Briefly, a single colony was picked from the streaked plate and incubated in a culture of 5 ml-LB medium containing 50 µg/ml Kanamycin overnight in a 37° C. shaker at approximately 300 rpm. The bacterial cells were harvested by centrifugation at 6000×g for 15 minutes at 4° C., and the pellet was resuspended in 300 µl of buffer P1. 300 µl of buffer P2 was added, mixed by inverting the tube 4-6 times, and incubated at RT (room temperature) for 5 minutes. 300 µl of chilled buffer P3 was added, mixed immediately by inverting 4-6 times, incubated on ice for 5 minutes, and centrifuged at maximum speed for 10 minutes. Supernatant containing plasmid DNA was removed promptly. A Qiagen-tip 20 was equilibrated by applying 1 ml of buffer QBT and allowed to empty by gravity flow. The supernatant was applied to the Qiagen-tip 20 and allowed to enter the resin by gravity flow. The Qiagen-tip 20 was washed with 2×2 ml of buffer QC and the DNA was eluted with 800 µl of buffer QF and the eluate was collected in a 1.5 ml Eppendorf tube. The DNA was precipitated by adding 0.7 volumes of isopropanol, mixed, and centrifuged immediately at 15000×g for 30 minutes in a microcentrifuge. The supernatant was decanted, and the DNA pellet was washed in 1 ml of 70% ethanol and centrifuged at 15000×g for 10 minutes. The supernatant was decanted. The pellet was air-dried for 5-10 minutes and the DNA was re-dissolved in 100 µl or suitable volume of nuclease-free water. Plasmid DNA was quantitated by Nanodrop and stored at −20° C. until further use.

Example 2—Generation of NRK Cell Lines

Expression vectors expressing each of the FGFR fusions were constructed. The expression vector was then transfected into normal rat kidney epithelial cells (NRK) cells. The stable cell lines were selected in media containing kanamycin following transfections. These cells were then grown and mRNA was isolated and subjected to FGFR fusion assays to confirm the presence of the specific FGFR fusions mRNA.

Example 3—FGFR-Fusion Cell Line Maintenance

The below protocol describes an exemplary procedure for culturing and maintaining the NRK FGFR-fusion overexpressing cell lines. Cell lines include, but are not limited to: NRK/FGFR3:TACC3v1, NRK/FGFR3:TACC3 v3, NRK/FGFR3:BAIAP2L1, NRK/FGFR2: BICC1, NRK/FGFR2:CASP7, NRK/FGFR2:CCDC6, NRK/FGFR2: AFF3, NRK/FGFR2:OFD1, and NRK/EMPTY VECTOR (plasmid control).

Required equipment: biosafety cabinet, fitted with vacuum aspiration system; $CO_2$ Incubator, set to 37° C. with 5% $CO_2$; −80° C. freezer; liquid nitrogen tank; water bath, set to 37° C.; and a microscope.

Required materials: serological pipettes; tissue culture flasks (T75 VWR #BD353136 and/or T150 VWR #15705-074); tissue culture 0.2 µm filtering units (Thermo Scientific #566-0020); DMEM (Dulbecco's Modified Eagle Medium) cell culture media (Life Technologies, #11965-084); Fetal Bovine Serum (FBS),certified, heat inactivated (Life Technologies, #10082147); PenStrep antibiotic solution (Life Technologies #15140-122); Trypsin-EDTA 0.25% solution (Life Technologies, #25200-056); DPBS (Dulbecco's Phosphate buffered solution, no calcium, no magnesium) (Life Technologies, #14190136); cell freezing container for cryopreservation; hand held pipetman; cell freezing media (Life Technologies, #12648-010); 15 ml conical tubes (VWR #62406-2); and cryovials (VWR #89094-800).

To prepare the cell culture media, DMEM medium was prepared by combining 445 ml of DMEM, 50 ml of FBS, and 5 ml of PenStrep. The prepared media was passed through a 0.2 μm filter unit and stored at 4° C.

To thaw frozen cells, prepared DMEM medium was warmed in the 37° C. water bath for at least 15 minutes and 15 ml of warmed medium was placed into a T75 flask. Cells were removed from liquid nitrogen tank and placed immediately in a 37° C. water bath until just thawed. Cryovials were sprayed generously with 70% alcohol and the excess was wiped with paper towels. The entire content was aliquoted into the T75 flask containing DMEM. Flask was swirled gently to mix and placed in incubator for 24 hours. If the cells were not ready for splitting, the media was changed to freshly prepared DMEM to remove residual freezing media. If cells were ready to split, each cell line was propagated once the flask achieved 80% confluency (splitting ratio for each cell line was dependent upon the experimental needs).

To freeze the cell lines, the cells were removed from the culture flask and spun down in a 15 ml conical tube for 5 minutes at 1500 RPM at RT. The medium was aspirated and 6 ml of cell freezing medium was added. The cells were mixed by pipetting up and down several times, and 1 ml of cell solution was aliquoted into each of 5 cryovials. Cryovials with cells were placed in a cryofreezing container, which was stored in a −80° C. freezer overnight, followed by long term storage in a liquid nitrogen tank.

Example 4—FFPET SNP Assay

An exemplary workflow and protocol for performing a FFPET SNP assay is described below. A similar procedure is performed for FFPET fusion assays, the results of which are shown in FIGS. 2A-2I.

De-Parafinization of FFPET

Slides were subjected to increasing amounts of xylene followed by alcohol treatment in order to remove the paraffin.

FFPET RNA Extraction

The procedure for extracting RNA from breast cancer formalin fixed paraffin embedded tissue samples for downstream gene expression assay is described below.

Required equipment: centrifuge with plate adapter, capable of 1500×g; microcentrifuge; pipettors, positive-displacement or air-displacement; vortexer; NanoDrop 8000; heating block capable of incubation at 37° C., 56° C. and 80° C.; and pasteur pipette (Pipet Trans EX-FT 1.5 ml pk 500, VWR #14670-329).

Required Materials: AllPrep DNA/RNA FFPE Kit (Qiagen #80234); Absolute Ethanol (Sigma Aldrich #E7023); Isopropanol; Xylene; Nuclease Free Water (Non-DEPC treated) (from IDT or Ambion #AM9932); RNase-free Barrier (Filter) Tips; RNase-free; microtube (1.5 to 2 mL VWR #10011-724); and Qiagen AllPrep DNA/RNA FFPE Kit Handbook.

RNA was extracted using the AllPrep DNA/RNA FFPE Kit. Briefly, one 1-10 μm section was placed in a 1.5 ml reaction tube and 800 μl of HemoDe or Xylene were added. The sample was vortexed for 4 seconds 3 times, incubated for 2 minutes, vortexed for 4 seconds for 3 times and incubated for 5 minutes.

The sample was centrifuged for 2 minutes at maximum speed (12,000-14,000×g) and the supernatant was discarded by aspiration. Tubes were capped immediately to avoid tissue from drying.

The above steps were repeated.

800 μl ethanol abs. was added, the tube was flicked to dislodge the pellet, vortexed for 4 seconds 3 times, centrifuged for 2 minutes at maximum speed (12,000-14,000×g), and the supernatant was discarded by aspiration.

800 μl 70% ethanol was added, the tube was flicked to dislodge the pellet, vortexed for 4 seconds 3 times, centrifuged for 2 minutes at maximum speed, and the supernatant was discarded by aspiration. After removal of 70% ethanol, the tube was re-spun for 10-20 seconds and the residual fluid was carefully removed with a fine bore pipet.

The open tubes were incubated in a heating block for 5-15 minutes at 37° C. to air dry the tissue pellet.

The pellet was resuspended by adding 150 μl Buffer PKD and the tube was flicked to loosen the pellet. 10 μl proteinase K was added and the tube was mixed by vortexing.

Tubes were incubated at 56° C. for 15 minutes, incubated on ice for 3 minutes, and centrifuged for 15 minutes at 20,000×g.

The supernatant was carefully transferred without disturbing the pellet to a new 1.5 ml microcentrifuge tube for RNA purification. The supernatant was incubated at 80° C. for 15 minutes. The tube was briefly centrifuged to remove drops from the inside of the lid. 320 μl Buffer RLT was added to adjust binding conditions, and the tube was mixed by vortexing or pipetting. 1120 μl ethanol (96-100%) was added and the tube was mixed well by vortexing or pipetting.

700 μl of the sample, including any precipitate that may have formed, was transferred to an RNeasy MinElute spin column placed in a 2 ml collection tube, and centrifuged for 15 seconds at ≥8000×g (≥10,000 rpm). The flow-through was discarded. This step was repeated until the entire sample was passed through the RNeasy MinElute spin column.

350 μl Buffer FRN was added to the RNeasy MinElute spin column and centrifuged for 15 seconds at ≥8000×g (≥10,000 rpm). Flow-through was discarded.

10 μl DNase I stock solution was added to 70 μl Buffer RDD, mixed by gently inverting the tube, and centrifuged briefly to collect residual liquid from the sides of the tube.

The DNase I incubation mix (80 l) was added directly to the RNeasy MinElute spin column membrane, and placed on the benchtop (20-30° C.) for 15 minutes.

500 μl Buffer FRN was added to the RNeasy MinElute spin column and centrifuged for 15 seconds at ≥8000×g (≥10,000 rpm). The flow-through was saved for use in the next step, as it contains small RNAs.

The RNeasy MinElute spin column was placed in a new 2 ml collection tube (supplied). The flow-through from the previous step was applied to the spin column and centrifuged for 15 seconds at ≥8000×g (≥10,000 rpm). Flow-through was discarded.

500 μl Buffer RPE was added to the RNeasy MinElute spin column and centrifuged for 15 second at ≥8000×g (≥10,000 rpm) to wash the spin column membrane.

Flow-through was discarded.

500 μl Buffer RPE was added to the RNeasy MinElute spin column and centrifuged for 15 seconds at ≥8000×g (10,000 rpm) to wash the spin column membrane. Collection tube with the flow-through was discarded.

The RNeasy MinElute spin column was placed in a new 2 ml collection tube and centrifuged at full speed for 5 minutes. The collection tube with the flow-through was discarded.

The RNeasy MinElute spin column was placed in a new 1.5 ml collection tube, 30 μl RNase-free water was added directly to the spin column membrane, incubated for 1 minute at room temperature, and centrifuged at full speed for 1 minute to elute the RNA.

The RNA samples were immediately stored in −80° C. freezer.

cDNA Synthesis

Disclosed below is a procedure of cDNA synthesis for the FFPET SNP Assays using Real time PCR (RT-PCR) analysis.

Required equipment: centrifuge with plate adapter, capable of 1500×g, microcentrifuge; pipettors (preferred single and multi-channel pipettor), positive-displacement or air-displacement; vortexer; and GeneAmp® PCR System 9700 (ABI #4314879) or equivalent.

Required materials: High Capacity cDNA Reverse Transcriptase Kit with RNase Inhibitor, 200 reactions (ABI #4374966); Nuclease Free Water (Non-DEPC treated) (from IDT) or equivalent; RNase-free Barrier (Filter) Tips; RNase-free Microtube (1.5 to 2 mL VWR #10011-724); Micro-Amp™ Optical 96-Well Reaction Plates (Life Technologies, #4306736); and sealing film (VWR #60941-072).

Following the RNA extraction (disclosed above) RNA sample tube(s) were kept on ice.

The kit components were used to prepare 2×Reverse Transcription (RT) Master Mix for all reactions, including 1 negative (water) control. Components were thawed on ice for approximately 15 minutes, gently inverted to mix and centrifuged briefly to bring down the solution. All reagents were returned to the ice. Tubes were not vortexed.

One Master Mix was prepared on ice in a 1.5 ml tube for the appropriate number of reactions (#reactions+10%, per 20-μL reaction) by combining the following amount of reagent per one reaction: 2 μl 10×RT Buffer Mix; 0.8 μl 25×dNTP Mix; 2 μl 10λ RT Random Primers; 1 μl 50U/μL MultiScribe Reverse Transcriptase; 1 μl RNase inhibitor; and 3.2 μl Nuclease/RNase free H$_2$O.

The Master Mix was vortexed several times (5 to 10) to mix and centrifuged briefly (1500×g, 5 to 10 seconds). 10 μl of the reaction mix was added to the appropriate wells of a 96-well plate.

The RNA samples were diluted to a concentration of 20 ng/μl. 10 μL of each RNA sample was added, including the water negative control, to the appropriate corresponding wells of the 96-well plate to a final reaction volume of 20 μL. The wells were mixed gently by pipetting up and down 3 times, sealed with a plate seal, and centrifuged briefly (1500×g for 60 seconds). Plates were kept on ice until ready to load in thermocycler.

The reaction plate was loaded into ABI 9700 Thermal Cycler in Clean Lab or Workstation and run using the following reverse-transcription program with a reaction volume of 20 μl:

Step 1: 25° C. for 10 minutes
Step 2: 37° C. for 120 minutes
Step 3: 85° C. for 5 seconds
Step 4: 4° C. infinite hold Synthesized cDNA was stored at −20° C. for next step of Pre-amplification.

Preamplification Assay Pool Mixture Preparation

The preamp assay pool mixture associated with the FFPET SNP Assay Pre-amplification Protocol was prepared as described below.

Required equipment: microcentrifuge; pipettors, positive-displacement or air-displacement; and vortexer.

Required materials: Nuclease Free Water (Non-DEPC treated) (from IDT) or equivalent; IDTE pH 8.0 (1×TE Solution) (IDT Technologies); RNase-free Barrier (Filter) Tips; and RNase-free Tubes (1.5 to 2 mL VWR #10011-724).

All TaqMan SNP Assays are ordered from Applied Biosystems, Life Technologies, Inc.

100 μL of 20×SNP assays were prepared.

To prepare 0.2×Preamp Assay Pool, all assays were thawed on ice for approximately 15 minutes. The following volume of components was added to a 1.5 ml tube:

TABLE 4

| Target | Stock Concentration | Volume Needed for 200 ul Preamp Stock (ul) |
|---|---|---|
| Preamp Stock 1 | | |
| FGFR3 S249C | 20X | 2 |
| IDTE | | 198 |
| Total Volume | | 200 |
| Preamp Stock 2 | | |
| FGFR3 R248C | 20X | 2 |
| IDTE | | 198 |
| Total Volume | | 200 |
| Preamp Stock 3 | | |
| FGFR3 Y373C | 20X | 2 |
| IDTE | | 198 |
| Total Volume | | 200 |

Note:
The above volumes are for the preparation of 200 μl of 0.2X preamp assay pool. Volumes can be adjusted accordingly depending on the number of samples being tested.

The 0.2×PreAmp Assay Pool was vortexed briefly to mix (5 to 10 seconds) and centrifuged briefly (1500×g, 5-10 seconds). 100 μL of PreAmp Primer Pool was aliquoted into 1.5 ml tubes and stored at −20° C.

Pre-Amplification for the Breast Cancer Formalin-Fixed Paraffin Embedded Tissue SNP Assay Using Real Time PCR (RT-PCR) Analysis Required equipment: centrifuge with plate adapter, capable of 1500×g; microcentrifuge; pipettors, positive-displacement or air-displacement; vortexer; GeneAmp® PCR System 9700 (ABI #4314879) or equivalent.

Required Materials: TaqMan® PreAmp Master Mix (2×) (Life Technologies #4391128); 0.2×Pooled Assay Mix (see Assay Preparation and Handling Protocol); 1×IDTE Buffer (10 mM Tris/0.1 mM EDTA, pH7.5, from IDT) or equivalent; Nuclease Free Water (Non-DEPC treated) (from IDT) or equivalent; RNase-free Barrier (Filter) Tips; RNase-free Microtube (1.5 to 2 mL VWR #10011-724); MicroAmp™ Optical 96-Well Reaction Plates (Life Technologies, #4306736); MicroAmp® Optical Adhesive Film (Applied Biosystems PN 4311971); deep well plates (VWR #47734-788); foil seals (VWR #60941-126).

Samples were prepared by placing the cDNA and 0.2× assay mix pool on ice to thaw, approximately 5 minutes, and centrifuging the plate briefly (1500×g for 5 to 10 seconds).

The kit components were used to prepare 2×PreAmp Master Mix. The kit components were allowed to thaw on ice for approximately 5 minutes. After all reagents were thawed, the tubes were gently inverted to mix and briefly centrifuged to bring down the solution. All reagents were returned to the ice. The tubes were not vortexed.

In a Clean Lab or Biosafety hood, each Master Mix was prepared for the appropriate number of reactions on ice by combining the required volumes of reagents as indicated Table 5 below (#reactions+10%):

TABLE 5

| Component | Volume (μL) for One Reaction |
|---|---|
| Master Mix 1 | |
| 2X TaqMan PreAmp Master Mix | 12.5 |
| 0.2X Assay Pool 1 | 6.25 |
| Total volume | 18.75 |

TABLE 5-continued

| Component | Volume (μL) for One Reaction |
|---|---|
| Master Mix 2 | |
| 2X TaqMan PreAmp Master Mix | 12.5 |
| 0.2X Assay Pool 2 | 6.25 |
| Total volume | 18.75 |
| Master Mix 3 | |
| 2X TaqMan PreAmp Master Mix | 12.5 |
| 0.2X Assay Pool 3 | 6.25 |
| Total volume | 18.75 |

Assay pools contain primers and probes.

To prevent cross-priming of SNP assays, all 5 assays were split into 3 preamp reaction per sample.

Each Master Mix was vortexed several times (5 to 10) to mix, followed by a brief centrifuge (1500×g, 5 to 10 seconds). 18.75 μL of each Master Mix was aliquoted to the appropriate wells in a 96-well reaction plate. 6.25 μL of each cDNA samples, including water negative control well, was transferred into the appropriate wells in the Master Mix reaction plate for each preamp reaction. The sample was mixed gently by pipetting up and down 3 times and the cap was closed. The plate was briefly centrifuged (1500×g for 60 seconds) and kept on ice until ready to load in thermocycler.

The reaction plate ABI 9700 Thermal Cycler was loaded and run using the following program:
Step 1: 95° C. for 10 minutes
Step 2: 95° C. for 15 seconds
Step 3: 60° C. for 4 minutes
Step 4: Set Step 2-3 for 10 cycles
If a gold or silver block was used, max mode was selected and Ramp rate was set at 77%.
If an aluminum block was used, standard mode (no rate change) was selected.
Step 5: 4° C. infinite hold
Reaction volume set to 25 μL The PreAmp reaction plate was centrifuged briefly (1500×g for 60 seconds) after PreAmp completion. 100 μl of IDTE was added to the appropriate wells of a new deep 96-well plate and 25 μL of each PreAmp product was transferred to the corresponding wells to have final dilution volume of 125 μL. The each well was mixed by pipetting up and down 3 times, the plate was sealed with foil adhesive, the plate was centrifuged briefly (1500×g for 5 to 10 seconds), and the PreAmp product was stored at −20° C. until further use.

FFPET SNP Assay Real Time PCR

Disclosed below is the procedure for the Formalin-Fixed Paraffin Embedded Tissue SNP Assay using Real time PCR analysis.

Required equipment: centrifuge with plate adapter, capable of 1500×g; microcentrifuge; pipettors (preferred single and multi-channel pipettor), positive-displacement or air-displacement; vortexer; and ABI ViiA 7 real time PCR instrument (Life Technologies).

Required materials: TaqMan Genotyping Master Mix (Life Technologies #4371355); SNP Assays; Nuclease Free Water (Non-DEPC treated, from IDT) or equivalent; RNase-free Barrier (Filter) Tips; RNase-free Microtube (1.5 to 2 mL VWR #10011-724); MicroAmp® Optical Adhesive Film (Applied Biosystems PN 4311971); and MicroAmp™ Optical 384-Well Reaction Plates.

Table 15 lists the sequences of the probes used during the Real Time PCR assays.

To prepare the samples, in a Clean Lab or Workstation, SNP assays were placed on ice to thaw for approximately 5 minutes. All reagents protected from light, to protect exposure of the fluorescent probes. Diluted PreAmp plates were placed on ice to thaw in a Dirty Lab or Workstation after preparing Genotyping Master Mix.

To prepare genotyping master mix, the Genotyping Master Mix was thawed on ice for approximately 5 minutes. The Master Mix (MM) was prepared in the required number of tubes on ice. The required volumes of reagents were combined in the appropriate labeled tubes as indicated in Table 6 below (#reactions+10%):

TABLE 6

| Component | Volume (μL) for One Reaction |
|---|---|
| 2X Genotyping Master Mix | 10 |
| 20X SNP Assay | 1 |
| RNase-free Water | 4 |
| Total volume | 15 |

20X SNP assay mix contains primers, probes, and blocking oligos.

The Master Mix was vortexed several times (5 to 10) to mix and then centrifuged briefly (1500×g, 5 to 10 seconds). 15 μl of each Master Mix was added to the appropriate wells of a MicroAmp™ Optical 384-Well Reaction Plates. The reaction plates were sealed with optical adhesive film.

The plate with 1:5 diluted PreAmp product was placed on ice for approximately 5-10 minutes to thaw. Using a multi-channel pipettor, 5 μL of each diluted PreAmp product was transferred to the appropriate corresponding wells. The reaction plate was sealed with optical adhesive film and centrifuged briefly (1500×g for 60 seconds). Plates were kept on ice until ready to load in thermocycler.

The following conditions were run using the viiA 7 Software with the volume set at 20 μl:

TABLE 7

| Stage | Repetitions | Process | Temperature | Time |
|---|---|---|---|---|
| 1 | 1 | Initial | 60° C. | 0.5 minutes |
| 2 | 1 | DNApol Activation | 95° C. | 10 minutes |
| 3 | 40 | Denature | 95° C. | 15 seconds |
| | | Anneal/Extend | 60° C. | 1 minutes |
| 4 | 1 | Post-Read | 60° C. | 30 seconds |

FGFR SNP-Specific qRT-PCR

The detection of rare somatic mutations in an excess of wild type alleles is increasingly important in cancer diagnosis. When the mutations of interest are close to each other, detection becomes challenging. To aid in the identification of FGFR SNPs from FFPET, a SNP-specific qRT-PCR assay was developed, in which SNP-specific amplification using Taqman MGB probes combined with the 3' dideoxy wild type (WT) allele blocker was used. The assay prevented non-specific binding, improved the number of on-target amplification, minimized the false positive signals from the WT alleles, and increased the sensitivity of the assay. This RNA based SNP detection assay, combined with the pre-amplification step in the assay, boosts the low or the rare mutant signals.

Figure 3:
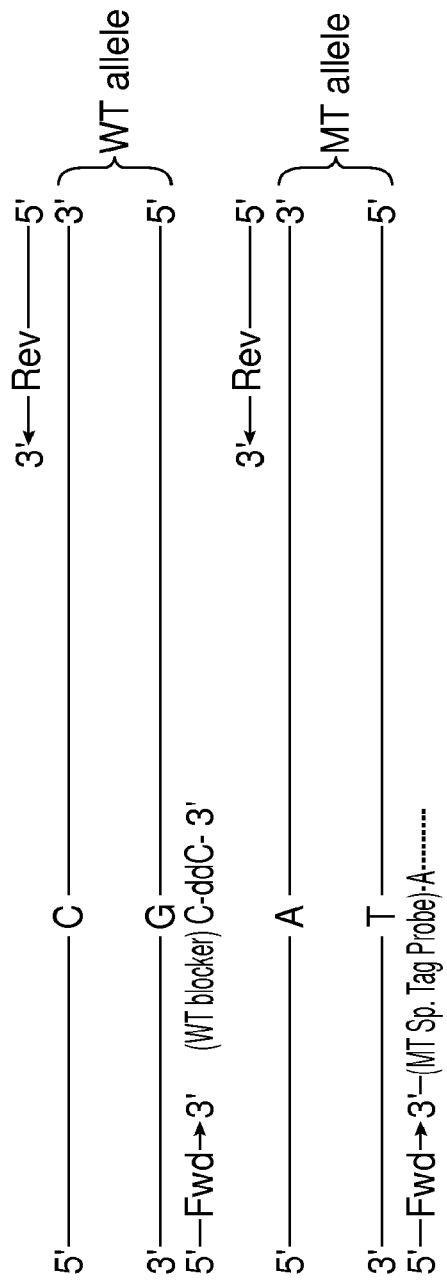
FIG. 3 illustrates an exemplary strategy for SNP-specific qRT-PCR using a 3' dideoxy wild type (WT) blocker oligonucleotide.
Figure 4:
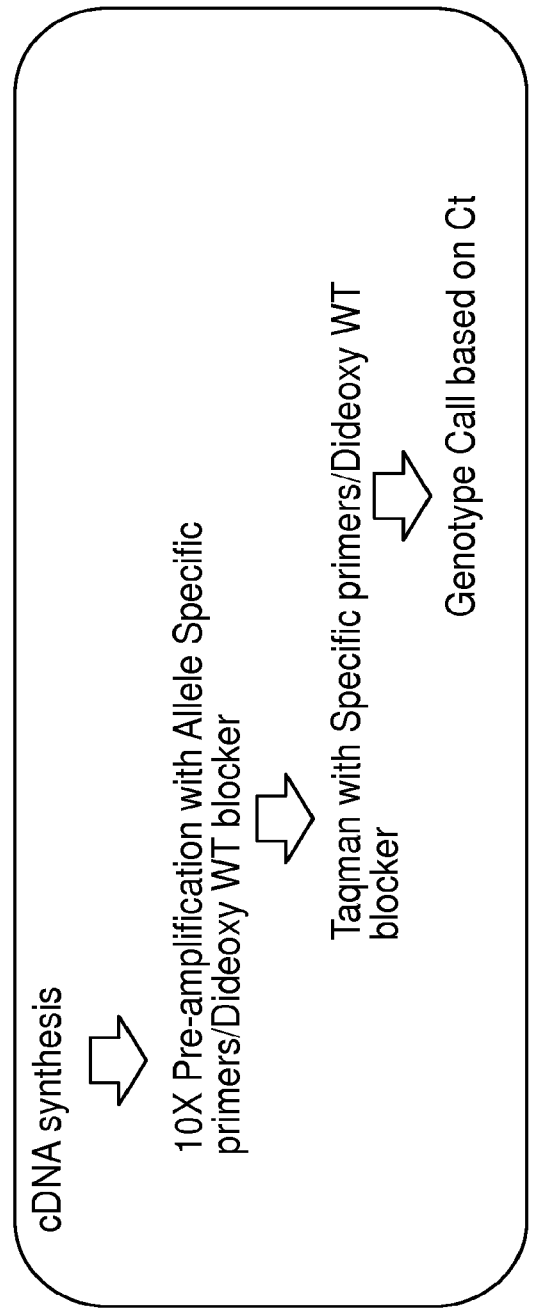
FIG. 4 illustrates an exemplary analytical validation strategy for detecting FGFR SNPs. Experiments were performed on engineered RK3E cell lines expressing the FGFR fusions and diluted into a wild type cell line harboring no FGFR3/FGFR2 fusions.
Figure 5C:
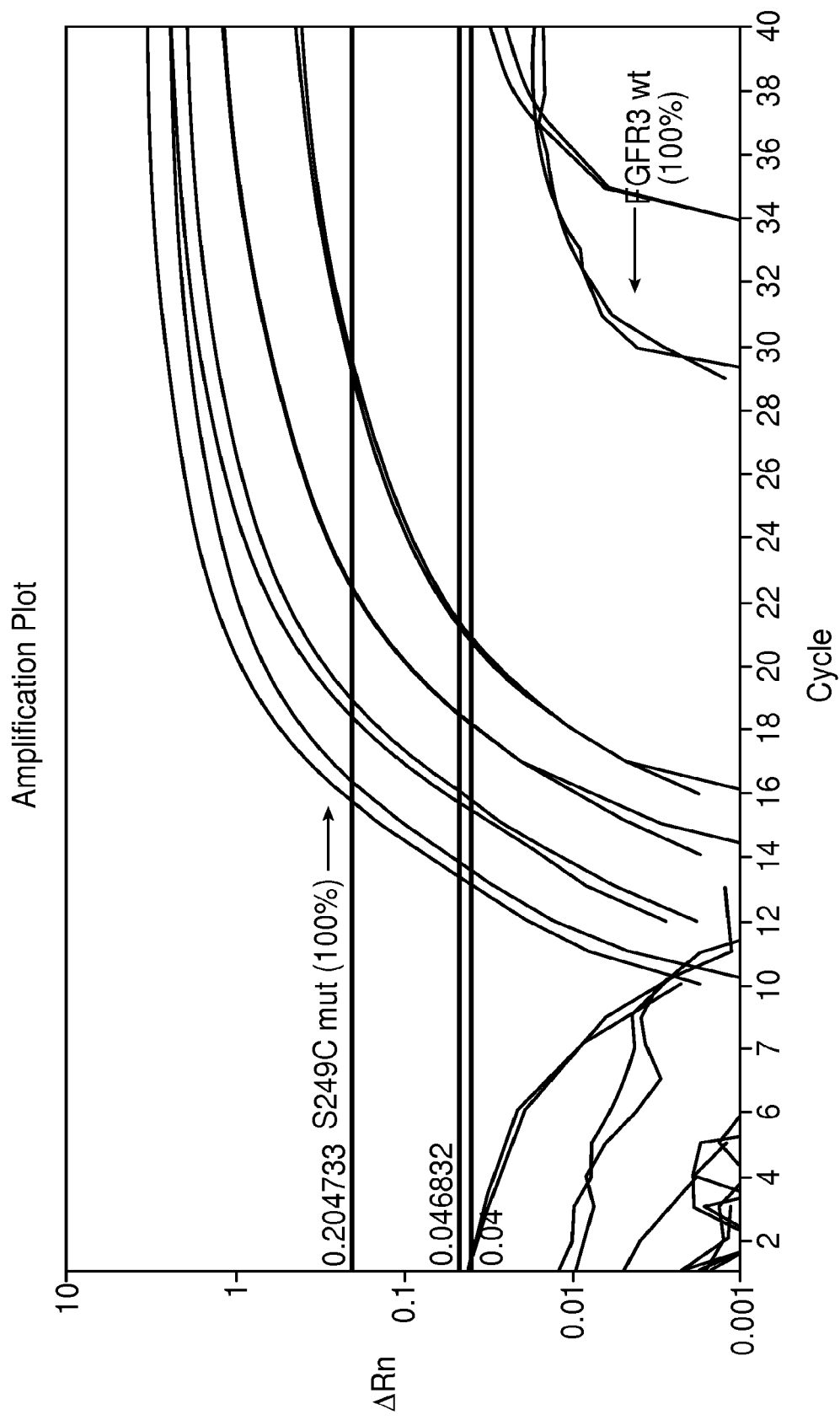
Figure 6B:
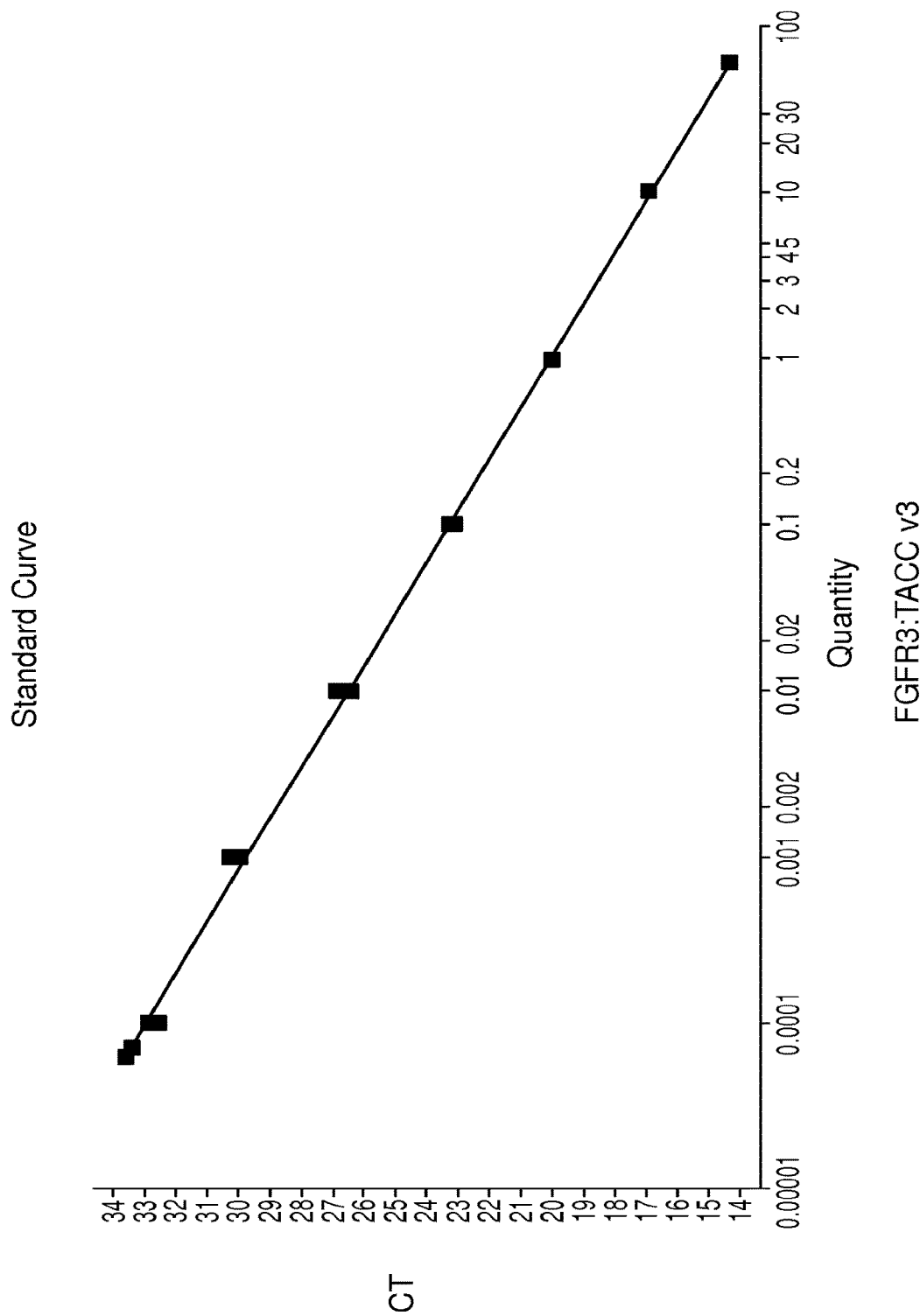
Figure 6H:
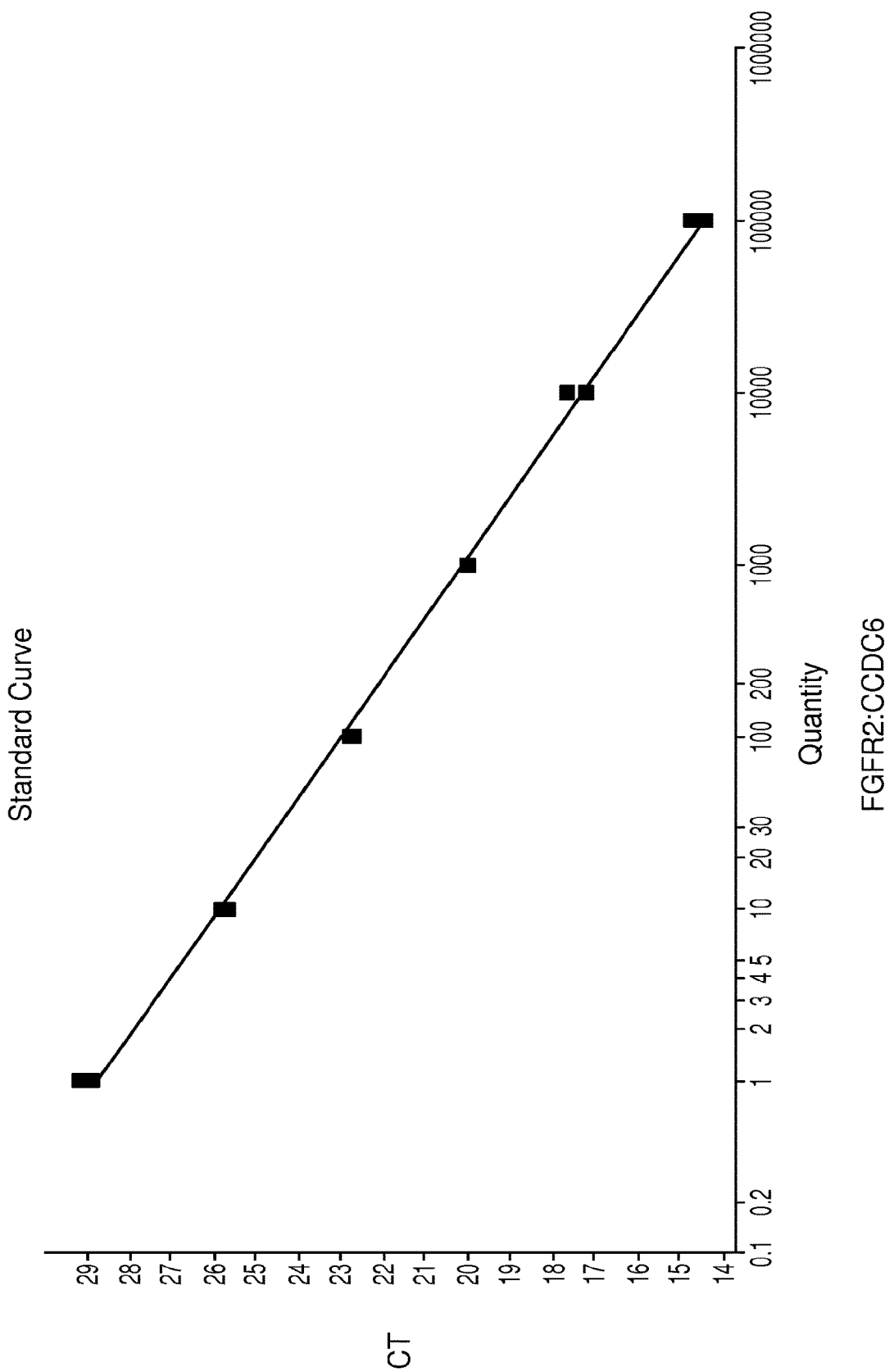
Figure 6I:
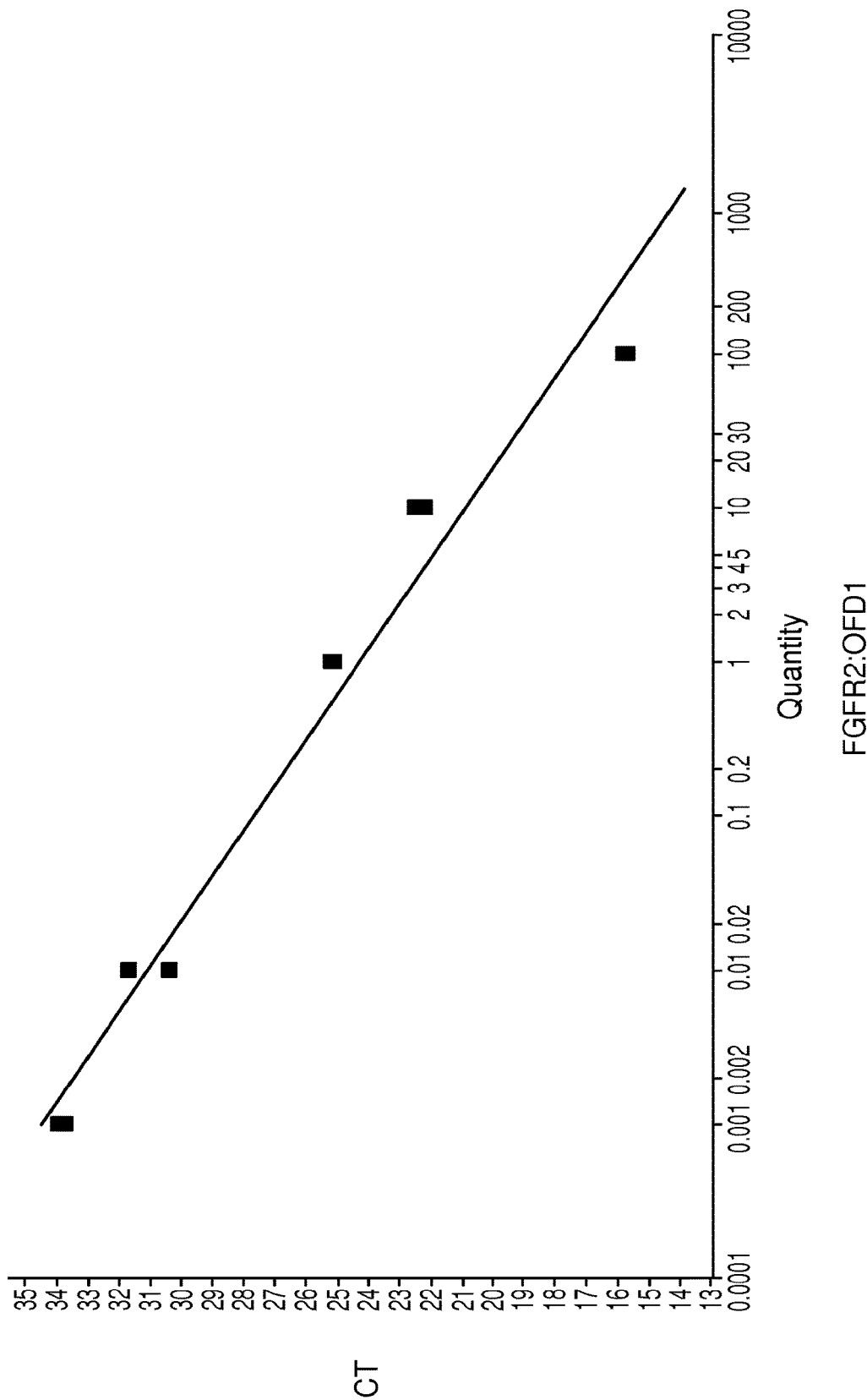

An exemplary strategy for SNP-specific qRT-PCR using a 3' dideoxy WT blocker oligonucleotide is shown in FIG. 3, and an exemplary FFPE sample validation strategy is illustrated in FIG. 4. Briefly, qRT-PCR was performed using the FGFR SNP primers in the presence of a 3' dideoxy WT blocker oligonucleotide, which was complementary to, and contained a short stretch of nucleotides flanking, the WT allele. Binding of the blocker oligonucleotide to the WT allele prevented applification of the WT allele, while the FGFR SNP primers bound to and specifically amplified the FGFR SNP. The 3' dideoxy WT blocker oligonucleotides used in the FGFR SNP-specific qRT-PCR are shown in Table 8. The FGFR SNP primers used in the FGFR SNP-specific qRT-PCR were: SEQ ID NO:31 and SEQ ID NO:32 (FGFR3 R248C); SEQ ID NO:33 and SEQ ID NO:34 (FGFR3 S249C); SEQ ID NO:35 and SEQ ID NO:36 (FGFR3 G370C); and SEQ ID NO:37 and SEQ ID NO:38 (FGFR3 Y373). Table 15 lists the sequences of the probes used during the real time PCR assays.

TABLE 8

| Target | 3' dideoxy WT blocker oligonucleotide |
|---|---|
| FGFR3 R248C | TGGAGCGCTCCCCGCA-ddC (SEQ ID NO: 39) |
| FGFR3 S249C | GACGTGCTGGAGRGCTC-ddC (SEQ ID NO: 40)* |
| FGFR3 G370C | CTGACGAGGCGGGCAG-ddC (SEQ ID NO: 41) |
| FGFR3 Y373 | GTGTGTATGCAGGCATCCTCAG-ddC (SEQ ID NO: 42) |

*R can be A or G. 3' WT blocking oligo will have 50% A and 50% G at that particular position during the synthesis (purified by manufacturer to provide A or G at that particular position).

Samples for validation studies were prepared as shown in Table 9. Exemplary validation data of the SNP-specific qRT-PCR using a 3' dideoxy WT blocker oligonucleotide for FGFR3 G370C, FGFR3 Y373, FGFR3 S249C, and FGFR3 R248C is illustrated in FIGS. 5A-5D, respectively. Raw Ct (cycle threshold) data for the FFPE samples with SNP-specific qRT-PCR with 3' dideoxy WT blocker oligonucleotides are shown in Table 10. The data derived from DNA and RNA using different platforms/techniques suggests that SNP-specific PCR with the 3' blocking nucleotide is a robust, reliable and a sensitive assay. The validation data suggests that one mutant allele/SNP can be detected in a large excess of WT-bearing genomic DNA, thus emphasizing the sensitivity and the specificity of each assay.

TABLE 9

| Sample | % Mutant |
|---|---|
| 1 | 100 |
| 2 | 20 |
| 3 | 4 |
| 4 | 0.8 |
| 5 | 0 (100% WT) |

RNA from Stable cell lines expressing each FGFR3 SNPs (R248C, S249C, G370C, Y373C) and FGFR3 WT

TABLE 10

| | FGFR3 SNPs-SNP-Specific PCR with Dideoxy WT Blocker (Ct *) | | | | | Janssen R&D |
|---|---|---|---|---|---|---|
| Pt Id# | R248C | S249C | G370C | Y373C | FMI/NGS | ver1.0 |
| 7502 | >35 | 28.03 | >35 | >35 | S249C | S249C |
| 10000305 | >35 | >35 | >35 | >35 | WT | WT |
| 33000127 | >35 | 20.92 | >35 | >35 | S249C | S249C |
| 33000118 | >35 | 29.35 | >35 | >35 | S249C | S249C |
| 10000306 | >35 | >35 | >35 | 24.30 | Y373C | Y373C |

TABLE 10-continued

| | FGFR3 SNPs-SNP-Specific PCR with Dideoxy WT Blocker (Ct *) | | | | | Janssen R&D |
|---|---|---|---|---|---|---|
| Pt Id# | R248C | S249C | G370C | Y373C | FMI/NGS | ver1.0 |
| 34000226 | >35 | >35 | >35 | >35 | WT | WT |
| 16446 | >35 | 28.03 | >35 | >35 | S249C | S249C |

*Mean of two Cts
FMI/NGS = Next generation Sequencing technique wherein DNA is used as an template to identify the mutations (without 3' blocking oligonucleotide); Janssen R&D = performed on RNA template (without the 3' blocking oligonucleotide); SNP-specific PCR performed on RNA template with the 3' blocking nucleotide.

Example 5—Validation of Custom FGFR Fusion Gene Detection Assay

Generation of Positive Controls for FGFR Fusion Assays

FGFR fusion "synthetic mini-genes," plasmids encoding FGFR fusions, and stable cell lines containing FGFR fusions were generated. Briefly, Synthetic mini genes were artificially constructed by linking a series of nucleotides, of about 100 base pairs, to each other corresponding to the target DNA sequence of the gene of interest. Plasmids encoding FGFR fusions were generated by cloning cDNA encoding the various FGFR fusion genes into an expression vector. Stable cell lines containing FGFR fusions were generated by transfecting plasmids encoding FGFR genes into normal rat kidney epithelial cells (NRK cells). The stable cell lines were selected under the G418 antibiotic. The FGFR fusion Taqman assay was performed on the total RNA isolated from these cell lines to confirm the successful generation of stable cell line(s) expressing the FGFR fusion(s). The stable cell lines expressing FGFR fusions are used a positive control. Table 15 lists the sequences of the probes used during the real time PCR assays.

Analysis of Lower Limit of Quantitation and Efficiency of FGFR Fusion Assays

To determine the lower limit of quantitation (LLOQ) and efficiency of the FGFR fusion gene assays, FGFR fusion products were generated by TaqMan PCR (as described in Example 4) and confirmed by Sanger Sequencing (FIGS. 2A-2I). 100 µg of fusion positive DNA was mixed with normal human cDNA (confirmed fusion-negative), serially diluted 1:10, and analyzed using the Applied Biosystems ViiA7 Software v1.1. Efficiency standard curves are shown in FIGS. 6A-6I. FGFR fusion LLOQ and efficiency are shown in Table 11.

TABLE 11

| Assay | LLOQ | Efficiency |
|---|---|---|
| FGFR3:TACC3 V1 | 1.0 fgm | 104% |
| FGFR3:TACC3 V3 | 10.0 fgm | 104% |
| FGFR3:TACC3 Intron | 0.1 fgm | 103% |
| FGFR3:BAIAP2L1 | 1.0 fgm | 101% |
| FGFR2:AFF3 | 0.1 fgm | 106% |
| FGFR2:BICC1 | 10.0 fgm | 105% |
| FGFR2:CASP7 | 0.1 fgm | 109% |
| FGFR2:CCDC6 | 1.0 fgm | 106% |
| FGFR2:OFD1 | 0.1 fgm | 96.6% |

The FGFR fusion gene assay was next validated in fusion gene-positive cell lines. FGFR fusion gene expression, serial dilutions were prepared by spiking fusion protein-positive cells lines into a fusion protein-negative cell line. For example, a 1:2 serial dilution was prepared for both FGFR3:TACC3v1 and FGFR3:BAIAP2L1 and spiked into 1 million BAF cells. RNA was isolated (using Qiagen Rneasy kit), followed by RT-PCR, preamplification of cDNA, and TaqMan Real Time PCR for the targeted FGFR fusion gene. As shown in Table 12, both the FGFR3:TACC3v1 and FGFR3:BAIAP2L1 Fusion Gene TaqMan assays are able to detect the fusion target in 31 out of 1 million fusion-negative cells (sensitivity of 0.003%).

TABLE 12

|  | FGFR-fusion Cell Count | Percent of Fusion-Positive Cells vs Background | RT112 FGFR3:TACC3v1 Average Ct (n = 2) | SW780 FGFR3:BAIAP2L1 Average Ct (n = 2) |
|---|---|---|---|---|
| Positive Control | 1.00E+06 | 100% | 17.56 | 20.35 |
|  | 1000 | 0.1000% | 27.95 | 28.61 |
|  | 500 | 0.0500% | 29.11 | 28.91 |
|  | 250 | 0.0250% | 29.62 | 30.14 |
|  | 125 | 0.0125% | 30.26 | 31.43 |
|  | 62.5 | 0.0063% | 31.19 | 31.69 |
| LLOD | 31.25 | 0.0031% | 32.59 | 32.97 |
|  | 15.6 | 0.0016% | 34.91 | >40 |
|  | 0 | 0.0000% | 0.00 | >40 |

RT112 and SW780 = commercially available bladder cancer cell lines harboring the FGFR fusions (from American Type Culture Collection).

Example 6—Validation of Custom FGFR SNP Detection Assay

Evaluation of FGFR3 Mutations in Bladder Cancer

The R248C, S249C, and Y373C SNPs were observed in approximately 8%, approximately 61%, and approximately 19% of bladder cancer samples tested, respectively.

Example 7—Analysis of Cancer Samples

Figure 7:
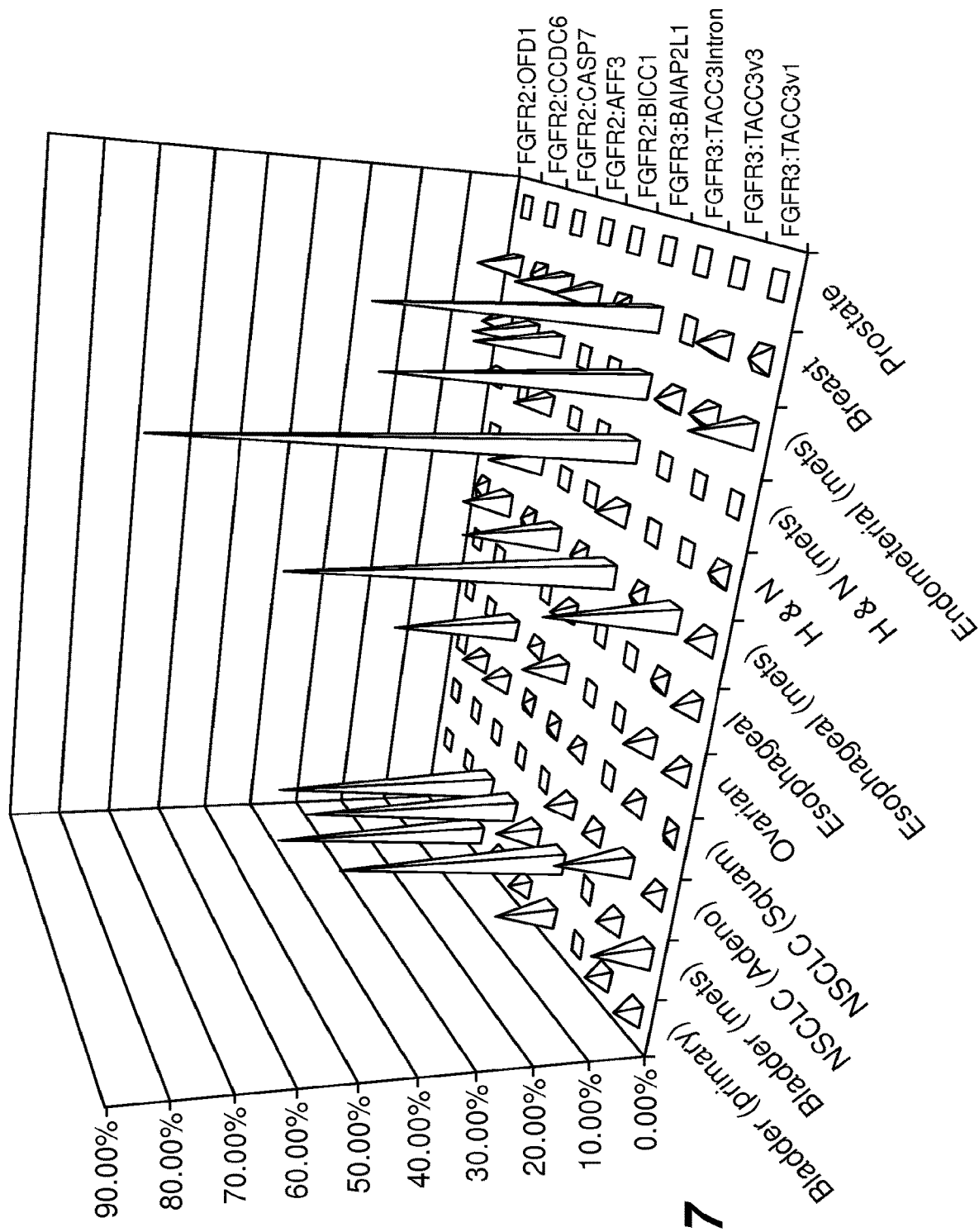
FIG. 7 is an exemplary representation of FGFR fusion gene status in bladder (primary and metastatic), NSCLC (adenocarcinoma and squamous), ovarian, esophageal (primary and metastatic), head and neck (H&N; primary and metastatic), endometrial (metastatic), breast, and prostate cancer.

Samples were analyzed using the same procedure as described in example 4. The results are shown in Table 13 and FIG. 7. Table 13 shows the FGFR fusion prevalence in different cancers. FGFR fusions detected in FFPE samples from different cancers such as bladder (primary and metastatic), NSCLC (adenocarcinoma and squamous), ovarian, esophageal (primary and metastatic), head and neck (H&N; primary and metastatic), endometrial (metastatic), breast, and prostate cancer using the qRT-PCR method. All FGFR fusions tested were negative for prostate cancer samples. FGFR3:TACC3intron fusion was negative in bladder (primary), NSCLC (squamous), ovarian and esophageal (primary), H&N (primary and metastatic) and breast. FGFR2:OFD1 fusion was negative in bladder (primary and metastatic), NSCLC (adenocarcinoma), ovarian and esophageal (primary and metastatic). FGFR2:CCDC6 fusion was negative in bladder (primary and metastatic), NSCLC (adenocarcinoma), ovarian and esophageal (primary) and H&N (primary and metastatic)

Figure 8:
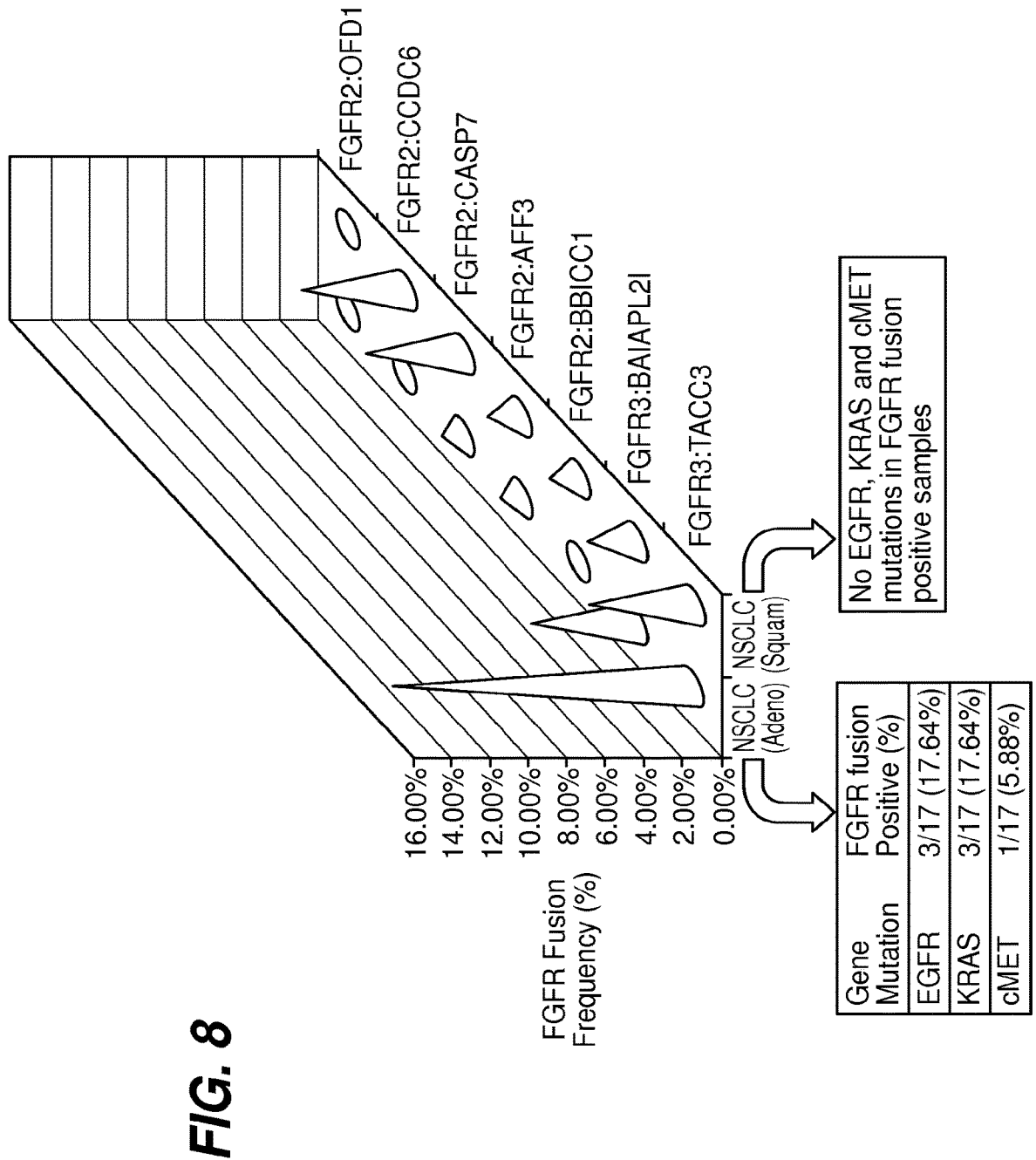
FIG. 8 is an exemplary representation of FGFR fusion gene and mutation status in NSCLC adenocarcinoma and squamous cell carcinoma.

FIG. 8 is an exemplary representation of FGFR fusion gene and mutation status in NSCLC adenocarcinoma and squamous cell carcinoma. In FGFR fusion positive NSCLC adenocarcinoma samples, 3/17 samples were positive for EGFR mutation, 3/17 samples were positive for KRAS mutation, and 1/17 samples were positive for cMET mutation. No EGFR, KRAS, or cMET mutations, however, were observed in FGFR fusion positive NSCLC squamous cell carcinoma samples.

TABLE 13

|  | Bladder primary (%) | Bladder Mets (%) | NSCLC Adeno (%) | NSCLC Squamous (%) | Ovarian (%) | Eso Primary (%) | Eso Mets (%) | H&N Primary (%) | H&N Mets (%) | Endo Mets (%) | Breast (%) | Prostate (%) |
|---|---|---|---|---|---|---|---|---|---|---|---|---|
| FGFR3: TACC3v1 | 1/22 (4.55) | 5/48 (10.47) | 3/89 (3.37) | 2/125 (1.60) | 4/94 (4.26) | 2/41 (4.88) | 2/42 (4.76) | 1/37 (2.70) | 0/40 (0.00) | 5/46 (10.87) | 3/112 (2.69) | 0/72 (0.00) |
| FGFR3: TACC3v3 | 1/22 (4.55) | 2/48 (4.20) | 9/89 (13.90) | 5/129 (3.38) | 5/94 (5.32) | 1/41 (2.44) | 10/42 (23.81) | 0/37 (0.00) | 0/40 (0.00) | 2/46 (4.35) | 6/112 (5.36) | 0/72 (0.00) |
| FGFR3: TACC3Intron | 0/22 (0.00) | 0/48 (0.00) | 3/89 (3.37) | 0/125 (0.00) | 0/94 (0.00) | 0/41 (0.00) | 1/42 (2.38) | 0/37 (0.00) | 0/40 (0.00) | 2/46 (4.35) | 0/112 (0.00) | 0/72 (0.00) |
| FGFR3: BAIAP2L1 | 2/17 (11.77) | 19/44 (43.18) | 5/89 (5.62) | 3/115 (2.61) | 1/94 (1.06) | 0/41 (0.00) | 25/42 (59.52) | 2/37 (5.41) | 34/40 (85.00) | 22/46 (47.83) | 56/112 (50.00) | 0/72 (0.00) |
| FGFR2: BICC1 | 1/22 (4.55) | 4/48 (8.33) | 0/89 (0.00) | 2/123 (1.63) | 8/94 (8.51) | 2/41 (4.88) | 1/42 (2.40) | 0/37 (0.00) | 0/40 (0.00) | 0/46 (0.00) | 3/112 (2.70) | 0/72 (0.00) |
| FGFR2: AFF3 | 1/17 (5.88) | 19/44 (43.18) | 1/89 (1.12) | 2/111 (1.80) | 2/94 (2.31) | 0/41 (0.00) | 8/42 (19.05) | 0/37 (0.00) | 0/40 (0.00) | 0/46 (0.00) | 10/112 (8.90) | 0/72 (0.00) |
| FGFR2: CASP7 | 7/16 (43.75) | 20/45 (44.44) | 1/89 (1.12) | 6/114 (5.26) | 24/94 (25.53) | 2/41 (4.88) | 1/42 (2.40) | 4/37 (10.81) | 3/40 (7.50) | 8/46 (17.40) | 12/112 (10.70) | 0/72 (0.00) |
| FGFR2: CCDC6 | 0/22 (0.00) | 0/48 (0.00) | 0/89 (0.00) | 6/109 (5.50) | 0/94 (0.00) | 0/41 (0.00) | 4/42 (9.52) | 0/37 (0.00) | 0/40 (0.00) | 6/46 (13.04) | 3/112 (2.70) | 0/72 (0.00) |
| FGFR2: OFD1 | 0/17 (0.00) | 0/44 (0.00) | 0/89 (0.00) | 1/121 (0.83) | 0/94 (0.00) | 0/41 (0.00) | 1/42 (2.40) | 0/37 (0.00) | 3/40 (7.50) | 3/46 (6.52) | 10/112 (8.90) | 0/72 (0.00) |

Eso = Esophageal;
Endo = Endometerial

Example 8—Treatment of Patients with Advanced Solid Tumors

Figure 9A:
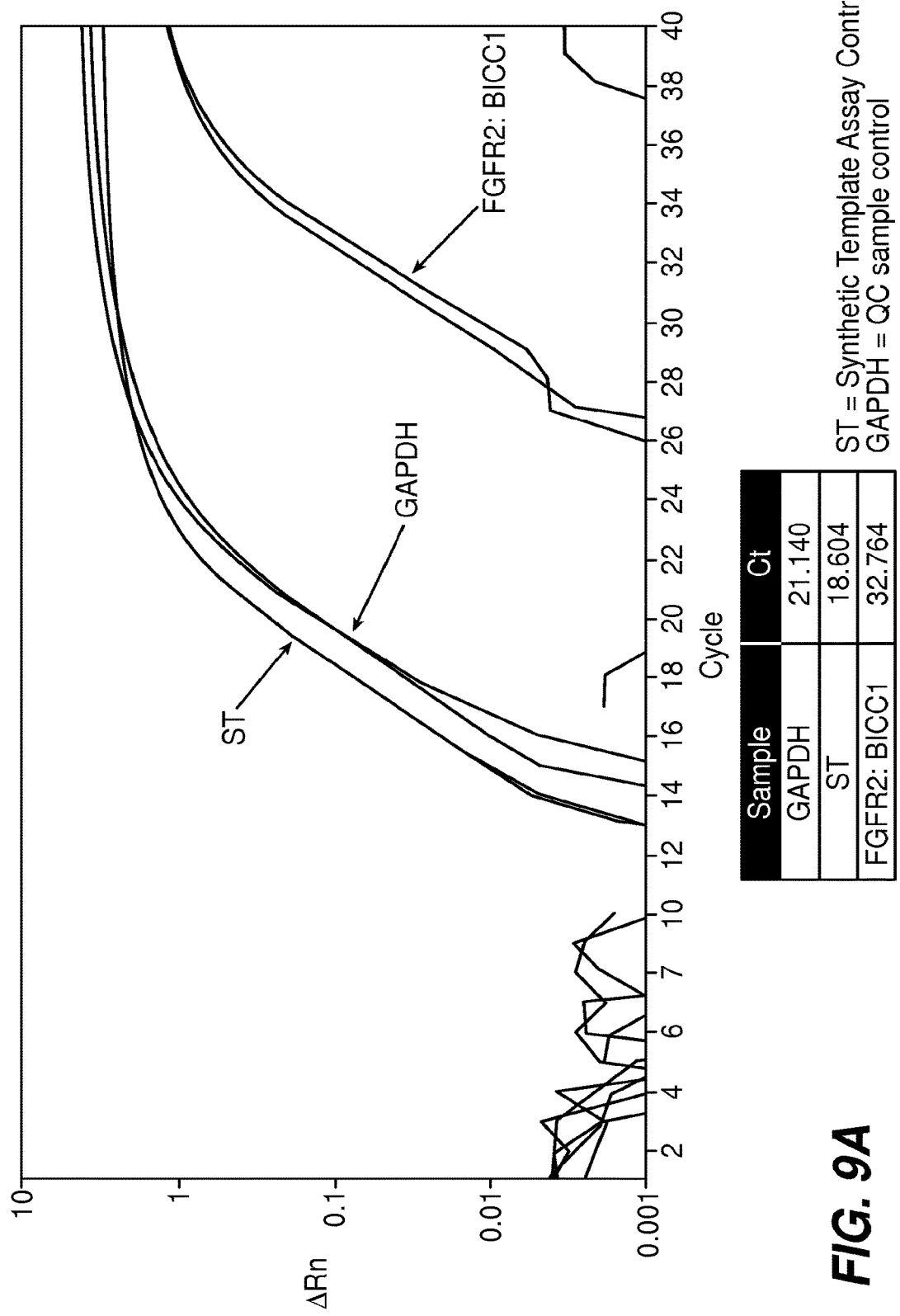
Figure 9B:
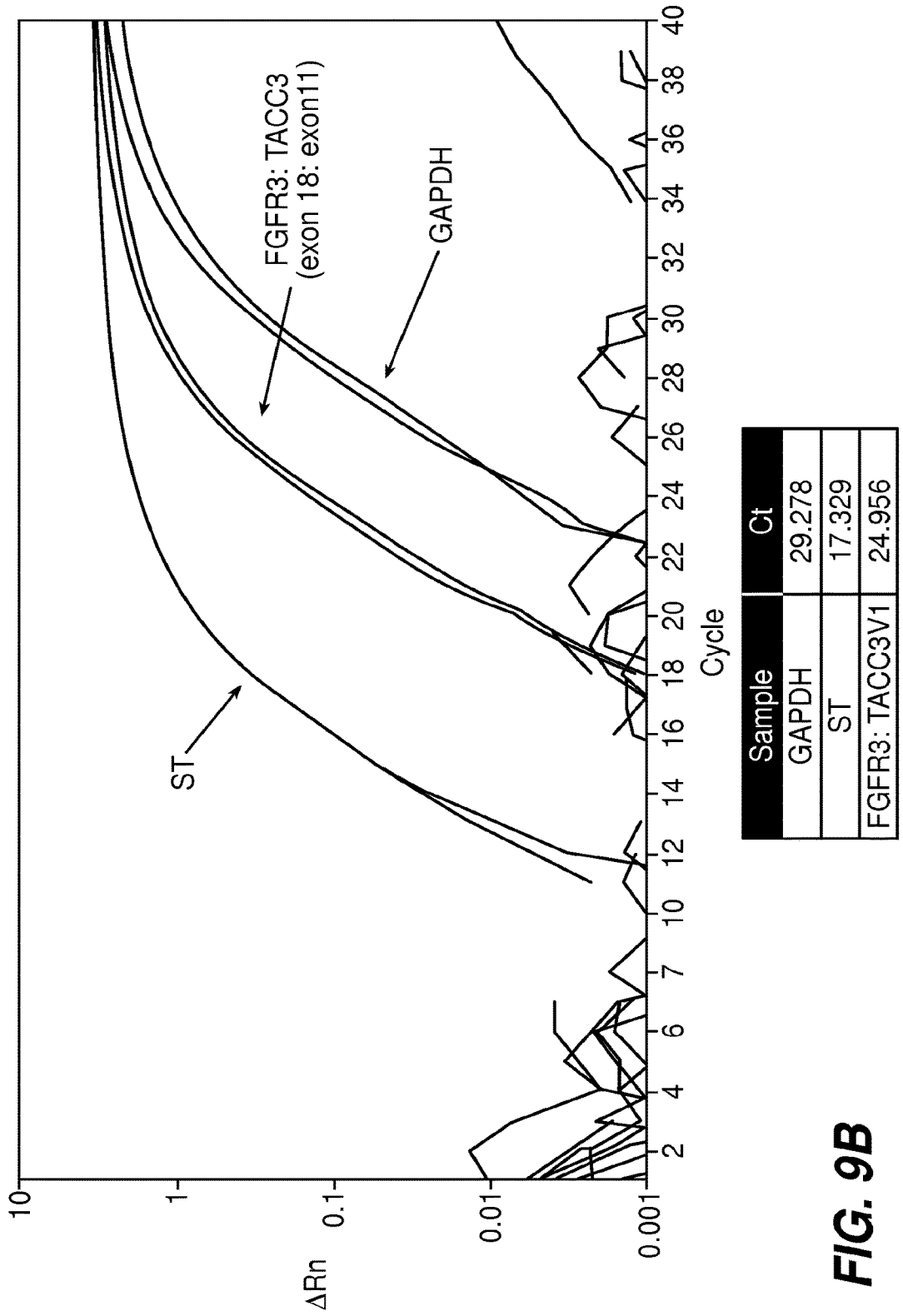
Figure 9C:
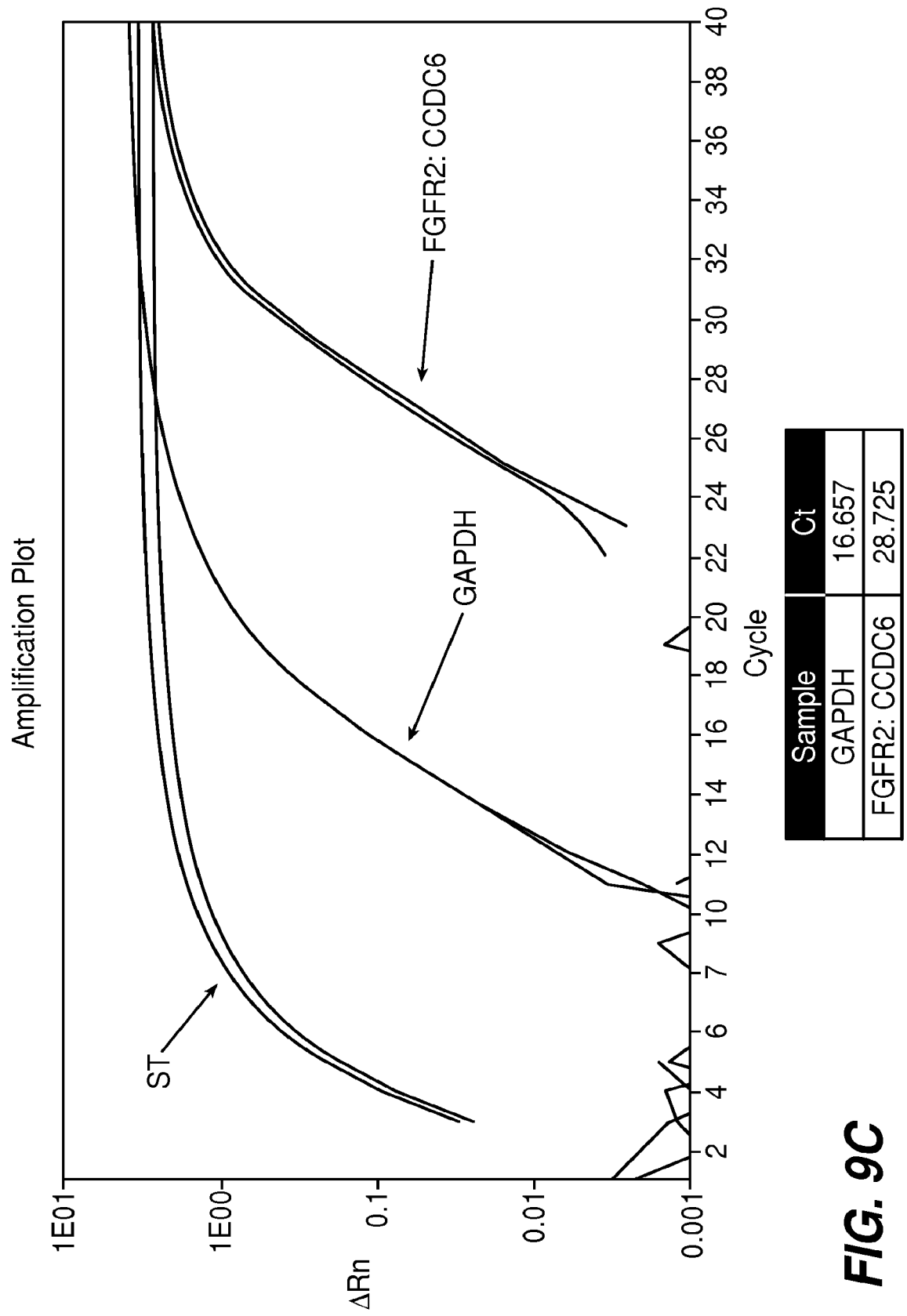
Figure 9D:
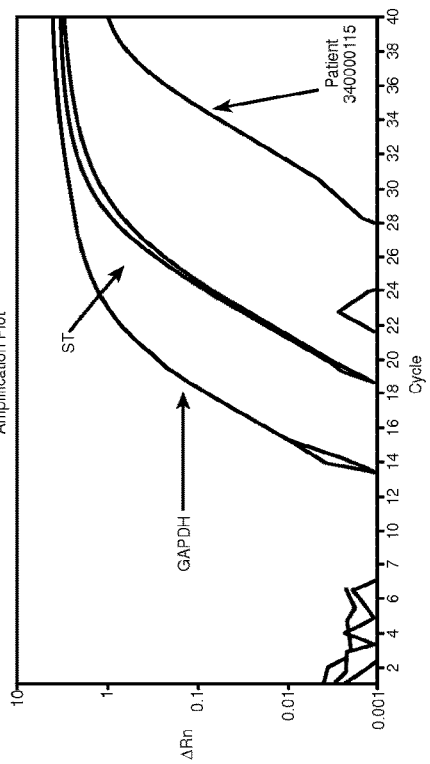
Figure 9D:
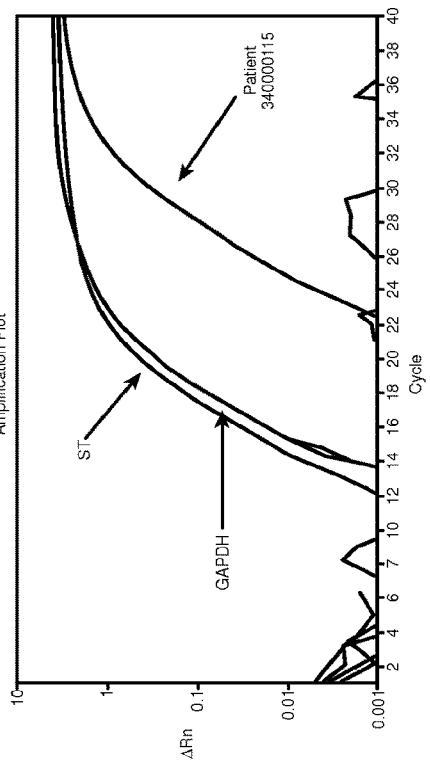
Figure 9D:
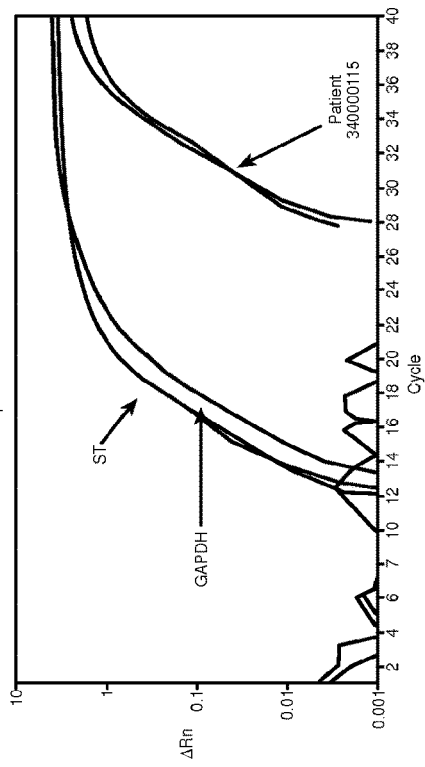

A clinical trial was conducted in which patients having various solid tumors expressing the FGFR3:TACC3 v1, FGFR3:TACC3 v3, FGFR2:CCDC6 and FGFR2:BICC1 fusion genes were treated with JNJ-42756493. FIGS. 9A-9D illustrates exemplary results from phase I patient samples, in which FGFR fusions in Phase I JNJ-427493 (EDI10001) trial samples were detected using the qRT-PCR assay. All FGFR fusion assays were run simultaneously with positive controls (ST) and GAPDH for quality control assessment of the RNA. FIG. 9A) Graphical representation of the qRT-PCR data generated for pt #1000081: positive only for FGFR2:BICC1 fusion (inset shows details of the Ct values for FGFR2:BICC1 fusion, ST-positive control and GAPDH). FIG. 9B) Graphical representation of the qRT-PCR data generated for pt #33000158: positive only for FGFR3:TACC3v1 fusion (inset shows details of the Ct values for FGFR3:TACC3v1 fusion, ST-positive control and GAPDH). FIG. 9C) Graphical representation of the qRT-PCR data generated for pt #34000123: positive only for FGFR2:CCDC6 fusion (inset shows details of the Ct values for FGFR2:CCDC6 fusion, ST-positive control and GAPDH). FIG. 9D) Graphical representation of the qRT-PCR data generated for pt #340000115: positive for FGFR3:TACC3v1, FGFR3:TACC #v3 and FGFR2:CCDC6 fusions (inset shows details of the Ct values for FGFR fusions, ST-positive controls and GAPDH).

Figure 10:
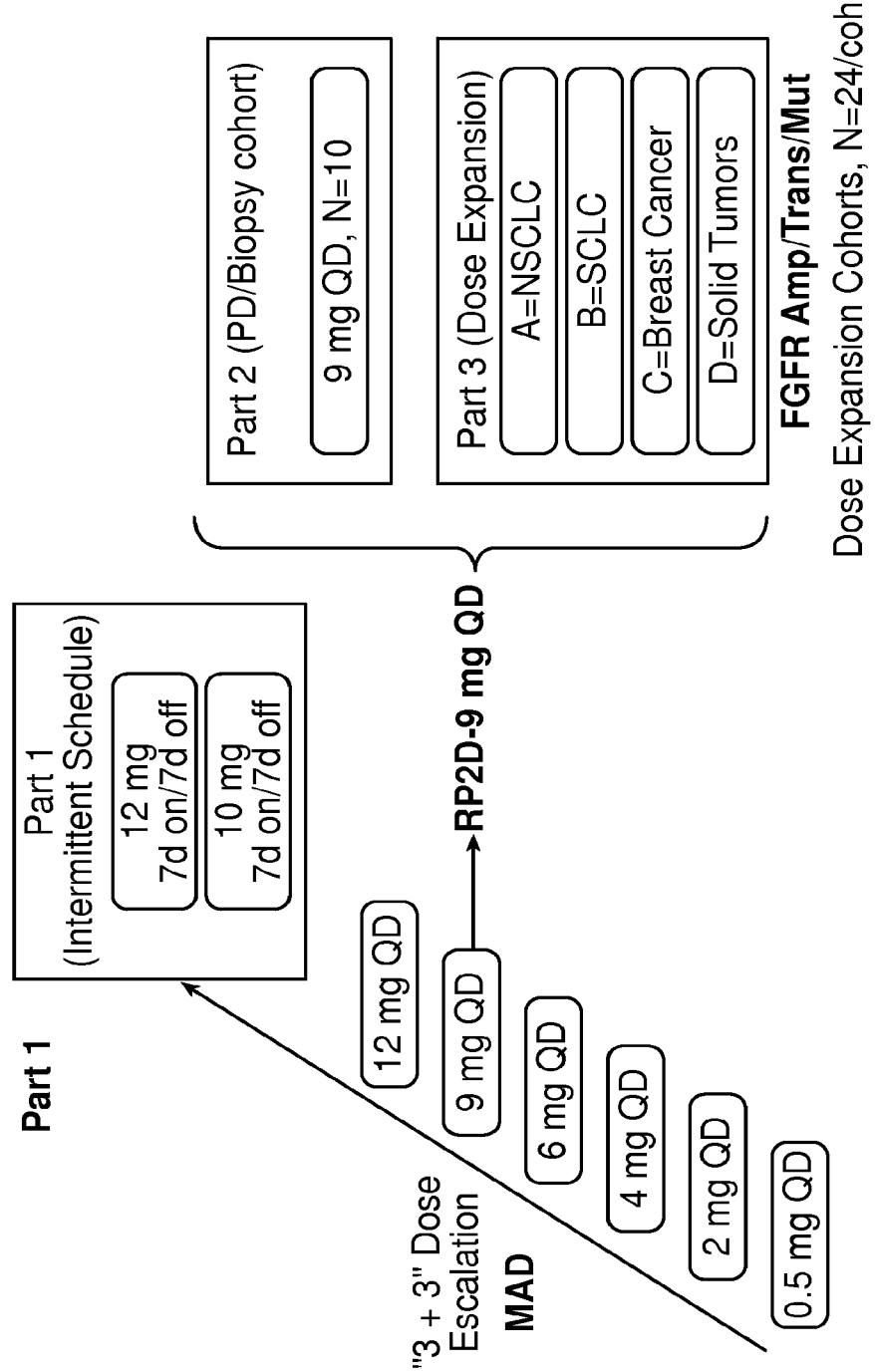
FIG. 10 represents an exemplary Phase I Study design for a First-In-Human Study of JNJ-42756493 in patients with advanced solid tumor.

FIG. 10 represents an exemplary Phase I Study design for a First-In-Human Study of JNJ-42756493 in patients with advanced solid tumor. Shown is a graphical depiction of a traditional 3+3 design dose escalation method for the phase I clinical trial. The dose escalation phase aimed to establish the maximum tolerated dose (MTD) and recommended Phase II dose (RPD). The Part 1 arm was used to determine the intermittent dosing schedule, i.e., 7 days on and seven days off (10 mg/kg and 12 mg/kg). The Part 2 arm was used to determine the PD biomarkers (pharmacodynamics biomarkers; makers examined to link the effect of the drug to the target and biological tumor response) wherein the biopsy and blood sample were tested. The Part 3 arm was used the dose expansion cohort and included accrual of additional patients in specific indications (NSCLC, SCLC, breast and solid tumors) with different eligibility criteria (FGFR aberrations: translocation/mutation/amplifications) to further characterize the toxicity profiles of the JNJ493.

Evaluation of Clinical Activity

Figure 11:
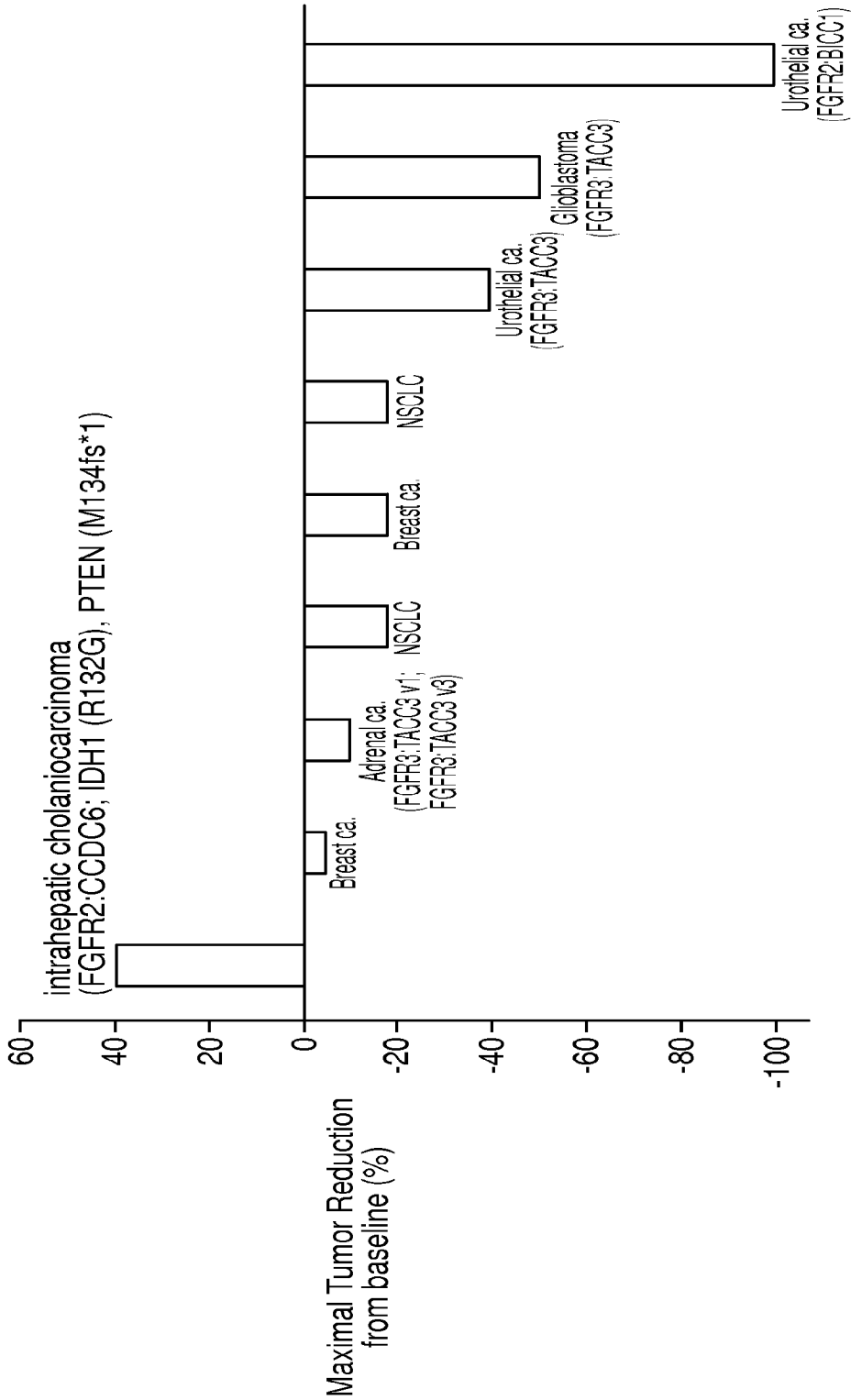
FIG. 11 represents the maximal inhibitory percentage reduction of sum of the diameters of targeted lesions from baseline with dose level greater than or equal to 6 mg. Solid tumor patients were treated with the FGFR inhibitor JNJ-42756493 at different doses administered either as a daily regimen or as an intermittent dosing regimen (7 days on –7 days off). Doses and tumor types are indicated. Reduction in tumor was measured as per the RECIST criteria. Patients whose tumors harbor FGFR gene translocations and mutations appear to be more sensitive to the FGFR inhibitor JNJ-42756493.

Significant clinical responses (RECIST) were observed at 9 mg dosing once a day (QD), 12 mg QD and 12 mg 7d on/off in patients with the FGFR fusion genes. (FIG. 11; represents all dosing regimens).

Example 9—Generation of FGFR Fusion Stably Transfected RK3E Cells

FGFR Fusion Overexpressing Cell Lines

Figure 12:
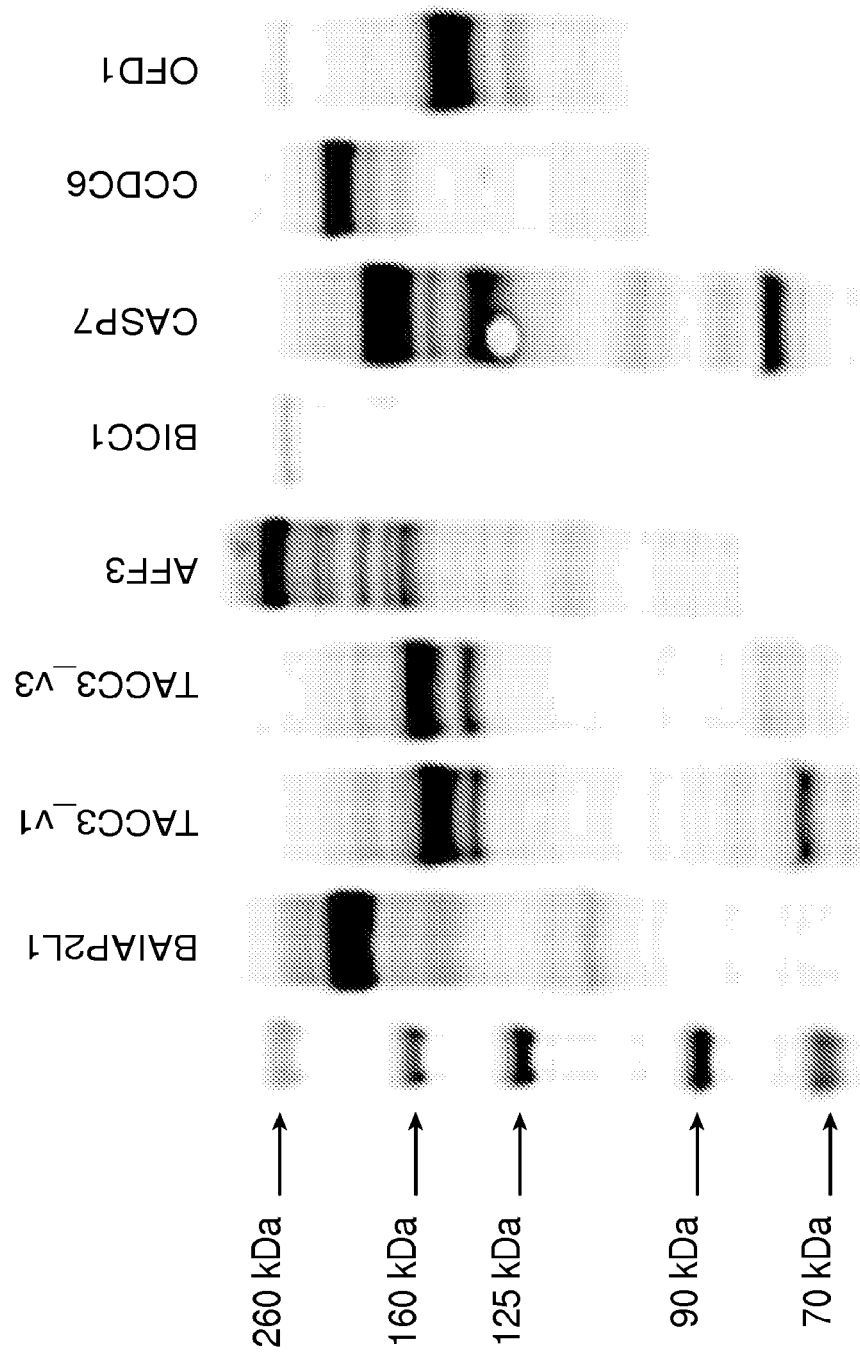
FIG. 12 illustrates the expression of various FGFR fusions in RK3E cells stably transfected with the indicated FGFR fusion.

RK3E (rat kidney epithelial cells) cells were purchased from ATCC (Manassas, VA, USA) and cultured in DMEM supplemented with FBS and antibiotics (Invitrogen, Grand Island, NY, USA). FGFR fusion gene constructs were designed and cloned into the pReceiver expression vector (Genecopoeia, Rockville, MD, USA), which contains an HA-tag. Clones were transfected into RK3E cells using the Amaxa Cell Line Nucleofector (Lonza, Basel, Switzerland) following the manufacturer's protocol. The stably transfected cells were selected in complete medium with 800 ug/ml of G418 (Invitrogen). Overexpression of the fusions in the stably transfected cells was confirmed by real-time PCR and immunoblotting using an anti-pFGFR antibody (FIG. 12). As shown in FIG. 12, the stable cell lines showed expression of active FGFR fusion kinases, as exhibited by the expression of phosphorylation of FGFR.

Colony Formation Assay

Figure 13A:
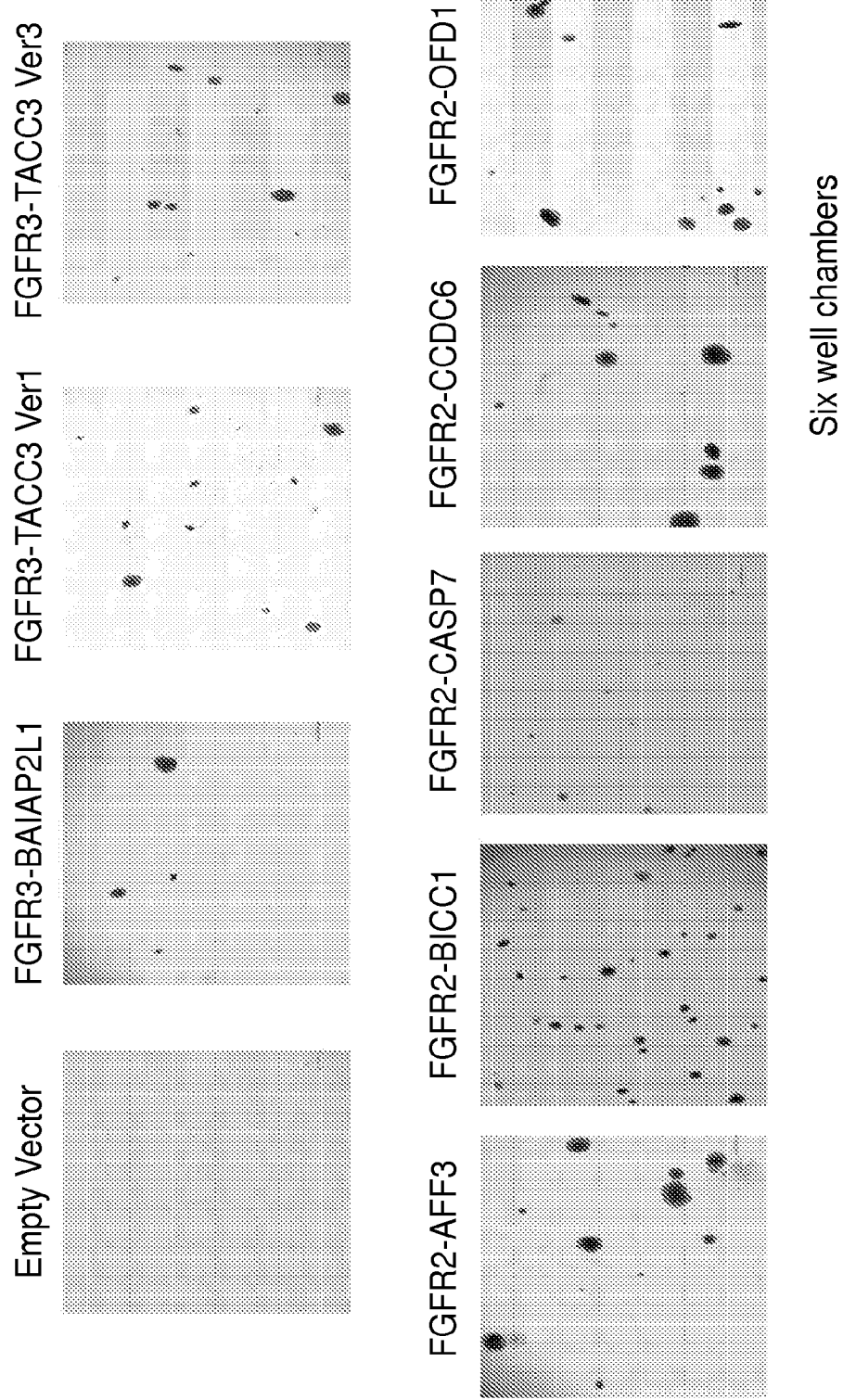
FIGS. 13A-13B illustrate colony formation assays in RK3E cells stably transfected with the indicated FGFR fusion.
Figure 13B:
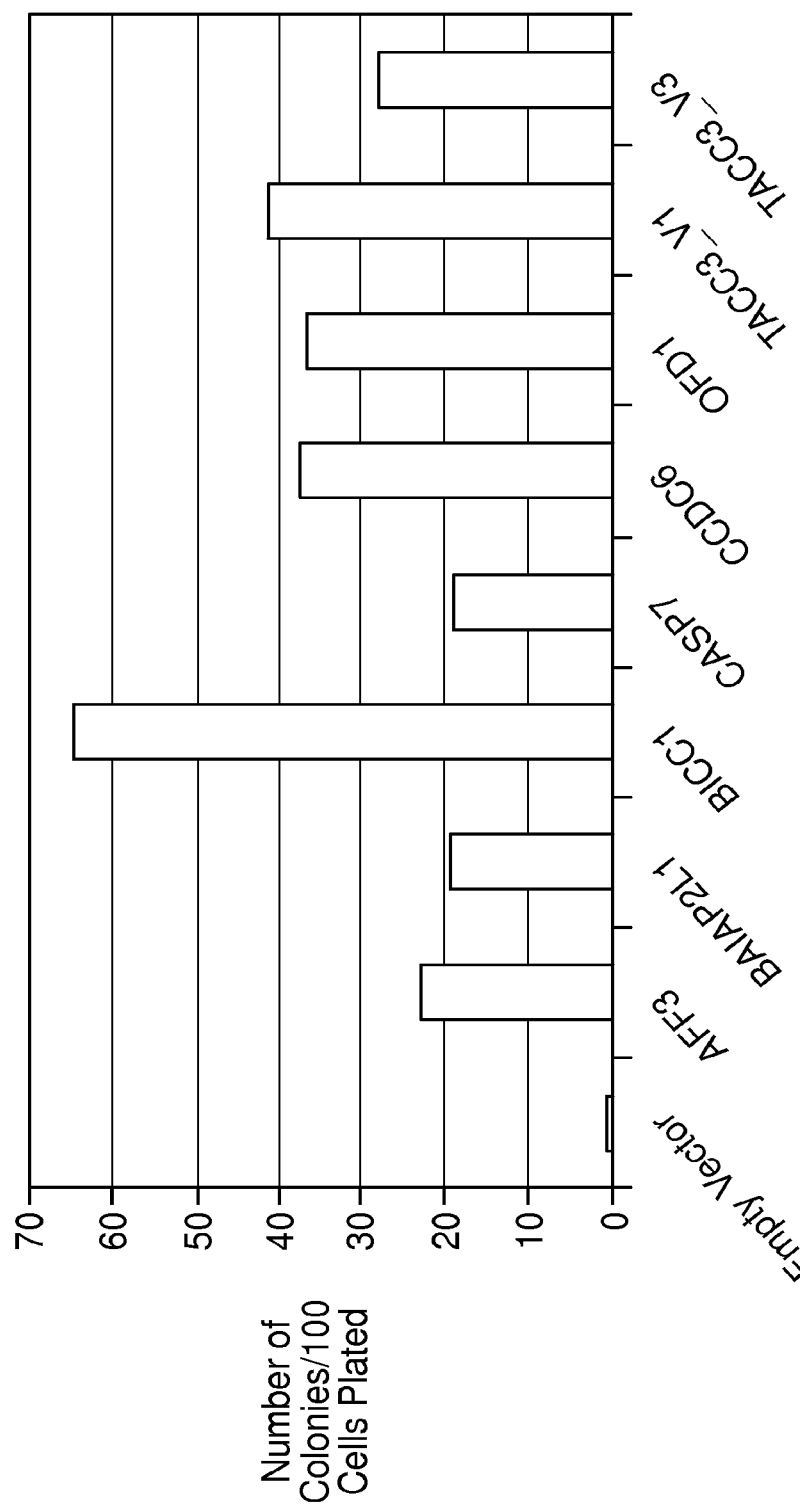
Figure 14A:
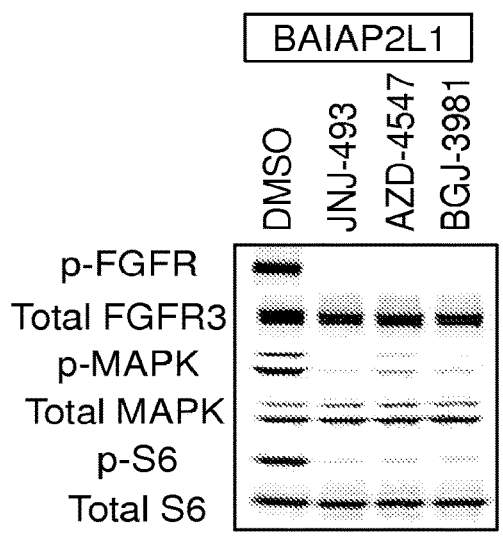
FIGS. 14A-14H illustrate the expression of exemplary downstream targets in RK3E cells stably transfected with the indicated FGFR fusion.
Figure 14B:
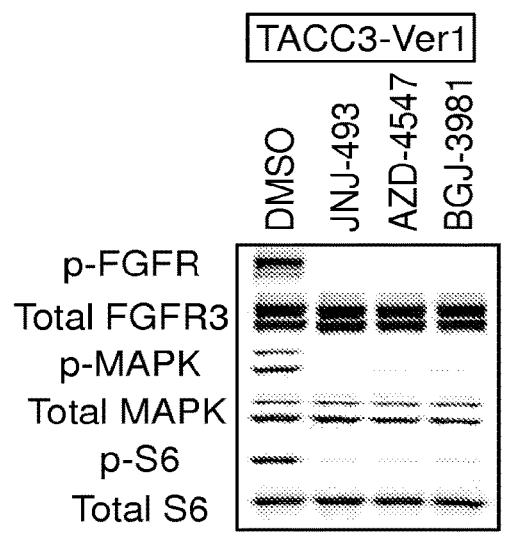
Figure 14C:
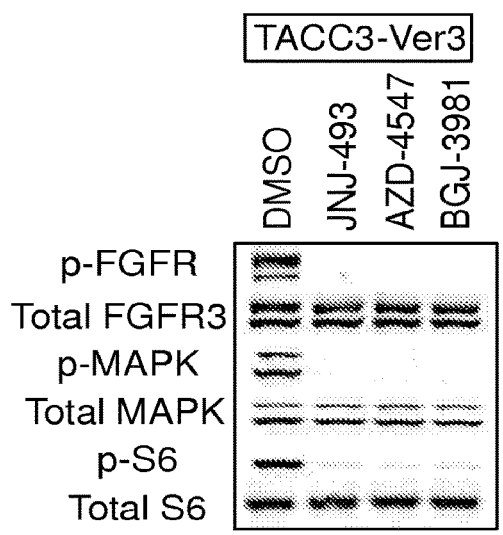
Figure 14D:
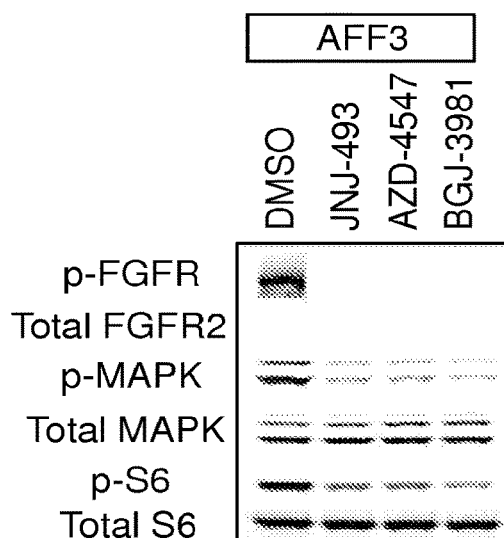
Figure 14E:
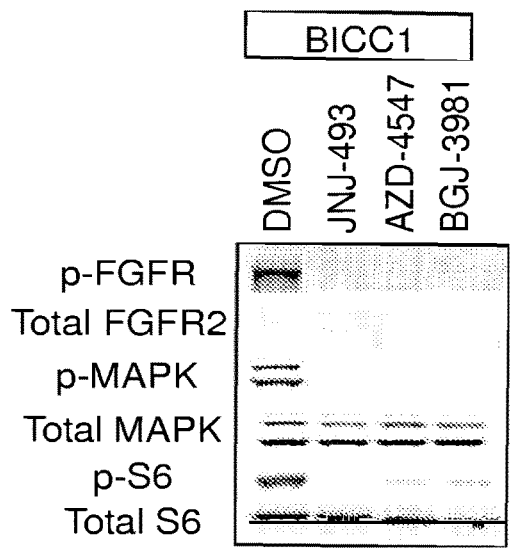
Figure 14F:
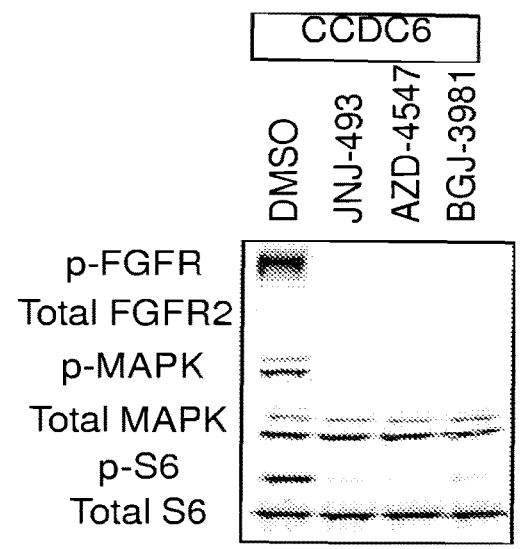
Figure 14G:
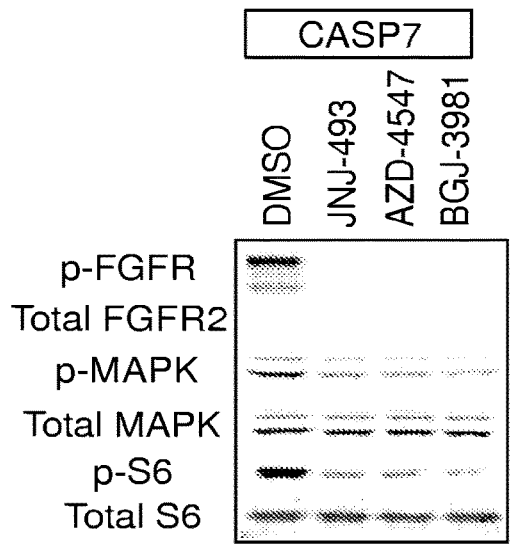
Figure 14H:
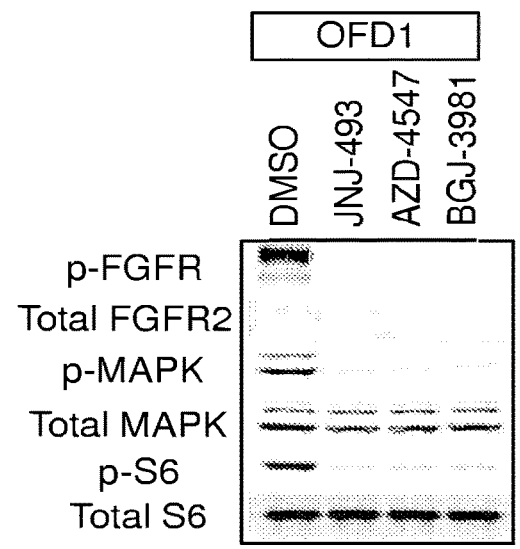

Anchorage-independent growth of the FGFR fusion stably transfected RK3E cells was tested. 1 ml culture medium with 0.8% low melting point agarose was first plated into each of three wells of a six-well plate. After the agar solidified, each well received another 1 ml of 0.4% agar in culture medium containing 100 cells. After 14 days, colonies were fixed and stained with 0.1% cresyl crystal violet. The number of colonies was determined microscopically by manual counting from triplicate wells for each cell line. A representative view of each fusion-overexpressing cell line is shown in FIG. 13A. Anchorage-independent cell growth in soft-agar could be detected in the FGFR fusion stably transfected cells, but not in the empty vector control. FIG. 13B represents a quantitative analysis of colonies in soft agar for the FGFR fusion stably transfected RK3E cells and empty vector control. All experiments were carried out in duplicate and the results are expressed as colonies/100 cells plated. All of the FGFR fusions tested induced anchorage independent growth, highlighting their transforming ability Downstream Target Expression FGFR fusion stably transfected RK3E cells were plated in complete growth medium, serum starved overnight, then re-fed with 0.5% FBS growth media. Cells were treated with 1 µM of JNJ-42756493, AZD4547 or NVP-BGJ398 in the presence of ligands for 1 hour. For immunoblotting, whole cell lysates were collected in RIPA buffer (Thermo Scientific, Waltham, MA, USA) and sample protein concentration was assayed using BCA Protein Assay (Thermo Scientific). Equal amounts of protein (30 µg per lane) were loaded onto on 4-12% Bis-Tris gels (Invitrogen) before an SDS-page was performed. Proteins were transferred to nitrocellulose membranes and probed with antibodies against p-FGFR, total-FGFR2, p-MAPK, total-MAPK, p-S6, total S6, B-actin (Cell Signaling Technology, Danvers, MA, USA), and total-FGFR3 (Santa Cruz, Dallas, TX, USA). The membranes were blocked with Odyssey blocking buffer for 1 h at room temperature and incubated overnight at 4° C. in a primary antibody solution diluted in Odyssey blocking buffer (1:1000). After three washes in 0.1% Tween tris buffered saline (TBST), the membranes were probed with goat anti-mouse or donkey anti-rabbit IR-Dye 670 or 800 cw labeled secondary antisera in Odyssey blocking buffer for 1 h at room temperature. Washes were repeated after secondary labeling and the membranes were imaged using a LiCor Odyssey scanner and the Odyssey 3.0 analytical software (LiCor, Lincoln, NE, USA). Effects of JNJ-42756493 was compared with AZD4547 and NVP-BGJ398. As shown in FIGS. 14A-14H, treatment with JNJ-42756493, AZD4547 and NVP-BGJ398 (lanes 2-4 in each blot) inhibited phosphorylation of FGFR and downstream targets i.e. MAPK and S6.

Drug Response Testing for FGFR-Fusion Overexpressing Cell Lines

FGFR fusion stably transfected RK3E cells were seeded into 96 well plates (1000 cells/well) in triplicates in complete growth medium plus and the ligands FGF-1 and FGF-2. After 24 hours, cells were serum starved overnight, then re-fed with 0.5% FBS growth media. 72 hours after plating, cells were treated with various concentrations of an 18 point 1:3 dilution series, starting at 10 µM, of JNJ493, AZD4547 (AZD), and NVP-BGJ398 (NVS). The Microtiter plates were then incubated for 72 hours and assayed for adenosine triphosphate (ATP; a marker of metabolically active cells) content using the Cell Titer-Glo® Luminescent Cell Viability assay (Promega Corp., Madison, WI, USA) following the manufacturer's instructions, with modifications. Briefly, cells were allowed to equilibrate to room temperature, at which time a 1:1 mixture of Cell Titer-Glo® reagent was added. Cells were then placed on an orbital shaker for 2 minutes and incubated for 10 minutes at room temperature to stabilize the luminescent signal. The luminescence was quantified and measurements were conducted using an Envision Multilabel plate reader (Perkin Elmer; Waltham, MA, USA). $IC_{50}$ values (shown in Table 14) were calculated using GraphPad Prism 5.0. As shown in Table 14, cells harboring the FGFR fusions showed sensitivity to the FGFR inhibitor JNJ-42756493, AZD4547 and NVP-BGJ398 in vitro, with JNJ-42756493 exhibiting enhanced sensitivity (nanomolar concentration range) when compared to AZD4547 and NVP-BGJ398, whereas the empty vector control did not.

TABLE 14

| Stimulated | Proliferation (IC50) | | |
| --- | --- | --- | --- |
| RK3E-Transgene | JNJ493 (nM) | AZD (nM) | NVS (nM) |
| Vector | 7010 | 8011 | >10 µM |
| AFF3 | 0.1133 | 2.809 | 2.273 |
| BAIA2PL1 | 0.3211 | 11.54 | 5.162 |
| BICC1 | 0.3303 | 6.448 | 18.19 |
| CASP7 | 0.4718 | 4.107 | 241.5 |
| CCDC6 | 0.1894 | 13.36 | 10.72 |
| OFD1 | 0.2303 | 7.259 | 15.99 |
| TACC3-V1 | 0.2915 | 16.53 | 2.594 |
| TACC3-V3 | 0.2706 | 8.664 | 4.092 |
| FGFR2 | >10 µM | 6501 | >10 µM |
| FGFR3 | >10 µM | 5686 | 6344 |
| KRAS | 1621 | 1478 | 2136 |

AZD = AZD4547;
NVS = NVP-BGJ398

TABLE 15

| Target | Probe Sequences |
| --- | --- |
| FGFR3TACC3 V1 | TCCACCGACGTAAAGG (SEQ ID NO: 43) |
| FGFR3TACC3 V3 | TCCACCGACGTGCCAG (SEQ ID NO: 44) |
| FGFR2BICC1 | CCAATGAGATCATGGAGG (SEQ ID NO: 45) |
| FGFR3TACC3 Intron | CCTTCTGGCCCAGGTG (SEQ ID NO: 46) |
| FGFR3BAIAP2L1 | CACCGACAATGTTATGG (SEQ ID NO: 47) |
| FGFR2AFF3 | TCACAACCAATGAGGAGAGT (SEQ ID NO: 48) |
| FGFR2CASP7 | CTGCCATCTCATTGGT (SEQ ID NO: 49) |
| FGFR2CCDC6 | AATGAGCAAGCCAGGGC (SEQ ID NO: 50) |
| FGFR2OFD1 | AAGTTGTGTCTCATTGGTT (SEQ ID NO: 51) |
| FGFR3 R248C | CTGGAGTGCTCCCC (SEQ ID NO: 52) |
| FGFR3 5249C | AGCGCTGCCCGCA (SEQ ID NO: 53) |
| FGFR3 G370C | GCGTGCAGTGTGTAT (SEQ ID NO: 54) |
| FGFR3 Y373 | CTGCACACACACTGC (SEQ ID NO: 55) |

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

The disclosures of each patent, patent application, and publication cited or described in this document are hereby incorporated herein by reference, in its entirety.

Nucleotide Sequence of FGFR Fusion Genes

The nucleotide sequences for the FGFR fusion cDNA that were engineered into expression vectors is provided in Table 16. The underlined sequences correspond to either FGFR3 or FGFR2, the sequences in normal font represent the fusion partners and the sequence in italic fonts represent the intron sequence of the FGFR3 gene.

TABLE 16

| FGFR3: TACC3 v1 (3271 base pairs) (SEQ ID NO: 56) | >ATGGGCGCCCCTGCCTGCGCCCTCGCGCTCTGCGTGGCCGTGGCCATCGTGGCCGGCGCC TCCTCGGAGTCCTTGGGGACGGAGCAGCGCGTCGTGGGGCGAGCGGCAGAAGTCCCGGGCC CAGAGCCCGGCCAGCAGGAGCAGTTGGTCTTCGGCAGCGGGGATGCTGTGGAGCTGAGCTG TCCCCCGCCCGGGGGTGGTCCCATGGGGCCCACTGTCTGGGTCAAGGATGGCACAGGGCTG GTGCCCTCGGAGCGTGTCCTGGTGGGGCCCCAGCGGCTGCAGGTGCTGAATGCCTCCCACG AGGACTCCGGGGCCTACAGCTGCCGGCAGCGGCTCACGCAGCGCGTACTGTGCCACTTCAG TGTGCGGGTGACAGACGCTCCATCCTCGGGAGATGACGAAGACGGGGAGGACGAGGCTGAG GACACAGGTGTGGACACAGGGGCCCCTTACTGGACACGGCCCGAGCGGATGGACAAGAAGC TGCTGGCCGTGCCGGCCGCCAACACCGTCCGCTTCCGCTGCCCAGCCGCTGGCAACCCCAC TCCCTCCATCTCCTGGCTGAAGAACGGCAGGGAGTTCCGCGGCGAGCACCGCATTGGAGGC ATCAAGCTGCGGCATCAGCAGTGGAGCCTGGTCATGGAAAGCGTGGTGCCCTCGGACCGCG GCAACTACACCTGCGTCGTGGAGAACAAGTTTGGCAGCATCCGGCAGACGTACACGCTGGA CGTGCTGGAGCGCTCCCCGCACCGGCCCATCCTGCAGGCGGGGCTGCCGGCCAACCAGACG GCGGTGCTGGGCAGCGACGTGGAGTTCCACTGCAAGGTGTACAGTGACGCACAGCCCCACA TCCAGTGGCTCAAGCACGTGGAGGTGAATGGCAGCAAGGTGGGCCCGGACGGCACACCCTA CGTTACCGTGCTCAAGACGGCGGGCGCTAACACCACCGACAAGGAGCTAGAGGTTCTCTCC TTGCACAACGTCACCTTTGAGGACGCCGGGGAGTACACCTGCCTGGCGGGCAATTCTATTG GGTTTTCTCATCACTCTGCGTGGCTGGTGGTGCTGCCAGCCGAGGAGGAGCTGGTGGAGGC |

TABLE 16-continued

| | |
|---|---|
| | TGACGAGGCGGGCAGTGTGTATGCAGGCATCCTCAGCTACGGGGTGGGCTTCTTCCTGTTC |
| | ATCCTGGTGGTGGCGGCTGTGACGCTCTGCCGCCTGCGCAGCCCCCCCAAGAAAGGCCTGG |
| | GCTCCCCCACCGTGCACAAGATCTCCCGCTTCCCGCTCAAGCGACAGGTGTCCCTGGAGTC |
| | CAACGCGTCCATGAGCTCCAACACACCACTGGTGCGCATCGCAAGGCTGTCCTCAGGGGAG |
| | GGCCCCACGCTGGCCAATGTCTCCGAGCTCGAGCTGCCTGCCGACCCCAAATGGGAGCTGT |
| | CTCGGGCCCGGCTGACCCTGGGCAAGCCCCTTGGGGAGGGCTGCTTCGGCCAGGTGGTCAT |
| | GGCGGAGGCCATCGGCATTGACAAGGACCGGGCCGCCAAGCCTGTCACCGTAGCCGTGAAG |
| | ATGCTGAAAGACGATGCCACTGACAAGGACCTGTCGGACCTGGTGTCTGAGATGGAGATGA |
| | TGAAGATGATCGGGAAACACAAAAACATCATCAACCTGCTGGGCGCCTGCACGCAGGGCGG |
| | GCCCCTGTACGTGCTGGTGGAGTACGCGGCCAAGGGTAACCTGCGGGAGTTTCTGCGGGCG |
| | CGGCGGCCCCCGGGCCTGGACTACTCCTTCGACACCTGCAAGCCGCCCGAGGAGCAGCTCA |
| | CCTTCAAGGACCTGGTGTCCTGTGCCTACCAGGTGGCCCGGGGCATGGAGTACTTGGCCTC |
| | CCAGAAGTGCATCCACAGGGACCTGGCTGCCCGCAATGTGCTGGTGACCGAGGACAACGTG |
| | ATGAAGATCGCAGACTTCGGGCTGGCCCGGGACGTGCACAACCTCGACTACTACAAGAAGA |
| | CGACCAACGGCCGGCTGCCCGTGAAGTGGATGGCGCCTGAGGCCTTGTTTGACCGAGTCTA |
| | CACTCACCAGAGTGACGTCTGGTCCTTTGGGGTCCTGCTCTGGGAGATCTTCACGCTGGGG |
| | GGCTCCCCGTACCCCGGCATCCCTGTGGAGGAGCTCTTCAAGCTGCTGAAGGAGGGCCACC |
| | GCATGGACAAGCCCGCCAACTGCACACACGACCTGTACATGATCATGCGGGAGTGCTGGCA |
| | TGCCGCGCCCTCCCAGAGGCCCACCTTCAAGCAGCTGGTGGAGGACCTGGACCGTGTCCTT |
| | ACCGTGACGTCCACCGACGTAAAGGCGACACAGGAGGAGAACCGGGAGCTGAGGAGCAGGT |
| | GTGAGGAGCTCCACGGGAAGAACCTGGAACTGGGGAAGATCATGGACAGGTTCGAAGAGGT |
| | TGTGTACCAGGCCATGGAGGAAGTTCAGAAGCAGAAGGAACTTTCCAAAGCTGAAATCCAG |
| | AAAGTTCTAAAAGAAAAAGACCAACTTACCACAGATCTGAACTCCATGGAGAAGTCCTTCT |
| | CCGACCTCTTCAAGCGTTTTGAGAAACAGAAAGAGGTGATCGAGGGCTACCGCAAGAACGA |
| | AGAGTCACTGAAGAAGTGCGTGGAGGATTACCTGGCAAGGATCACCCAGGAGGGCCAGAGG |
| | TACCAAGCCCTGAAGGCCCACGCGGAGGAGAAGCTGCAGCTGGCAAACGAGGAGATCGCCC |
| | AGGTCCGGAGCAAGGCCCAGGCGGAAGCGTTGGCCCTCCAGGCCAGCCTGAGGAAGGAGCA |
| | GATGCGCATCCAGTCGCTGGAGAAGACAGTGGAGCAGAAGACTAAAGAGAACGAGGAGCTG |
| | ACCAGGATCTGCGACGACCTCATCTCCAAGATGGAGAAGATCTGA |
| FGFR3: TACC3 v3 (3376 base pairs) (SEQ ID NO: 57) | >ATGGGCGCCCTGCCTGCGCCCTCGCGCTCTGCGTGGCCGTGGCCATCGTGGCCGGCGCC |
| | TCCTCGGAGTCCTTGGGGACGGAGCAGCGCGTCGTGGGGCGAGCGGCAGAAGTCCCGGGCC |
| | CAGAGCCCGGCCAGCAGGAGCAGTTGGTCTTCGGCAGCGGGGATGCTGTGGAGCTGAGCTG |
| | TCCCCCGCCCGGGGGTGGTCCCATGGGGCCCACTGTCTGGGTCAAGGATGGCACAGGCCTG |
| | GTGCCCTCGGAGCGTGTCCTGGTGGGGCCCCAGCGGCTGCAGGTGCTGAATGCCTCCCACG |
| | AGGACTCCGGGGCCTACAGCTGCCGGCAGCGGCTCACGCAGCGCGTACTGTGCCACTTCAG |
| | TGTGCGGGTGACAGACGCTCCATCCTCGGGAGATGACGAAGACGGGGAGGACGAGGCTGAG |
| | GACACAGGTGTGGACACAGGGGCCCCTTACTGGACACGGCCCGAGCGGATGGACAAGAAGC |
| | TGCTGGCCGTGCCGGCCGCCAACACCGTCCGCTTCCGCTGCCCAGCCGCTGGCAACCCCAC |
| | TCCCTCCATCTCCTGGCTGAAGAACGGCAGGGAGTTCCGCGGCGAGCACCGCATTGGAGGC |
| | ATCAAGCTGCGGCATCAGCAGTGGAGCCTGGTCATGGAAAGCGTGGTGCCCTCGGACCGCG |
| | GCAACTACACCTGCGTCGTGGAGAACAAGTTTGGCAGCATCCGGCAGACGTACACGCTGGA |
| | CGTGCTGGAGCGCTCCCCGCACCGGCCCATCCTGCAGGCGGGGCTGCCGGCCAACCAGACG |
| | GCGGTGCTGGGCAGCGACGTGGAGTTCCACTGCAAGGTGTACAGTGACGCACAGCCCCACA |
| | TCCAGTGGCTCAAGCACGTGGAGGTGAATGGCAGCAAGGTGGGCCCGGACGGCACACCCTA |
| | CGTTACCGTGCTCAAGACGGCGGGCGCTAACACCACCGACAAGGAGCTAGAGGTTCTCTCC |
| | TTGCACAACGTCACCTTTGAGGACGCCGGGGAGTACACCTGCCTGGCGGGCAATTCTATTG |
| | GGTTTTCTCATCACTCTGCGTGGCTGGTGGTGCTGCCAGCCGAGGAGGAGCTGGTGGAGGC |
| | TGACGAGGCGGGCAGTGTGTATGCAGGCATCCTCAGCTACGGGGTGGGCTTCTTCCTGTTC |
| | ATCCTGGTGGTGGCGGCTGTGACGCTCTGCCGCCTGCGCAGCCCCCCCAAGAAAGGCCTGG |
| | GCTCCCCCACCGTGCACAAGATCTCCCGCTTCCCGCTCAAGCGACAGGTGTCCCTGGAGTC |
| | CAACGCGTCCATGAGCTCCAACACACCACTGGTGCGCATCGCAAGGCTGTCCTCAGGGGAG |
| | GGCCCCACGCTGGCCAATGTCTCCGAGCTCGAGCTGCCTGCCGACCCCAAATGGGAGCTGT |
| | CTCGGGCCCGGCTGACCCTGGGCAAGCCCCTTGGGGAGGGCTGCTTCGGCCAGGTGGTCAT |
| | GGCGGAGGCCATCGGCATTGACAAGGACCGGGCCGCCAAGCCTGTCACCGTAGCCGTGAAG |
| | ATGCTGAAAGACGATGCCACTGACAAGGACCTGTCGGACCTGGTGTCTGAGATGGAGATGA |
| | TGAAGATGATCGGGAAACACAAAAACATCATCAACCTGCTGGGCGCCTGCACGCAGGGCGG |
| | GCCCCTGTACGTGCTGGTGGAGTACGCGGCCAAGGGTAACCTGCGGGAGTTTCTGCGGGCG |
| | CGGCGGCCCCCGGGCCTGGACTACTCCTTCGACACCTGCAAGCCGCCCGAGGAGCAGCTCA |
| | CCTTCAAGGACCTGGTGTCCTGTGCCTACCAGGTGGCCCGGGGCATGGAGTACTTGGCCTC |
| | CCAGAAGTGCATCCACAGGGACCTGGCTGCCCGCAATGTGCTGGTGACCGAGGACAACGTG |
| | ATGAAGATCGCAGACTTCGGGCTGGCCCGGGACGTGCACAACCTCGACTACTACAAGAAGA |
| | CGACCAACGGCCGGCTGCCCGTGAAGTGGATGGCGCCTGAGGCCTTGTTTGACCGAGTCTA |
| | CACTCACCAGAGTGACGTCTGGTCCTTTGGGGTCCTGCTCTGGGAGATCTTCACGCTGGGG |
| | GGCTCCCCGTACCCCGGCATCCCTGTGGAGGAGCTCTTCAAGCTGCTGAAGGAGGGCCACC |
| | GCATGGACAAGCCCGCCAACTGCACACACGACCTGTACATGATCATGCGGGAGTGCTGGCA |
| | TGCCGCGCCCTCCCAGAGGCCCACCTTCAAGCAGCTGGTGGAGGACCTGGACCGTGTCCTT |
| | ACCGTGACGTCCACCGACGTGCCAGGCCCACCCCAGGTGTTCCCGCGCCTGGGGCCCAC |
| | CCTGTCCACCGGACCTATAGTGGACCTGCTCCAGTACAGCCAGAAGGACCTGGATGCAGT |
| | GGTAAAGGCGACACAGGAGGAGAACCGGGAGCTGAGGAGCAGGTGTGAGGAGCTCCACGGG |
| | AAGAACCTGGAACTGGGGAAGATCATGGACAGGTTCGAAGAGGTTGTGTACCAGGCCATGG |
| | AGGAAGTTCAGAAGCAGAAGGAACTTTCCAAAGCTGAAATCCAGAAAGTTCTAAAAGAAAA |
| | AGACCAACTTACCACAGATCTGAACTCCATGGAGAAGTCCTTCTCCGACCTCTTCAAGCGT |
| | TTTGAGAAACAGAAAGAGGTGATCGAGGGCTACCGCAAGAACGAAGAGTCACTGAAGAAGT |
| | GCGTGGAGGATTACCTGGCAAGGATCACCCAGGAGGGCCAGAGGTACCAAGCCCTGAAGGC |
| | CCACGCGGAGGAGAAGCTGCAGCTGGCAAACGAGGAGATCGCCCAGGTCCGGAGCAAGGCC |
| | CAGGCGGAAGCGTTGGCCCTCCAGGCCAGCCTGAGGAAGGAGCAGATGCGCATCCAGTCGC |
| | TGGAGAAGACAGTGGAGCAGAAGACTAAAGAGAACGAGGAGCTGACCAGGATCTGCGACGA |
| | CCTCATCTCCAAGATGGAGAAGATCTGA |

TABLE 16-continued

| FGFR3<br>Intron: TACC3<br>(4463 base pairs)<br>(SEQ ID NO: 58) | >ATGGGCGCCCTGCCTGCGCCCTCGCGCTCTGCGTGGCCGTGGCCATCGTGGCCGGCGCC<br>TCCTCGGAGTCCTTGGGGACGGAGCAGCGCGTCGTGGGGCGAGCGGCAGAAGTCCCGGGCC<br>CAGAGCCCGGCCAGCAGGAGCAGTTGGTCTTCGGCAGCGGGGATGCTGTGGAGCTGAGCTG<br>TCCCCCGCCCGGGGGTGGTCCCATGGGGCCCACTGTCTGGGTCAAGGATGGCACAGGGCTG<br>GTGCCCTCGGAGCGTGTCCTGGTGGGGCCCCAGCGGCTGCAGGTGCTGAATGCCTCCCACG<br>AGGACTCCGGGGCCTACAGCTGCCGGCAGCGGCTCACGCAGCGCGTACTGTGCCACTTCAG<br>TGTGCGGGTGACAGACGCTCCATCCTCGGGAGATGACGAAGACGGGGAGGACGAGGCTGAG<br>GACACAGGTGTGGACACAGGGGCCCCTTACTGGACACGGCCCGAGCGGATGGACAAGAAGC<br>TGCTGGCCGTGCCGGCCGCCAACACCGTCCGCTTCCGCTGCCCAGCCGCTGGCAACCCCAC<br>TCCCTCCATCTCCTGGCTGAAGAACGGCAGGGAGTTCCGCGGCGAGCACCGCATTGGAGGC<br>ATCAAGCTGCGGCATCAGCAGTGGAGCCTGGTCATGGAAAGCGTGGTGCCCTCGGACCGCG<br>GCAACTACACCTGCGTCGTGGAGAACAAGTTTGGCAGCATCCGGCAGACGTACACGCTGGA<br>CGTGCTGGAGCGCTCCCCGCACCGGCCCATCCTGCAGGCGGGGCTGCCGGCCAACAGACG<br>GCGGTGCTGGGCAGCGACGTGGAGTTCCACTGCAAGGTGTACAGTGACGCACAGCCCCACA<br>TCCAGTGGCTCAAGCACGTGGAGGTGAATGGCAGCAAGGTGGGCCCGGACGGCACACCCTA<br>CGTTACCGTGCTCAAGACGGCGGGCGCTAACACCACCGACAAGGAGCTAGAGGTTCTCTCC<br>TTGCACAACGTCACCTTTGAGGACGCCGGGGAGTACACCTGCCTGGCGGGCAATTCTATTG<br>GGTTTTCTCATCACTCTGCGTGGCTGGTGGTGCTGCCAGCCGAGGAGGAGCTGGTGGAGGC<br>TGACGAGGCGGGCAGTGTGTATGCAGGCATCCTCAGCTACGGGGTGGGCTTCTTCCTGTTC<br>ATCCTGGTGGTGGCGGCTGTGACGCTCTGCCGCCTGCGCAGCCCCCCCAAGAAAGGCCTGG<br>GCTCCCCCACCGTGCACAAGATCTCCCGCTTCCCGCTCAAGCGACAGGTGTCCCTGGAGTC<br>CAACGCGTCCATGAGCTCCAACACACCACTGGTGCGCATCGCAAGGCTGTCCTCAGGGGAG<br>GGCCCCACGCTGGCCAATGTCTCCGAGCTCGAGCTGCCTGCCGACCCCAAATGGGAGCTGT<br>CTCGGGCCCGGCTGACCCTGGGCAAGCCCCTTGGGGAGGGCTGCTTCGGCCAGGTGGTCAT<br>GGCGGAGGCCATCGGCATTGACAAGGACCGGGCCGCCAAGCCTGTCACCGTAGCCGTGAAG<br>ATGCTGAAAGACGATGCCACTGACAAGGACCTGTCGGACCTGGTGTCTGAGATGGAGATGA<br>TGAAGATGATCGGGAAACACAAAAACATCATCAACCTGCTGGGCGCCTGCACGCAGGGCGG<br>GCCCCTGTACGTGCTGGTGGAGTACGCGGCCAAGGGTAACCTGCGGGAGTTTCTGCGGGCG<br>CGGCGGCCCCCGGGCCTGGACTACTCCTTCGACACCTGCAAGCCGCCCGAGGAGCAGCTCA<br>CCTTCAAGGACCTGGTGTCCTGTGCCTACCAGGTGGCCCGGGGCATGGAGTACTTGGCCTC<br>CCAGAAGTGCATCCACAGGGACCTGGCTGCCCGCAATGTGCTGGTGACCGAGGACAACGTG<br>ATGAAGATCGCAGACTTCGGGCTGGCCCGGGACGTGCACAACCTCGACTACTACAAGAAGA<br>CGACCAACGGCCGGCTGCCCGTGAAGTGGATGGCGCCTGAGGCCTTGTTTGACCGAGTCTA<br>CACTCACCAGAGTGACGTCTGGTCCTTTGGGGTCCTGCTCTGGGAGATCTTCACGCTGGGG<br>GGCTCCCCGTACCCCGGCATCCCTGTGGAGGAGCTCTTCAAGCTGCTGAAGGAGGGCCACC<br>GCATGGACAAGCCCGCCAACTGCACACACGACCTGTACATGATCATGCGGGAGTGCTGGCA<br>TGCCGCGCCCTCCCAGAGGCCCACCTTCAAGCAGCTGGTGGAGGACCTGGACCGTGTCCTT<br>ACCGTGACGTCCACCGACgtgagtgctggctctggcctggtgccaccgcctatgccctc<br>cccctgccgtccccggccatcctgccccccagagtgctgaggtgtggggcgggcctt TCTG<br>GCCCAGGTGCCCTGCTGACCTGGACTGCTCAAGCTCTTCCCAGAGCCCAGGAAGTTCTGA<br>GAACCAAATGGTGTCTCCAGGAAAAGTGTCTGGCAGCCCTGAGCAAGCCGTGGAGGAAAAC<br>CTTAGTTCCTATTCCTTAGACAGAAGAGTTGACACCCGCCTCTGAGACCCTAGAAGACCCTT<br>GCAGGACAGAGTCCCAGCACAAAGCGGAGACTCCGCACGGAGCCGAGGAAGAATGCAAAGC<br>GGAGACTCCGCACGGAGCCGAGGAGGAATGCCGGCACGGTGGGGTCTGTGCTCCCGCAGCA<br>GTGGCCACTTCGCCTCCTGGTGCAATCCCTAAGGAAGCCTGCGGAGGAGCACCCCTGCAGG<br>GTCTGCCTGGCGAAGCCCTGGGCTGCCCTGCGGGTGTGGGCACCCCCGTGCCAGCAGATGG<br>CACTCAGACCCTTACCTGTGCACACACCTCTGCTCCTGAGAGCACAGCCCCAACCAACCAC<br>CTGGTGGCTGGCAGGGCCATGACCCTGAGTCCTCAGGAAGAAGTGGCTGCAGGCCAAATGG<br>CCAGCTCCTCGAGGAGCGGACCTGTAAAACTAGAATTTGATGTATCTGATGGCGCCACCAG<br>CAAAAGGGCACCCCCACCAAGGAGACTGGGAGAGAGGTTCCGGCCTCAAGCCTCCCTTGAGG<br>AAAGCAGCAGTGAGGCAGCAAAAGGCCCCGCAGGAGGTGGAGGAGGACGACGGTAGGAGCG<br>GAGCAGGAGAGGACCCCCCCATGCCAGCTTCTCGGGGCTCTTACCACCTCGACTGGGACAA<br>AATGGATGACCCAAACTTCATCCCGTTCGGAGGTGACACCAAGTCTGGTTGCAGTGAGGCC<br>CAGCCCCCAGAAAGCCTGAGACCAGGCTGGGCCAGCCAGCGGCTGAACAGTTGCATGCTG<br>GGCCTGCCACGGAGGAGCCAGGTCCCTGTCTGAGCCAGCAGCTGCATTCAGCCTCAGCGGA<br>GGACACGCCTGTGGTGCAGTTGGCAGCCGAGACCCCAACAGCAGAGAGCAAGGAGAGAGCC<br>TTGAACTCTGCCAGCACCTCGCTTCCCACAAGCTGTCCAGGCAGTGAGCCAGTGCCCACCC<br>ATCAGCAGGGGCAGCCTGCCTTGGAGCTGAAAGAGGAGAGCTTCAGAGACCCCGCTGAGGT<br>TCTAGGCACGGGCGCGGAGGTGGATTACCTGGAGCAGTTTGGAACTTCCTCGTTTAAGGAG<br>TCGGCCTTGAGGAAGCAGTCCTTATACCTCAAGTTCGACCCCCTCCTGAGGGACAGTCCTG<br>GTAGACCAGTGCCCGTGGCCACCGAGACCAGCAGCATGCACGGTGCAAATGAGACTCCCTC<br>AGGACGTCCGCGGGAAGCCAAGCTTGTGGAGTTCGATTTCTTGGGAGCACTGGACATTCCT<br>GTGCCAGGCCCACCCCCAGGTGTTCCCGCGCTGGGGGCCCACCCCTGTCCACCGGACCTA<br>TAGTGGACCCTGCTCCAGTACAGCCAGAAGGACCTGGATGCAGTGGTAAAGGCGACACAGGA<br>GGAGAACCGGGAGCTGAGGAGCAGGTGTGAGGAGCTCCACGGGAAGAACCTGGAACTGGGG<br>AAGATCATGGACAGGTTCGAAGAGGTTGTGTACCAGGCCATGGAGGAAGTTCAGAAGCAGA<br>AGGAACTTTCAAAAGCTGAAATCCAGAAAAGTTCTAAAAGAAAAAAGACCAACTTACCACAGA<br>TCTGAACTCCATGGAGAAGTCCTTCTCCGACCTCTTCAAGCGTTTTGAGAAACAGAAAGAG<br>GTGATCGAGGGCTACCGCAAGAACGAAGAGTCACTGAAGAAGTGCGTGGAGGATTACCTGG<br>CAAGGATCACCCAGGAGGGCCAGAGGTACCAAGCCCTGAAGGCCCACGCGGAGGAGAAGCT<br>GCAGCTGGCAAACGAGGAGATCGCCCAGGTCCGGAGCAAGGCCCAGGCGGAAGCGTTGGCC<br>CTCCAGGCCAGCCTGAGGAAGGAGCAGATGCGCATCCAGTCGCTGGAGAAGACAGTGGAGC<br>AGAAGACTAAAGAGAACGAGGAGCTGACCAGGATCTGCGACGACCTCATCTCCAAGATGGA<br>GAAGATCTGA |
| FGFR3: BAIAP2L1<br>(3765 base pairs)<br>(SEQ ID NO: 59) | >ATGGGCGCCCTGCCTGCGCCCTCGCGCTCTGCGTGGCCGTGGCCATCGTGGCCGGCGCC<br>TCCTCGGAGTCCTTGGGGACGGAGCAGCGCGTCGTGGGGCGAGCGGCAGAAGTCCCGGGCC<br>CAGAGCCCGGCCAGCAGGAGCAGTTGGTCTTCGGCAGCGGGGATGCTGTGGAGCTGAGCTG<br>TCCCCCGCCCGGGGGTGGTCCCATGGGGCCCACTGTCTGGGTCAAGGATGGCACAGGGCTG<br>GTGCCCTCGGAGCGTGTCCTGGTGGGGCCCCAGCGGCTGCAGGTGCTGAATGCCTCCCACG |

TABLE 16-continued

|   |   |
|---|---|
|   | AGGACTCCGGGGCCTACAGCTGCCGGCAGCGGCTCACGCAGCGCGTACTGTGCCACTTCAG |
|   | TGTGCGGGTGACAGACGCTCCATCCTCGGGAGATGACGAAGACGGGGAGGACGAGGCTGAG |
|   | GACACAGGTGTGGACACAGGGGCCCCTTACTGGACACGGCCCGAGCGGATGGACAAGAAGC |
|   | TGCTGGCCGTGCCGGCCGCCAACACCGTCCGCTTCCGCTGCCCAGCCGCTGGCAACCCCAC |
|   | TCCCTCCATCTCCTGGCTGAAGAACGGCAGGGAGTTCCGCGGCGAGCACCGCATTGGAGGC |
|   | ATCAAGCTGCGGCATCAGCAGTGGAGCCTGGTCATGGAAAGCGTGGTGCCCTCGGACCGCG |
|   | GCAACTACACCTGCGTCGTGGAGAACAAGTTTGGCAGCATCCGGCAGACGTACACGCTGGA |
|   | CGTGCTGGAGCGCTCCCCGCACCGGCCCATCCTGCAGGCGGGGCTGCCGGCCAACCAGACG |
|   | GCGGTGCTGGGCAGCGACGTGGAGTTCCACTGCAAGGTGTACAGTGACGCACAGCCCCACA |
|   | TCCAGTGGCTCAAGCACGTGGAGGTGAATGGCAGCAAGGTGGGCCCGGACGGCACACCCTA |
|   | CGTTACCGTGCTCAAGTCCTGGATCAGTGAGAGTGTGGAGGCCGACGTGCGCCTCCGCCTG |
|   | GCCAATGTGTCGGAGCGGGACGGGGGCGAGTACCTCTGTCGAGCCACCAATTTCATAGGCG |
|   | TGGCCGAGAAGGCCTTTTGGCTGAGCGTTCACGGGCCCCGAGCAGCCGAGGAGGAGCTGGT |
|   | GGAGGCTGACGAGGCGGGCAGTGTGTATGCAGGCATCCTCAGCTACGGGGTGGGCTTCTTC |
|   | CTGTTCATCCTGGTGGTGGCGGCTGTGACGCTCTGCCGCCTGCGCAGCCCCCCCAAGAAAG |
|   | GCCTGGGCTCCCCCACCGTGCACAAGATCTCCCGCTTCCCGCTCAAGCGACAGGTGTCCCT |
|   | GGAGTCCAACGCGTCCATGAGCTCCAACACACCACTGGTGCGCATCGCAAGGCTGTCCTCA |
|   | GGGGAGGGCCCCACGCTGGCCAATGTCTCCGAGCTCGAGCTGCCTGCCGACCCCAAATGGG |
|   | AGCTGTCTCGGGCCCGGCTGACCCTGGGCAAGCCCCTTGGGGAGGGCTGCTTCGGCCAGGT |
|   | GGTCATGGCGGAGGCCATCGGCATTGACAAGGACCGGGCCGCCAAGCCTGTCACCGTAGCC |
|   | GTGAAGATGCTGAAAGACGATGCCACTGACAAGGACCTGTCGGACCTGGTGTCTGAGATGG |
|   | AGATGATGAAGATGATCGGGAAACACAAAAACATCATCAACCTGCTGGGCGCCTGCACGCA |
|   | GGGCGGGCCCCTGTACGTGCTGGTGGAGTACGCGGCCAAGGGTAACCTGCGGGAGTTTCTG |
|   | CGGGCGCGGCGGCCCCCGGGCCTGGACTACTCCTTCGACACCTGCAAGCCGCCCGAGGAGC |
|   | AGCTCACCTTCAAGGACCTGGTGTCCTGTGCCTACCAGGTGGCCCGGGGCATGGAGTACTT |
|   | GGCCTCCCAGAAGTGCATCCACAGGGACCTGGCTGCCCGCAATGTGCTGGTGACCGAGGAC |
|   | AACGTGATGAAGATCGCAGACTTCGGGCTGGCCCGGGACGTGCACAACCTCGACTACTACA |
|   | AGAAGACGACCAACGGCCGGCTGCCCGTGAAGTGGATGGCGCCTGAGGCCTTGTTTGACCG |
|   | AGTCTACACTCACCAGAGTGACGTCTGGTCCTTTGGGGTCCTGCTCTGGGAGATCTTCACG |
|   | CTGGGGGGCTCCCCGTACCCCGGCATCCCTGTGGAGGAGCTCTTCAAGCTGCTGAAGGAGG |
|   | GCCACCGCATGGACAAGCCCGCCAACTGCACACACGACCTGTACATGATCATGCGGGAGTG |
|   | CTGGCATGCCGCGCCCTCCCAGAGGCCCACCTTCAAGCAGCTGGTGGAGGACCTGGACCGT |
|   | GTCCTTACCGTGACGTCCACCGACAATGTTATGGAACAGTTCAATCCTGGGCTGCGAAATT |
|   | TAATAAACCTGGGGAAAAATTATGAGAAAGCTGTAAACGCTATGATCCTGGCAGGAAAAGC |
|   | CTACTACGATGGAGTGGCCAAGATCGGTGAGATTGCCACTGGGTCCCCCGTGTCAACTGAA |
|   | CTGGGACATGTCCTCATAGAGATTTCAAGTACCCACAAGAAACTCAACGAGAGTCTTGATG |
|   | AAAATTTTAAAAAATTCCACAAAGAGATTATCCATGAGCTGGAGAAGAAGATAGAACTTGA |
|   | CGTGAAATATATGAACGCAACTCTAAAAAGATACCAAACAGAACACAAGAATAAATTAGAG |
|   | TCTTTGGAGAAATCCCAAGCTGAGTTGAAGAAGATCAGAAGGAAAAGCCAAGGAAGCCGAA |
|   | ACGCACTCAAATATGAACACAAAGAAATTGAGTATGTGGAGACCGTTACTTCTCGTCAGAG |
|   | TGAAATCCAGAAATTCATTGCAGATGGTTGCAAAGAGGCTCTGCTTGAAGAGAAGAGGCGC |
|   | TTCTGCTTTCTGGTTGATAAGCACTGTGGCTTTGCAAACCACATACATTATTATCACTTAC |
|   | AGTCTGCAGAACTACTGAATTCCAAGCTGCCTCGGTGGCAGGAGACCTGTGTTGATGCCAT |
|   | CAAAGTGCCAGAGAAAATCATGAATATGATCGAAGAAATAAAGACCCCAGCCTCTACCCCC |
|   | GTGTCTGGAACTCCTCAGGCTTCACCCATGATCGAGAGAAGCAATGTGGTTAGGAAAGATT |
|   | ACGACACCCTTTCTAAATGCTCACCAAAGATGCCCCCCGCTCCTTCAGGCAGAGCATATAC |
|   | CAGTCCCTTGATCGATATGTTTAATAACCCAGCCACGGCTGCCCCGAATTCACAAAGGGTA |
|   | AATAATTCAACAGGTACTTCCGAAGATCCCAGTTTACAGCGATCAGTTTCGGTTGCAACGG |
|   | GACTGAACATGATGAAGAAGCAGAAAGTGAAGACCATCTTCCCGCACACTGCGGGCTCCAA |
|   | CAAGACCTTACTCAGCTTTGCACAGGGAGATGTCATCACGCTGCTCATCCCCGAGGAGAAG |
|   | GATGGCTGGCTCTATGGAGAACACGACGTGTCCAAGGCGAGGGGTTGGTTCCCGTCGTCGT |
|   | ACACGAAGTTGCTGGAAGAAAATGAGACAGAAGCAGTGACCGTGCCCACGCCAAGCCCCAC |
|   | ACCAGTGAGAAGCATCAGCACCGTGAACTTGTCTGAGAATAGCAGTGTTGTCATCCCCCCA |
|   | CCCGACTACTTGGAATGCTTGTCCATGGGGGCAGCTGCCGACAGGAGAGCAGATTCGGCCA |
|   | GGACGACATCCACCTTTAAGGCCCCAGCGTCCAAGCCCGAGACCGCGGCTCCTAACGATGC |
|   | CAACGGGACTGCAAAGCCGCCTTTTCTCAGCGGAGAAAACCCCTTTGCCACTGTGAAACTC |
|   | CGCCCGACTGTGACGAATGATCGCTCGGCACCCATCATTCGATGA |
| FGFR2: BICC1<br>(5830 base pairs)<br>(SEQ ID NO: 60) | >ATGGTCAGCTGGGGTCGTTTCATCTGCCTGGTCGTGGTCACCATGGCAACCTTGTCCCTG<br>GCCCGGCCCTCCTTCAGTTTAGTTGAGGATACCACATTAGAGCCAGAAGAGCCACCAACCA<br>AATACCAAATCTCTCAACCAGAAGTGTACGTGGCTGCGCCAGGGGAGTCGCTAGAGGTGCG<br>CTGCCTGTTGAAAGATGCCGCCGTGATCAGTTGGACTAAGGATGGGGTGCACTTGGGGCCC<br>AACAATAGGACAGTGCTTATTGGGGAGTACTTGCAGATAAAGGGCGCCACGCCTAGAGACT<br>CCGGCTCTATGCTTGTACTGCCAGTAGGACTGTAGACAGTGAAACTTGGTACTTCATGGT<br>GAATGTCACAGATGCCATCTCATCCGGAGATGATGAGGATGACACCGATGGTCGGAAGAT<br>TTTGTCAGTGAGAACAGTAACAACAAGAGAGCACCATACTGGACCAACACAGAAAAGATGG<br>AAAAGCGGCTCCATGCTGTGCCTGCGGCCAACACTGTCAAGTTTCGCTGCCCAGCCGGGG<br>GAACCCAATGCCAACCATGCGGTGGCTGAAAAACGGGAAGGAGTTTAAGCAGGAGCATCGC<br>ATTGGAGGCTACAAGGTACGAAACCAGCACTGGAGCCTCATTATGGAAAGTGTGGTCCCAT<br>CTGACAAGGGAAATTATACCTGTGTAGTGGAGAATGAATACGGGTCCATCAATCACACGTA<br>CCACCTGGATGTTGTGGAGCGATCGCCTCACCGGCCCATCCTCCAGGCCGGACTGCCGGCA<br>AATGCCTCCACAGTGGTCGGAGGAGACGTAGAGTTTGTCTGCAAGGTTTACAGTGATGCCC<br>AGCCCCACATCCAGTGGATCAAGCACGTGGAAAAGAACGGCAGTAAATACGGGCCCGACGG<br>GCTGCCCTACCTCAAGGTTCTCAAGGCCGCCGGTGTTAACACCACGGACAAAGAGATTGAG<br>GTTCTCTATATTCGGAATGTAACTTTTGAGGACGCTGGGGAATATACGTGCTTGGCGGGTA<br>ATTCTATTGGGATATCCTTTCACTCTGCATGGTTGACAGTTCTGCCAGCGCCTGGAAGAGA<br>AAAGGAGATTACAGCTTCCCCAGACTACCTGGAGATAGCCATTTACTGCATAGGGGTCTTC<br>TTAATCGCCTGTATGTGGTAACAGTCATCCTGTGCCGAATGAAGAACACGACCAAGAAGC<br>CAGACTTCAGCAGCCAGCCGGCTGTGCACAAGCTGACCAAACGTATCCCCCTGCGGAGACA<br>GGTAACAGTTTCGGCTGAGTCCAGCTCCTCCATGAACTCCAACACCCCGCTGGTGAGGATA |

TABLE 16-continued

| | |
|---|---|
| | ACAACACGCCTCTCTTCAACGGCAGACACCCCCATGCTGGCAGGGGTCTCCGAGTATGAAC |
| | TTCCAGAGGACCCAAAATGGGAGTTTCCAAGAGATAAGCTGACACTGGGCAAGCCCCTGGG |
| | AGAAGGTTGCTTTGGGCAAGTGGTCATGGCGGAAGCAGTGGGAATTGACAAAGACAAGCCC |
| | AAGGAGGCGGTCACCGTGGCCGTGAAGATGTTGAAAGATGATGCCACAGAGAAAGACCTTT |
| | CTGATCTGGTGTCAGAGATGGAGATGATGAAGATGATTGGGAAACACAAGAATATCATAAA |
| | TCTTCTTGGAGCCTGCACACAGGATGGGCCTCTCTATGTCATAGTTGAGTATGCCTCTAAA |
| | GGCAACCTCCGAGAATACCTCCGAGCCCGGAGGCCACCCGGGATGGAGTACTCCTATGACA |
| | TTAACCGTGTTCCTGAGGAGCAGATGACCTTCAAGGACTTGGTGTCATGCACCTACCAGCT |
| | GGCCAGAGGCATGGAGTACTTGGCTTCCCAAAAATGTATTCATCGAGATTTAGCAGCCAGA |
| | AATGTTTTGGTAACAGAAAACAATGTGATGAAAATAGCAGACTTTGGACTCGCCAGAGATA |
| | TCAACAATATAGACTATTACAAAAAGACCACCAATGGGCGGCTTCCAGTCAAGTGGATGGC |
| | TCCAGAAGCCCTGTTTGATAGAGTATACACTCATCAGAGTGATGTCTGGTCCTTCGGGGTG |
| | TTAATGTGGGAGATCTTCACTTTAGGGGGCTCGCCCTACCCAGGGATTCCCGTGGAGGAAC |
| | TTTTTAAGCTGCTGAAGGAAGGACACAGAATGGATAAGCCAGCCAACTGCACCAACGAACT |
| | GTACATGATGATGAGGGACTGTTGGCATGCAGTGCCCTCCCAGAGACCAACGTTCAAGCAG |
| | TTGGTAGAAGACTTGGATCGAATTCTCACTCTCACAACCAATGAGATCATGTGGAGGAAACAA |
| | ATACGCAGATTGCTTGGCCATCAAAACTGAAGATCGGAGCCAAATCCAAGAAAGATCCCCA |
| | TATTAAGGTTTCTGGAAAGAAAGAAGATGTTAAAGAAGCCAAGGAAATGATCATGTCTGTC |
| | TTAGACACAAAAAGCAATCGAGTCACACTGAAGATGGATGTTTCACATACAGAACATTCAC |
| | ATGTAATCGGCAAAGGTGGCAACAATATTAAAAAAGTGATGGAAGAAACCGGATGCCATAT |
| | CCACTTTCCAGATTCCAACAGGAATAACCAAGCAGAAAAAAGCAACCAGGTATCTATAGCG |
| | GGACAACCAGCAGGAGTAGAATCTGCCCGAGTTAGAATTCGGGAGCTGCTTCCTTTGGTGC |
| | TGATGTTTGAGCTACCAATTGCTGGAATTCTTCAACCGGTTCCTGATCCTAATTCCCCCTC |
| | TATTCAGCATATATCACAAACGTACAATATTTCAGTATCATTTAAACAGCGTTCCCGAATG |
| | TATGGTGCTACTGTCATAGTACGAGGGTCTCAGAATAACACTAGTGCTGTGAAGGAAGGAA |
| | CTGCCATGCTGTTAGAACATCTTGCTGGGAGCTTAGCATCAGCTATTCCTGTGAGCACACA |
| | ACTAGATATTGCAGCTCAACATCATCTCTTTATGATGGGTCGAAATGGGAGCAACATCAAA |
| | CATATCATGCAGAGAACAGGTGCTCAGATCCACTTTCCTGATCCCAGTAATCCACAAAAGA |
| | AATCTACCGTCTACCTCCAGGGCACCATTGAGTCTGTCTGTCTTGCAAGGCAATATCTCAT |
| | GGGTTGTCTTCCTCTTGTGTTGATGTTTGATATGAAGGAAGAAATTGAAGTAGATCCACAA |
| | TTCATTGCGCAGTTGATGGAACAGCTTGATGTCTTCATCAGTATTAAACCAAAGCCCAAAC |
| | AGCCAAGCAAGTCTGTGATTGTGAAAAGTGTTGAGCGAAATGCCTTAAATATGTATGAAGC |
| | AAGGAAATGTCTCCTCGGACTTGAAAGCAGTGGGGTTACCATAGCAACCAGTCCATCCCCA |
| | GCATCCTGCCCTGCCGGCCTGGCATGTCCCAGCCTGGATATCTTAGCTTCAGCAGGCCTTG |
| | GACTCACTGGACTAGGTCTTTTGGGACCCACCACCTTATCTCTGAACACTTCAACAACCCC |
| | AAACTCACTCTTGAATGCTCTTAATAGCTCAGTCAGTCCTTTGCAAAGTCCAAGTTCTGGT |
| | ACACCCAGCCCCACATTATGGGCACCCCCACTTGCTAATACTTCAAGTGCCACAGGTTTTT |
| | CTGCTATACCACACCTTATGATTCCATCTACTGCCCAAGCCACATTAACTAATATTTTGTT |
| | GTCTGGAGTGCCCACCTATGGGCACACAGCTCCATCTCCCCCTCCTGGCTTGACTCCTGTT |
| | GATGTCCATATCAACAGTATGCAGACCGAAGGCAAAAAAATCTCTGCTGCTTTAAATGGAC |
| | ATGCACAGTCTCCAGATATAAAATATGGTGCAATATCCACTTCATCACTTGGAGAAAAAGT |
| | GCTGAGTGCAAATCACGGGGATCCGTCCATCCAGACAAGTGGGTCTGAGCAGACATCTCCC |
| | AAATCAAGCCCCACTGAAGGTTGTAATGATGCTTTTGTTGAAGTAGGCATGCCTCGAAGTC |
| | CTTCCCATTCTGGGAATGCTGGTGACTTGAAACAGATGATGTGTCCCTCCAAGGTTTCCTG |
| | TGCCAAAAGGCAGACAGTGGAACTATTGCAAGGCACGAAAAACTCACACTTACACAGCACT |
| | GACAGGTTGCTCTCAGACCCTGAACTGAGTGCTACCGAAAGCCCTTTGGCTGACAAGAAGG |
| | CTCCAGGGAGTGAGCGCGCTGCAGAGAGGGCAGCAGCTGCCCAGCAAAACTCCGAAAGGGC |
| | CCACCTTGCTCCACGGTCATCATATGTCAACATGCAGGCATTTGACTATGAACAGAAGAAG |
| | CTATTAGCCACCAAAGCTATGTTAAAGAAACCAGTGGTGACGGAGGTCAGAACGCCCACAA |
| | ATACCTGGAGTGGCCTGGGTTTTTCTAAATCATGCCAGCTGAAACTATCAAGGAGTTGAG |
| | AAGGGCCAATCATGTGTCCTATAAGCCCACAATGACAACCACTTATGAGGGCTCATCCATG |
| | TCCCTTTCACGGTCCAACAGTCGTGAGCACTTGGGAGGTGGAAGCGAATCTGATAACTGGA |
| | GAGACCGAAATGGAATTGGACCTGGAAGTCATAGTGAATTTGCAGCTTCTATTGGCAGCCC |
| | TAAGCGTAAACAAACAAATCAACGGAACACTATCTCAGCAGTAGCAATTACATGGACTGC |
| | ATTTCCTCGCTGACAGGAAGCAATGGCTGTAACTTAAATAGCTCTTTCAAAGGTTCTGACC |
| | TCCCTGAGCTCTTCAGCAAACTGGGCCTGGGCAAATACACAGATGTTTTCCAGCAACAAGA |
| | GATCGATCTTCAGACATTCCTCACTCTCACAGATCAGGATCTGAAGGAGCTGGGAATAACT |
| | ACTTTTGGTGCCAGGAGGAAAATGCTGCTTGCAATTTCAGAACTAAATAAAAACCGAAGAA |
| | AGCTTTTTGAATCGCAAATGCACGCACCTCTTTCCTGGAAGGTGGAGCGAGTGGAAGGCT |
| | ACCCCGTCAGTATCACTCAGACATTGCTAGTGTCAGTGGCCGCTGGTAG |
| FGFR2: AFF3 (base pairs) (SEQ ID NO: 61) | >ATGGTCAGCTGGGGTCGTTTCATCTGCCTGGTCGTGGTCACCATGGCAACCTTGTCCCTG |
| | GCCCGGCCCTCCTTCAGTTTAGTTGAGGATACCACATTAGAGCCAGAAGAGCCACCAACCA |
| | AATACCAAATCTCTCAACCAGAAGTGTACGTGGCTGCGCCAGGGGAGTCGCTAGAGGTGCG |
| | CTGCCTGTTGAAAGATGCCGCCGTGATCAGTTGGACTAAGGATGGGGTGCACTTGGGGCCC |
| | AACAATAGGACAGTGCTTATTGGGGAGTACTTGCAGATAAAGGGCGCCACGCCTAGAGACT |
| | CCGGCCTCTATGCTTGTACTGCCAGTAGGACTGTAGACAGTGAAACTTGGTACTTCATGGT |
| | GAATGTCACAGATGCCATCTCATCCGGAGATGATGAGGATGACACCGATGGTGCGGAAGAT |
| | TTTGTCAGTGAGAACAGTAACAACAAGAGAGCACCATACTGGACCAACACAGAAAAGATGG |
| | AAAAGCGGCTCCATGCTGTGCCTGCGGCCAACACTGTCAAGTTTCGCTGCCCAGCCGGGGG |
| | GAACCCAATGCCAACCATGCGGTGGCTGAAAAACGGGAAGGAGTTTAAGCAGGAGCATCGC |
| | ATTGGAGGCTACAAGGTACGAAACCAGCACTGGAGCCTCATTATGGAAAGTGTGGTCCCAT |
| | CTGACAAGGGAAATTATACCTGTGTAGTGGAGAATGAATACGGGTCCATCAATCACACGTA |
| | CCACCTGGATGTTGTGGAGCGATCGCCTCACCGGCCCATCCTCCAAGCCGGACTGCCGGCA |
| | AATGCCTCCACAGTGGTCGGAGGAGACGTAGAGTTTGTCTGCAAGGTTTACAGTGATGCCC |
| | AGCCCCACATCCAGTGGATCAAGCACGTGGAAAAGAACGGCAGTAAATACGGGCCCGACGG |
| | GCTGCCCTACCTCAAGGTTCTCAAGGCCGCCGGTGTTAACACCACGGACAAAGAGATTGAG |
| | GTTCTCTATATTCGGAATGTAACTTTTGAGGACGCTGGGGAATATACGTGCTTGGCGGGTA |
| | ATTCTATTGGGATATCCTTTCACTCTGCATGGTTGACAGTTCTGCCAGCGCCTGGAAGAGA |
| | AAAGGAGATTACAGCTTCCCCAGACTACCTGGAGATAGCCATTTACTGCATAGGGGTCTTC |

TABLE 16-continued

|  | |
|---|---|
|  | TTAATCGCCTGTATGGTGGTAACAGTCATCCTGTGCCGAATGAAGAACACGACCAAGAAGC<br>CAGACTTCAGCAGCCAGCCGGCTGTGCACAAGCTGACCAAACGTATCCCCCTGCGGAGACA<br>GGTAACAGTTTCGGCTGAGTCCAGCTCCTCCATGAACTCCAACACCCCGCTGGTGAGGATA<br>ACAACACGCCTCTCTTCAACGGCAGACACCCCCATGCTGGCAGGGGTCTCCGAGTATGAAC<br>TTCCAGAGGACCCAAAATGGGAGTTTCCAAGAGATAAGCTGACACTGGGCAAGCCCCTGGG<br>AGAAGGTTGCTTTGGGCAAGTGGTCATGGCGGAAGCAGTGGGAATTGACAAAGACAAGCCC<br>AAGGAGGCGGTCACCGTGGCCGTGAAGATGTTGAAAGATGATGCCACAGAGAAAGACCTTT<br>CTGATCTGGTGTCAGAGATGGAGATGATGAAGATGATTGGGAAACACAAGAATATCATAAA<br>TCTTCTTGGAGCCTGCACACAGGATGGGCCTCTCTATGTCATAGTTGAGTATGCCTCTAAA<br>GGCAACCTCCGAGAATACCTCCGAGCCCGGAGGCCACCCGGGATGGAGTACTCCTATGACA<br>TTAACCGTGTTCCTGAGGAGCAGATGACCTTCAAGGACTTGGTGTCATGCACCTACCAGCT<br>GGCCAGAGGCATGGAGTACTTGGCTTCCCAAAAATGTATTCATCGAGATTTAGCAGCCAGA<br>AATGTTTTGGTAACAGAAAACAATGTGATGAAAATAGCAGACTTTGGACTCGCCAGAGATA<br>TCAACAATATAGACTATTACAAAAAGACCACCAATGGGCGGCTTCCAGTCAAGTGGATGGC<br>TCCAGAAGCCCTGTTTGATAGAGTATACACTCATCAGAGTGATGTCTGGTCCTTCGGGGTG<br>TTAATGTGGGAGATCTTCACTTTAGGGGCTCGCCCTACCCAGGGATTCCCGTGGAGGAAC<br>TTTTTAAGCTGCTGAAGGAAGGACACAGAATGGATAAGCCAGCCAACCTGCACCAACGAACT<br>GTACATGATGATGAGGGACTGTTGGCATGCAGTGCCCTCCCAGAGACCAACGTTCAAGCAG<br>TTGGTAGAAGACTTGGATCGAATTCTCACTCTCACAACCAATGAGGAGAGTAGATCTGGAG<br>AAACCAACAGCTGTGTTGAAGAAATAATCCGGGAGATGACCTGGCTTCCACCACTTTCTGC<br>TATTCAAGCACCTGGCAAAGTGGAACCAACCAAATTTCCATTTCCAAATAAGGACTCTCAG<br>CTTGTATCCTCTGGACACAATAATCCAAAGAAAGGTGATGCAGAGCCAGAGAGTCCAGACA<br>GTGGCACATCGAATACATCAATGCTGGAAGATGACCTTAAGCTAAGCAGTGATGAAGAGGA<br>GAATGAACAGCAGGCAGCTCAGAGAACGGCTCTCCGCGCTCTCTCTGACAGCGCCGTGGTC<br>CAGCAGCCCAACTGCAGAACCTCGGTGCCTTCCAGCAAGGGCAGCAGCAGCAGCAGCAGCA<br>GCGGCAGCAGCAGCTCCTCCAGCGACTCAGAGAGCAGCTCCGGATCTGACTCGGAGACCGA<br>GAGCAGCTCCAGCGAGAGTGAGGGCAGCAAGCCCCCCACTTCTCCAGCCCCGAGGCTGAA<br>CCGGCATCCTCTAACAAGTGGCAGCTGGATAAATGGCTAAACAAAGTTAATCCCCACAAGC<br>CTCCTATTCTGATCCAAAATGAAAGCCACGGGTCAGAGAGCAATCAGTACTACAACCCGGT<br>GAAAGAGGACGTCCAGGACTGTGGGAAAGTCCCCGACGTTTGCCAGCCCAGCCTGAGAGAG<br>AAGGAGATCAAGAGCACTTGCAAGGAGGAGCAAAGGCCAAGGACAGCCAACAAGGCCCCTG<br>GGAGTAAAGGCGTGAAGCAGAAGTCCCCGCCCGCGGCCGTGGCCGTGGCGGTGAGCGCAGC<br>CGCCCCGCCACCCGCAGTGCCCTGTGCGCCCGCGGAGAACGCGCCCGCGCCTGCCCGGAGG<br>TCCGCGGGCAAGAAGCCCACCAGGCGCACCGAGAGGACCTCAGCCGGGGACGGCGCCAACT<br>GCCACCGGCCCGAGGAGCCCGCGGCCGCGGACGCGCTGGGGACGAGCGTGGTGGTCCCCCC<br>GGAGCCCACCAAAACCAGGCCCTGTGGCAACAACAGAGCGAGCCACCGCAAGGAGCTGCGC<br>TCCTCCGTGACCTGCGAGAAGCGCCGCACGCGGGGGCTAAGCAGGATCGTCCCCAAATCCA<br>AGGAGTTCATTGAGACAGAGTCGTCATCTTCATCCTCCTCCTCGGACTCCGACCTGGAGTC<br>CGAGCAGGAGGAGTACCCCTCTGTCCAAAGCACAGACCGTGGCTGCCTCTGCCTCCTCCGGG<br>AATGATCAGAGGCTGAAGGAGGCCGCTGCCAACGGGGGCAGTGGTCCTAGGGCCCCTGTAG<br>GCTCCATCAACGCCAGGACCACCAGTGACATCGCCAAGGAGCTGGAGGAGCAGTTCTACAC<br>ACTGGTCCCCTTTGGCCGGAACGAACTTCTCTCCCCTCTAAAGGACAGTGATGAGATCAGG<br>TCTCTCTGGGTCAAAATCGACCTGACCCTCCTGTCCAGGATCCCAGAACCTGCCCCAGG<br>AGCCAGGGGTATTGAGCGCCCCTGCCACCAAGGACTCTGAGAGCGCACCGCCCAGCCACAC<br>CTCGGACACACCTGCAGAAAAGGCTTTGCCAAAATCCAAGAGGAAACGCAAGTGTGACAAC<br>GAAGACGACTACAGGGAGATCAAGAAGTCCCAGGGAGAGAAGACAGCTCTTCAAGACTGG<br>CCACCTCCACCAGTAATACTTTGTCTGCAAACCACTGCAACATGAACATCAACAGTGTGGC<br>AATACCAATAAATAAAAATGAAAAAATGCTTCGGTCGCCCATCTCACCCCTCTCTGATGCA<br>TCTAAACACAAATACACCAGCGAGGACTTAACTTCTTCCAGCCGACCTAATGGCAACAGTT<br>TGTTTACTTCAGCCTCTTCCAGCAAAAAGCCTAAGGCCGACAGCCAGCTGCAGCCTCACGG<br>CGGAGACCTCACGAAAGCAGCTCACAACAATTCTGAAAACATTCCCCTCCACAAGTCACGG<br>CCGCAGACGAAGCCGTGGTCTCCAGGCTCCAACGGCCACAGGGACTGCAAGAGGCAGAAAC<br>TTGTCTTCGATGATATGCCTCGCAGTGCCGATTATTTTATGCAAGAAGCTAAACGAATGAA<br>GCATAAAGCAGATGCAATGGTGGAAAAGTTTGGAAAGGCTTTGAACTATGCTGAAGCAGCA<br>TTGTCGTTTATCGAGTGTGGAAATGCAATGGAACAAGGCCCCATGGAATCCAAATCTCCTT<br>ATACGATGTATTCAGAAACAGTAGAGCTCATCAGGTATGCTATGAGACTAAAAACCCACTC<br>AGGCCCCAATGCCACACCAGAAGACAAACAACTGGCTGCATTATGTTACCGATGCCTGGCC<br>CTCCTGTACTGGCGGATGTTTCGACTCAAAAAGGCACCACGCTGTAAAGTATTCAAAAGCAC<br>TAATCGACTATTTCAAGAACTCATCTAAAGCGCCCAAGCCCCATCTCCGTGGGGGCCAG<br>TGGAAAGAGCACTGGAACCCCATCCCCCATGTCTCCCAACCCCTCTCCCGCCAGCTCCGTG<br>GGGTCTCAGGGCAGCCTCTCCAACGCCAGCGCCCTGTCCCCGTCGACCATCGTCAGCATCC<br>CACAGCGCATCCACCAGATGGCGGCCAACCACGTCAGCATCACCAACAGCATCCTGCACAG<br>CTACGACTACTGGGAGATGGCCGACAACCTGGCCAAGGAAAACCGAGAATTCTTCAACGAC<br>CTGGATCTGCTCATGGGGCCGGTCACCCTGCACAGCAGCATGGAGCACCTGGTCCAGTACT<br>CCCAACAGGGCCTGCACTGGCTGCGGAACAGCGCCCACCTGTCATAG |
| FGFR2: CASP7<br>(3213 base pairs)<br>(SEQ ID NO: 62) | >ATGGTCAGCTGGGGTCGTTTCATCTGCCTGGTCGTGGTCACCATGGCAACTTGTCCCTG<br>GCCCGGCCCTCCTTCAGTTTAGTTGAGGATACCACATTAGAGCCAGAAGAGCCACCAACCA<br>AATACCAAATCTCTCAACCAGAAGTGTACGTGGCTGCGCCAGGGGAGTCGCTAGAGGTGCG<br>CTGCCTGTTGAAAGATGCCGCCGTGATCAGTTGGACTAAGGATGGGGTGCACTTGGGGCCC<br>AACAATAGGACAGTGCTTATTGGGGAGTACTTGCAGATAAAGGGCGCCACGCCTAGAGACT<br>CCGGCCTCTATGCTTGTACTGCCAGTAGGACTGTAGACAGTGAAACTTGGTACTTCATGGT<br>GAATGTCACAGATGCCATCTCATCCGGAGATGATGAGGATGACACCGATGGTGCGGAAGAT<br>TTTGTCAGTGAGAACAGTAACAACAAGAGAGCACCATACTGGACCAACACAGAAAAGATGG<br>AAAAGCGGCTCCATGCTGTGCCTGCGGCCAACACTGTCAAGTTTCGCTGCCCAGCCGGAGG<br>GAACCCAATGCCAACCATGCGGTGGCTGAAAAACGGGAAGGAGTTTAAGCAGGAGCATCGC<br>ATTGGAGGCTACAAGGTACGAAACCAGCACTGGAGCCTCATTATGGAAAGTGTGGTCCCAT<br>CTGACAAGGGAAATTATACCTGTGTAGTGGAGAATGAATACGGGTCCATCAATCACACGTA<br>CCACCTGGATGTTGTGGAGCGATCGCCTCACCGGCCCATCCTCCAAGCCGGACTGCCGGCA<br>AATGCCTCCACAGTGGTCGGAGGAGACGTAGAGTTTGTCTGCAAGGTTTACAGTGATGCCC |

TABLE 16-continued

```
                    AGCCCCACATCCAGTGGATCAAGCACGTGGAAAAGAACGGCAGTAAATACGGGCCCGACGG
                    GCTGCCCTACCTCAAGGTTCTCAAGGCCGCCGGTGTTAACACCACGGACAAAGAGATTGAG
                    GTTCTCTATATTCGGAATGTAACTTTTGAGGACGCTGGGGAATATACGTGCTTGGCGGGTA
                    ATTCTATTGGGATATCCTTTCACTCTGCATGGTTGACAGTTCTGCCAGCGCCTGGAAGAGA
                    AAAGGAGATTACAGCTTCCCCAGACTACCTGGAGATAGCCATTTACTGCATAGGGGTCTTC
                    TTAATCGCCTGTATGGTGGTAACAGTCATCCTGTGCCGAATGAAGAACACGACCAAGAAGC
                    CAGACTTCAGCAGCCAGCCGGCTGTGCACAAGCTGACCAAACGTATCCCCCTGCGGAGACA
                    GGTAACAGTTTCGGCTGAGTCCAGCTCCTCCATGAACTCCAACACCCCGCTGGTGAGGATA
                    ACAACACGCCTCTCTTCAACGGCAGACACCCCCATGCTGGCAGGGGTCTCCGAGTATGAAC
                    TTCCAGAGGACCCAAAATGGGAGTTTCCAAGAGATAAGCTGACACTGGGCAAGCCCCTGGG
                    AGAAGGTTGCTTTGGGCAAGTGGTCATGGCGGAAGCAGTGGGAATTGACAAAGACAAGCCC
                    AAGGAGGCGGTCACCGTGGCCGTGAAGATGTTGAAAGATGATGCCACAGAGAAAGACCTTT
                    CTGATCTGGTGTCAGAGATGGAGATGATGAAGATGATTGGGAACACAAGAATATCATAAA
                    TCTTCTTGGAGCCTGCACACAGGATGGGCCTCTCTATGTCATAGTTGAGTATGCCTCTAAA
                    GGCAACCTCCGAGAATACCTCCGAGCCCGGAGGCCACCCGGGATGGAGTACTCCTATGACA
                    TTAACCGTGTTCCTGAGGAGCAGATGACCTTCAAGGACTTGGTGTCATGCACCTACCAGCT
                    GGCCAGAGGCATGGAGTACTTGGCTTCCCAAAAATGTATTCATCGAGATTTAGCAGCCAGA
                    AATGTTTTGGTAACAGAAAACAATGTGATGAAAATAGCAGACTTTGGACTCGCCAGAGATA
                    TCAACAATATAGACTATTACAAAAAGACCACCAATGGGCGGCTTCCAGTCAAGTGGATGGC
                    TCCAGAAGCCCTGTTTGATAGAGTATACACTCATCAGAGTGATGTCTGGTCCTTCGGGGTG
                    TTAATGTGGGAGATCTTCACTTTAGGGGGCTCGCCCTACCCAGGGATTCCCGTGGAGGAAC
                    TTTTTAAGCTGCTGAAGGAAGGACACAGAATGGATAAGCCAGCCAACTGCACCAACGAACT
                    GTACATGATGATGAGGGACTGTTGGCATGCAGTGCCCTCCCAGAGACCAACGTTCAAGCAG
                    TTGGTAGAAGACTTGGATCGAATTCTCACTCTCACAACCAATGAGATGGCAGATGATCAGG
                    GCTGTATTGAAGAGCAGGGGGTTGAGGATTCAGCAAATGAAGATTCAGTGGATGCTAAGCC
                    AGACCGGTCCTCGTTTGTACCGTCCCTCTTCAGTAAGAAGAAGAAAAATGTCACCATGCGA
                    TCCATCAAGACCACCCGGGACCGAGTGCCTACATATCAGTACAACATGAATTTTGAAAAGC
                    TGGGCAAATGCATCATAATAAACAACAAGAACTTTGATAAAGTGACAGGTATGGGCGTTCG
                    AAACGGAACAGACAAAGATGCCGAGGCGCTCTTTCAAGTGCTTCCGAAGCCTGGGTTTTGAC
                    GTGATTGTCTATAATGACTGCTCTTGTGCCAAGATGCAAGATCTGCTTAAAAAAGCTTCTG
                    AAGAGGACCATACAAATGCCGCCTGCTTCGCCTGCATCCTCTTAAGCCATGGAAGAAAAA
                    TGTAATTTATGGGAAAGATGGTGTCACACCAATAAAGGATTTGACAGCCCACTTTAGGGGG
                    GATAGATGCAAAACCCTTTTAGAGAAACCCAAACTCTTCTTCATTCAGGCTTGCCGAGGGA
                    CCGAGCTTGATGATGGCATCCAGGCCGACTCGGGGCCCATCAATGACACAGATGCTAATCC
                    TCGATACAAGATCCCAGTGGAAGCTGACTTCCTCTTCGCCTATTCCACGGTTCCAGGCTAT
                    TACTCGTGGAGGAGCCCAGGAAGAGGCTCCTGGTTTGTGCAAGCCCTCTGCTCCATCCTGG
                    AGGAGCACGGAAAAGACCTGGAAATCATGCAGATCCTCACCAGGGTGAATGACAGAGTTGC
                    CAGGCACTTTGAGTCTCAGTCTGATGACCCACACTTCCATGAGAAGAAGCAGATCCCCTGT
                    GTGGTCTCCATGCTCACCAAGGAACTCTACTTCAGTCAATAG

FGFR2: CCDC6       >ATGGTCAGCTGGGGTCGTTTCATCTGCCTGGTCGTGGTCACCATGGCAACCTTGTCCCTG
(3423 base pairs)  GCCCGGCCCTCCTTCAGTTTAGTTGAGGATACCACATTAGAGCCAGAAGAGCCACCAACCA
(SEQ ID NO: 63)    AATACCAAATCTCTCAACCAGAAGTGTACGTGGCTGCGCCAGGGGAGTCGCTAGAGGTGCG
                    CTGCCTGTTGAAAGATGCCGCCGTGATCAGTTGGACTAAGGATGGGGTGCACTTGGGGCCC
                    AACAATAGGACAGTGCTTATTGGGGAGTACTTGCAGATAAAGGGCGCCACGCCTAGAGACT
                    CCGGCCTCTATGCTTGTACTGCCAGTAGGACTGTAGACAGTGAAACTTGGTACTTCATGGT
                    GAATGTCACAGATGCCATCTCATCCGGAGATGATGAGGATGACACCGATGGTGCGGAAGAT
                    TTTGTCAGTGAGAACAGTAACAACAAGAGAGCACCATACTGGACCAACACAGAAAAGATGG
                    AAAAGCGGCTCCATGCTGTGCCTGCGGCCAACACTGTCAAGTTTCGCTGCCCAGCCGGGGG
                    GAACCCAATGCCAACCATGCGGTGGCTGAAAAACGGGAAGGAGTTTAAGCAGGAGCATCGC
                    ATTGGAGGCTACAAGGTACGAAACCAGCACTGGAGCCTCATTATGGAAAGTGTGGTCCCAT
                    CTGACAAGGGAAATTATACCTGTGTAGTGGAGAATGAATACGGGTCCATCAATCACACGTA
                    CCACCTGGATGTTGTGGAGCGATCGCCTCACCGGCCCATCCTCCAAGCCGGACTGCCGGCA
                    AATGCCTCCACAGTGGTCGGAGGAGACGTAGAGTTTGTCTGCAAGGTTTACAGTGATGCCC
                    AGCCCCACATCCAGTGGATCAAGCACGTGGAAAAGAACGGCAGTAAATACGGGCCCGACGG
                    GCTGCCCTACCTCAAGGTTCTCAAGGCCGCCGGTGTTAACACCACGGACAAAGAGATTGAG
                    GTTCTCTATATTCGGAATGTAACTTTTGAGGACGCTGGGGAATATACGTGCTTGGCGGGTA
                    ATTCTATTGGGATATCCTTTCACTCTGCATGGTTGACAGTTCTGCCAGCGCCTGGAAGAGA
                    AAAGGAGATTACAGCTTCCCCAGACTACCTGGAGATAGCCATTTACTGCATAGGGGTCTTC
                    TTAATCGCCTGTATGGTGGTAACAGTCATCCTGTGCCGAATGAAGAACACGACCAAGAAGC
                    CAGACTTCAGCAGCCAGCCGGCTGTGCACAAGCTGACCAAACGTATCCCCCTGCGGAGACA
                    GGTAACAGTTTCGGCTGAGTCCAGCTCCTCCATGAACTCCAACACCCCGCTGGTGAGGATA
                    ACAACACGCCTCTCTTCAACGGCAGACACCCCCATGCTGGCAGGGGTCTCCGAGTATGAAC
                    TTCCAGAGGACCCAAAATGGGAGTTTCCAAGAGATAAGCTGACACTGGGCAAGCCCCTGGG
                    AGAAGGTTGCTTTGGGCAAGTGGTCATGGCGGAAGCAGTGGGAATTGACAAAGACAAGCCC
                    AAGGAGGCGGTCACCGTGGCCGTGAAGATGTTGAAAGATGATGCCACAGAGAAAGACCTTT
                    CTGATCTGGTGTCAGAGATGGAGATGATGAAGATGATTGGGAACACAAGAATATCATAAA
                    TCTTCTTGGAGCCTGCACACAGGATGGGCCTCTCTATGTCATAGTTGAGTATGCCTCTAAA
                    GGCAACCTCCGAGAATACCTCCGAGCCCGGAGGCCACCCGGGATGGAGTACTCCTATGACA
                    TTAACCGTGTTCCTGAGGAGCAGATGACCTTCAAGGACTTGGTGTCATGCACCTACCAGCT
                    GGCCAGAGGCATGGAGTACTTGGCTTCCCAAAAATGTATTCATCGAGATTTAGCAGCCAGA
                    AATGTTTTGGTAACAGAAAACAATGTGATGAAAATAGCAGACTTTGGACTCGCCAGAGATA
                    TCAACAATATAGACTATTACAAAAAGACCACCAATGGGCGGCTTCCAGTCAAGTGGATGGC
                    TCCAGAAGCCCTGTTTGATAGAGTATACACTCATCAGAGTGATGTCTGGTCCTTCGGGGTG
                    TTAATGTGGGAGATCTTCACTTTAGGGGGCTCGCCCTACCCAGGGATTCCCGTGGAGGAAC
                    TTTTTAAGCTGCTGAAGGAAGGACACAGAATGGATAAGCCAGCCAACTGCACCAACGAACT
                    GTACATGATGATGAGGGACTGTTGGCATGCAGTGCCCTCCCAGAGACCAACGTTCAAGCAG
                    TTGGTAGAAGACTTGGATCGAATTCTCACTCTCACAACCAATGAGCAAGCCAGGGCTGAGC
                    AGGAAGAAGAATTCATTAGTAACACTTTATTCAAGAAAATTCAGGCTTTGCAGAAGGAGAA
                    AGAAACCCTTGCTGTAAATTATGAGAAAGAAGAAGAATTCCTCACTAATGAGCTCTCCAGA
```

TABLE 16-continued

| | |
|---|---|
| | AAATTGATGCAGTTGCAGCATGAGAAAGCCGAACTAGAACAGCATCTTGAACAAGAGCAGG
AATTTCAGGTCAACAAACTGATGAAGAAAATTAAAAAACTGGAGAATGACACCATTTCTAA
GCAACTTACATTAGAACAGTTGAGACGGGAGAAGATTGACCTTGAAAATACATTGGAACAA
GAACAAGAAGCACTAGTTAATCGCCTCTGGAAAAGGATGGATAAGCTTGAAGCTGAAAAGC
GAATCCTGCAGGAAAATTAGACCAGCCCGTCTCTGCTCCACCATCGCCTAGAGATATCTC
CATGGAGATTGATTCTCCAGAAAATATGATGCGTCACATCAGGTTTTTAAAGAATGAAGTG
GAACGGCTGAAGAAGCAACTGAGAGCTGCTCAGTTACAGCATTCAGAGAAAATGGCACAGT
ATCTGGAGGAGGAACGTCACATGAGAGAAGAGAACTTGAGGCTCCAGAGGAAGCTGCAGAG
GGAGATGGAGAGAAGAGAAGCCCTCTGTCGACAGCTCTCCGAGAGTGAGTCCAGCTTAGAA
ATGGACGACGAAAGGTATTTTAATGAGATGTCTGCACAAGGATTAAGACCTCGCACTGTGT
CCAGCCCGATCCCTTACACACCTTCTCCGAGTTCAAGCAGGCCTATATCACCTGGTCTATC
ATATGCAAGTCACACGGTTGGTTTCACGCCACCAACTTCACTGACTAGAGCTGGAATGTCT
TATTACAATTCCCCGGGTCTTCACGTGCAGCACATGGGAACATCCCATGGTATCACAAGGC
CTTCACCACGGAGAAGCAACAGTCCTGACAAATTCAAACGGCCCACGCCGCCTCCATCTCC
CAACACACAGACCCCAGTCCAGCCACCTCCGCCTCCACCTCCGCCACCCATGCAGCCCACG
GTCCCCTCAGCAGCCACCTCGCAGCCTACTCCTTCGCAACATTCGGCGCACCCCTCCTCCC
AGCCTTAA |
| FGFR2: OFD1
(5229 base pairs)
(SEQ ID NO: 64) | >ATGGTCAGCTGGGGTCGTTTCATCTGCCTGGTCGTGGTCACCATGGCAACCTTGTCCCTG
GCCCGGCCCTCCTTCAGTTTAGTTGAGGATACCACATTAGAGCCAGAAGAGCCACCAACCA
AATACCAAATCTCTCAACCAGAAGTGTACGTGGCTGCGCCAGGGGAGTCGCTAGAGGTGCG
CTGCCTGTTGAAAGATGCCGCCGTGATCAGTTGGACTAAGGATGGGGTGCACTTGGGGCCC
AACAATAGGACAGTGCTTATTGGGGAGTACTTGCAGATAAAGGGCGCCACGCCTAGAGACT
CCGGCCTCTATGCTTGTACTGCCAGTAGGACTGTAGACAGTGAAACTTGGTACTTCATGGT
GAATGTCACAGATGCCATCTCATCCGGAGATGATGAGGATGACACCGATGGTGCGGAAGAT
TTTGTCAGTGAGAACAGTAACAACAAGAGAGCACCATACTGGACCAACACAGAAAAGATGG
AAAAGCGGCTCCATGCTGTGCCTGCGGCCAACACTGTCAAGTTTCGCTGCCCAGCCGGGGG
GAACCCAATGCCAACCATGCGGTGGCTGAAAAACGGGAAGGAGTTTAAGCAGGAGCATCGC
ATTGGAGGCTACAAGGTACGAAACCAGCACTGGAGCCTCATTATGGAAAGTGTGGTCCCAT
CTGACAAGGGAAATTATACCTGTGTAGTGGAGAATGAATACGGGTCCATCAATCACACGTA
CCACCTGGATGTTGTGGAGCGATCGCCTCACCGGCCCATCCTCCAAGCCGGACTGCCGGCA
AATGCCTCCACAGTGGTCGGAGGAGACGTAGAGTTTGTCTGCAAGGTTTACAGTGATGCCC
AGCCCCACATCCAGTGGATCAAGCACGTGGAAAAGAACGGCAGTAAATACGGGCCGACGG
GCTGCCCTACCTCAAGGTTCTCAAGGCCGCCGGTGTTAACACCACGGACAAAGAGATTGAG
GTTCTCTATATTCGGAATGTAACTTTTGAGGACGCTGGGGAATATACGTGCTTGGCGGGTA
ATTCTATTGGGATATCCTTTCACTCTGCATGGTTGACAGTTCTGCCAGCGCCTGGAAGAGA
AAAGGAGATTACAGCTTCCCCAGACTACCTGGAGATAGCCATTTACTGCATAGGGGTCTTC
TTAATCGCCTGTATGGTGGTAACAGTCATCCTGTGCCGAATGAAGAACACGACCAAGAAGC
CAGACTTCAGCAGCCAGCCGGCTGTGCACAAGCTGACCAAACGTATCCCCCTGCGGAGACA
GGTAACAGTTTCGGCTGAGTCAGCTCCTCCATGAACTCCAACACCCCGCTGGTGAGGATA
ACAACACGCCTCTCTTCAACGGCAGACACCCCCATGCTGGCAGGGGTCTCCGAGTATGAAC
TTCCAGAGGACCCAAAATGGGAGTTTCCAAGAGATAAGCTGACACTGGGCAAGCCCCTGGG
AGAAGGTTGCTTTGGGCAAGTGGTCATGGCGGAAGCAGTGGGAATTGACAAAGACAAGCCC
AAGGAGGCGGTCACCGTGGCCGTGAAGATGTTGAAAGATGATGCCACAGAGAAAGACCTTT
CTGATCTGGTGTCAGAGATGGAGATGATGAAGATGATTGGGAAACACAAGAATATCATAAA
TCTTCTTGGAGCCTGCACACAGGATGGGCCTCTCTATGTCATTGTTGAGTATGCCTCTAAA
GGCAACCTCCGAGAATACCTCCGAGCCCGGAGGCCACCCGGGATGGAGTACTCCTATGACA
TTAACCGTGTTCCTGAGGAGCAGATGACCTTCAAGGACTTGGTGTCATGCACCTACCAGCT
GGCCAGAGGCATGGAGTACTTGGCTTCCCAAAAATGTATTCATCGAGATTTAGCAGCCAGA
AATGTTTTGGTAACAGAAAACAATGTGATGAAAATAGCAGACTTTGGACTCGCCAGAGATA
TCAACAATATAGACTATTACAAAAAGACCACCAATGGGCGGCTTCCAGTCAAGTGGATGGC
TCCAGAAGCCCTGTTTGATAGAGTATACACTCATCAGAGTGATGTCTGGTCCTTCGGGGTG
TTAATGTGGGAGATCTTCACTTTAGGGGGCTCGCCCTACCCAGGGATTCCCGTGGAGGAAC
TTTTTAAGCTGCTGAAGGAAGGACACAGAATGGATAAGCCAGCCAACTGCACCAACGAACT
GTACATGATGATGAGGGACTGTTGGCATGCAGTGCCCTCCCAGACCAACGTTCAAGCAG
TTGGTAGAAGACTTGGATCGAATTCTCACTCTCACAACCAATGAGACAACTTCGAAACC
AGCTAATTCATGAGTTGATGCACCCTGTATTGAGTGGAGAACTGCAGCCTCGGTCCATTTC
AGTAGAAGGGAGCTCCCTCTTAATAGGCGCCTCTAACTCTTTAGTGGCAGATCACTTACAA
AGATGTGGCTATGAATATTCACTTTCTGTTTTCTTTCCAGAAAGTGGTTTGGCAAAAGAAA
AGGTATTTACTATGCAGGATCTATTACAACTCATTAAAATCAACCCTACTTCCAGTCTCTA
CAAATCACTGGTTTCAGGATCTGATAAAGAAAATCAAAAAGGTTTTCTTATGCATTTTTTA
AAAGAATTGGCAGAATATCATCAAGCTAAAGAGAGTTGTAATATGGAAACTCAGACAAGTT
CGACATTTAACAGAGATTCTCTGGCTGAGAAGCTTCAGCTTATTGATGATCAGTTTGCAGA
TGCTTACCCTCAGCGTATCAAGTTCGAATCTTTAGAAATAAAGCTAAATGAGTATAAGAGA
GAAATAGAAGAGCAACTTCGGGCAGAAATGTGTCAAAAGTTGAAGTTTTTTAAAGATACCG
AGATAGCAAAATTAAAATGGAAGCAAAAAAAAGTATGAAAAGGAGTTAACCATGTTCCA
GAATGATTTTGAAAAAGCTTGTCAAGCAAATCTGAAGCTCTCGTTCTTCGGGAAAAGAGT
ACCCTTGAAAGAATTCACAAGCACCAAGAGATTGAAACAAAAGAAATTTATGCTCAAAGGC
AACTTTTACTAAAAGATATGGATTTGCTAAGAGGAAGAAGAGCAGAGCTGAAGCAAAGAGT
TGAAGCTTTTGAATTGAACCAGAAGCTCCAGGAAGAAAAACATAAAAGCATAACTGAGGCA
CTTAGGAGACAGGAGCAGAATATAAAGAGTTTTGAGGAGACCTATGACCGAAAGCTCAAGA
ATGAACTTCTAAAGTATCAACTTGAACTGAAGGATGACTACATCATTAGAACTAATCGACT
GATTGAAGATGAAAGGAAGAATAAAGAAAAAGCTGTTCATTTGCAAGAGGAGCTCATAGCT
ATTAATTCAAAAAGGAGGAACTCAATCAATCTGTAAATCGTGTGAAGAACTTGAGCTTG
AATTAGAGTCTGTCAAAGCCCAGTCTTTGGCAATAACAAAACAAACCATATGCTGAATGA
AAAGGTTAAAGAGATGAGTGATTATTCACTACTAAAAGAAGAGAAATGGAGCTTCTGGCA
CAAAATAAATTACTTAAACAACAACTGGAAGAGAGTAGAAATGAAAACCTGCGTCTCCTAA
ACCGCCTAGCTCAGCCGGCTCCTGAACTTGCAGTCTTTCAGAAAGAACTACGGAAAGCCGA
AAAGGCTATAGTGGTTGAGCATGAGGAGTTCGAAAGCTGCAGGCAAGCTCTGCACAAACAA
CTGCAAGACGAAATTGAGCATTCTGCACAGCTGAAGGCCCAGATTCTAGGTTACAAAGCTT |

TABLE 16-continued

```
CTGTAAAGAGTTTAACTACTCAGGTTGCCGATTTAAAATTGCAACTGAAGCAAACTCAGAC
AGCCCTAGAGAATGAAGTGTACTGCAATCCAAAGCAGTCTGTGATCGATCGTTCTGTCAAT
GGATTAATAAATGGCAATGTGGTGCCTTGCAATGGTGAGATAAGTGGGGATTTCTTGAACA
ATCCTTTTAAACAGGAAAACGTTCTAGCACGTATGGTTGCATCAAGGATCACAAATTATCC
AACTGCATGGGTGGAGGGTAGTTCCCCTGATTCTGACCTTGAGTTTGTAGCCAATACTAAG
GCAAGGGTCAAAGAGCTTCAGCAAGAGGCCGAACGCTTGGAAAAGGCTTTCAGAAGTTACC
ATCGGAGAGTCATTAAAAACTCTGCCAAAAGCCCACTAGCAGCAAAGAGCCCACCATCTCT
GCACTTGCTGGAAGCCTTCAAAAAACATTACTTCCAGTTCCCCGGAAAGACATATTTTTGGA
GAGGACAGAGTTGTCTCTGAGCAGCCTCAAGTGGGCACACTTGAAGAAAGGAATGACGTCG
TGGAAGCACTGACAGGCAGTGCAGCCTCGAGGCTCCGCGGGGGCACTTCCTCCAGACGCCT
CTCTTCCACACCCTTCCAAAAGCAAAAGAAGCCTCGAAAGTGAAATGTATCTGGAAGGT
CTGGGCAGATCACACATTGCTTCCCCCAGTCCTTGTCCTGACAGAATGCCCCTACCATCAC
CCACTGAGTCTAGGCACAGCCTCTCCATCCCTCCTGTCTCCAGCCCTCCGGAGCAGAAAGT
GGGTCTTTATCGAAGACAAACTGAACTTCAAGACAAAAGTGAATTTTCAGATGTGGACAAG
CTAGCTTTTAAGGATAATGAGGAGTTTGAATCATCTTTTGAATCTGCAGGGAACATGCCAA
GGCAGTTGGAAATGGGCGGGCTTTCTCCTGCCGGGGATATGTCTCATGTGGACGCTGCTGC
AGCTGCTGTGCCCCTCTCATATCAGCACCCAAGTGTAGATCAGAAACAAATTGAAGAACAA
AAGGAAGAAGAAAAAATACGGGAACAGCAAGTGAAAGAACGAAGGCAGAGAGAAGAAAGAA
GGCAGAGTAACCTACAAGAAGTTTTAGAAAGGGAACGAAGAGAACTAGAAAAACTGTATCA
GGAAAGGAAGATGATTGAAGAATCACTGAAGATTAAAATAAAAAAGGAATTAGAAATGGAA
AATGAATTAGAAATGAGTAATCAAGAAATAAAAGACAAATCTGCTCACAGTGAAAATCCTT
TAGAGAAATACATGAAAATCATCCAGCAGGAGCAAGACCAGGAGTCGGCAGATAAGAGCTC
AAAAAAGATGGTCCAAGAAGGCTCCCTAGTGGACACGCTGCAATCTAGTGACAAAGTCGAA
AGTTTAACAGGCTTTTCTCATGAAGAACTAGACGACTCTTGGTAA
```

---

What is claimed:

1. A method of treating bladder cancer in a patient, the method comprising:
   determining that a fibroblast growth factor receptor (FGFR) single nucleotide polymorphism FGFR3 Y373C is present in a biological sample from the patient, and
   administering a FGFR inhibitor to the patient,
   wherein the FGFR inhibitor comprises a compound having Structural Formula I:

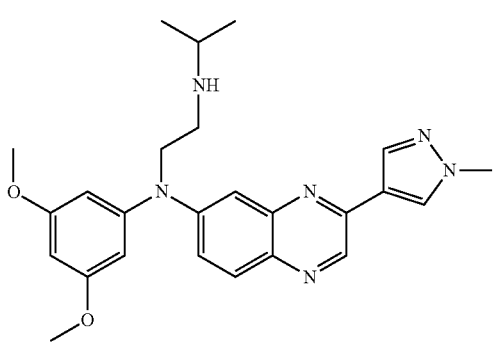
(I)

or a pharmaceutically acceptable salt thereof, thereby treating said bladder cancer.

2. The method of claim 1, wherein the FGFR inhibitor is a compound having Structural Formula I:

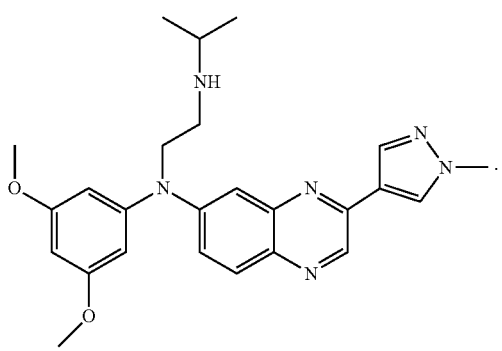
(I)

3. The method of claim 1, wherein the patient has been diagnosed with metastatic bladder cancer.

4. The method of claim 1, further comprising determining that one or more additional FGFR mutants from a FGFR mutant gene panel are present in the biological sample, wherein the one or more additional FGFR mutants comprise
   a) a FGFR fusion gene comprising FGFR3:TACC3 v1, FGFR3:TACC3 v3, FGFR3:TACC3 Intron, FGFR3:BAIAP2L1, FGFR2:BICC1, FGFR2:AFF3, FGFR2:CASP7, FGFR2:CCDC6, or FGFR2:OFD1, or any combination thereof,
   b) a FGFR single nucleotide polymorphism comprising FGFR3 R248C, FGFR3 S249C or FGFR3 G370C, or any combination thereof, or
   c) any combination of a) and b).

5. The method of claim 4, wherein the one or more additional FGFR mutants comprise one or more of: FGFR3 R248C, FGFR3 S249C, FGFR3 G370C, FGFR3:TACC3 v1, FGFR3:TACC3 v3, FGFR3:BAIAP2L1, FGFR2:CASP7 and FGFR2:BICC1.

6. The method of claim 4, wherein the one or more additional FGFR mutants comprise one or more of: FGFR3 R248C, FGFR3 S249C, FGFR3 G370C, FGFR3:TACC3 v1 and FGFR3:TACC3 v3.

7. The method of claim 1, wherein the patient has been diagnosed with urothelial carcinoma.

8. The method of claim 1, wherein the patient has been diagnosed with advanced bladder cancer.

9. The method of claim 1 comprising administering the FGFR inhibitor to the patient according to a dosing regimen comprising a once daily dose of about 9 mg.

10. The method of claim 1 comprising administering the FGFR inhibitor to the patient according to a dosing regimen comprising a once daily dose of from about 0.5 mg to about 9 mg.

11. The method of claim 1 comprising administering the FGFR inhibitor to the patient according to a dosing regimen comprising a once daily dose of from about 4 mg to about 9 mg.

12. A method of treating bladder cancer in a patient, the method comprising:
   determining that a fibroblast growth factor receptor (FGFR) single nucleotide polymorphism FGFR3 Y373C is present in a biological sample from the patient, and administering a FGFR inhibitor to the patient,
   wherein the FGFR inhibitor comprises a compound having Structural Formula I:

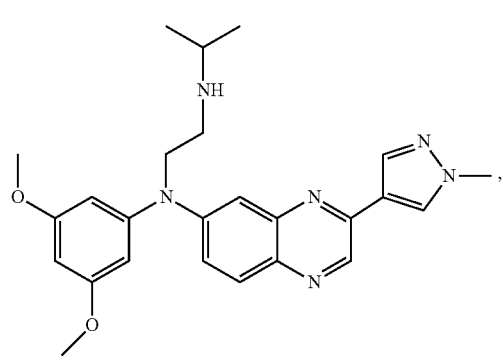
(I)

or a pharmaceutically acceptable salt thereof,
wherein the method comprises administering the FGFR inhibitor to the patient according to a dosing regimen comprising a once daily dose of from about 6 mg to about 9 mg, thereby treating said bladder cancer.

13. The method of claim 12, wherein the FGFR inhibitor is a compound having Structural Formula I:

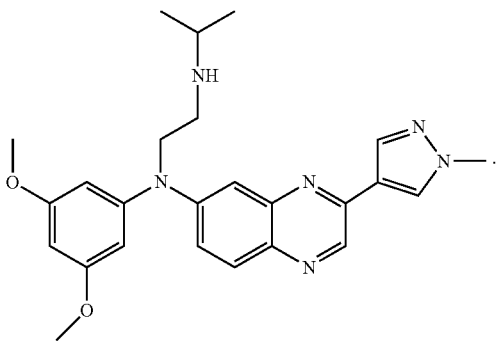

14. The method of claim 1, wherein the determining comprises amplifying a cDNA with a pair of primers that amplify FGFR3 Y373.

15. The method of claim 14, wherein the pair of primers have the sequences of SEQ ID NO: 29 and SEQ ID NO: 30 or SEQ ID NO: 37 and SEQ ID NO: 38.

16. The method of claim 14, wherein the determining comprises: isolating an RNA from the biological sample and synthesizing the cDNA from the isolated RNA.

17. The method of claim 16, further comprising pre-amplifying the cDNA prior to the amplifying.

18. The method of claim 14, wherein the cDNA is preamplified.

19. The method of claim 14, wherein the amplifying comprises performing a real-time PCR.

20. The method of claim 19, wherein the real-time PCR is performed with one or more probes comprising SEQ ID NO:55.

21. The method of claim 20, wherein the real-time PCR is further performed with one or more 3'comprising SEQ ID NO:42.

22. The method of claim 14, comprising sequencing the amplified cDNA.

23. The method of claim 4, wherein the determining comprises amplifying a cDNA with a pair of primers that amplify the one or more additional FGFR mutants from the FGFR mutant gene panel.

24. The method of claim 23, wherein one or more additional FGFR mutants and the pair of primers comprise:
FGFR3:TACC3 v1 and primers having the sequences of SEQ ID NO:5 and SEQ ID NO:6;
FGFR3:TACC3 v3 and primers having the sequences of SEQ ID NO:7 and SEQ ID NO:8;
FGFR3:TACC3 Intron and primers having the sequences of SEQ ID NO:9 and SEQ ID NO:10;
FGFR3:BAIAP2L1 and primers having the sequences of SEQ ID NO:11 and SEQ ID NO:12;
FGFR2:BICC1 and primers having the sequences of SEQ ID NO:13 and SEQ ID NO:14;
FGFR2:AFF3 and primers having the sequences of SEQ ID NO:15 and SEQ ID NO:16;
FGFR2:CASP7 and primers having sequences of SEQ ID NO:17 and SEQ ID NO:18;
FGFR2:CCDC6 and primers having the sequences of SEQ ID NO:19 and SEQ ID NO:20;
FGFR2:OFD1 and primers having the sequences of SEQ ID NO:21 and SEQ ID NO:22;
FGFR3 SC249C and primers having sequences of SEQ ID NO:25 and SEQ ID NO:26 or SEQ ID NO:33 and SEQ ID NO:34;
FGFR3 G370C and primers having the sequences of SEQ ID NO:27 and SEQ ID NO:28 or SEQ ID NO:35 and SEQ ID NO:36;
FGFR3 R248C and primers having the sequences of SEQ ID NO:23 and SEQ ID NO:24 or SEQ ID NO:31 and SEQ ID NO:32;
or any combination thereof.

25. The method of claim 23, wherein one or more additional FGFR mutants and the pair of primers comprise:
FGFR3:TACC3 v1 and primers having the sequences of SEQ ID NO:5 and SEQ ID NO:6;
FGFR3:TACC3 v3 and primers having the sequences of SEQ ID NO:7 and SEQ ID NO:8;
FGFR3:TACC3 Intron and primers having the sequences of SEQ ID NO:9 and SEQ ID NO:10;
FGFR3:BAIAP2L1 and primers having the sequences of SEQ ID NO:11 and SEQ ID NO:12;
FGFR2:BICC1 and primers having the sequences of SEQ ID NO:13 and SEQ ID NO:14;
FGFR2:CASP7 and primers having sequences of SEQ ID NO:17 and SEQ ID NO:18;
FGFR3 SC249C and primers having sequences of SEQ ID NO:25 and SEQ ID NO:26 or SEQ ID NO:33 and SEQ ID NO:34;
FGFR3 G370C and primers having the sequences of SEQ ID NO:27 and SEQ ID NO:28 or SEQ ID NO:35 and SEQ ID NO:36;
FGFR3 R248C and primers having the sequences of SEQ ID NO:23 and SEQ ID NO:24 or SEQ ID NO:31 and SEQ ID NO:32;
or any combination thereof.

* * * * *

UNITED STATES PATENT AND TRADEMARK OFFICE
CERTIFICATE OF CORRECTION

| | | |
|---|---|---|
| PATENT NO. | : 12,037,644 B2 | Page 1 of 3 |
| APPLICATION NO. | : 16/136201 | |
| DATED | : July 16, 2024 | |
| INVENTOR(S) | : Suso Jesus Platero et al. | |

It is certified that error appears in the above-identified patent and that said Letters Patent is hereby corrected as shown below:

In the Specification

Under Column no. 5, Line no. 35 (TABLE 2), Replace:
"RGFR3 Y373C*"
With:
--FGFR3 Y373C*--

Under Column no. 36, Line no. 39, Replace:
"mix (80 1) was"
With:
--mix (80 µl) was--

Under Column no. 37, Line no. 29, Replace:
"2 µl 10λ RT Random Primers;"
With:
--2 µl 10X RT Random Primers;--

Under Column no. 42, Line no. 38, Replace:
"100 µg of fusion"
With:
--100 pg of fusion--

Under Column no. 48, Line no. 24, TABLE 15-continued, Replace:
"FGFR3 5249C"
With:
--FGFR3 S249C--

Signed and Sealed this
Twenty-second Day of October, 2024

Katherine Kelly Vidal
*Director of the United States Patent and Trademark Office*

CERTIFICATE OF CORRECTION (continued)
U.S. Pat. No. 12,037,644 B2

In the Claims

Under Column no. 119, Claim 4, Line no. 62, Replace:
"combination thereof,"
With:
--combination thereof;--

Under Column no. 119, Claim 4, Line no. 65, Replace:
"combination thereof,"
With:
--combination thereof;--

Under Column no. 121, Claim 14, Line no. 22, Replace:
"amplify FGFR3 Y373."
With:
--amplify FGFR3 Y373C.--

Under Column no. 121, Claim 15, Line no. 24, Replace:
"SEQ ID NO: 30or"
With:
--SEQ ID NO: 30 or--

Under Column no. 121, Claim 21, Line no. 39, Replace:
"more 3'comprising SEQ ID NO:42."
With:
--more 3' blocking oligonucleotides comprising SEQ ID NO:42.--

Under Column no. 121, Claim 24, Line no. 48, Replace:
"wherein one"
With:
--wherein the one--

Under Column no. 122, Claim 24, Line no. 16, Replace:
"FGFR3 SC249C"
With:
--FGFR3 S249C--

Under Column no. 122, Claim 25, Line no. 26, Replace:
"wherein one"
With:
--wherein the one--

Under Column no. 122, Claim 25, Line nos. 32-33, Replace:
"SEQ ID NO:8; FGFR3:TACC3 Intron and primers having the sequences of SEQ ID NO:9 and SEQ ID NO:10; FGFR3:BAIAP2L1"

With:
--SEQ ID NO:8; FGFR3:BAIAP2L1--

Under Column no. 122, Claim 25, Line no. 40, Replace:
"FGFR3 SC249C"
With:
--FGFR3 S249C--